US012807620B2

(12) United States Patent
Deng et al.

(10) Patent No.: US 12,807,620 B2
(45) Date of Patent: Nov. 24, 2026

(54) NITROGEN-CONTAINING SPIRAL ORGANIC COMPOUND AND APPLICATION THEREOF IN ORGANIC LIGHT-EMITTING DEVICE AND PANEL

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Dongyang Deng, Shanghai (CN); Ying Liu, Shanghai (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

(*) Notice: Subject to any disclaimer, the term of this patent is extended or adjusted under 35 U.S.C. 154(b) by 1167 days.

(21) Appl. No.: 17/804,324

(22) Filed: May 27, 2022

(65) Prior Publication Data

US 2022/0298175 A1 Sep. 22, 2022

(30) Foreign Application Priority Data

Jan. 28, 2022 (CN) ......................... 202210108321.8

(51) Int. Cl.
*C07D 513/22* (2006.01)
*C07D 498/22* (2006.01)
(Continued)

(52) U.S. Cl.
CPC ......... *C07D 513/22* (2013.01); *C07D 498/22* (2013.01); *H10K 85/654* (2023.02);
(Continued)

(58) Field of Classification Search
CPC ................ C07D 498/20; C07D 513/20; C09K 2211/1011; C09K 2211/1029; C09K 2211/1044; C09K 2211/1059; C09K 2211/1062; C09K 2211/1066; C09K 2211/1088; H10K 85/615; H10K 85/636;
(Continued)

(56) References Cited

FOREIGN PATENT DOCUMENTS

| | | |
|---|---|---|
| CN | 106008537 B | 3/2018 |
| CN | 108409680 A | 8/2018 |

(Continued)

OTHER PUBLICATIONS

Bilgili et al. J. Phys. Chem. C 2021, 125, 4893-4908 (Year: 2021).*

(Continued)

*Primary Examiner* — Elizabeth M. Dahlburg
(74) *Attorney, Agent, or Firm* — KILPATRICK TOWNSEND & STOCKTON LLP

(57) ABSTRACT

A nitrogen-containing spiral organic compound is provided. The compound has a structure shown in Formula I or Formula II. A series of new TADF materials with excellent performance are developed. With the TADF materials used for mass products, the efficiency and service life of OLED devices are significantly improved and the driving voltage is reduced.

20 Claims, 1 Drawing Sheet

(51) Int. Cl.
*H10K 85/60* (2023.01)
*H10K 101/20* (2023.01)

(52) U.S. Cl.
CPC ....... *H10K 85/657* (2023.02); *H10K 85/6572* (2023.02); *H10K 85/6574* (2023.02); *H10K 85/6576* (2023.02); *H10K 2101/20* (2023.02)

(58) Field of Classification Search
CPC ............... H10K 85/654; H10K 85/657; H10K 85/6572; H10K 85/6574; H10K 2101/10
See application file for complete search history.

(56) References Cited

FOREIGN PATENT DOCUMENTS

| | | | | | |
|---|---|---|---|---|---|
| CN | 109824681 | A | | 5/2019 | |
| CN | 113801117 | A | | 12/2021 | |
| CN | 113845505 | A | | 12/2021 | |
| KR | 20170057852 | A | | 5/2017 | |
| KR | 20170059910 | A | | 5/2017 | |
| KR | 20190080063 | A | * | 7/2019 | ........... C07D 513/14 |

OTHER PUBLICATIONS

CN 108409680 A machine translation (Year: 2018).*
CN-113845505-A machine translation (Year: 2021).*
The State Intellectual Property Office of the People's Republic of China, First Office Action Issued in Application No. 202210108321.8, Nov. 22, 2022, 10 pages.

* cited by examiner

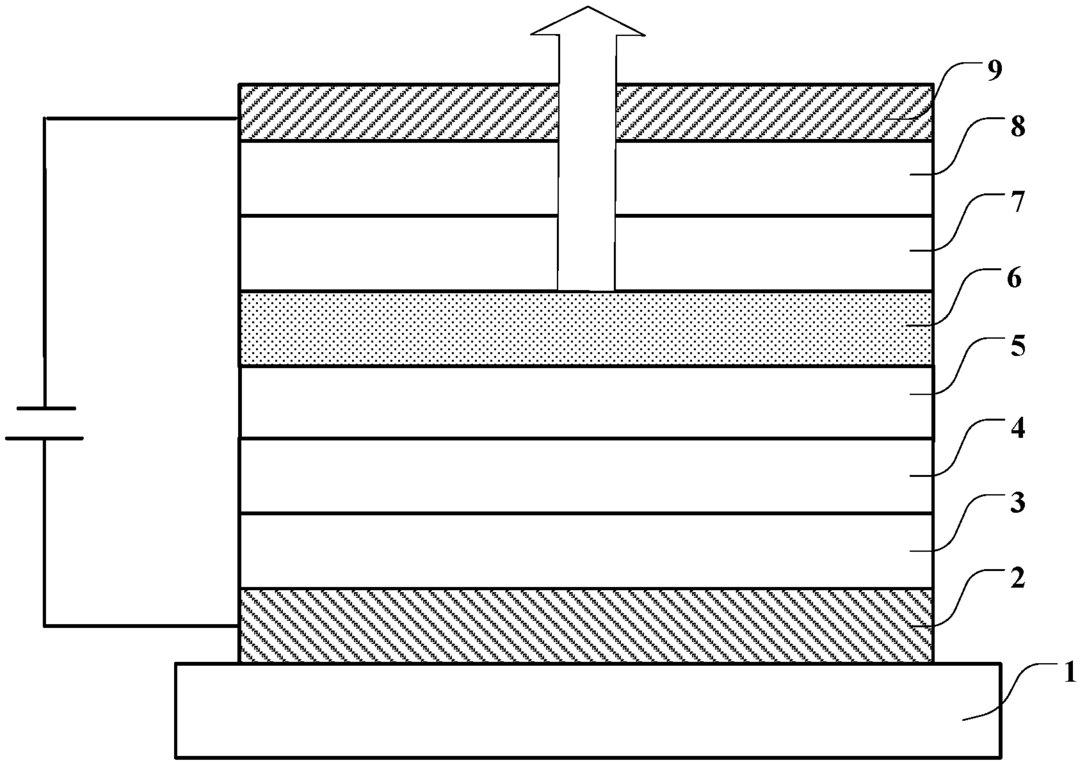
9
8
7
6
5
4
3
2
1

NITROGEN-CONTAINING SPIRAL ORGANIC COMPOUND AND APPLICATION THEREOF IN ORGANIC LIGHT-EMITTING DEVICE AND PANEL

CROSS REFERENCE OF RELATED APPLICATIONS

The present application claims the priority to Chinese Patent Application No. 202210108321.8, titled "NITROGEN-CONTAINING SPIRAL ORGANIC COMPOUND AND APPLICATION THEREOF IN ORGANIC LIGHT-EMITTING DEVICE AND PANEL", filed on Jan. 28, 2022 with the China National Intellectual Property Administration (CNIPA), which is incorporated herein by reference in its entirety.

FIELD

The present disclosure relates to the field of organic electroluminescent material, and in particular to a nitrogen-containing spiral organic compound and application thereof in an organic light-emitting device and panel.

BACKGROUND

According to the light-emitting mechanism, materials that can be used for an OLED light-emitting layer mainly include the following four types: a fluorescence material, a phosphor material, a triplet-trimer annihilation (TTA) material and a thermal activation delay fluorescence (TADF) material.

Theoretical maximum internal quantum yields of the fluorescence material and the TTA material are low and the cost of the phosphor material is high. Compared with the above three materials, the TADF materials have advantages. A theoretical maximum internal quantum yield of the TADF materials can reach 100%, and the TADF materials are mainly organic compounds without needing rare metallic elements. The TADF materials have a low production cost, and can be chemically modified with various methods to form various structures. However, there are few TADF materials found at present. Therefore, it is required to develop a TADF material having a high theoretical maximum internal quantum yield and low cost to improve comprehensive performance of OLED display devices.

SUMMARY

In view of the above, the problem to be solved by the present disclosure is to provide a nitrogen-containing spiral organic compound and application thereof in an organic light-emitting device and panel. With the prepared nitrogen-containing spiral-organic compound, the efficiency and the service life of OLED devices can be significantly improved and the driving voltage can be reduced.

A nitrogen-containing spiral organic compound is provided according to the present disclosure. The compound has a structure shown in Formula I or Formula II:

Formula I

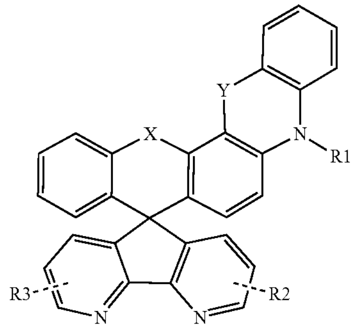

Formula II

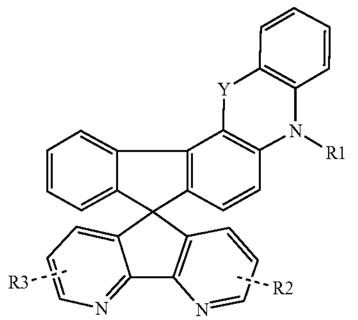

where X and Y are independently selected from O and S;

$R_1$ is selected from substituted or unsubstituted aryl and heteroaryl; and $R_2$ and $R_3$ are independently selected from H, substituted or unsubstituted aryl and heteroaryl, and $R_2$ and $R_3$ are not both H.

An organic light-emitting device is provided according to the present disclosure. The organic light-emitting device includes an anode, a cathode and an organic thin film layer between the anode and the cathode. The organic thin film layer includes a light-emitting layer, and the light-emitting layer includes at least one of the above-mentioned nitrogen-containing spiral organic compounds.

A display panel is provided according to the present disclosure. The display panel includes the above-mentioned organic light-emitting device.

BRIEF DESCRIPTION OF THE DRAWINGS

The FIGURE is a schematic structural diagram of an organic light-emitting device prepared according to the present disclosure.

DETAILED DESCRIPTION OF EMBODIMENTS

A nitrogen-containing spiral organic compound is provided according to the present disclosure The compound has a structure shown in Formula I or Formula II:

Formula I

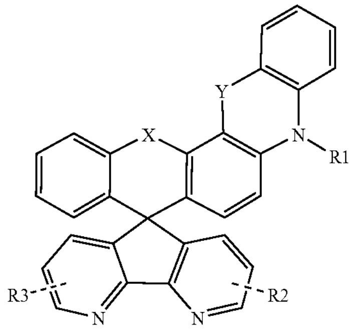

Formula II

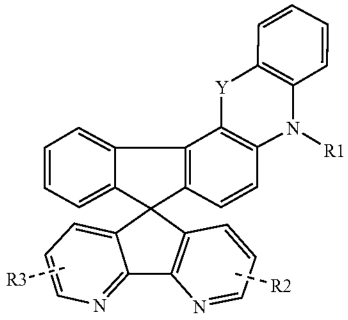

where X and Y are independently selected from O and S;

$R_1$ is selected from substituted or unsubstituted aryl and heteroaryl; and $R_2$ and $R_3$ are independently selected from H, and substituted or unsubstituted aryl and heteroaryl, and $R_2$ and $R_3$ are not both H.

In one embodiment, for the substituted aryl or heteroaryl, the substituent is one or more selected from halogen, cyano, C1-C6 alkyl, C1-C6 alkoxyl, substituted or unsubstituted aryl, substituted or unsubstituted heteroaryl, and arylamino.

In one embodiment, for the substituted aryl or heteroaryl, the substituent is one or more selected from F, Cl, Br, cyano, methyl, ethyl, n-propyl, isopropyl, n-butyl, isobutyl, t-butyl, methoxy, ethoxy, n-propoxy, and substituted or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl, and quinazolinyl.

In one embodiment, for the substituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl, and quinazolinyl, the substituent is one or more selected from phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl, and quinazolinyl.

In one embodiment, $R_1$ is selected from substituted or unsubstituted monocyclic aryl, monocyclic heteroaryl, fused ring aryl, and fused ring heteroaryl, or is a group formed by connecting any one or more of substituted or unsubstituted monocyclic aryl, monocyclic heteroaryl, fused ring aryl and fused ring heteroaryl through a single bond or an N atom.

The monocyclic aryl is phenyl.

The monocyclic heteroaryl is selected from pyridyl, pyrazinyl, pyrimidinyl, pyridazinyl, 1,2,3-triazinyl, 1,3,5-triazinyl, and 1,3,4-triazinyl.

The fused ring aryl is selected from naphthyl, anthracenyl, phenanthrenyl, pyrenyl and fluorenyl.

The fused ring heteroaryl is selected from carbazolyl, dibenzofuranyl, dibenzothiophenyl, quinolinyl, isoquinolinyl, quinoxalinyl and quinazolinyl.

In one embodiment, the one or more means one or two, one or three, or one or four.

In one embodiment, $R_1$ is selected from a first substituent-containing or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, quinolinyl, isoquinolinyl, quinoxalinyl, and quinazolinyl.

The first substituent is one or more selected from F, Cl, Br, cyano, methyl, ethyl, n-propyl, isopropyl, n-butyl, isobutyl, t-butyl, methoxy, ethoxy, n-propoxy, and a second substituent-containing or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl, and quinazolinyl.

The second substituent is one or more selected from phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl, and quinazolinyl.

In one embodiment, $R_1$ is selected from any of the following structures:

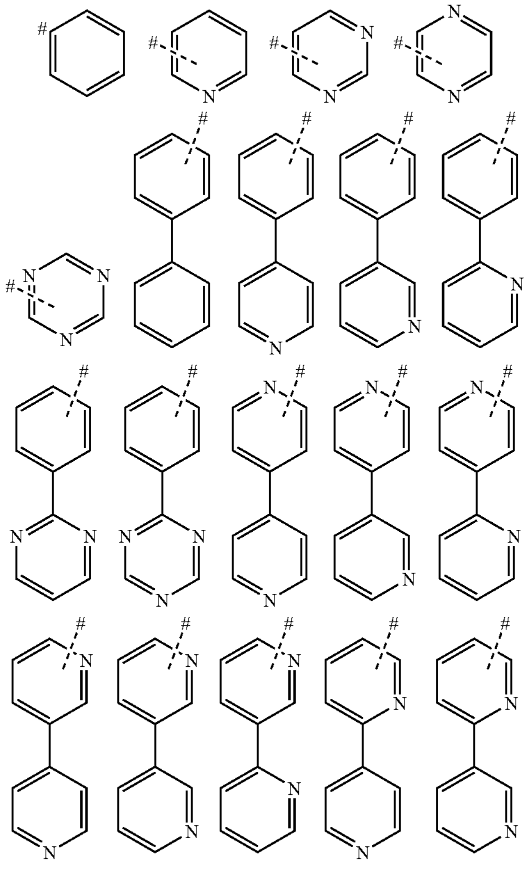

-continued

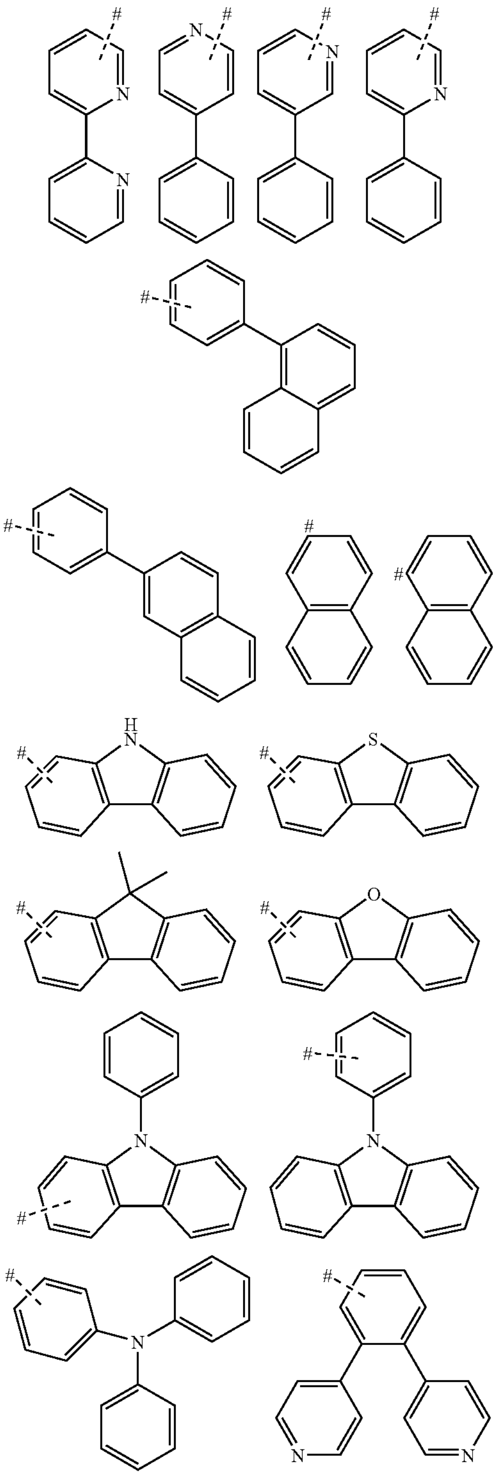

where #represents a connection position.

In one embodiment, $R_2$ and $R_3$ are independently selected from H, substituted or unsubstituted monocyclic aryl, monocyclic heteroaryl, fused ring aryl, and fused ring heteroaryl, or groups formed by connecting any one or more of substituted or unsubstituted monocyclic aryl, monocyclic heteroaryl, fused ring aryl and fused ring heteroaryl through a single bond or an N atom. In addition, $R_2$ and $R_3$ are not both H.

In one embodiment, the monocyclic aryl is phenyl.

The monocyclic heteroaryl is selected from pyridyl, pyrazinyl, pyrimidinyl, pyridazinyl, 1,2,3-triazine, 1,3,5-triazide, and 1,3,4-triazide.

The fused ring aryl is selected from naphthyl, anthracenyl, phenanthrenyl, pyrenyl and fluorenyl.

The fused ring heteroaryl is selected from carbazolyl, dibenzofuranyl, dibenzothiophenyl, quinolinyl, isoquinolinyl, quinoxalinyl and quinazolinyl.

In one embodiment, the one or more means one or two, one or three, or one or four.

In one embodiment, $R_2$ and $R_3$ are independently selected from H, first substituent-containing or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, quinolinyl, isoquinolinyl, quinoxalinyl, and quinazolinyl.

The first substituent is one or more selected from F, Cl, Br, cyano, methyl, ethyl, n-propyl, isopropyl, n-butyl, isobutyl, t-butyl, methoxy, ethoxy, n-propoxy, and second substituent-containing or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl, and quinazolinyl.

The second substituent is one or more selected from halogen, cyano, C1-C6 alkyl, C1-C6 alkoxyl, phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl, and quinazolinyl.

$R_2$ and $R_3$ are not both H.

In one embodiment, either or both of $R_2$ and $R_5$ are selected from any one of the following structures:

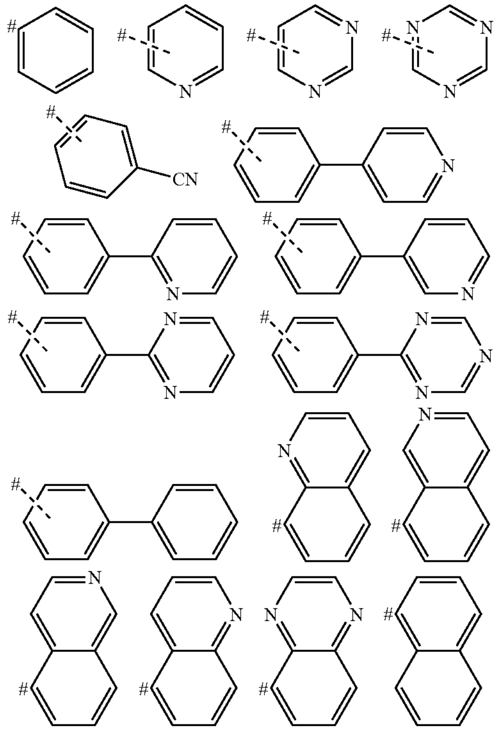

-continued
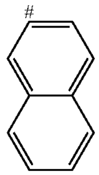
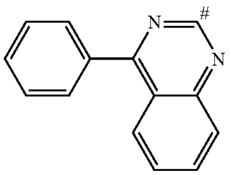
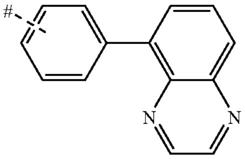
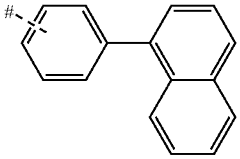
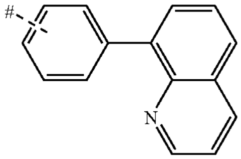
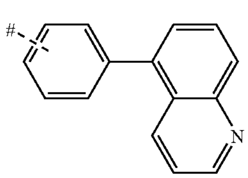
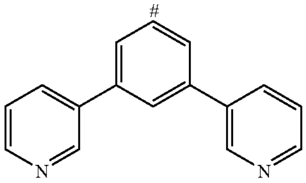
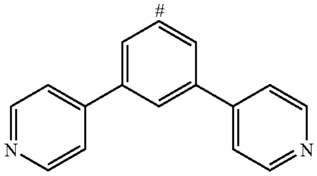
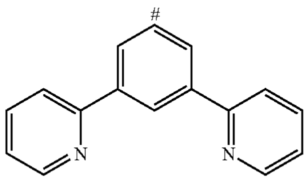
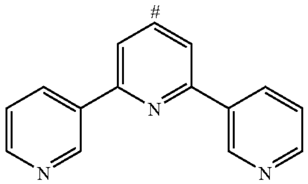
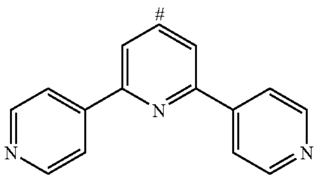
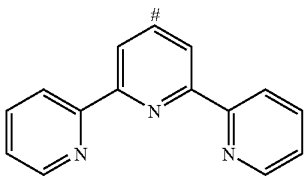
-continued
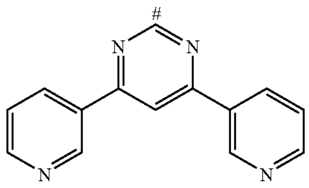
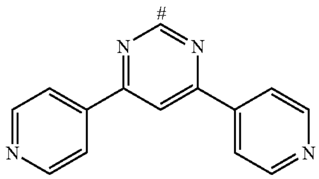
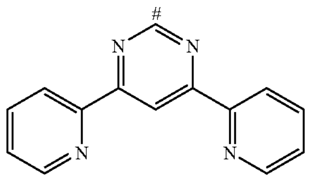
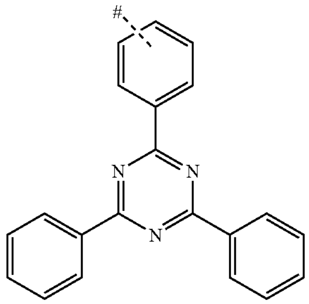
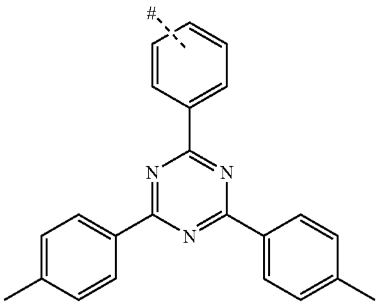
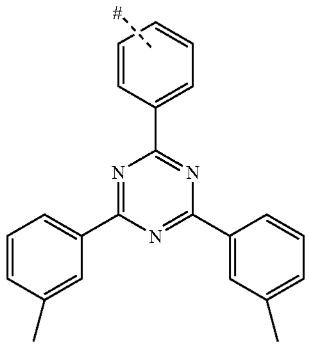

-continued
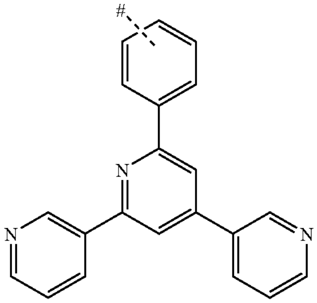
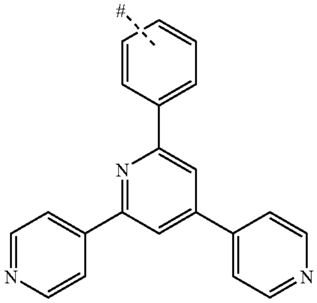
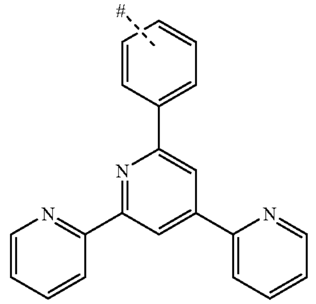
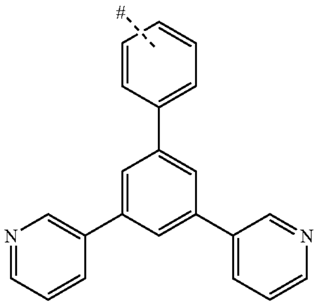
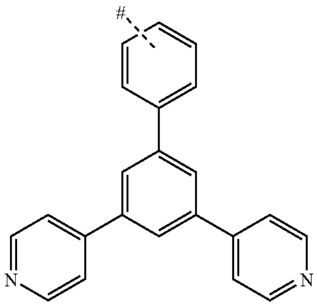
-continued
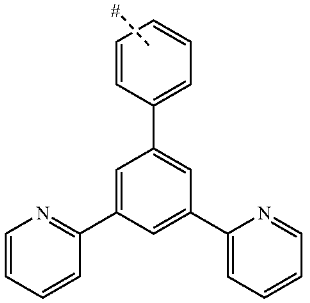
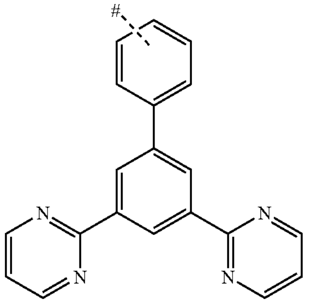
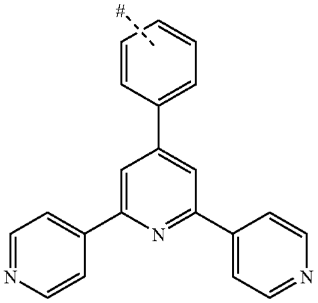
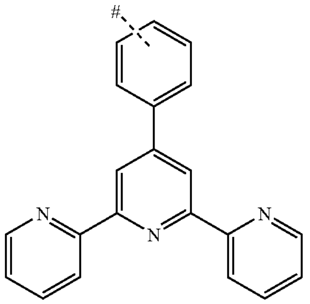
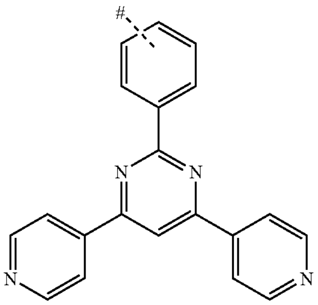

-continued
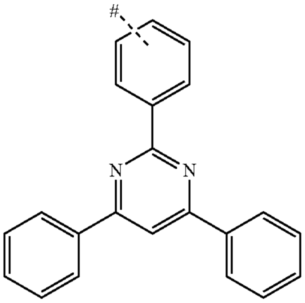
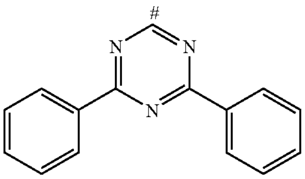
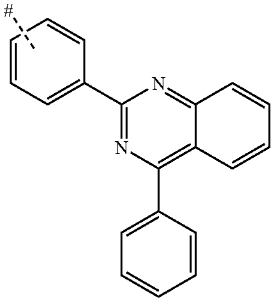
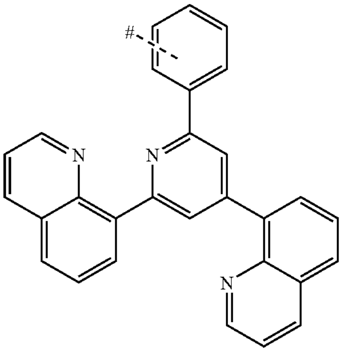
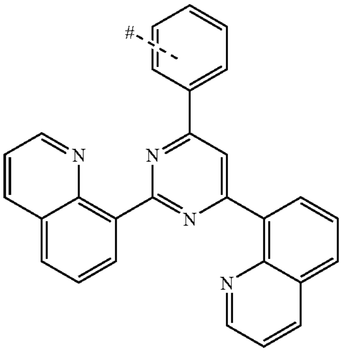
-continued
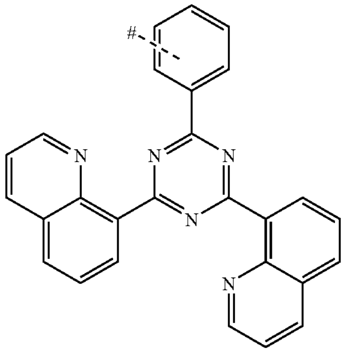
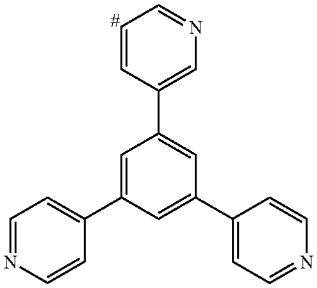
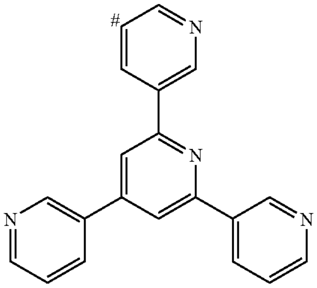
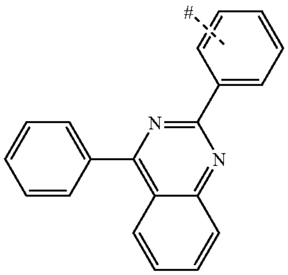
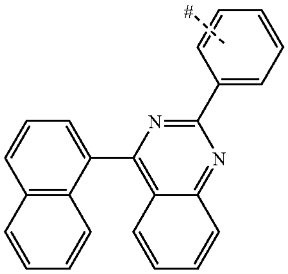

-continued
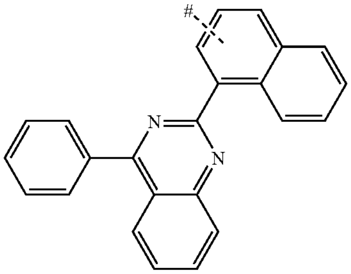
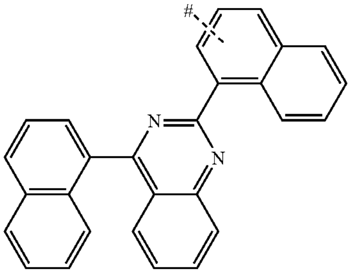
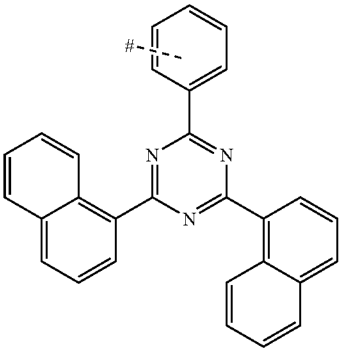
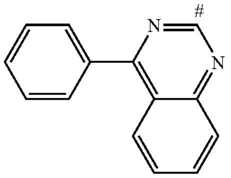
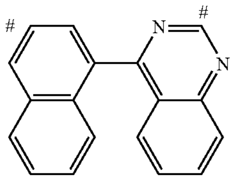
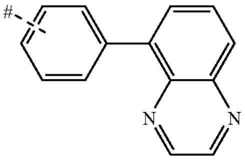
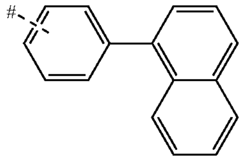
-continued
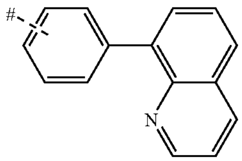
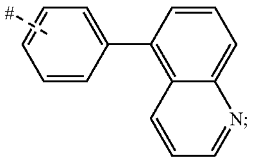
where #represents a connection position.
In one embodiment, $R_3$ is H.
In one embodiment, the nitrogen-containing spiral organic compound has any one of the following structures:
H1
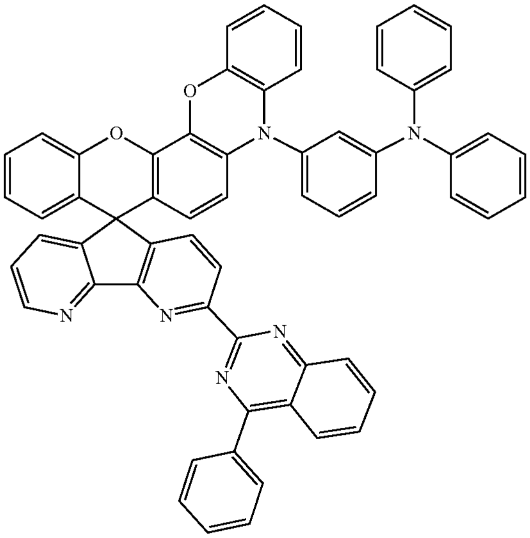
H2
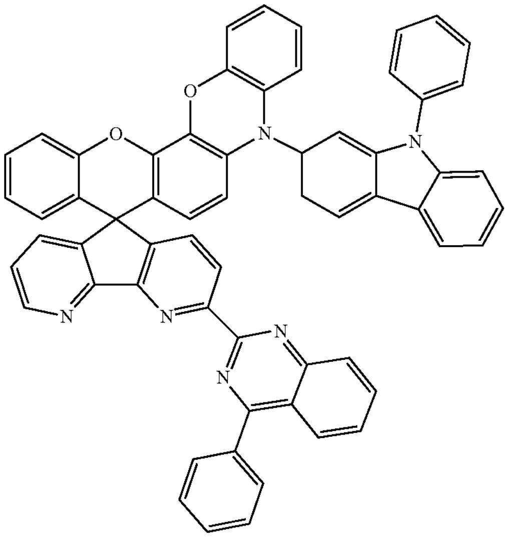

-continued
H3
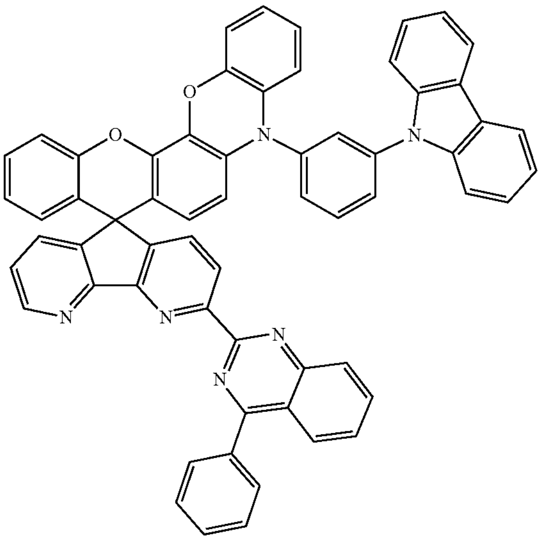
H4
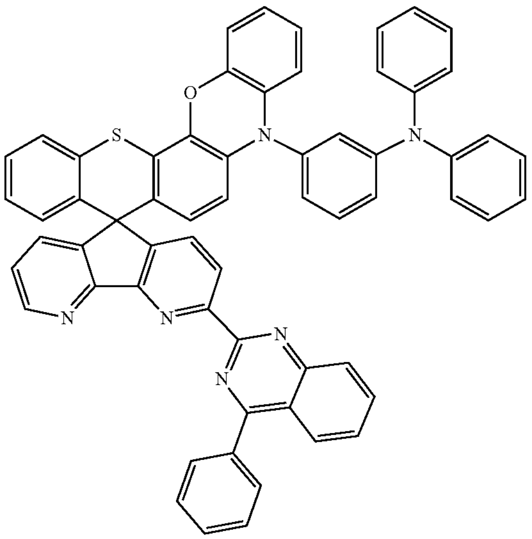
H5
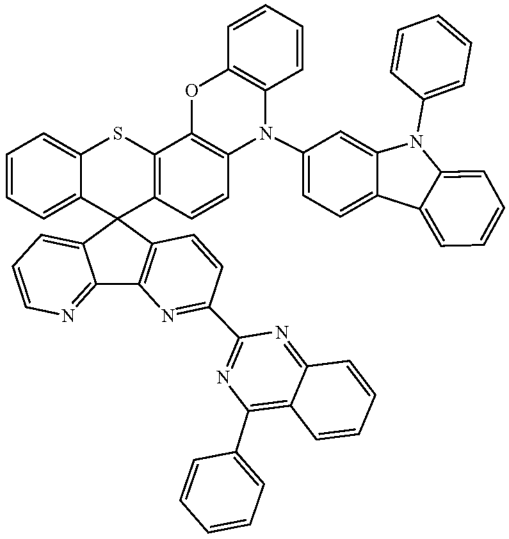
-continued
H6
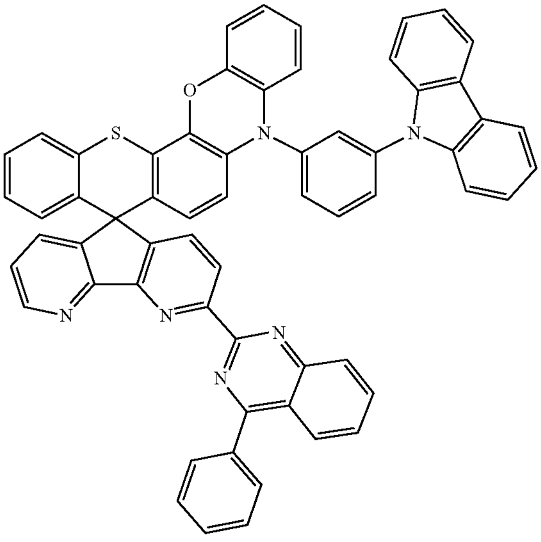
H7
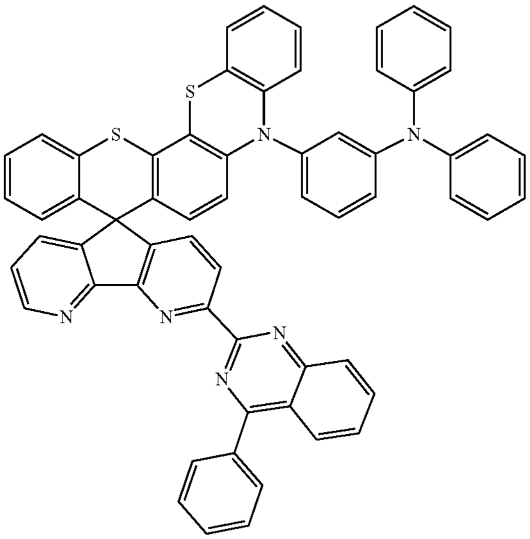
H8
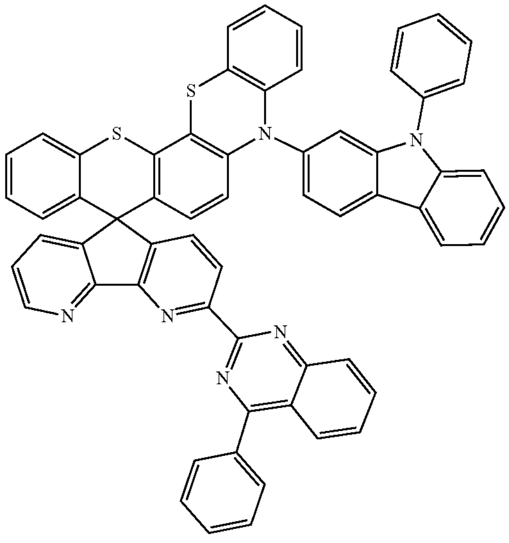

-continued
H9
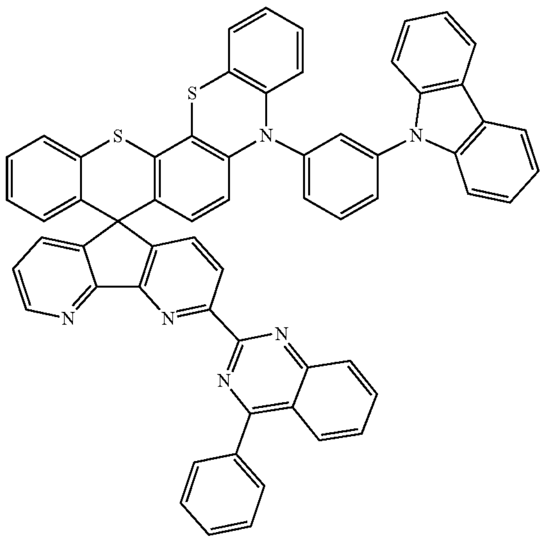
H10
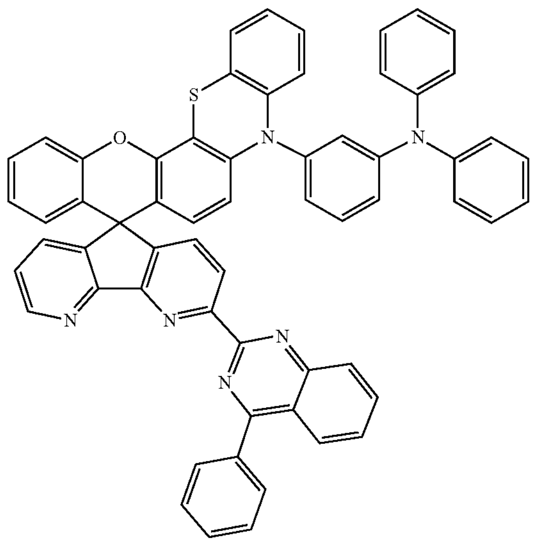
H11
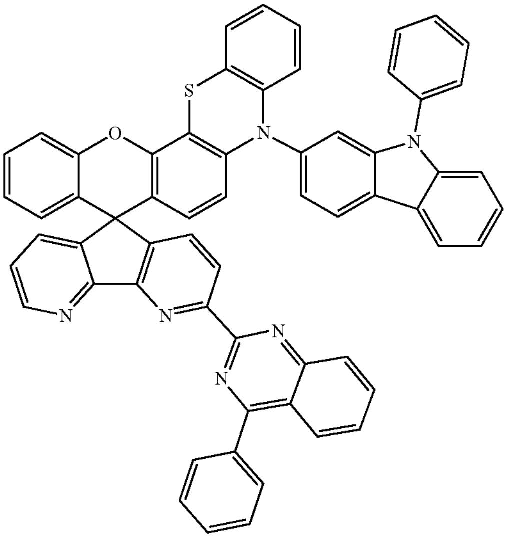
-continued
H12
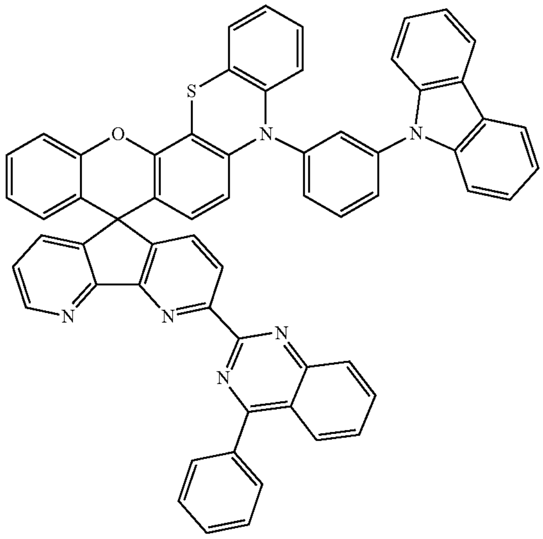
H13
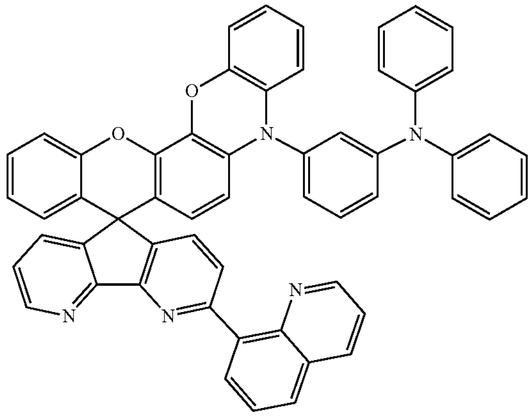
H14
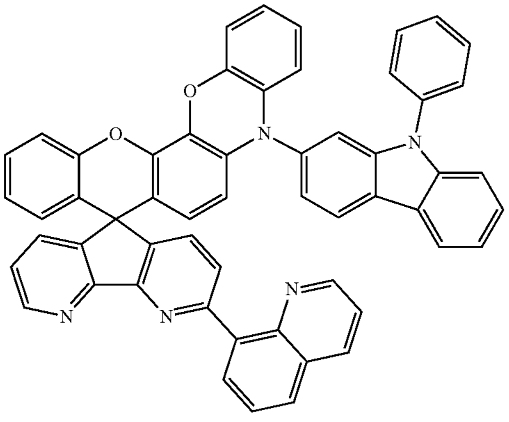

H15
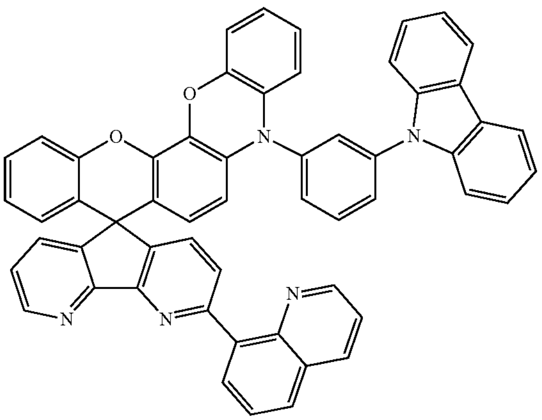
H16
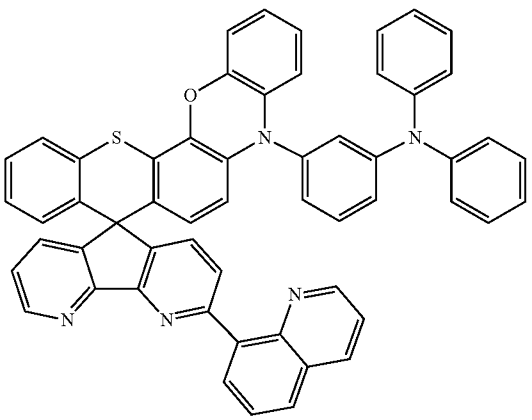
H17
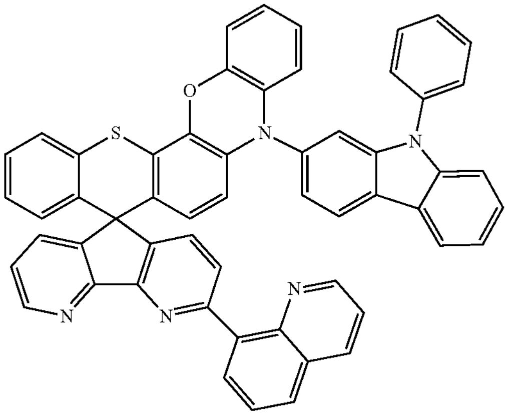
H18
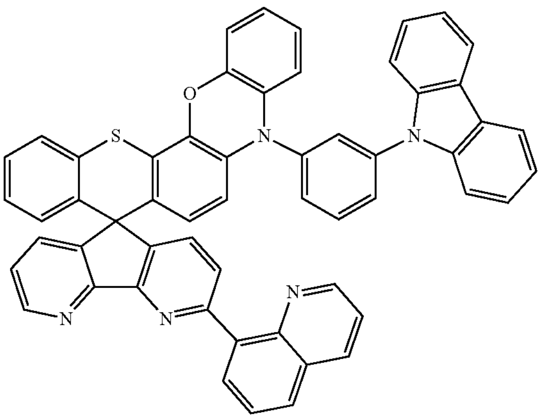
H19
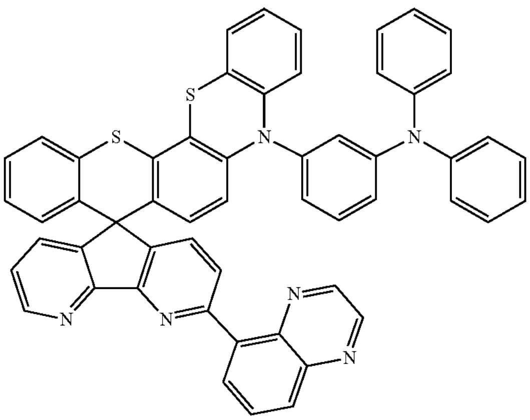
H20
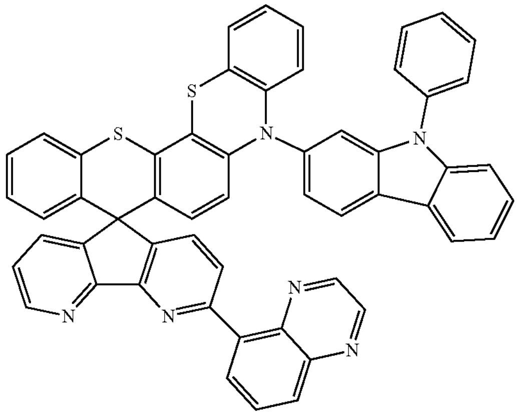

-continued
H21
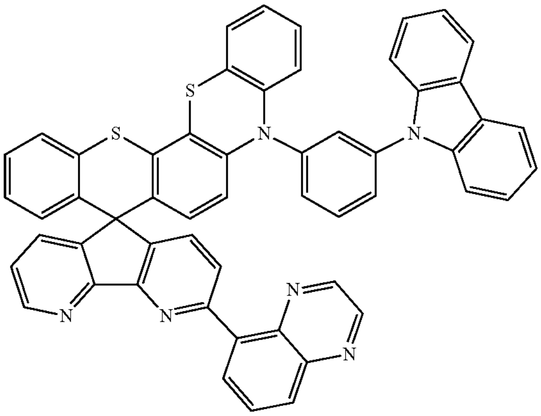
H22
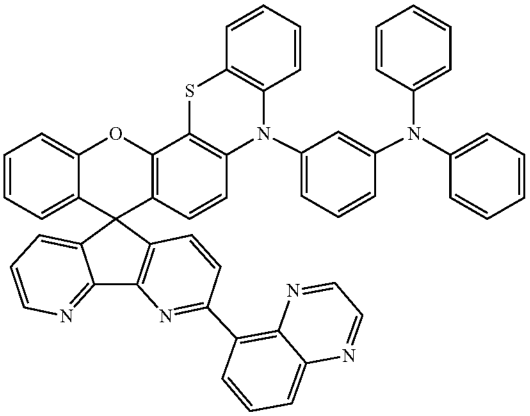
H23
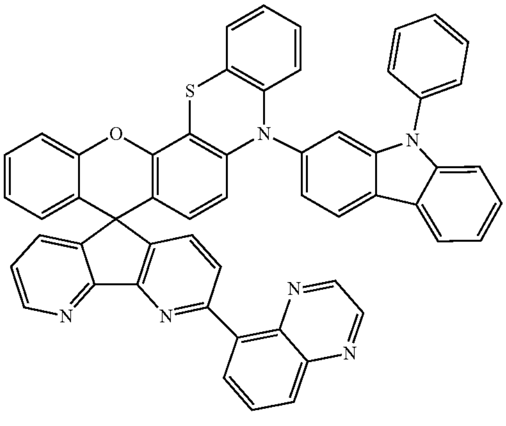
-continued
H24
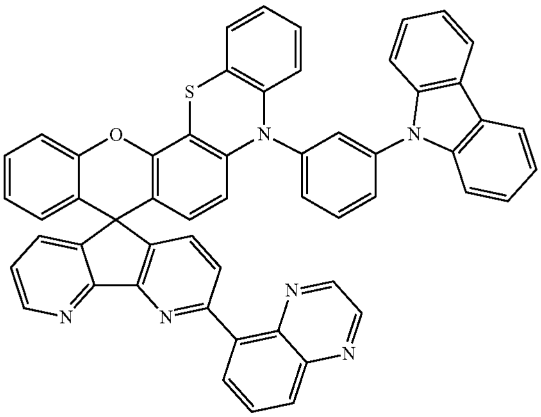
H25
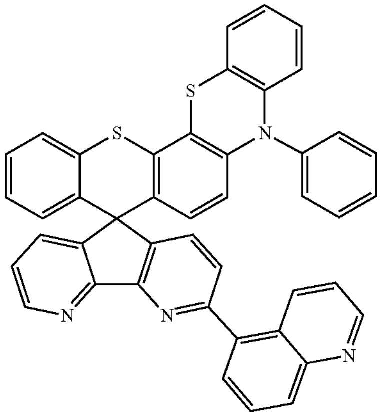
H26
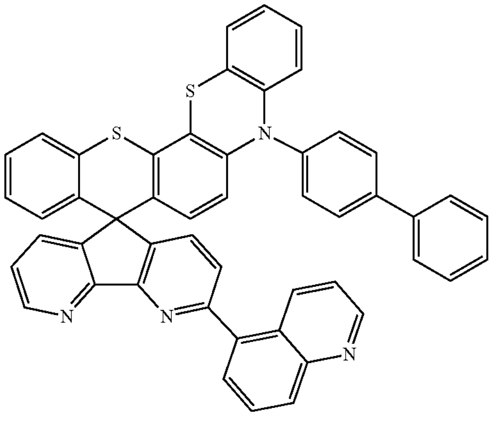

-continued
H27
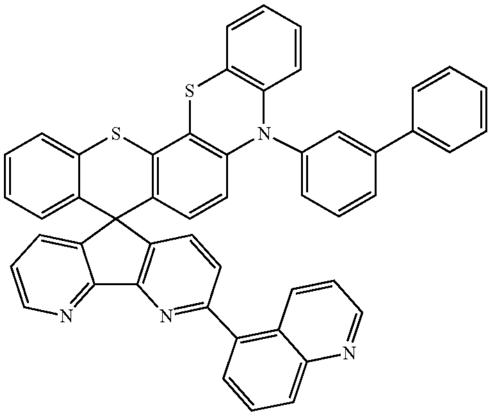
H28
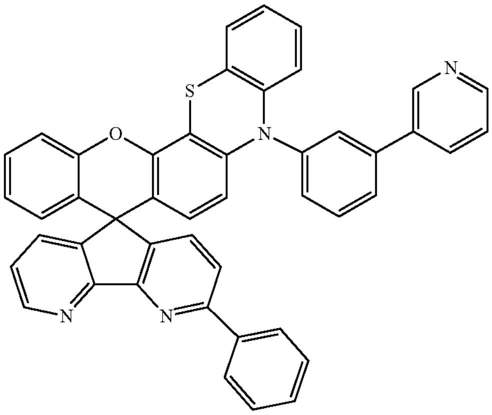
H29
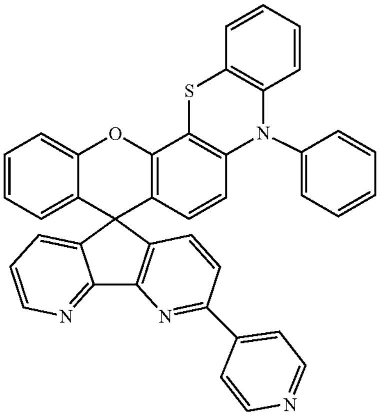
-continued
H30
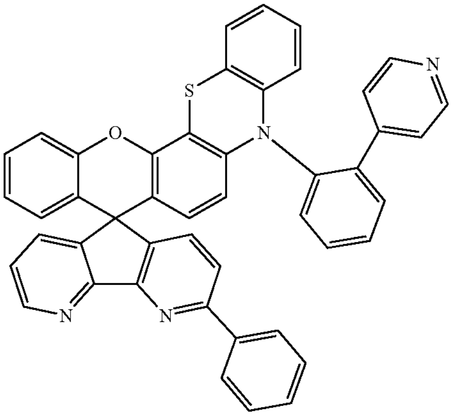
H31
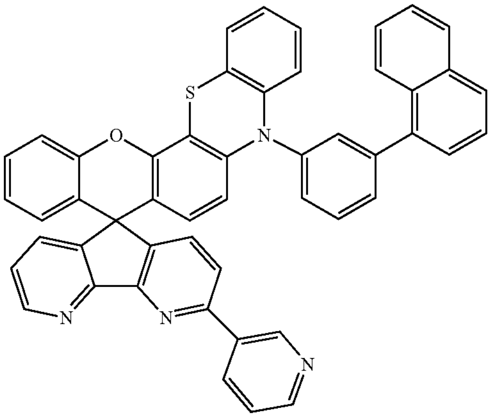
H32
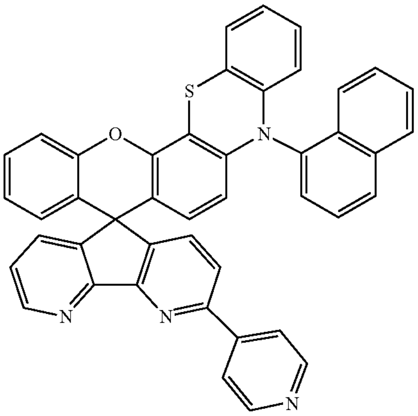

-continued
H33
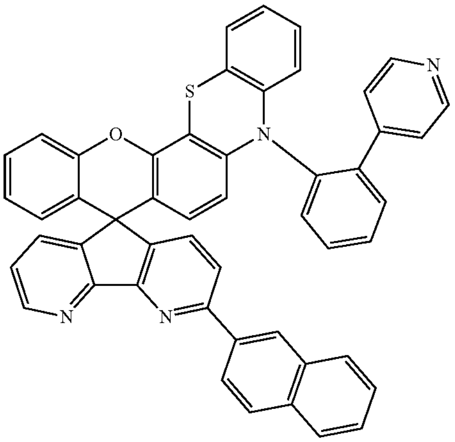
H34
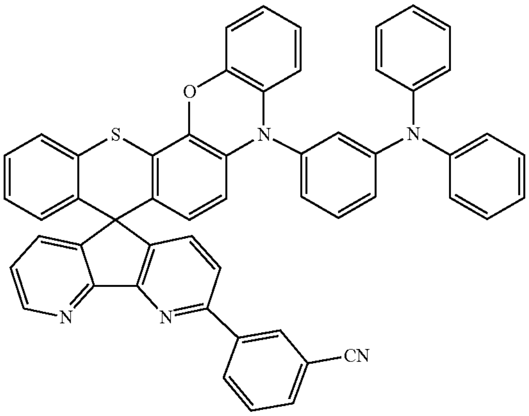
H35
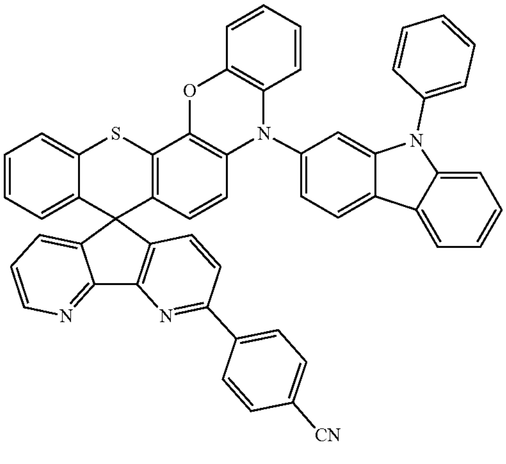
-continued
H36
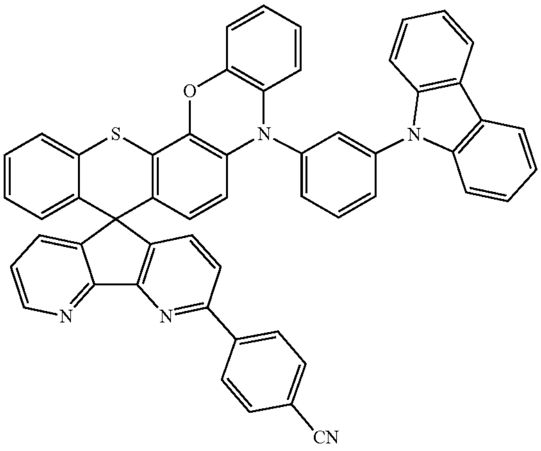
H37
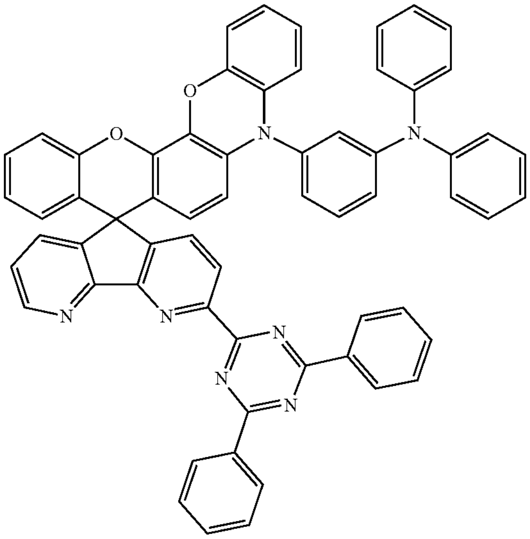
H38
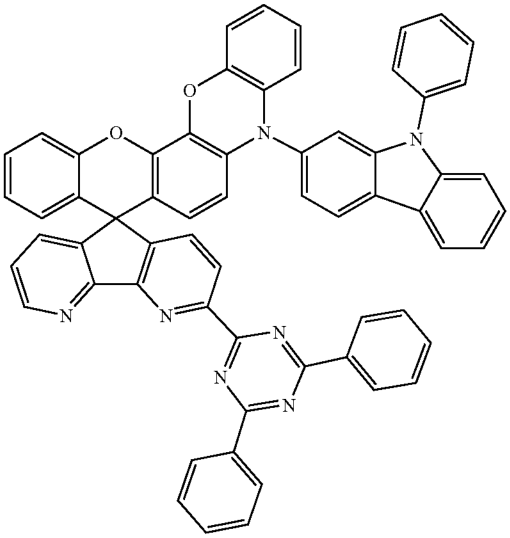

-continued
H39
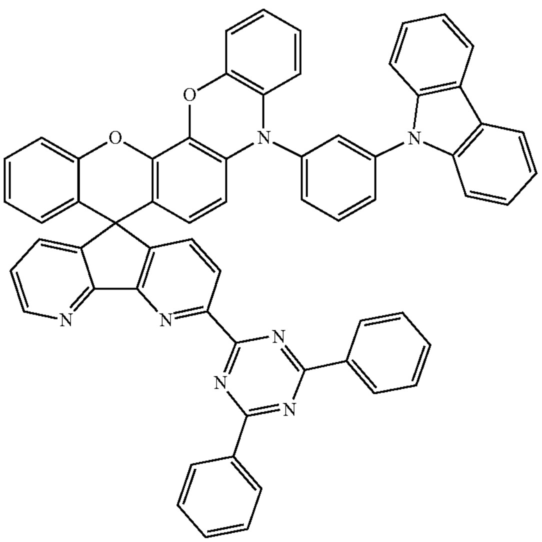
H40
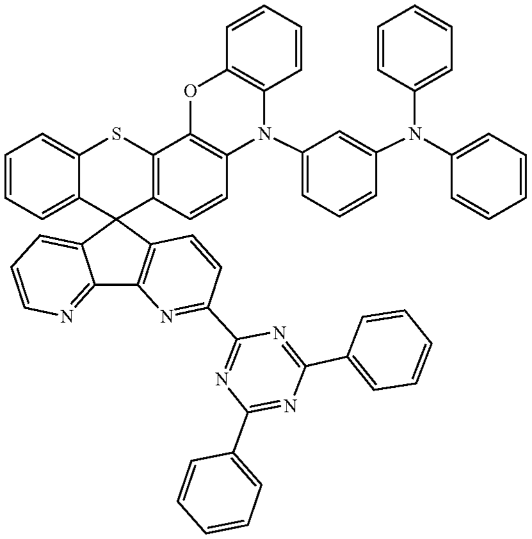
H41
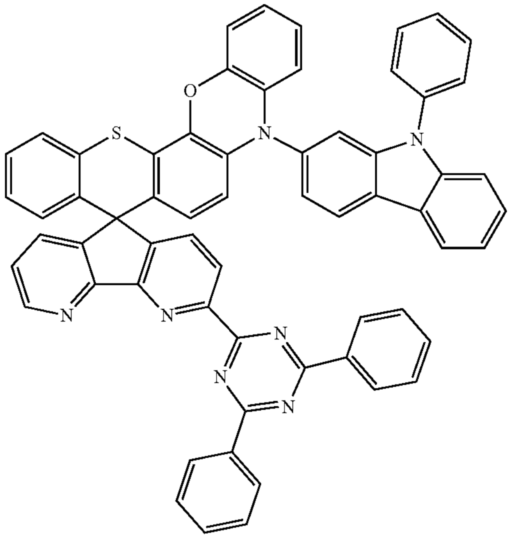
-continued
H42
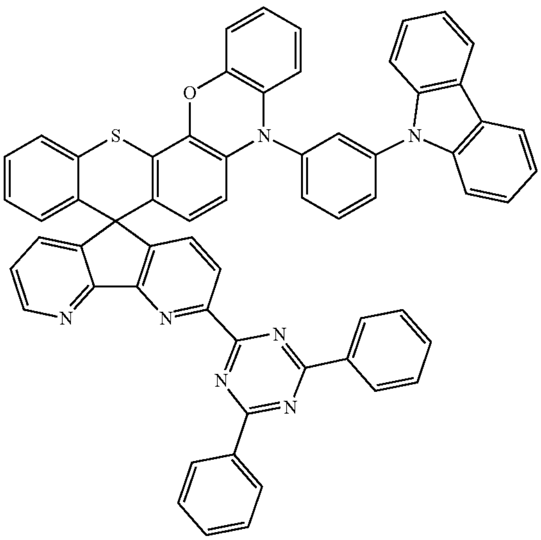
H43
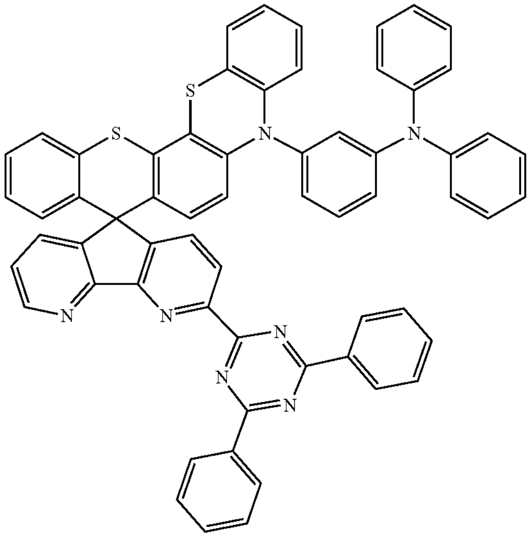
H44
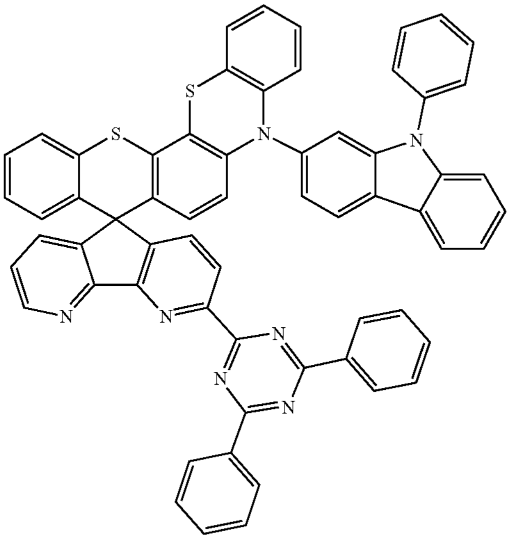

-continued
H45
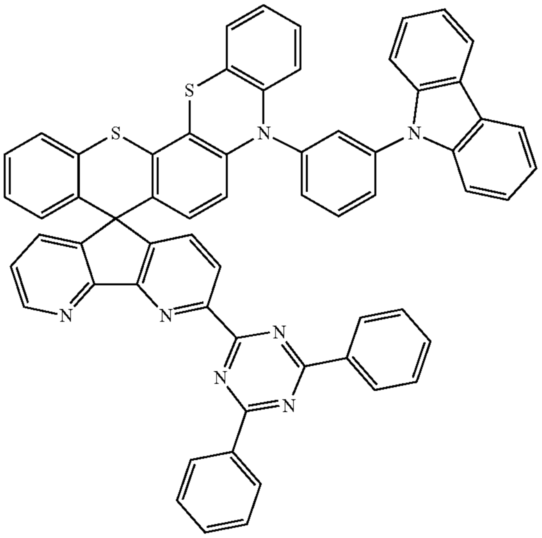
H46
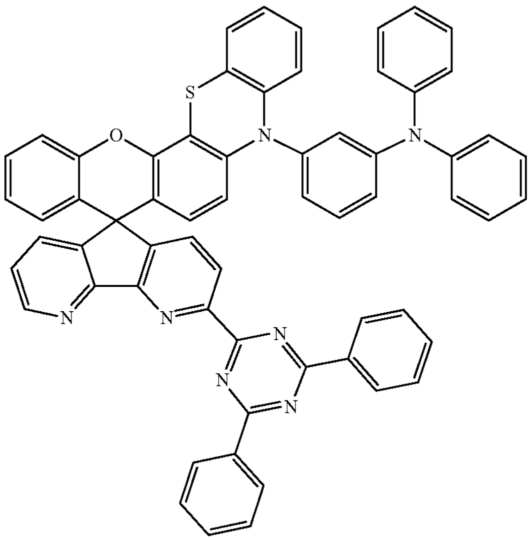
H47
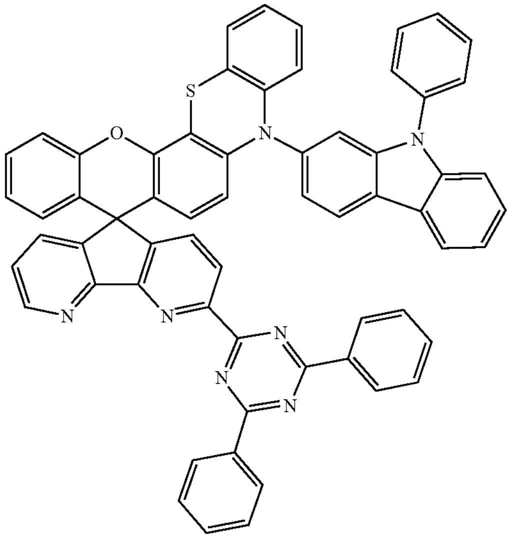
-continued
H48
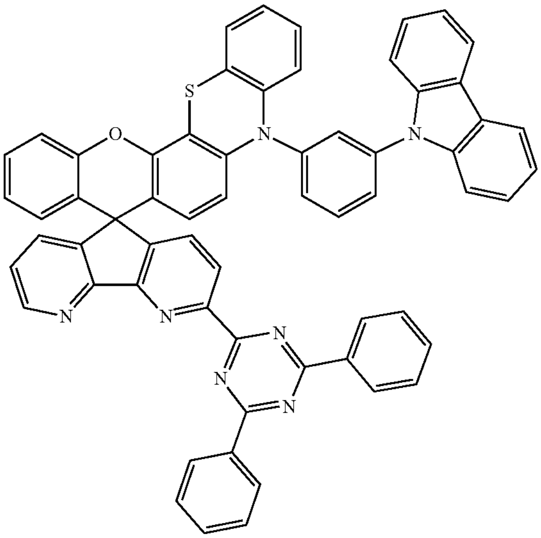
H49
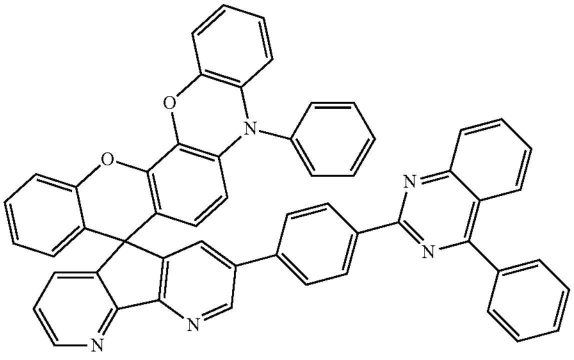
H50
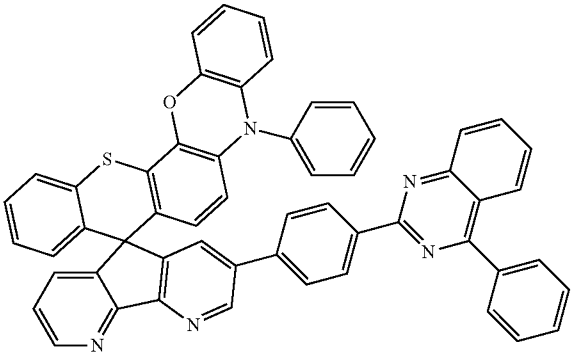

-continued
H51
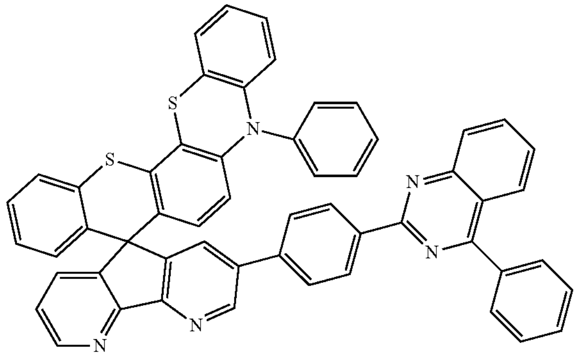
H52
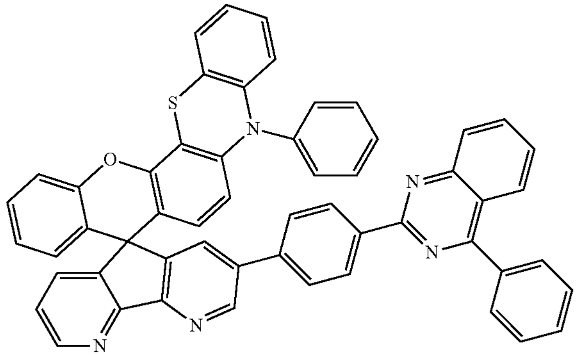
H53
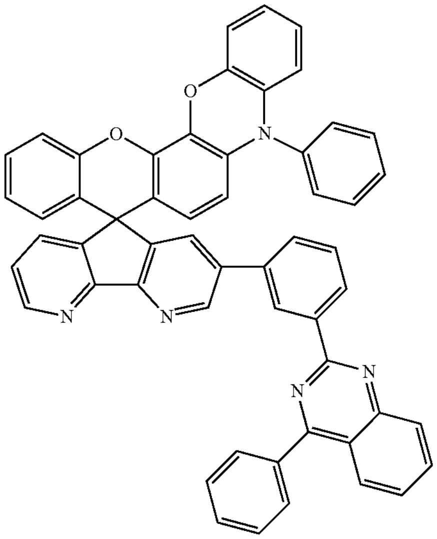
-continued
H54
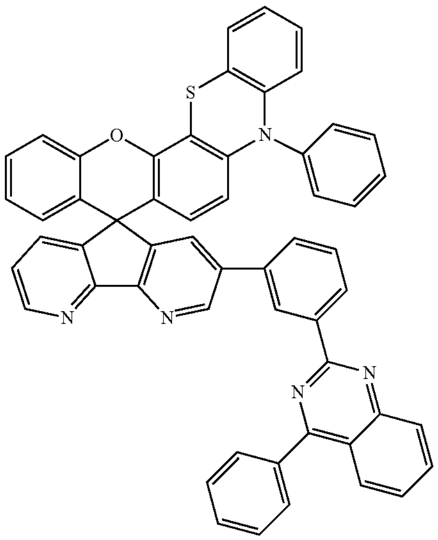
H55
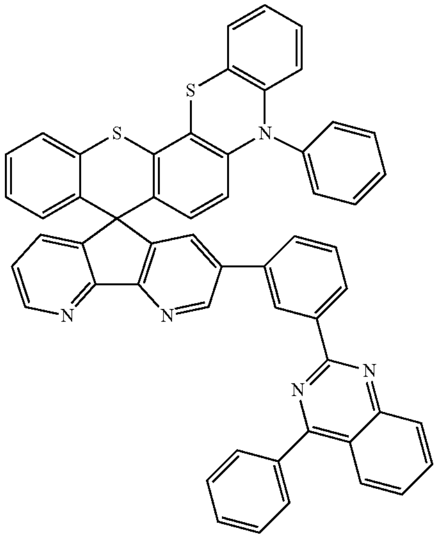
H56
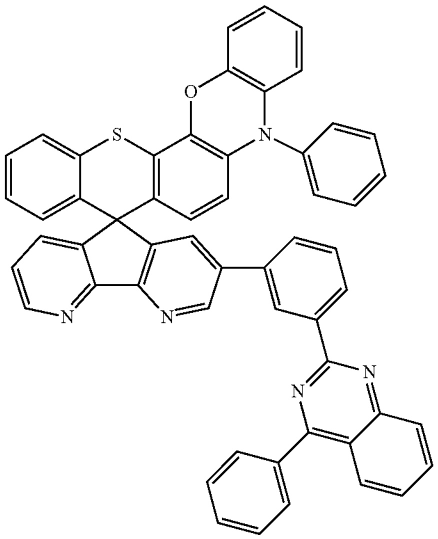

-continued
H57
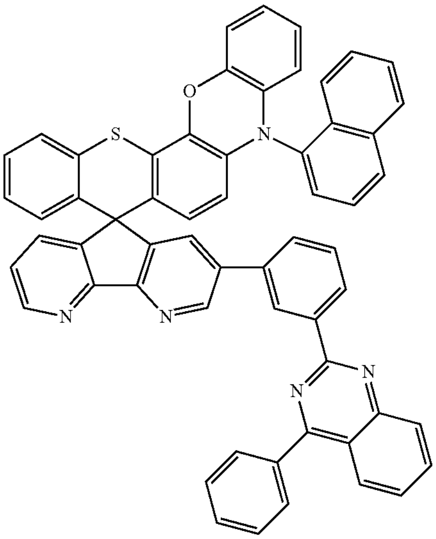
H58
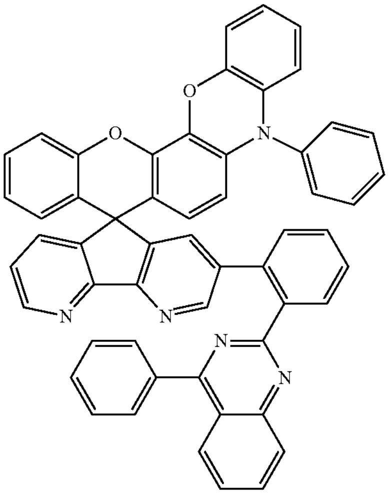
H59
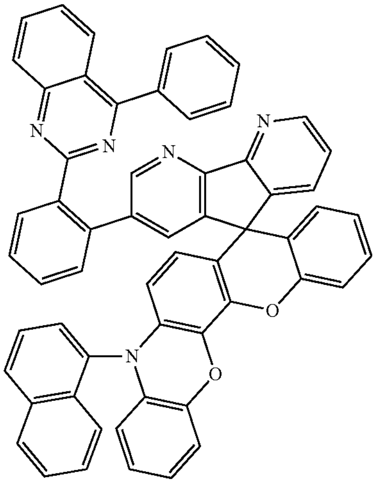
-continued
H60
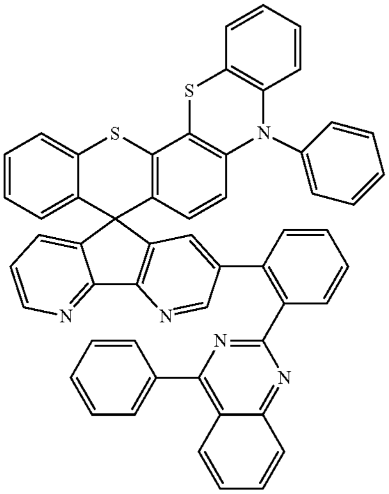
H61
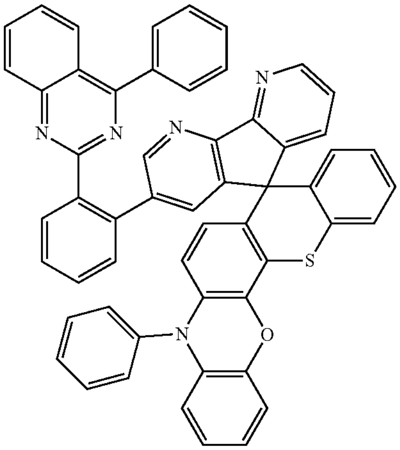
H62
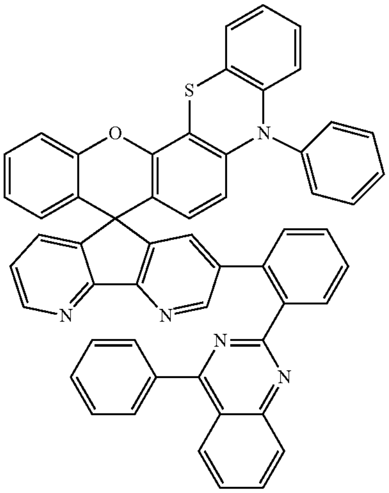

-continued
H63
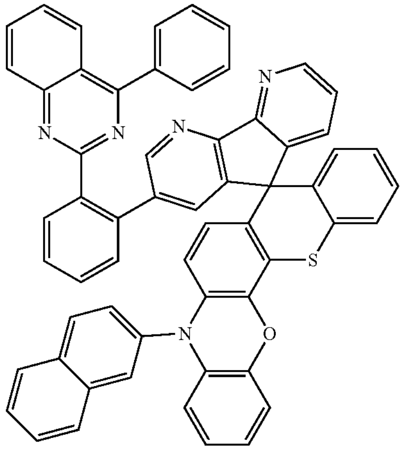
H64
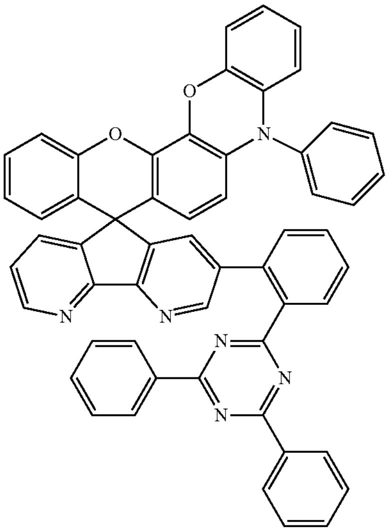
H65
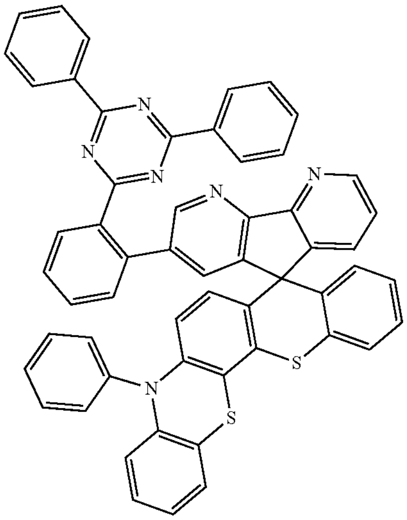
-continued
H66
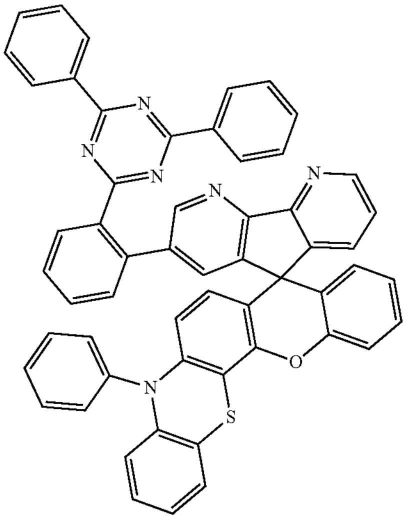
H67
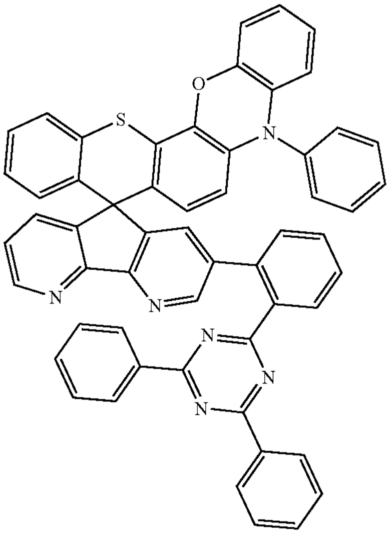
H68
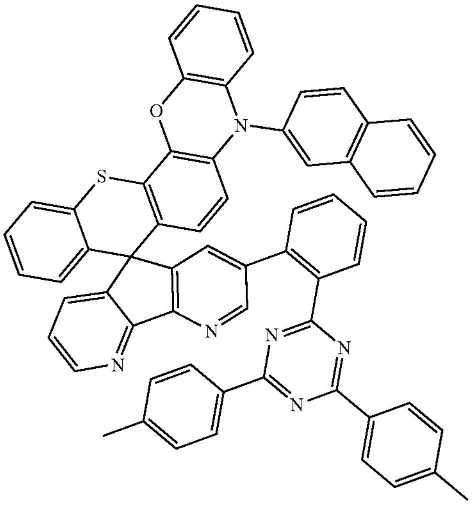

-continued
H69
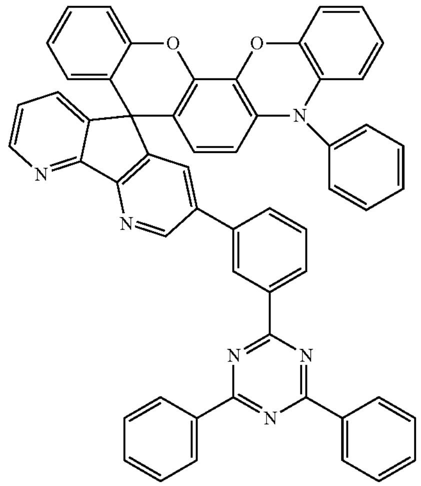
H70
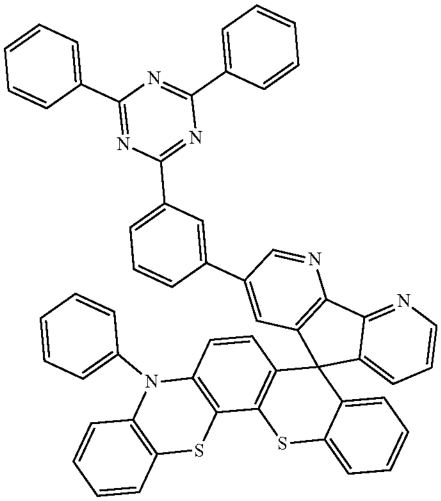
H71
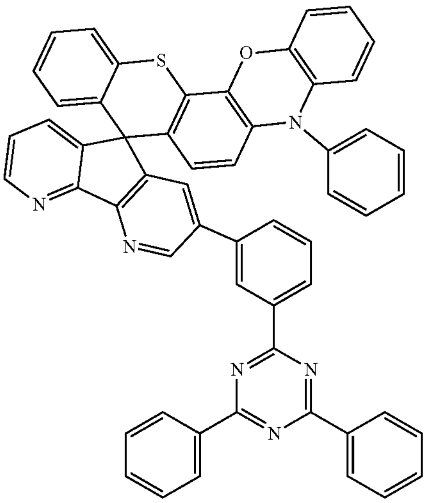
-continued
H72
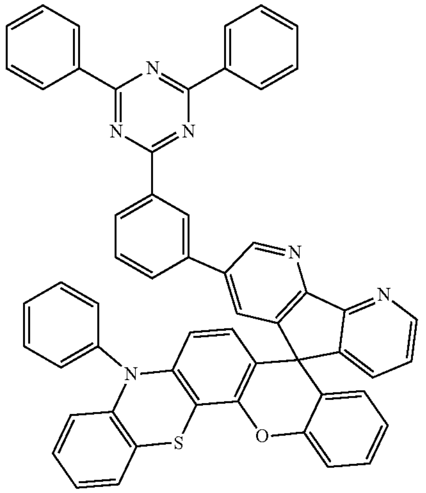
H73
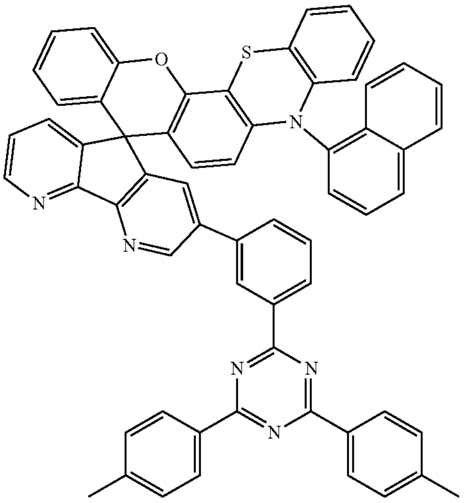
H74
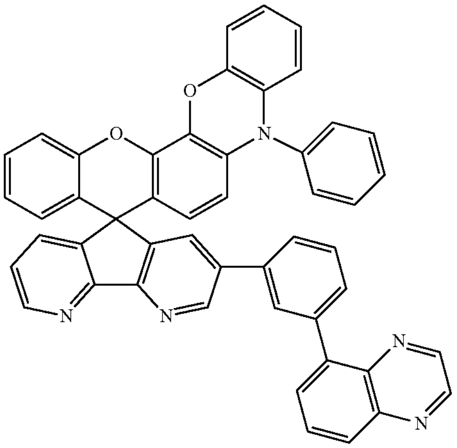

-continued
H75
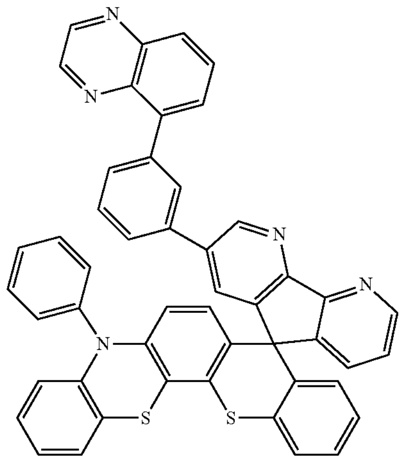
H76
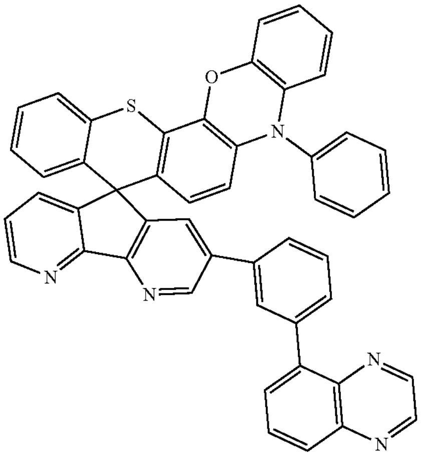
H77
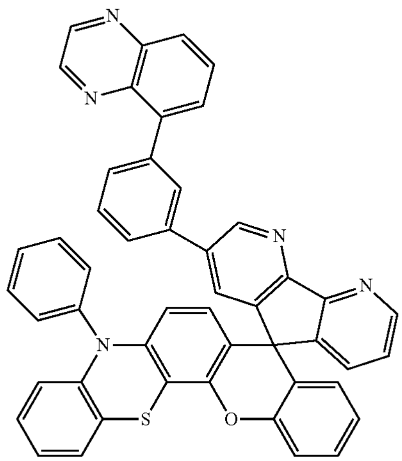
-continued
H78
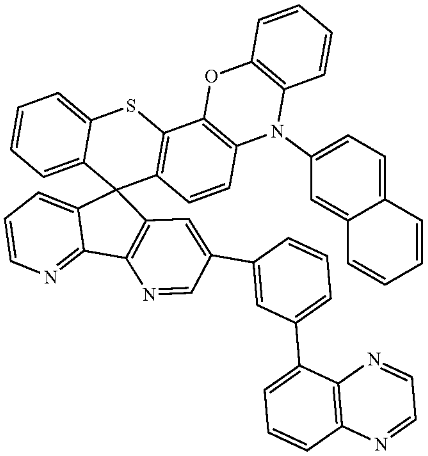
H79
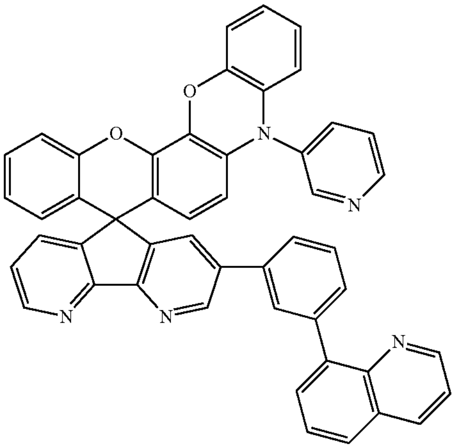
H80
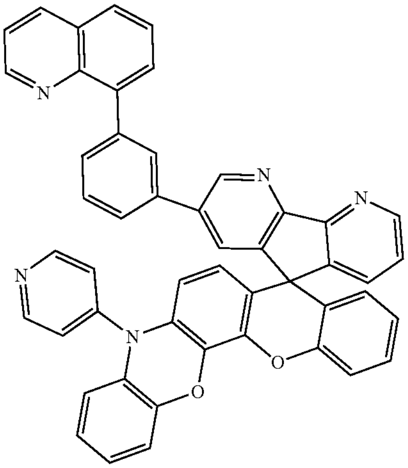

-continued
H81
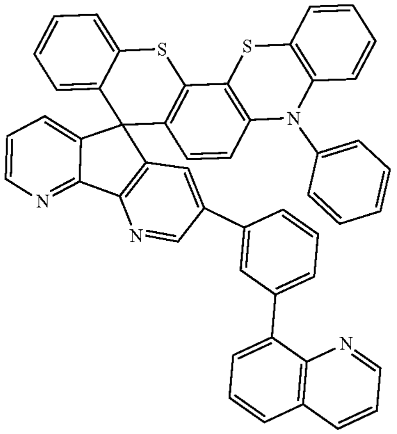
H82
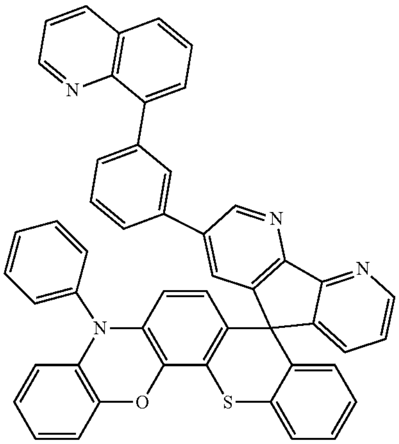
H83
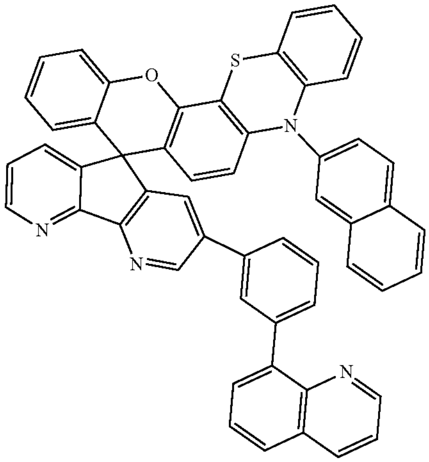
-continued
H84
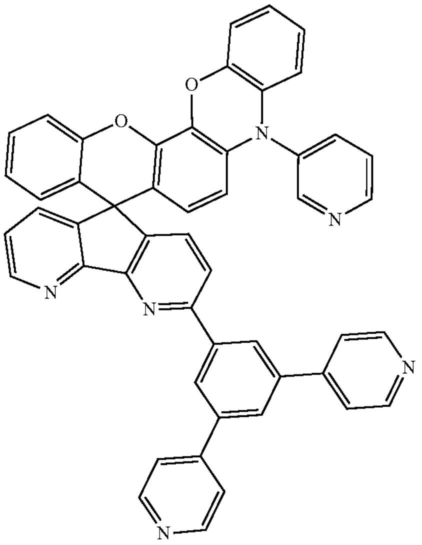
H85
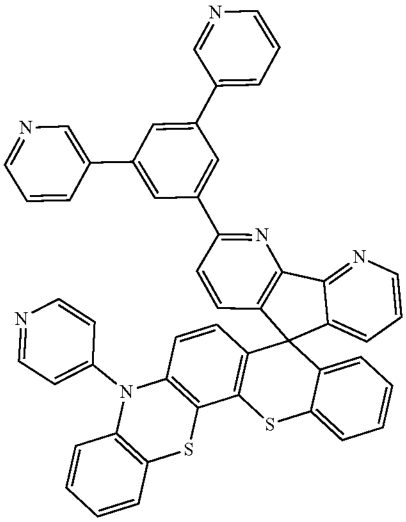
H86
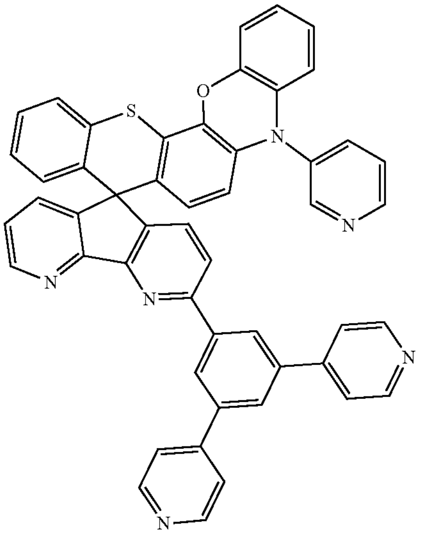

-continued
H87
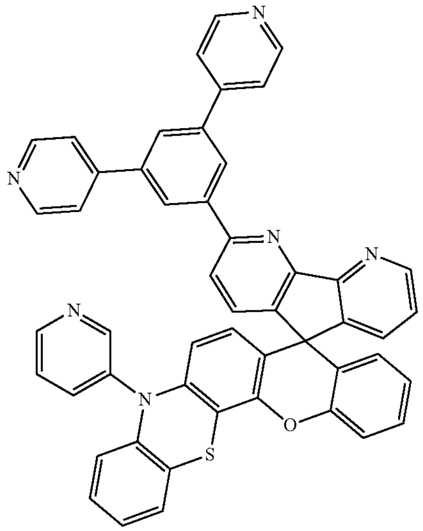
H88
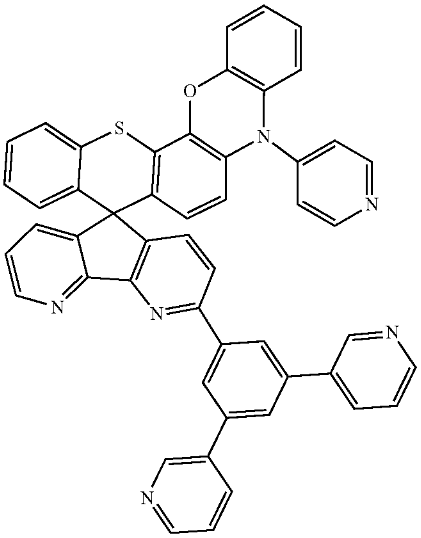
H89
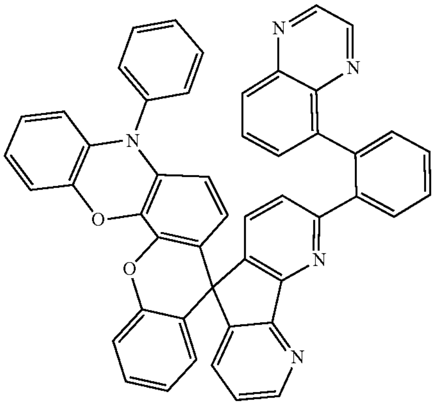
-continued
H90
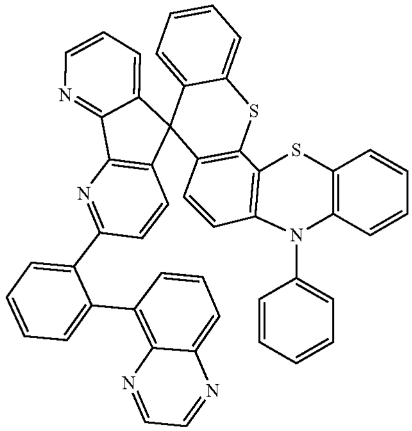
H91
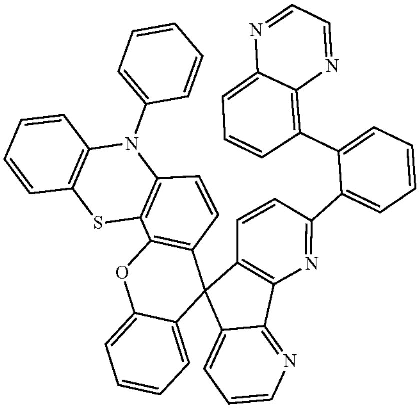
H92
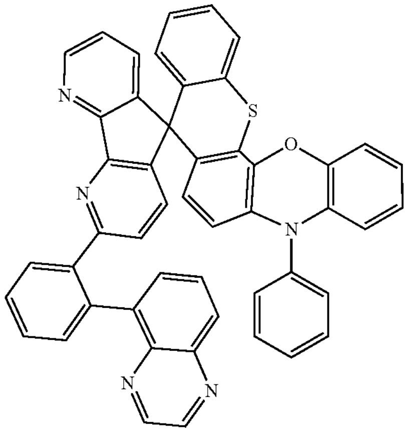

-continued
H93
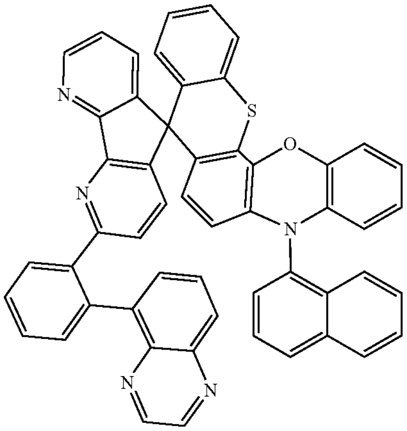
H94
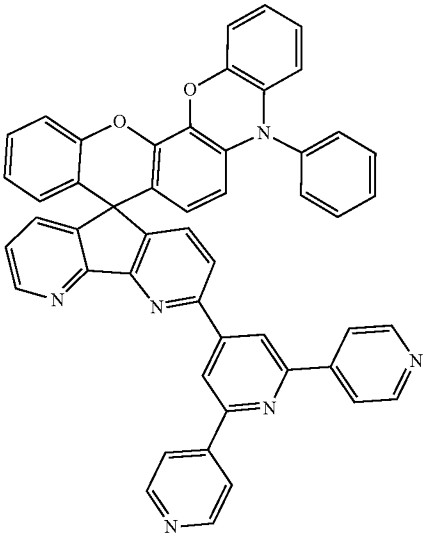
H95
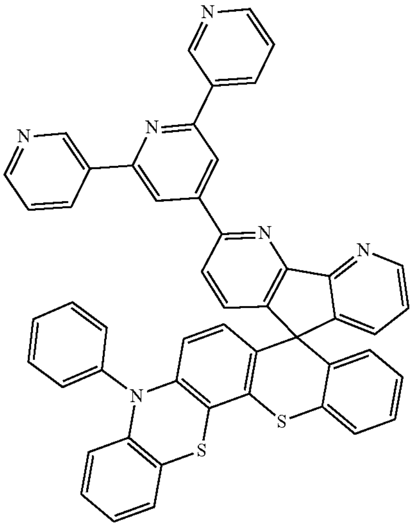
-continued
H96
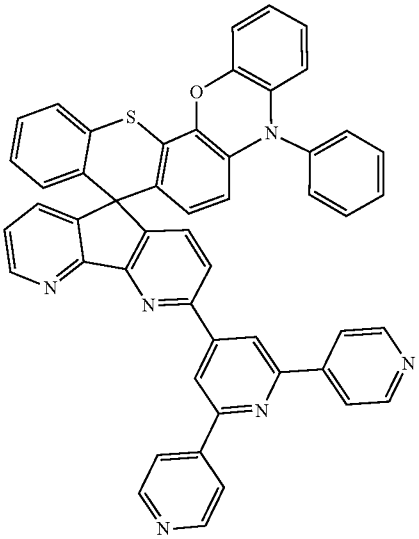
H97
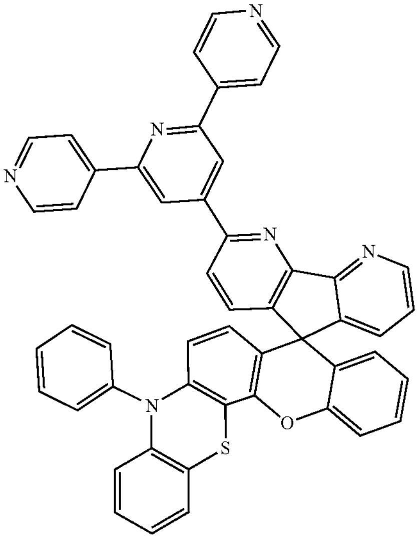
H98
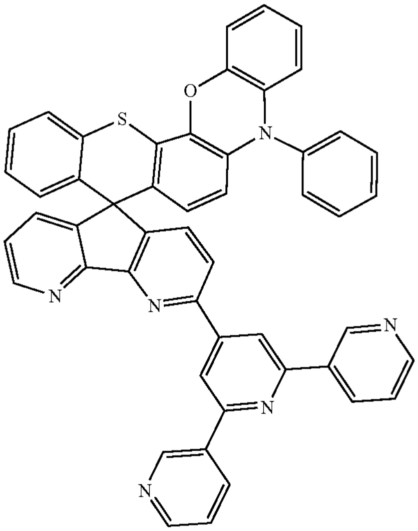

-continued
H99
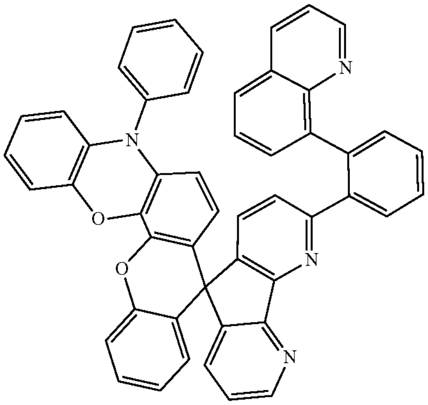
H100
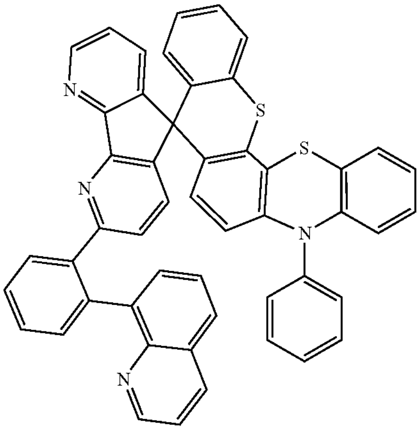
H101
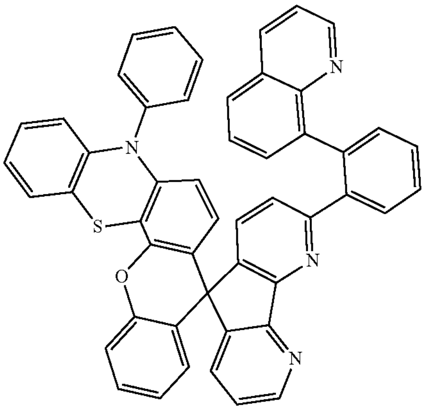
-continued
H102
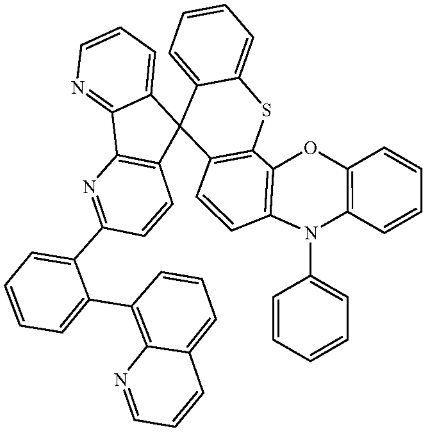
H103
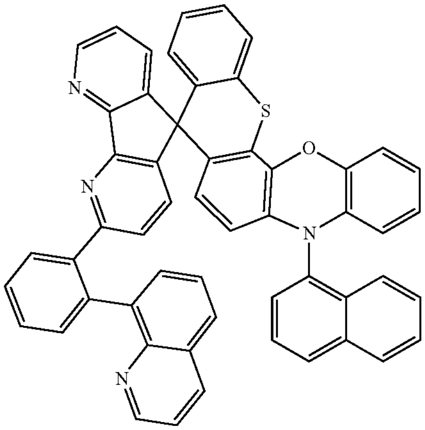
H104
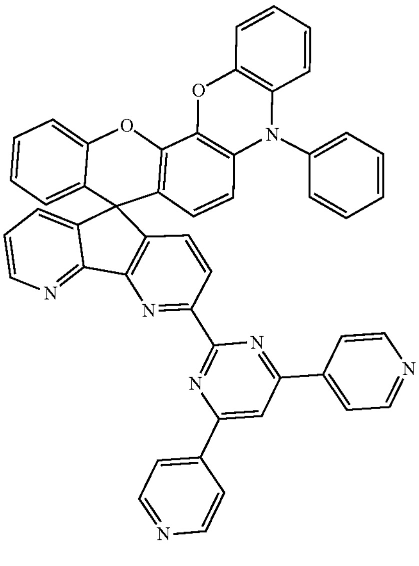

-continued
H105
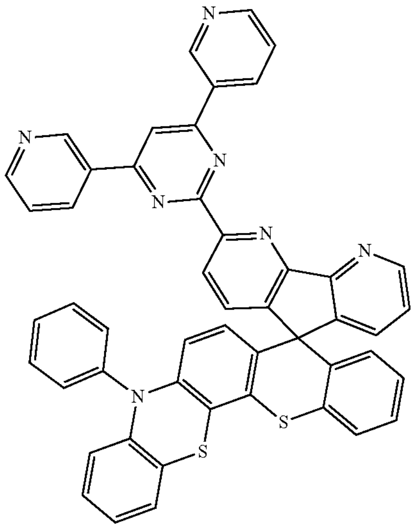
H106
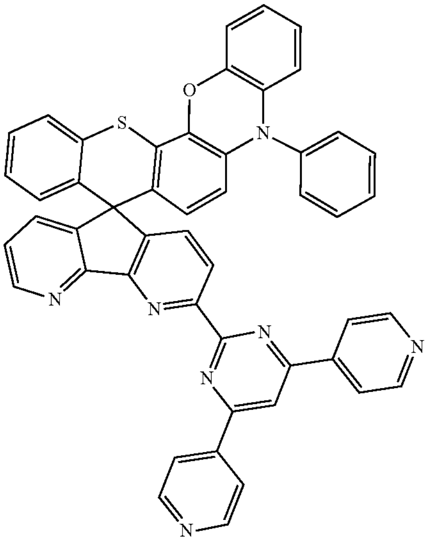
H107
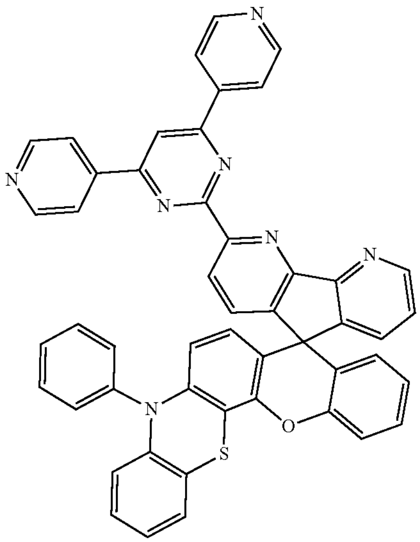
-continued
H108
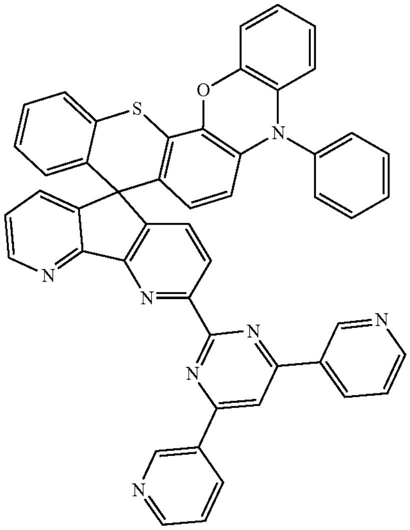
H109
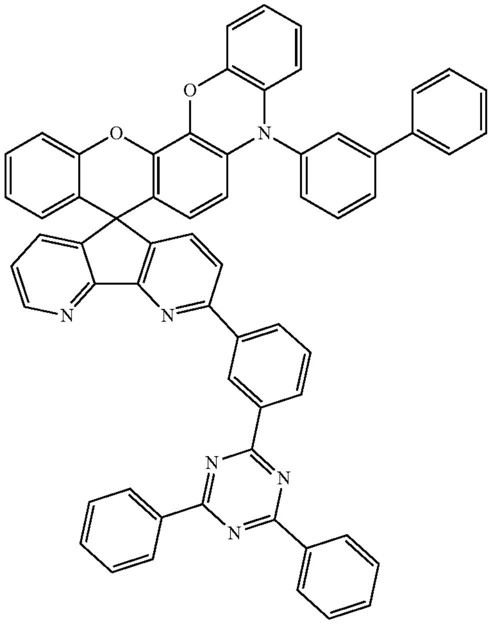

-continued
H110
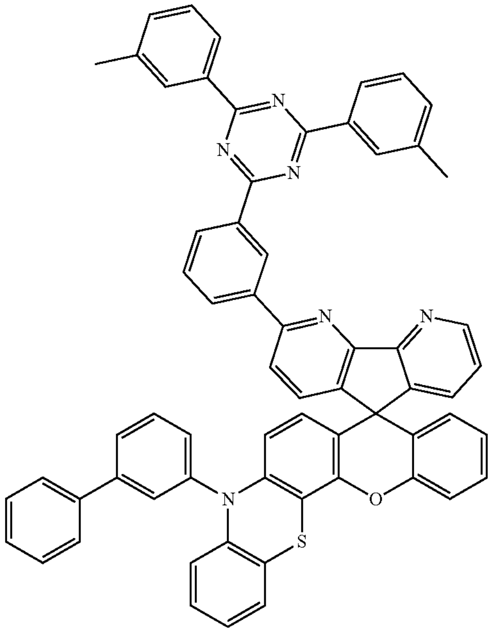
-continued
H112
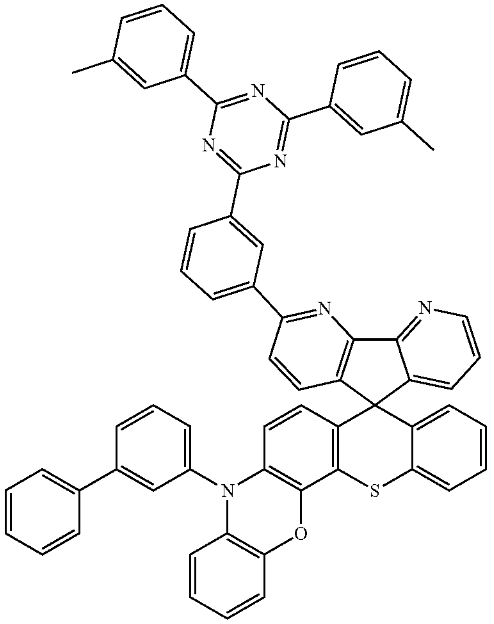
H111
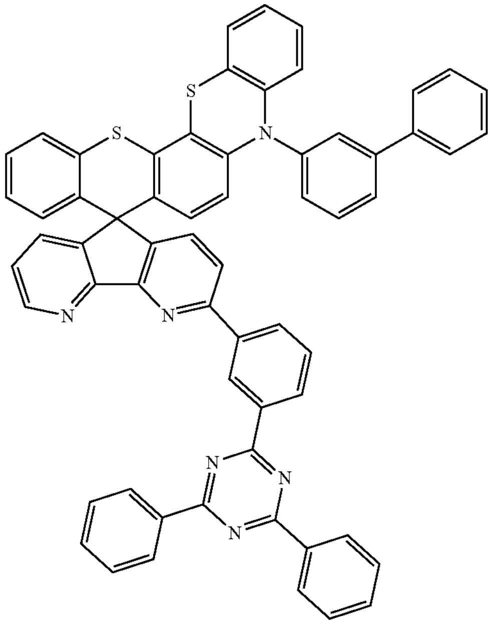
H113
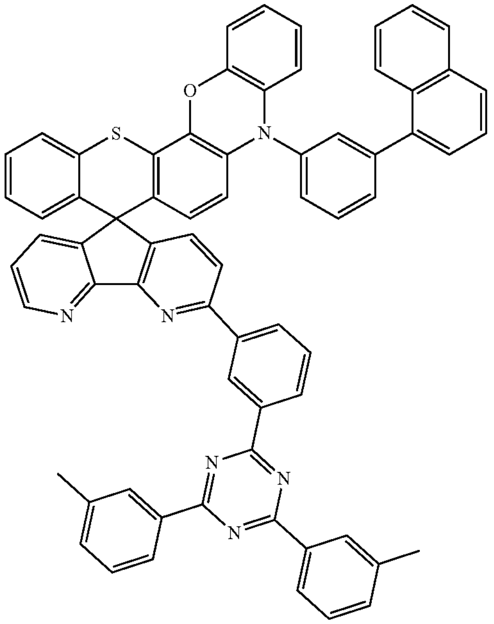

-continued
H114
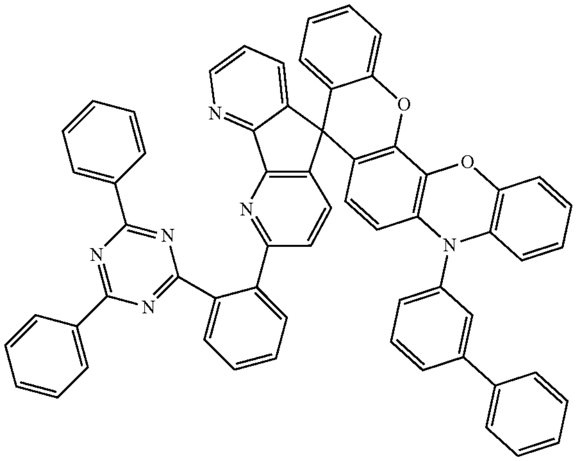
H115
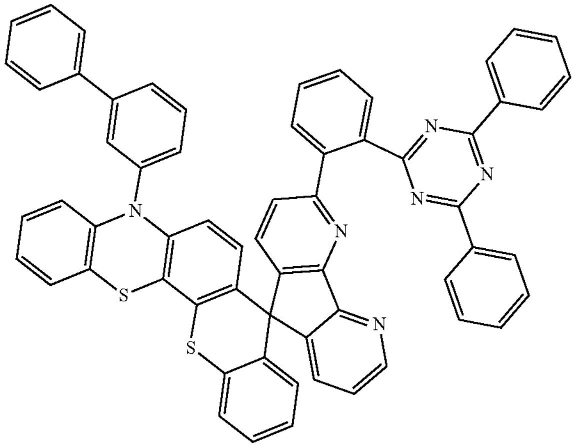
H116
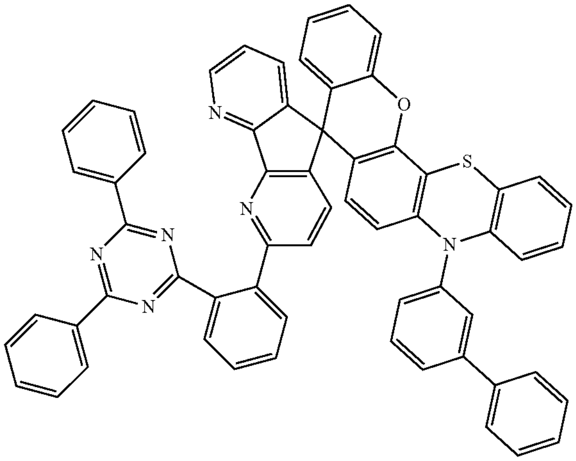
-continued
H117
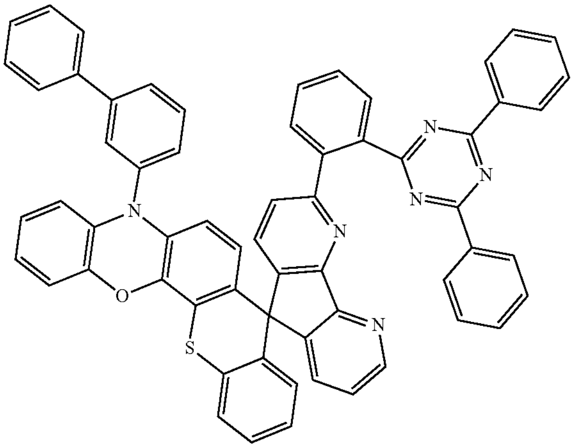
H118
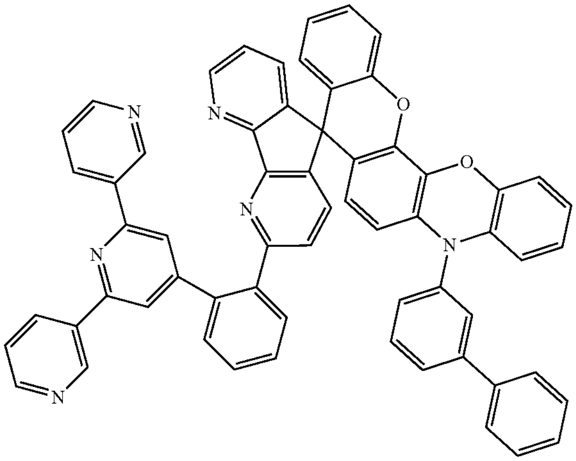
H119
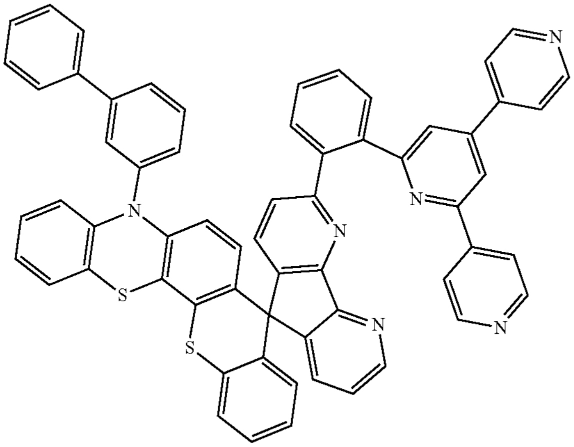

-continued
H120
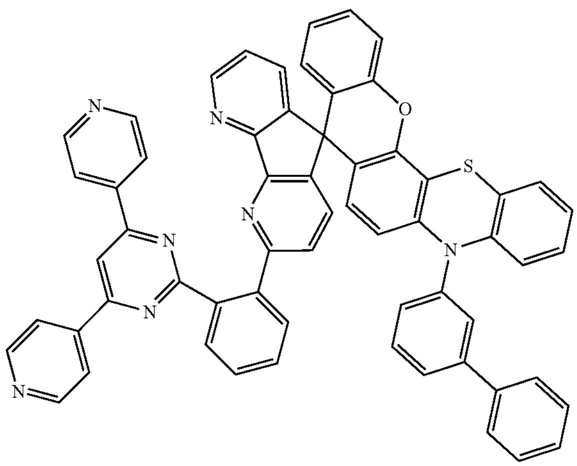
H121
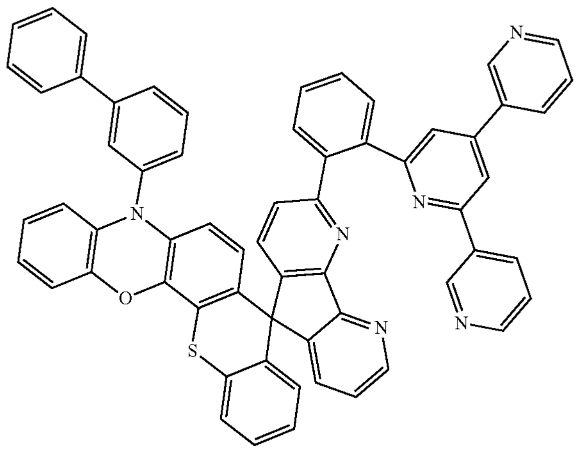
H122
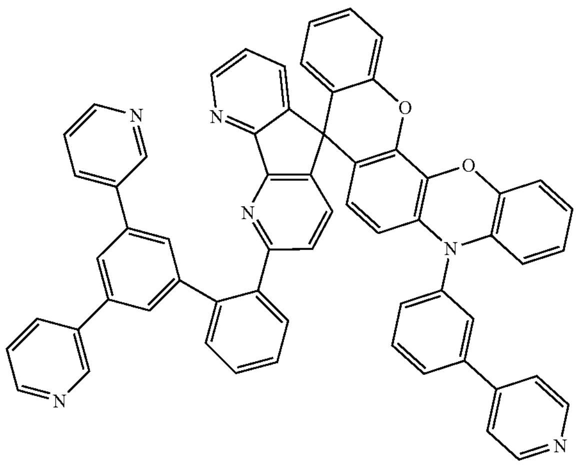
-continued
H123
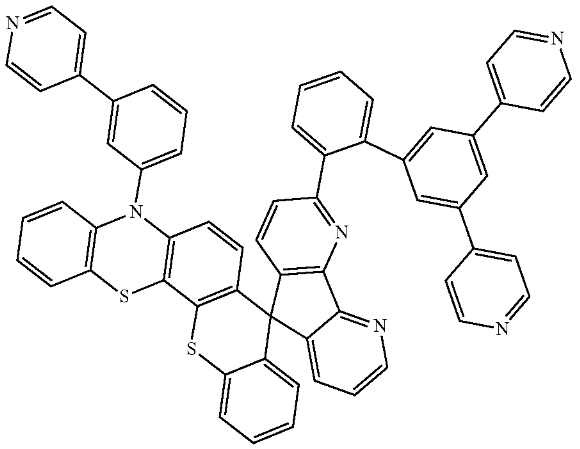
H124
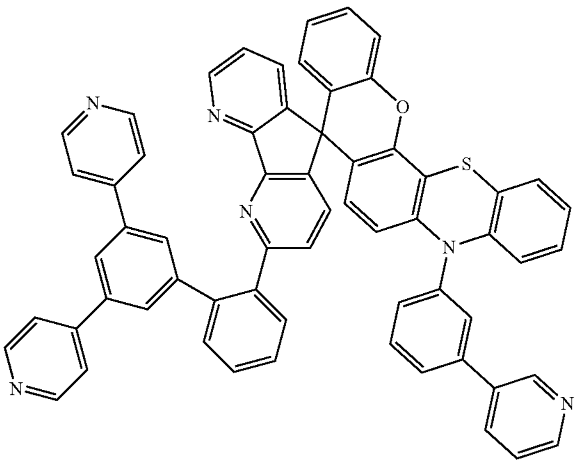
H125
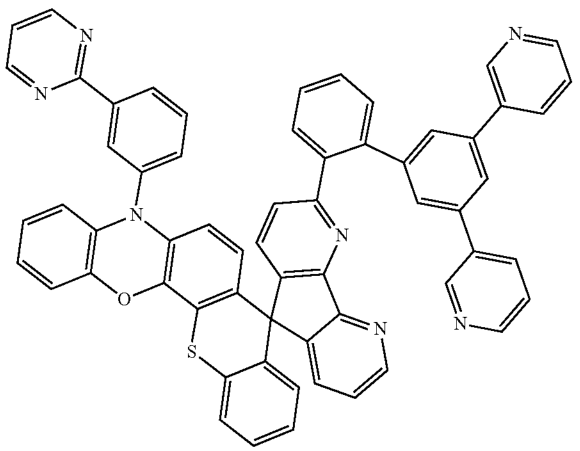

-continued
H126
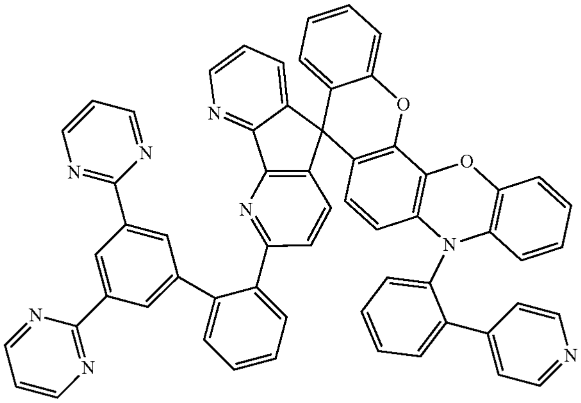
H127
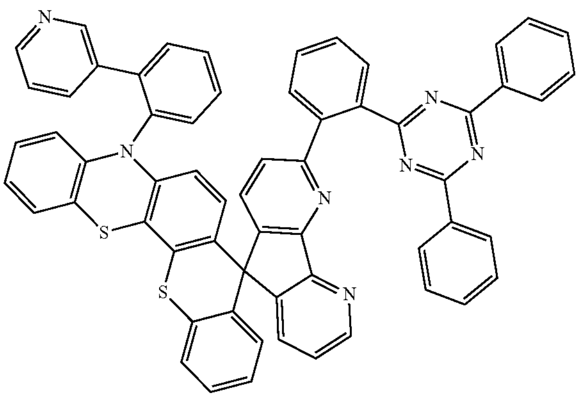
H128
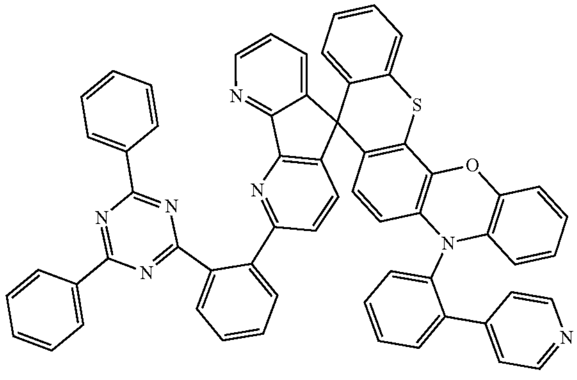
H129
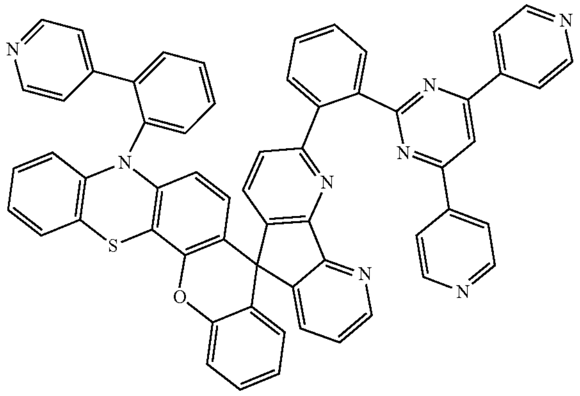
-continued
H130
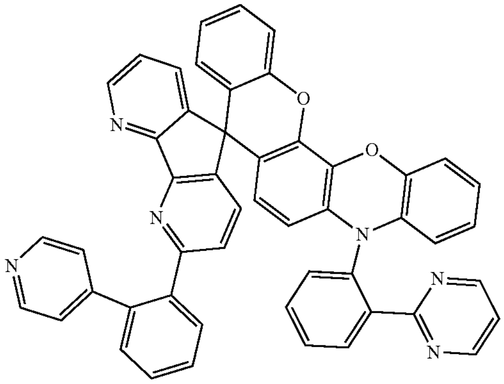
H131
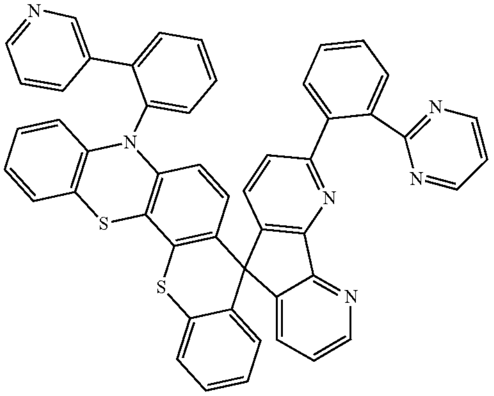
H132
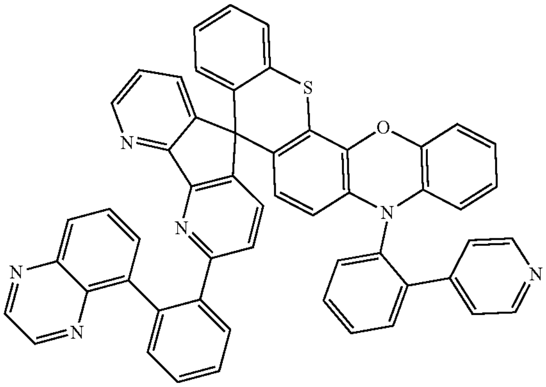
H133
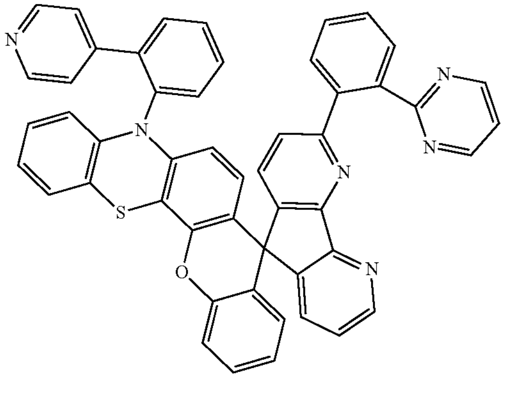

-continued
H134
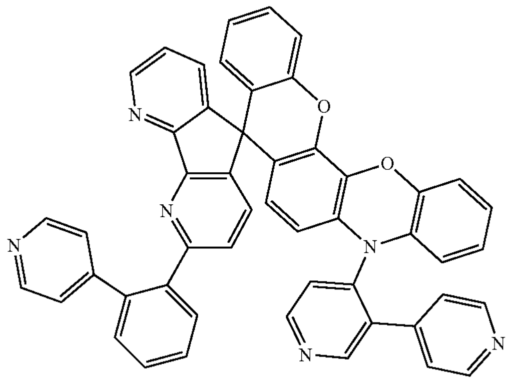
H135
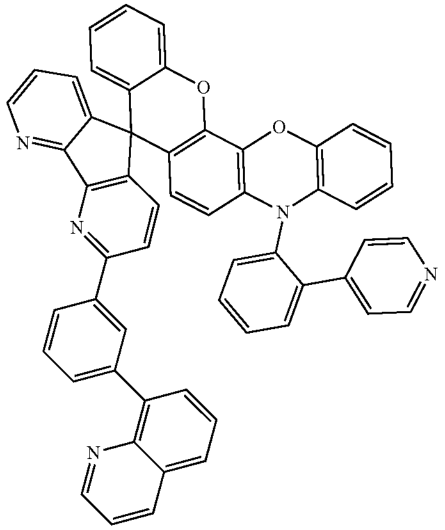
H136
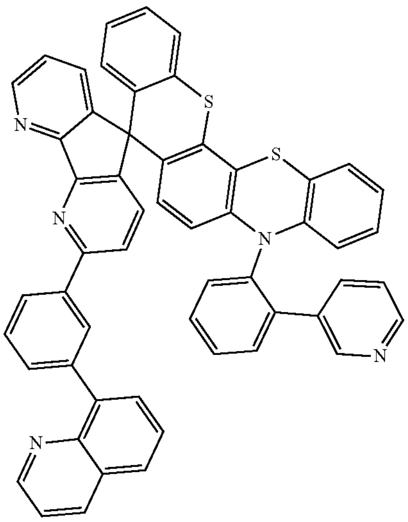
-continued
H137
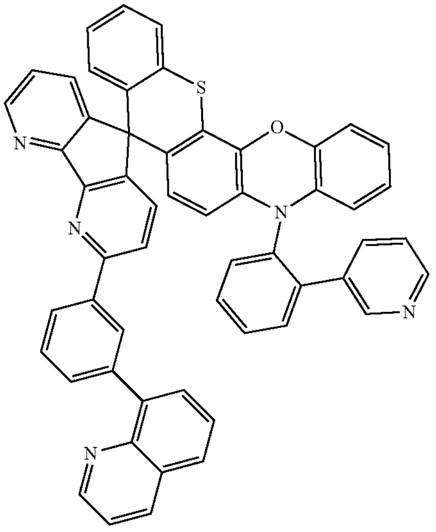
H138
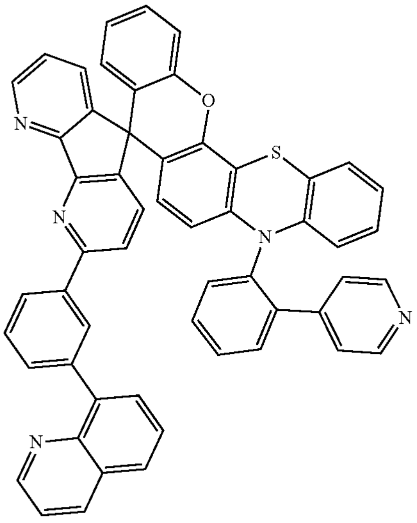
H139
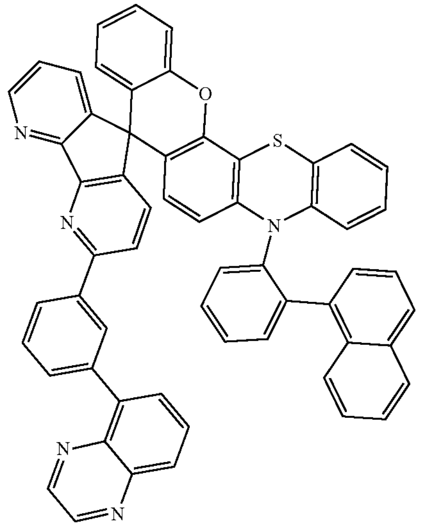

H140
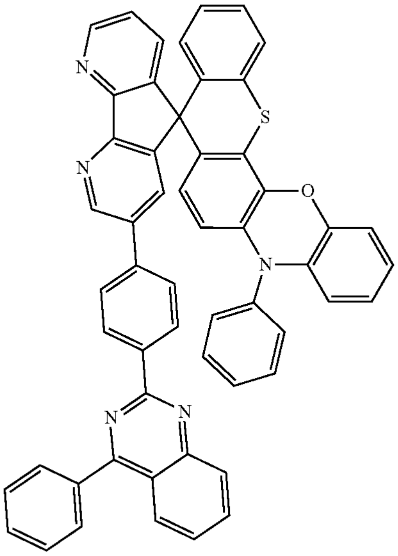
H141
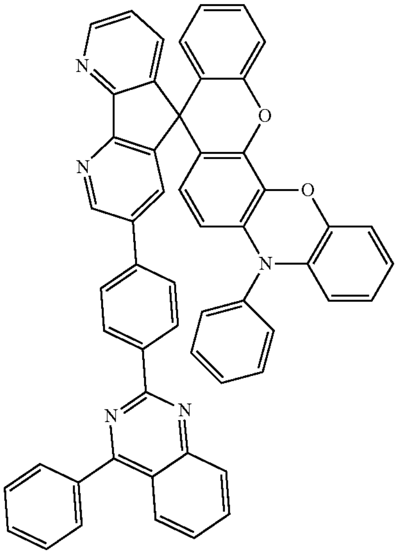
H142
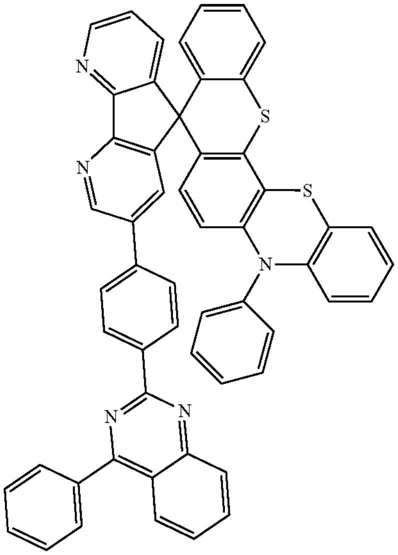
H143
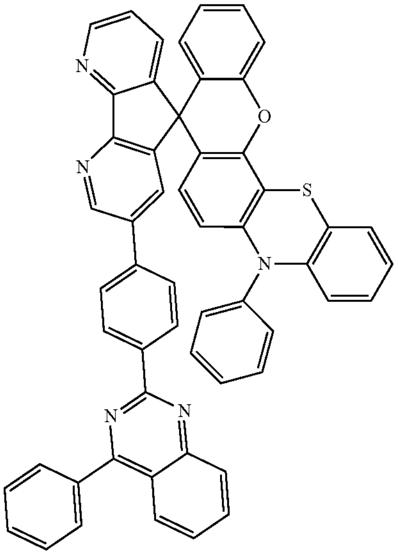
H144
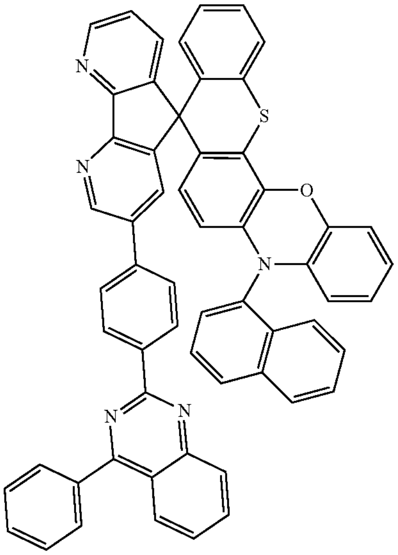

-continued
H145
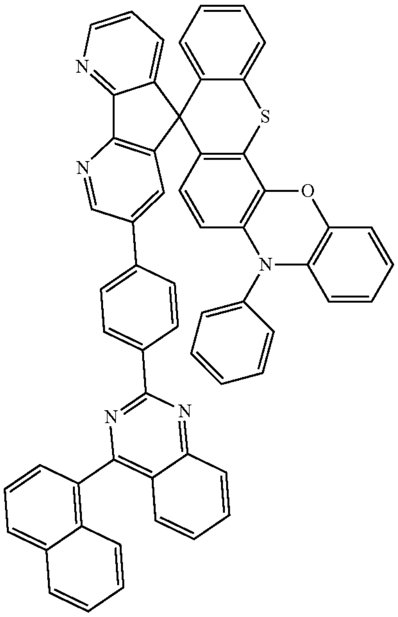
H146
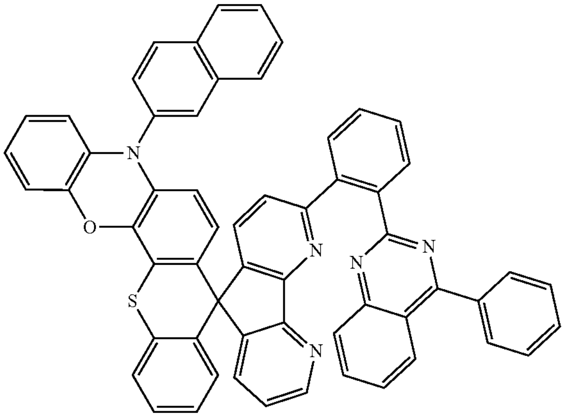
H147
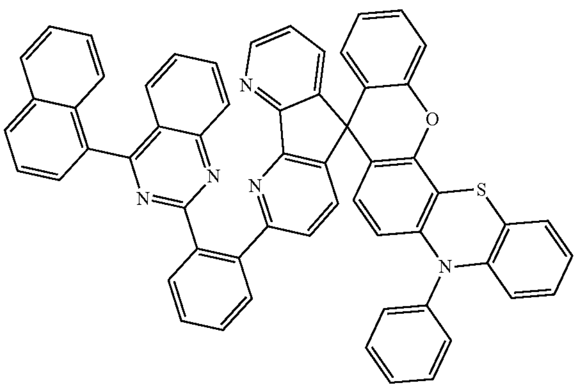
-continued
H148
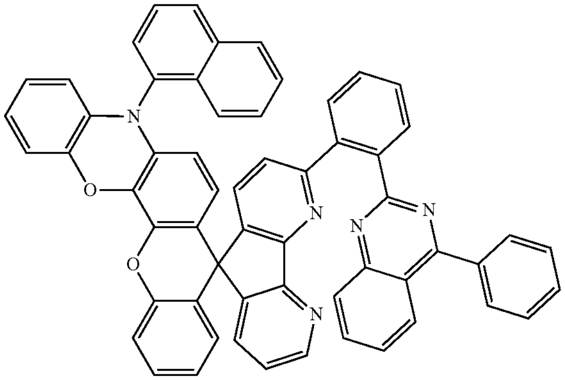
H149
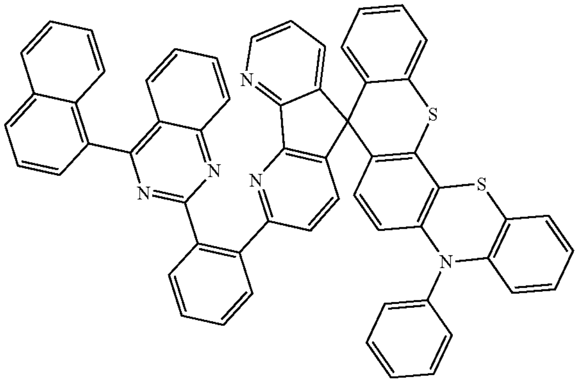
H150
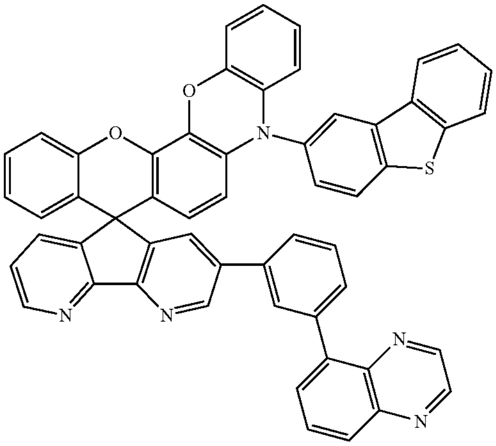

-continued
H151
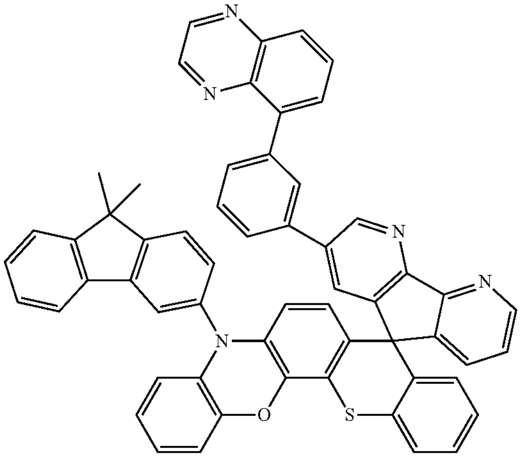
H152
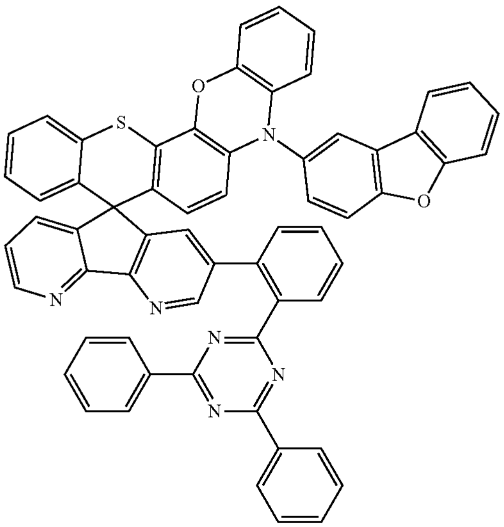
H153
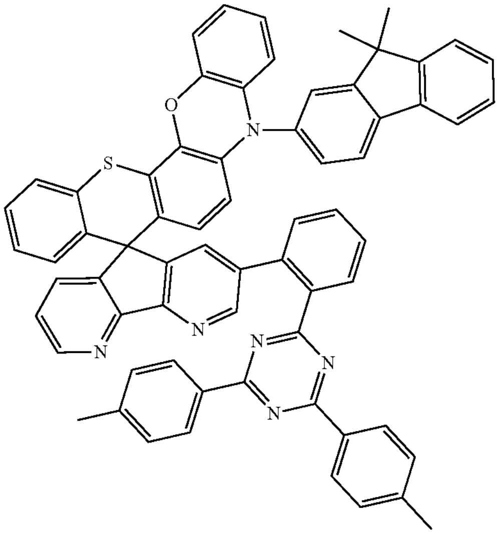
H154
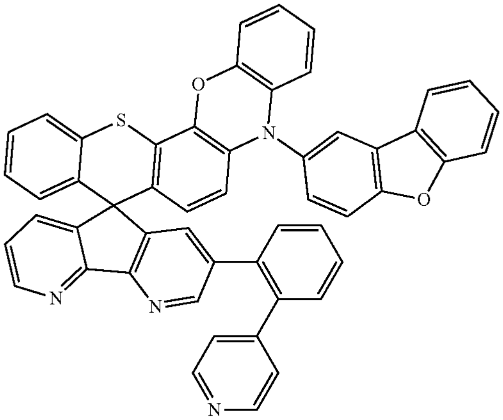
H155
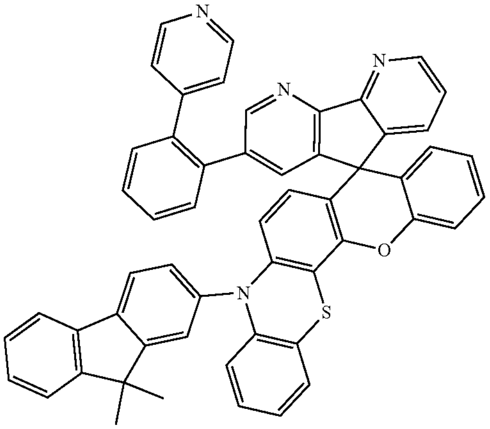
.
In one embodiment, the nitrogen-containing spiral organic compound has any one of the following structures:
L01
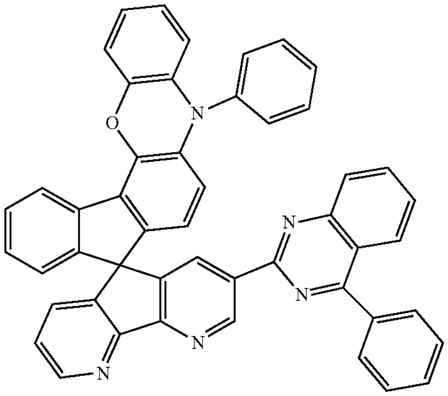

-continued
L02
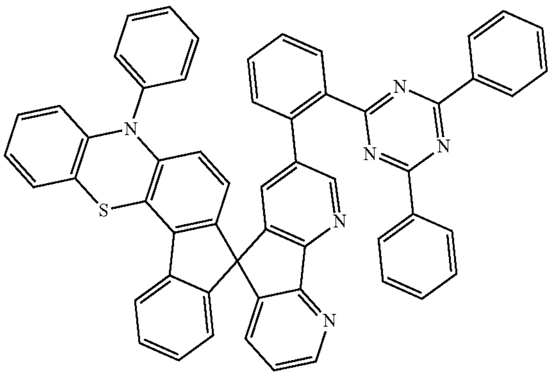
L03
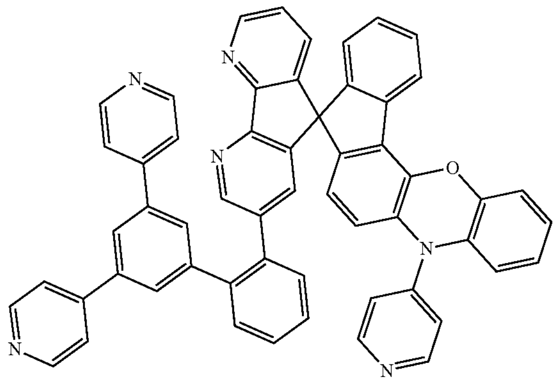
L04
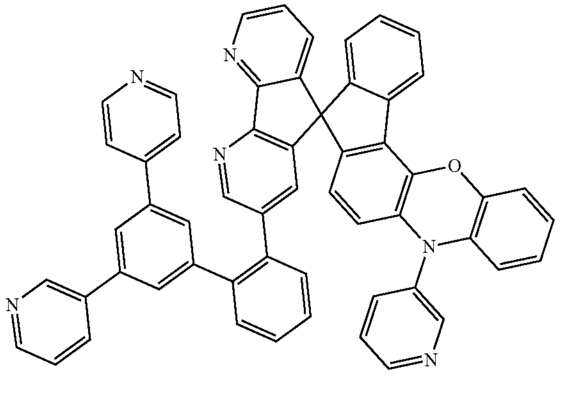
L05
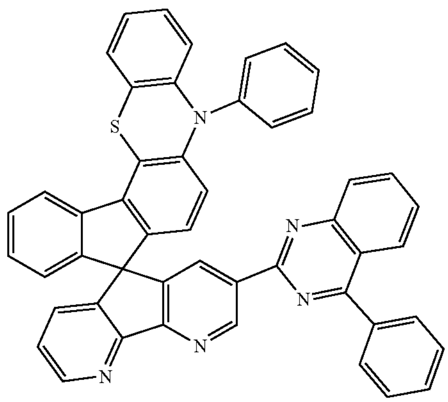
-continued
L06
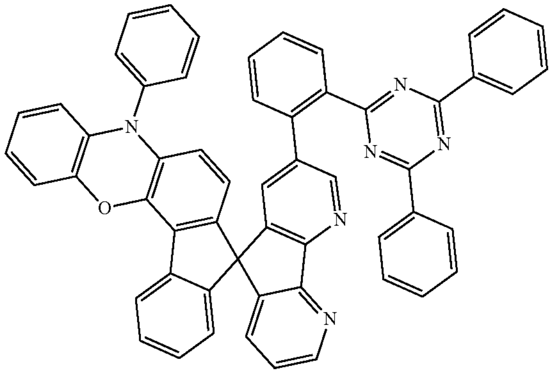
L07
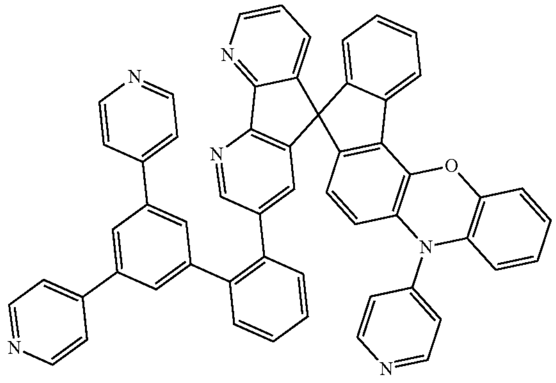
L08
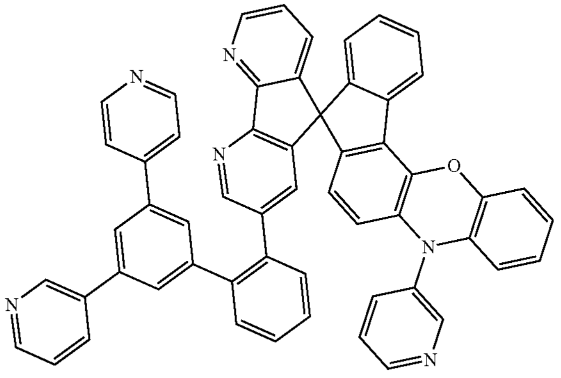
L09
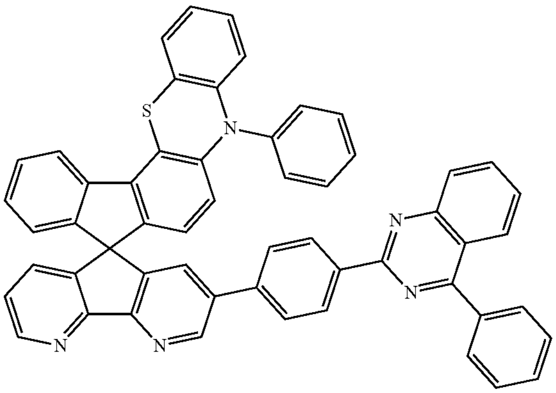

-continued
L10
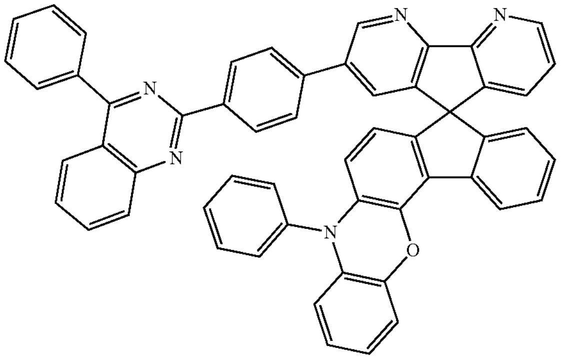
L11
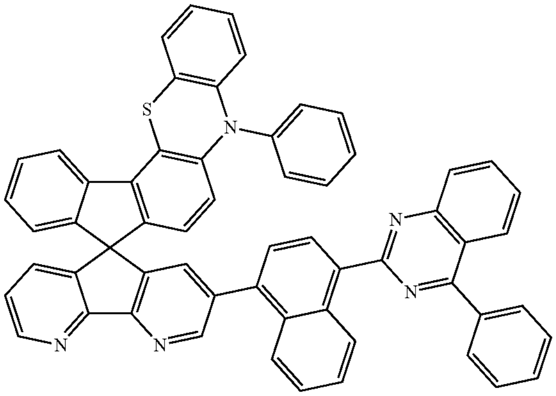
L12
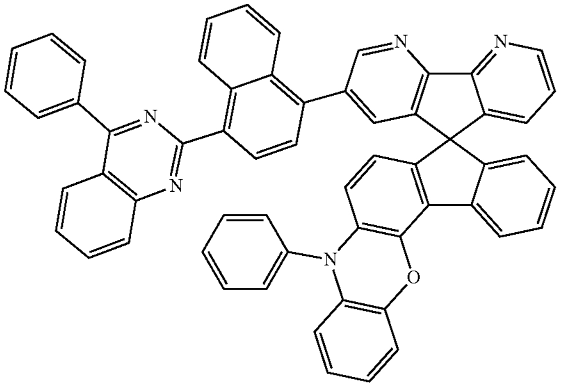
-continued
L13
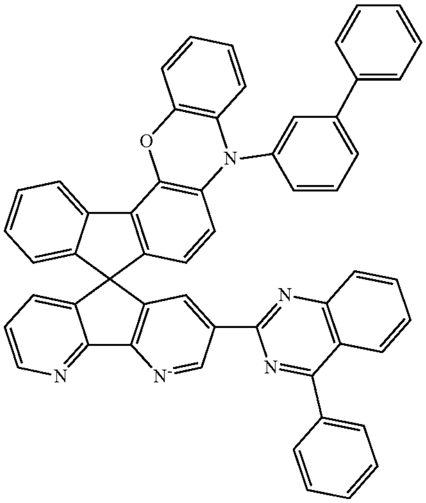
L14
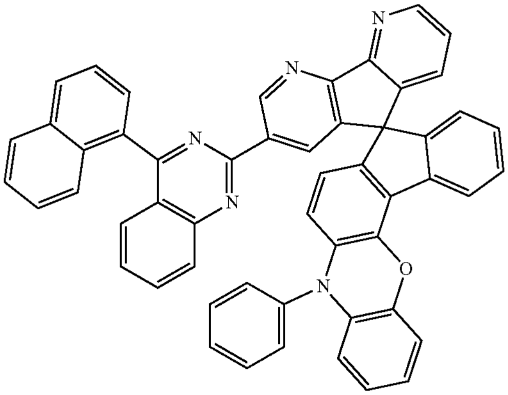
L15
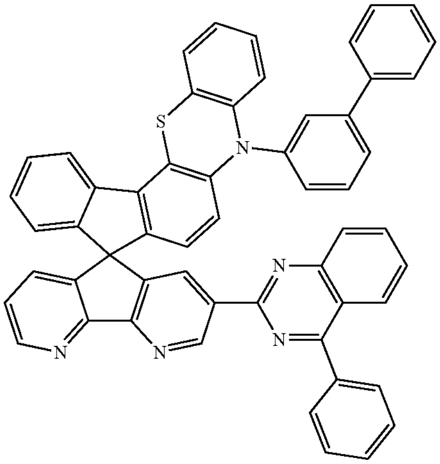

-continued
L16
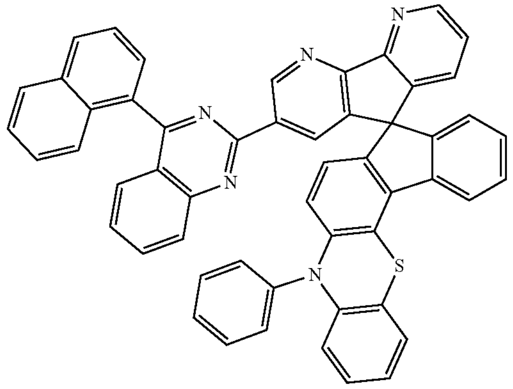
L17
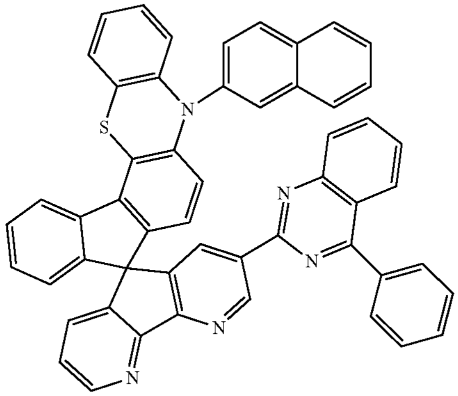
L18
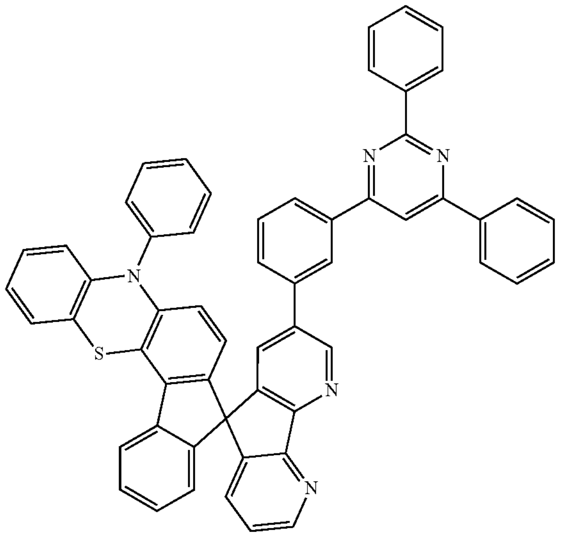
-continued
L19
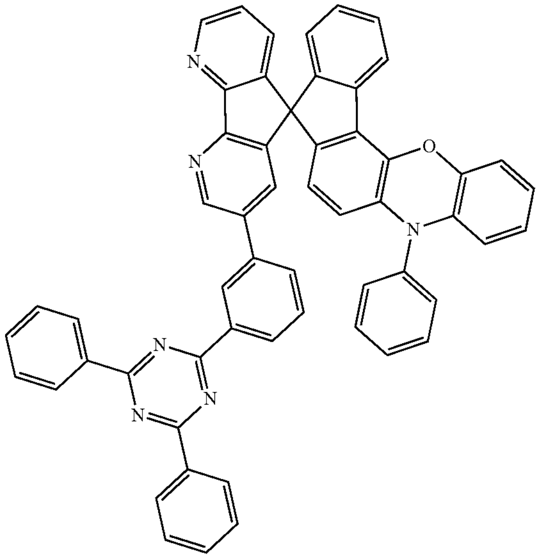
L20
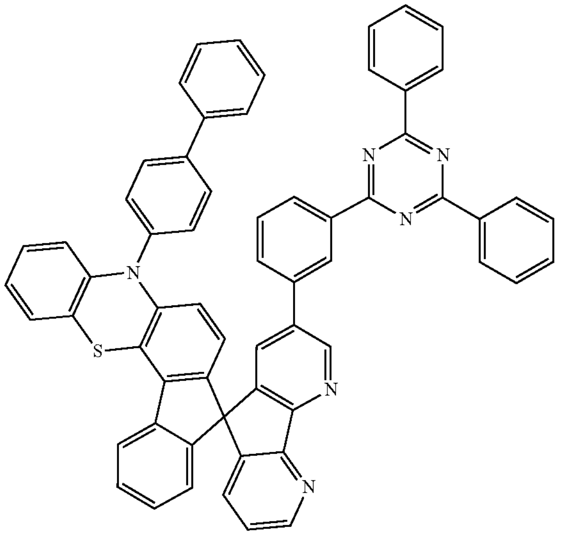

-continued
L21
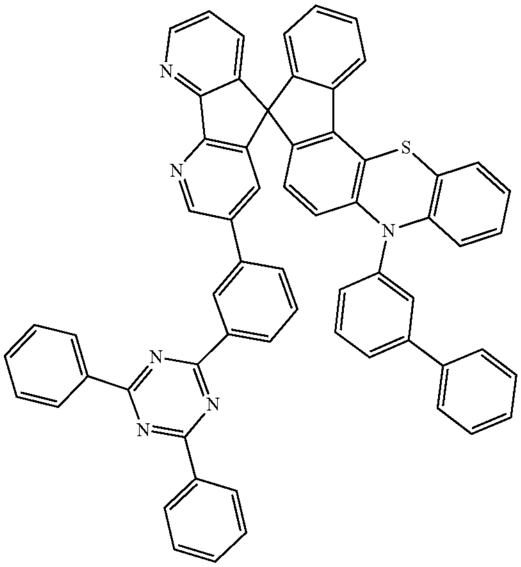
-continued
L23
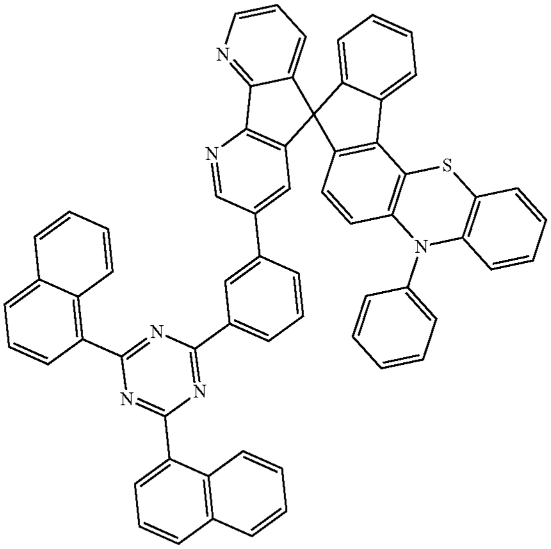
L22
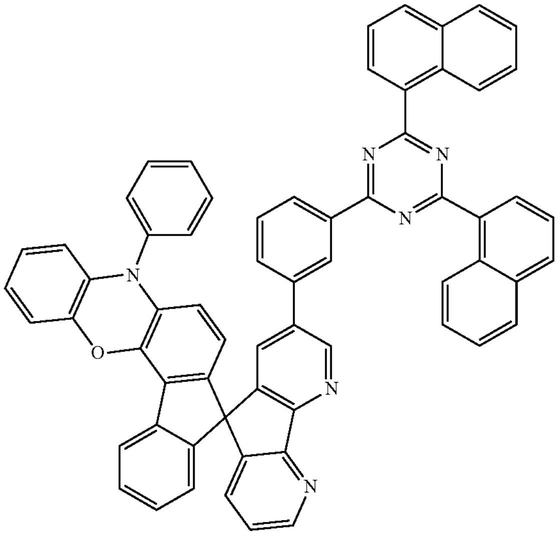
L24
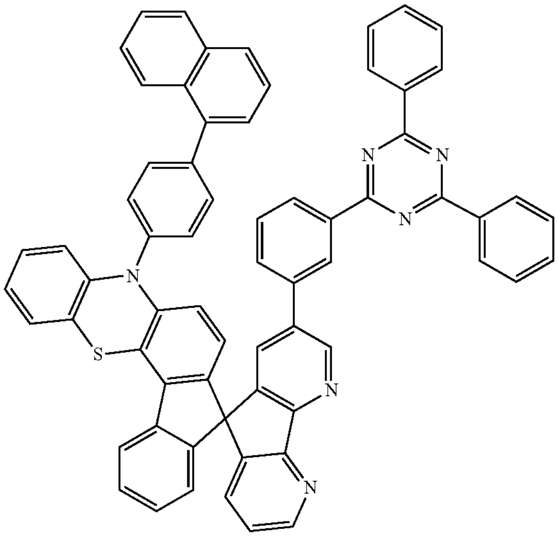

-continued
L25
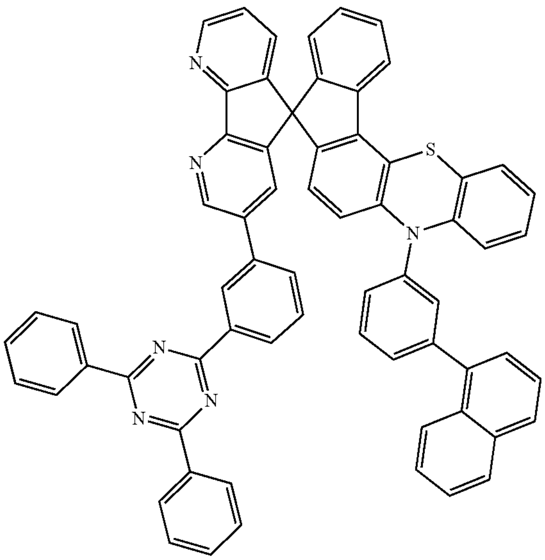
L26
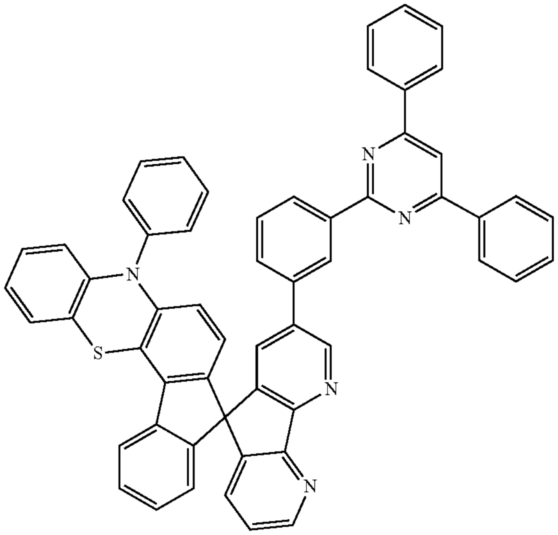
-continued
L27
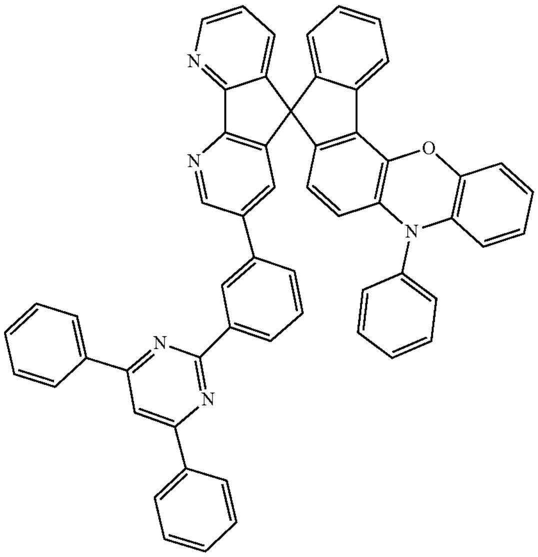
L28
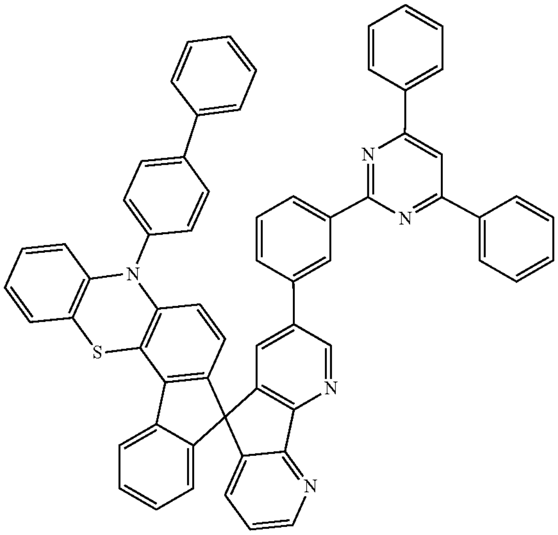

-continued
L29
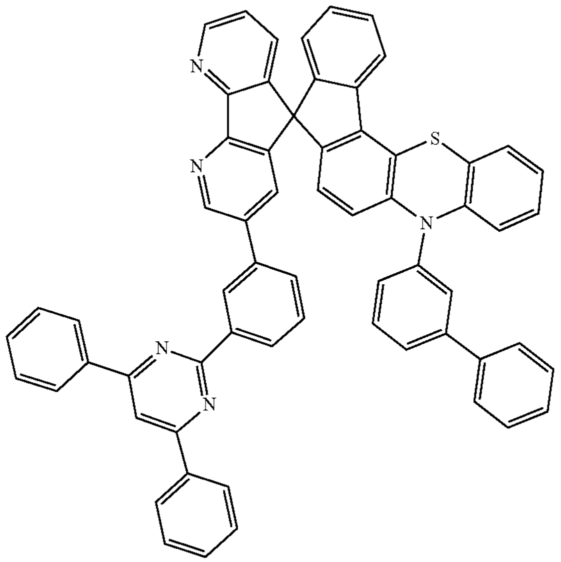
L30
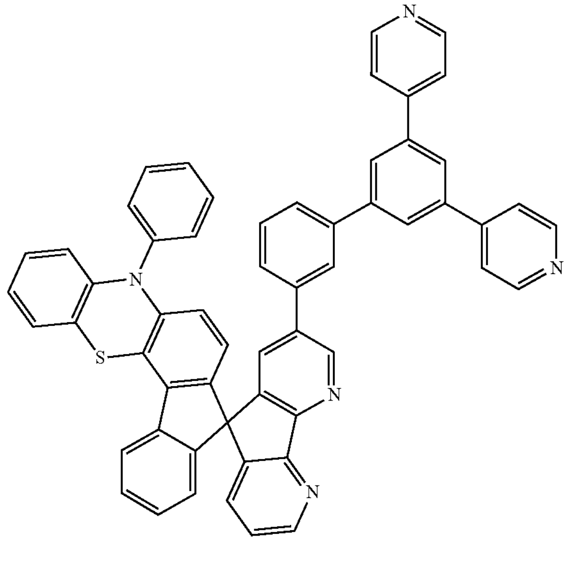
-continued
L31
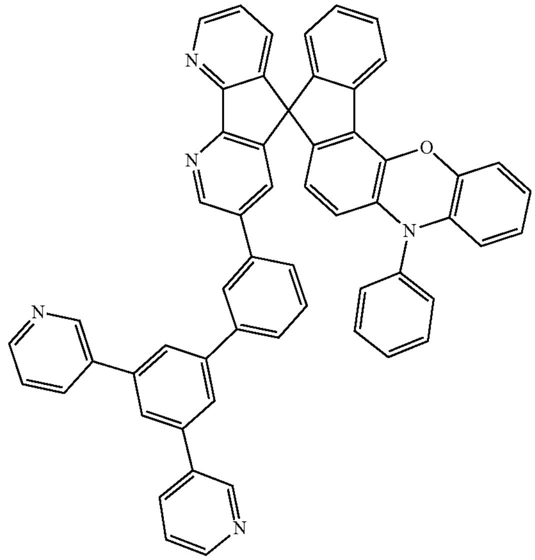
L32
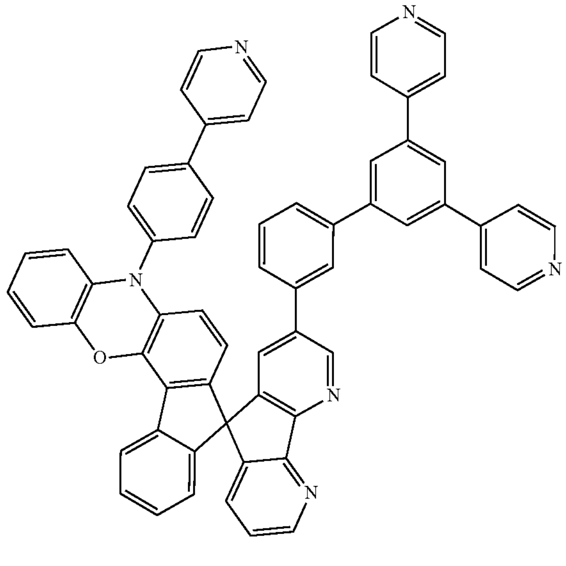

-continued
L33
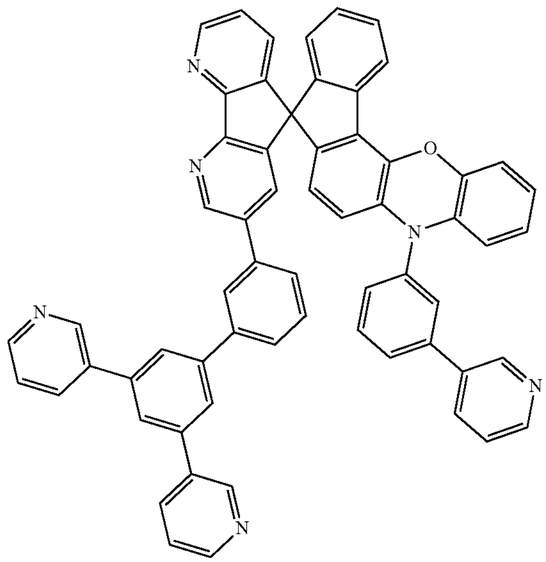
L34
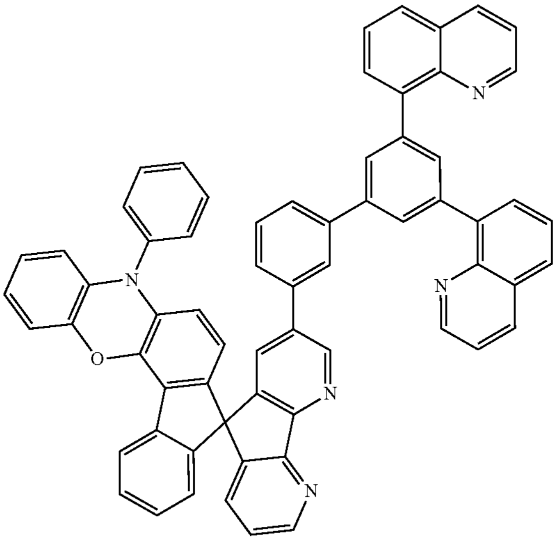
-continued
L35
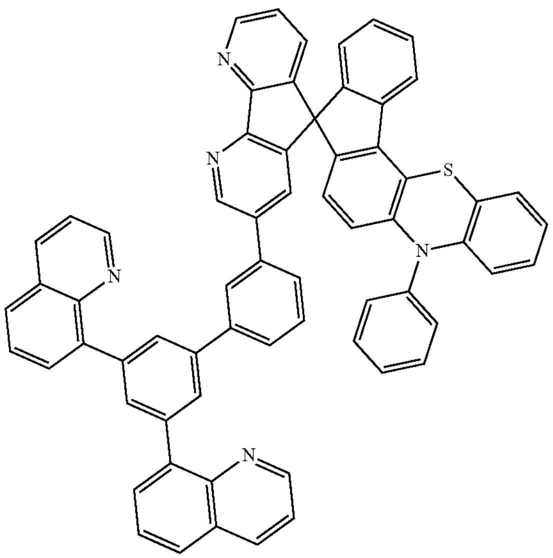
L36
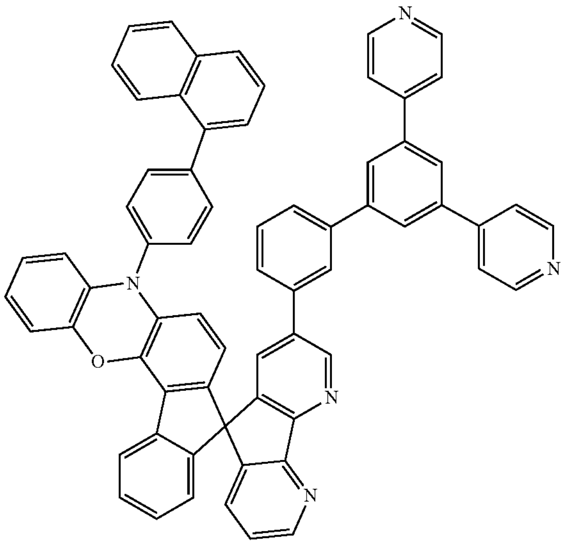

-continued
L37
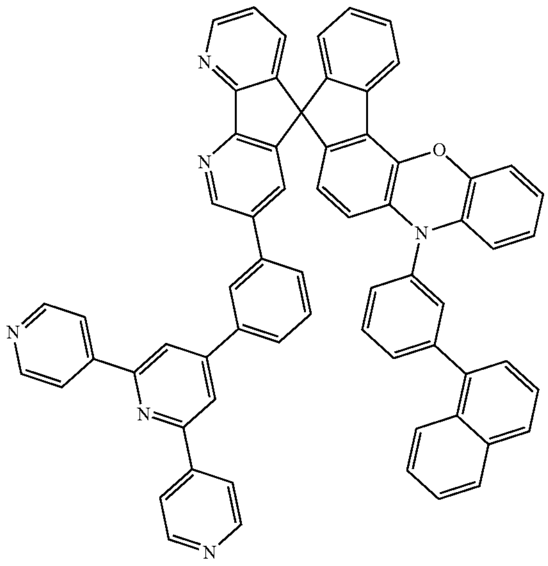
L38
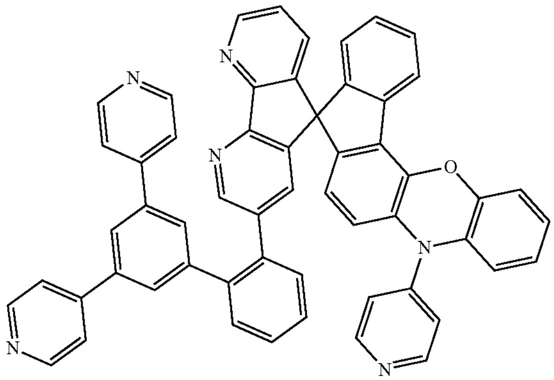
L39
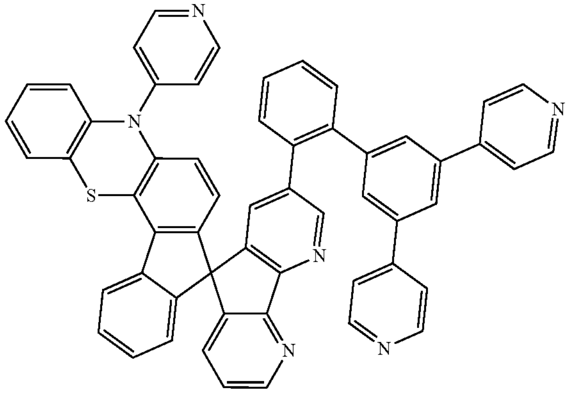
-continued
L40
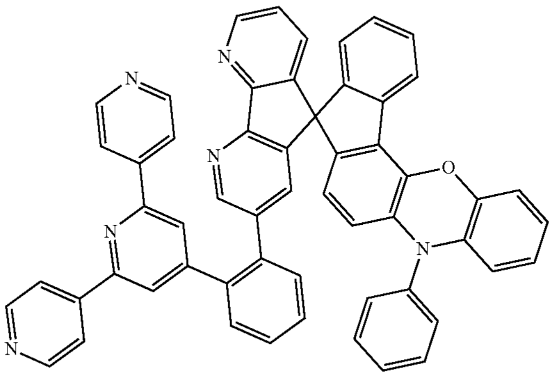
L41
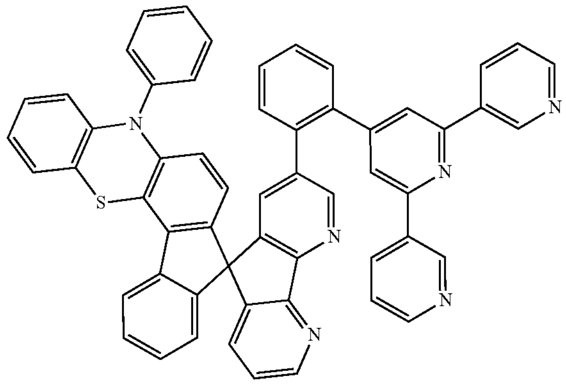
L42
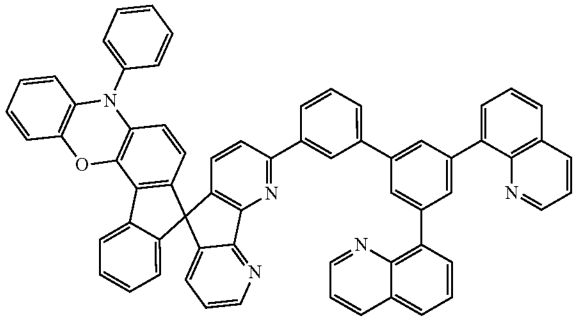
L43
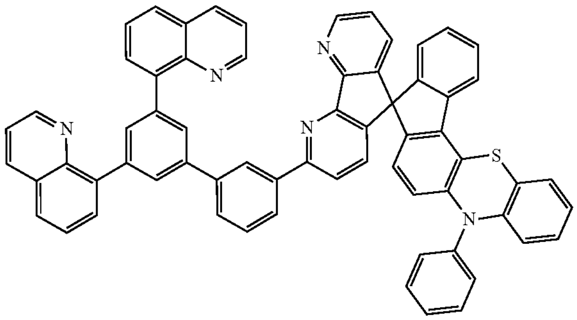

-continued
L44
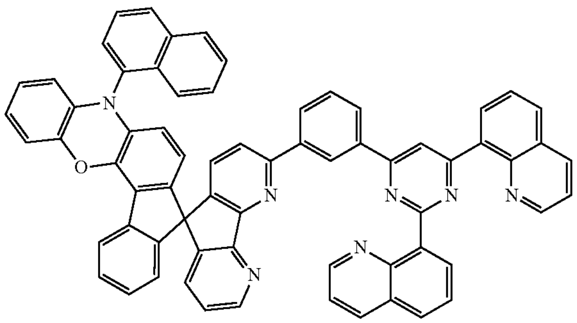
L45
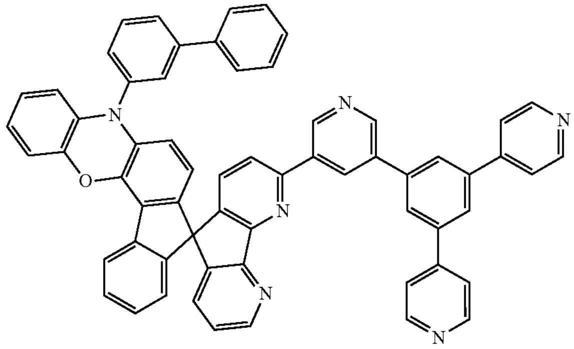
L46
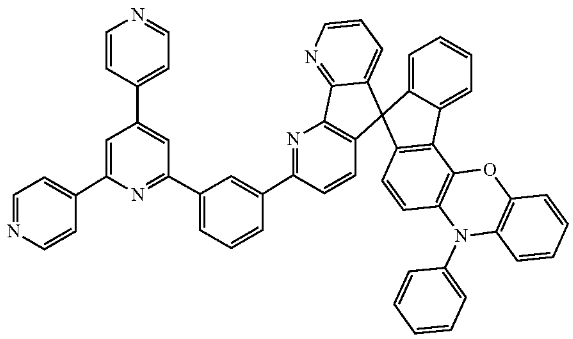
L47
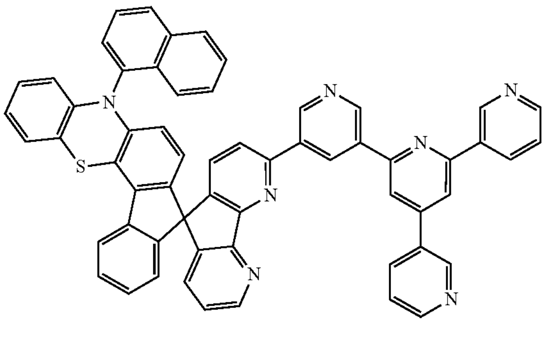
-continued
L48
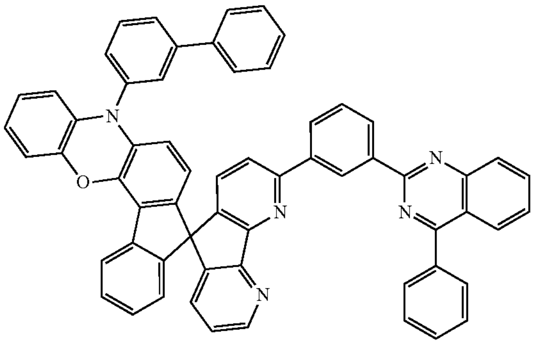
L49
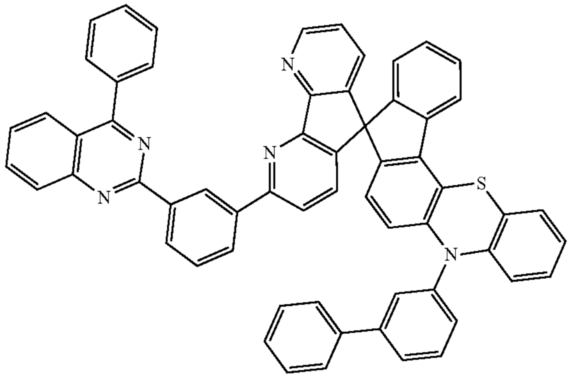
L50
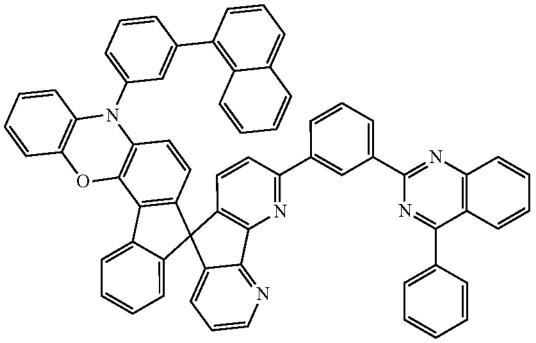
L51
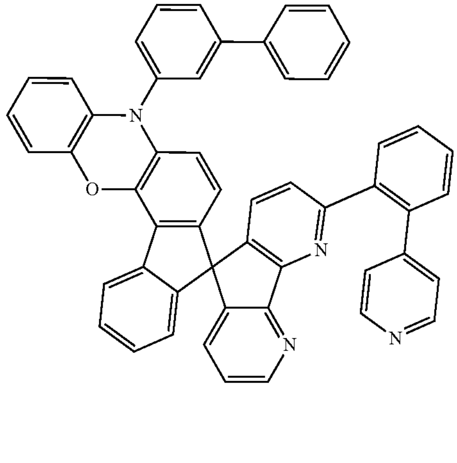

-continued
L52
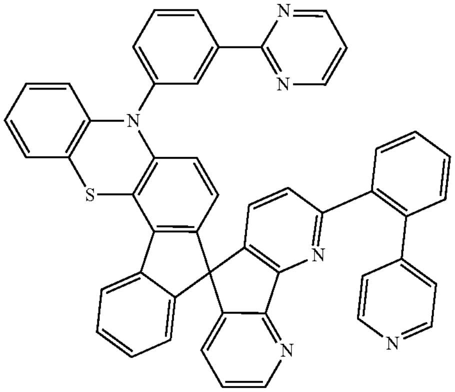
L53
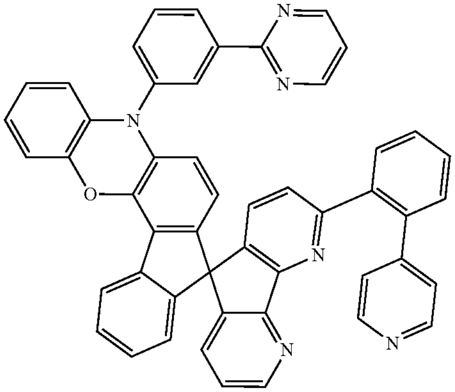
L54
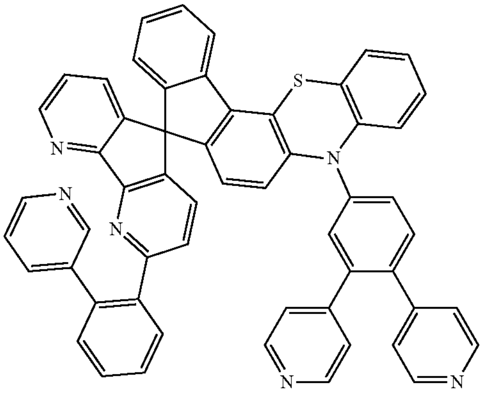
L55
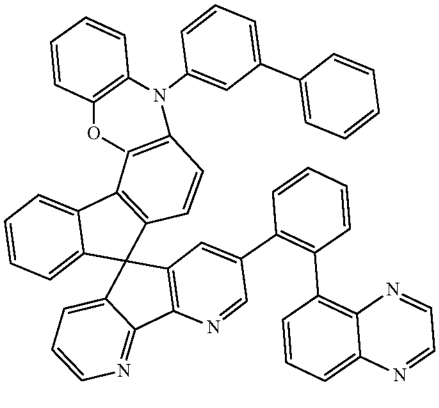
-continued
L56
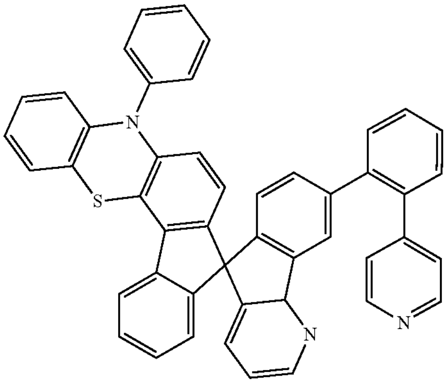
L57
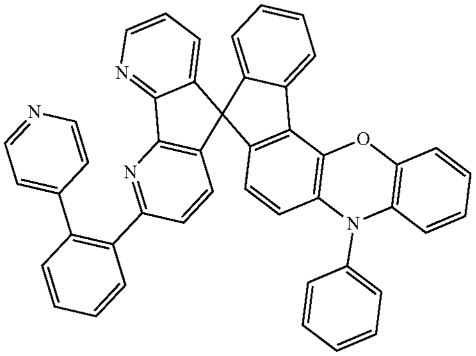
L58
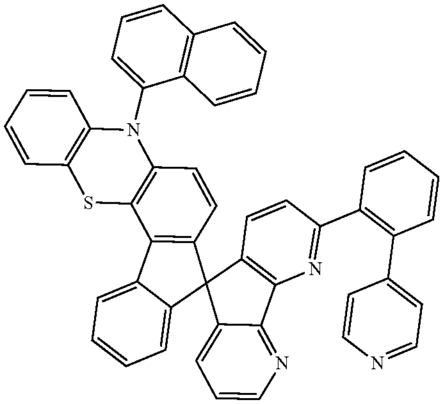
L59
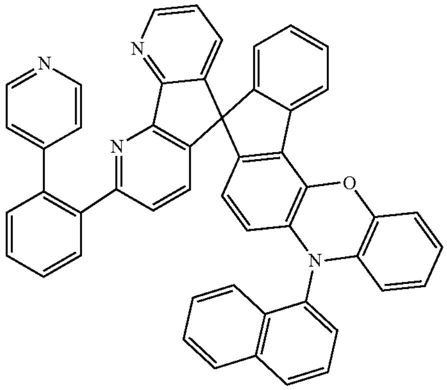

-continued
L60
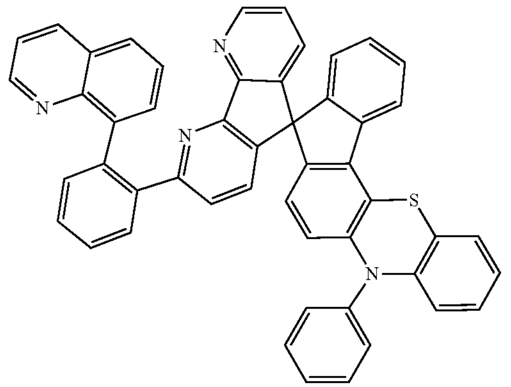
L61
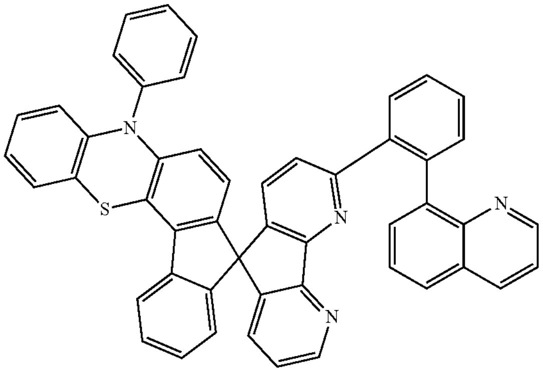
L62
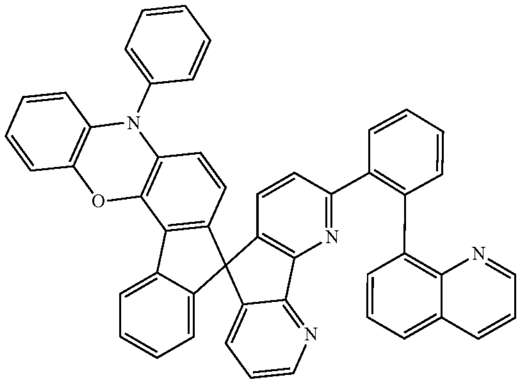
L63
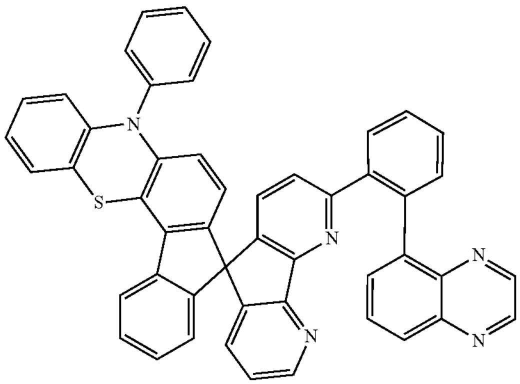
-continued
L64
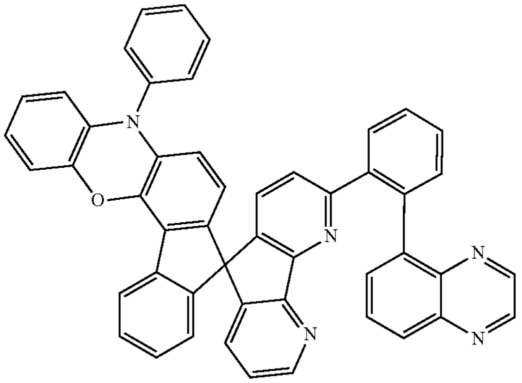
L65
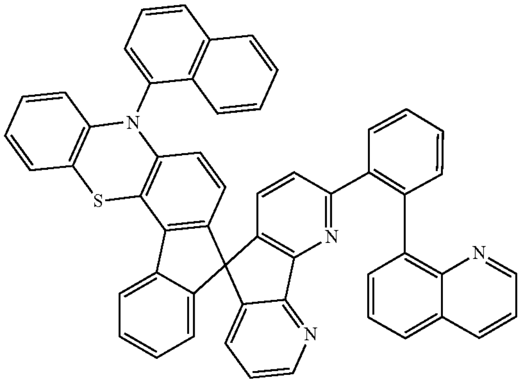
L66
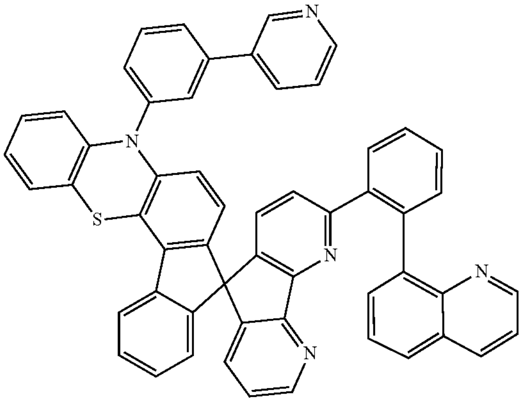
L67
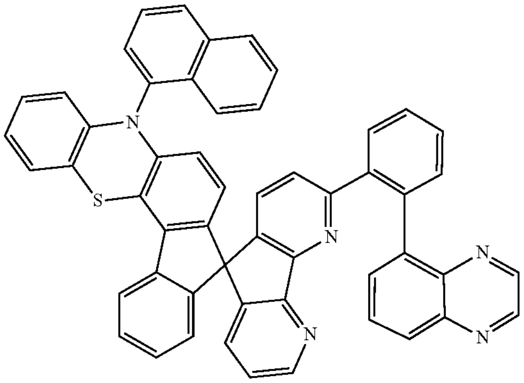

-continued
L68
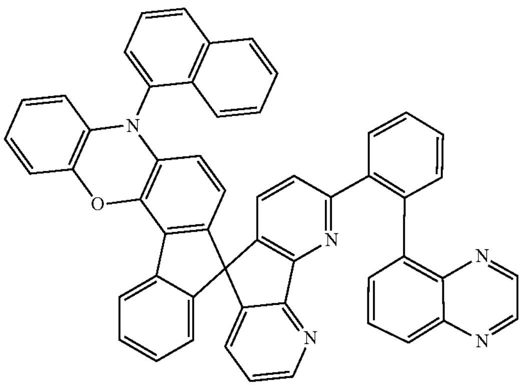
L69
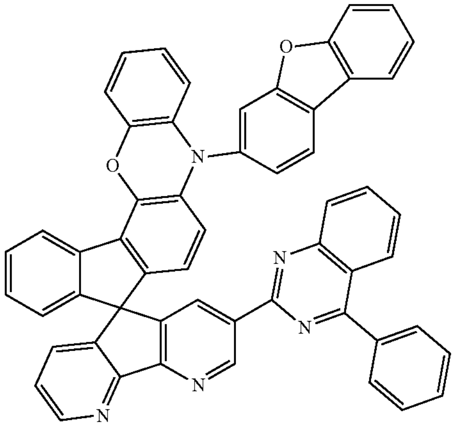
L70
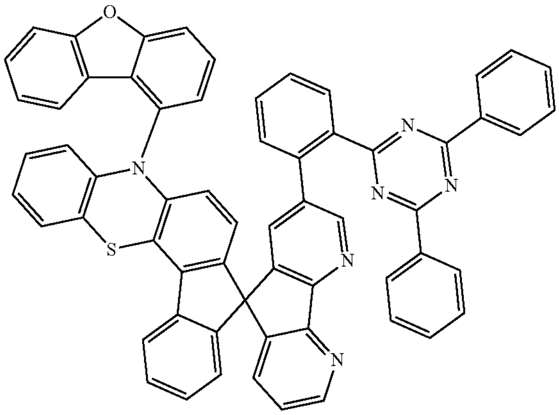
-continued
L71
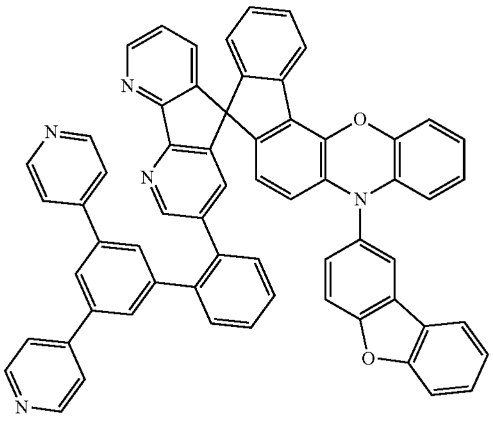
L72
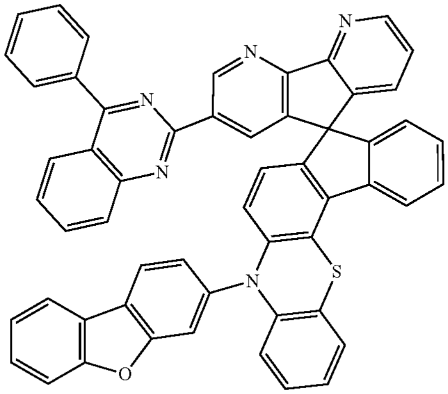
L73
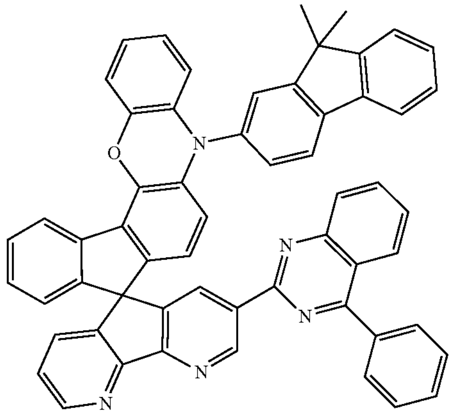

-continued

L74

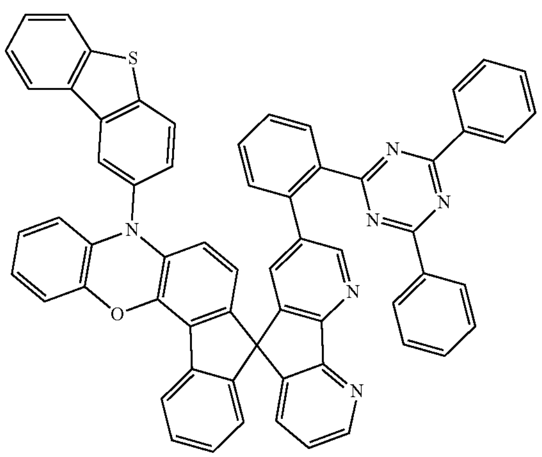

L75

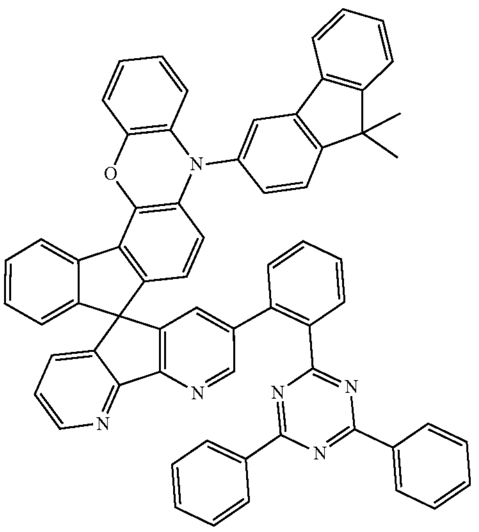

L76

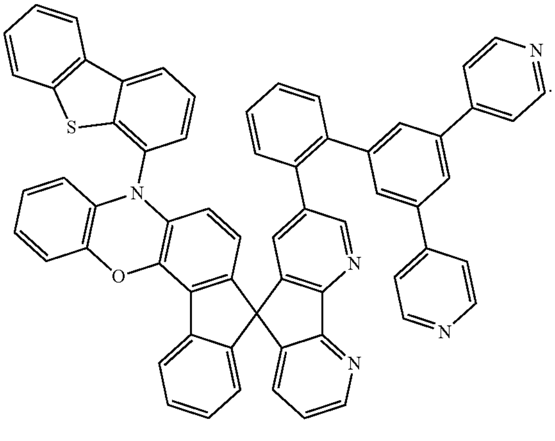

A method of preparing the nitrogen-containing spiral organic compound is provided according to the present disclosure. The compound represented by Formula I is synthesized according to the following route:

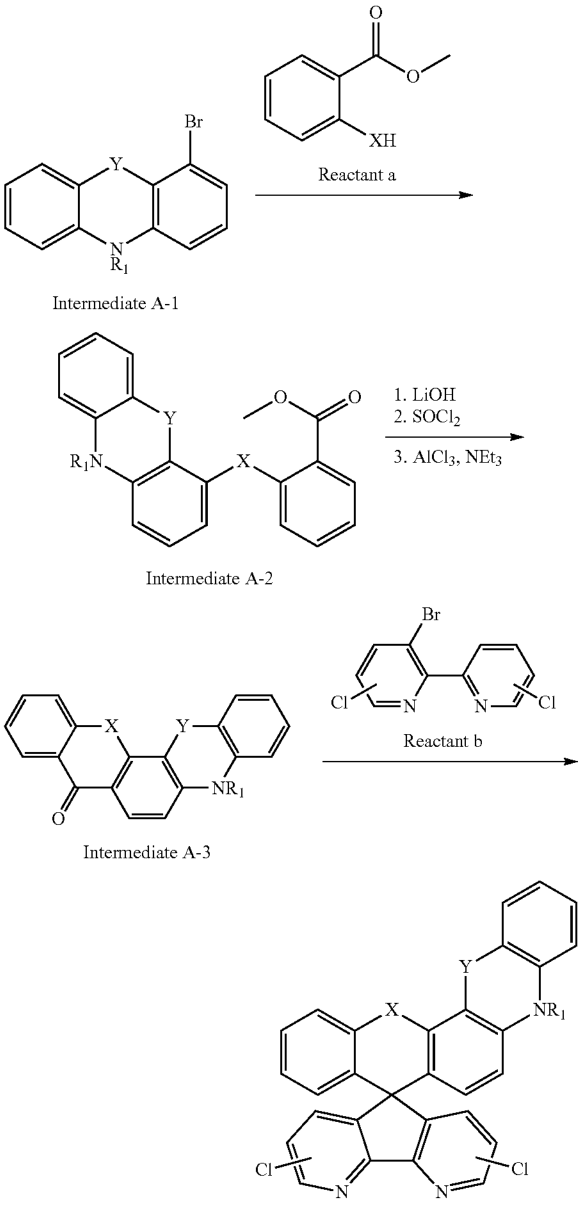

Intermediate A-1

Intermediate A-2

Intermediate A-3

Intermediate A

The compound represented by Formula II is synthesized according to the following route:

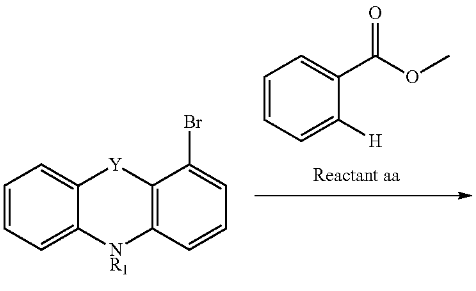

Intermediate B-1

-continued

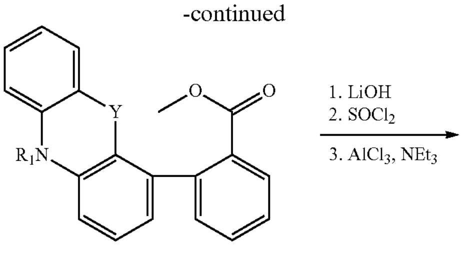

Intermediate B-2

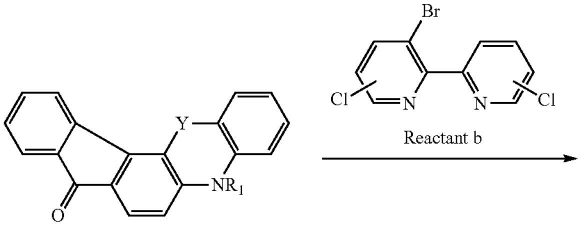

Intermediate B-3

Reactant b

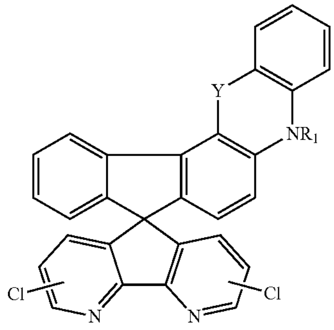

Intermediate B

After the intermediate A or the intermediate B is prepared, a substitution reaction is performed to prepare the nitrogen-containing spiral organic compound represented by Formula I or Formula II.

The nitrogen-containing spiral organic compounds provided by the present disclosure have thermal activation delayed fluorescence (TADF) property and can be applied to a light-emitting layer material.

An organic light-emitting device is provided by the present disclosure. The organic light-emitting device includes an anode, a cathode and an organic thin film layer between the anode and the cathode. The organic thin film layer includes a light-emitting layer, and the light-emitting layer includes at least one of the above-mentioned nitrogen-containing spiral organic compounds.

In one embodiment, the organic light-emitting device includes an anode, a cathode and an organic thin film layer between the anode and the cathode. The organic thin film layer includes a phosphorescent light-emitting layer, and the phosphorescent light-emitting layer includes at least one of the above-mentioned nitrogen-containing spiral organic compounds.

A display panel is provided by the present disclosure. The display panel includes the above-mentioned organic light-emitting device.

The organic light-emitting device according to the present disclosure may be those well known. In one embodiment, in the present disclosure, the organic light-emitting device includes a substrate, an ITO anode, a first hole transport layer, a second hole transport layer, an electron barrier layer, a light-emitting layer, a first electron transport layer, a second electron transport layer, a cathode (a magnesium silver electrode with a mass ratio of magnesium to silver of 1:9) and a cap layer (CPL).

In one embodiment, in the present disclosure, a material of the anode of the organic light-emitting device may be selected from metals such as copper, gold, silver, iron, chromium, nickel, manganese, palladium, platinum and an alloy thereof, metal oxided such as indium oxide, zinc oxide, indium tin oxide (ITO), indium zinc oxide (IZO), and a conductive polymer such as polydibenzothiophenyl, polypyrrole, poly(3-methylthiophene). In addition to the above materials that facilitate hole injection and a combination thereof, known materials suitable for the anode are further included.

In one embodiment, in the present disclosure, a material of the cathode of the organic light-emitting device may be selected from metals such as aluminum, magnesium, silver, indium, tin, titanium and an alloy thereof, such as a multilayer metal material such as LiF/Al, $LiO_2$/Al, and $BaF_2$/Al. In addition to the above materials that facilitate electron injection and a combination thereof, known materials suitable for the cathode are further included.

In one embodiment, in the present disclosure, the organic photoelectric device, for example, the organic thin film layer in the organic light-emitting device, at least includes one light-emitting layer (EML), and may further includes other functional layers, including a hole injection layer (HIL), a hole transport layer (HTL), an electron barrier layer (EBL), a hole barrier layer (HBL), an electron transport layer (ETL) and an electron injection layer (EIL).

In one embodiment, in the present disclosure, the organic light-emitting device may be prepared by the following method:

forming an anode on a transparent or opaque smooth substrate, forming an organic thin film layer on the anode, and forming an cathode on the organic thin film layer.

In one embodiment, in the present disclosure, the organic thin film layer may be formed with a known film forming method such as evaporation deposition, sputtering, spin coating, impregnation, and ion plating.

A display device is provided by the present disclosure. The display device includes the above-mentioned display panel.

In the present disclosure, the organic light-emitting device (OLED device) may be used in the display device. The organic light-emitting display device may be a display screen of a mobile phone, a display screen of a computer, a display screen of a television, a display screen of an intelligent watch, a display panel of a smart car, a VR or AR helmet display screen, and display screens of various intelligent devices.

Compared with the prior art, a nitrogen-containing spiral organic compound is provided according to the present disclosure. The compound has the structure shown in the Formula I or the Formula II. A series of new TADF materials with excellent performance are developed according to the present disclosure. With the TADF materials used for mass products, the efficiency and the service life of OLED devices can be significantly improved and the driving voltage can be reduced.

The present embodiment will be clearly and completely described below in combination with embodiments of the examples. Apparently, the examples described are only some examples of the present disclosure, rather than all the examples.

Preparation of the Intermediate A

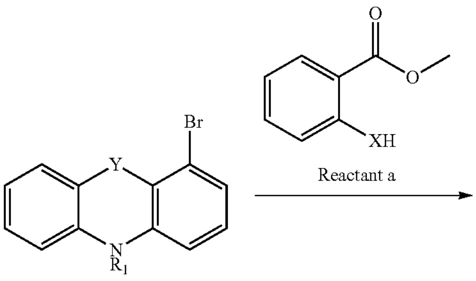

Intermediate A-1

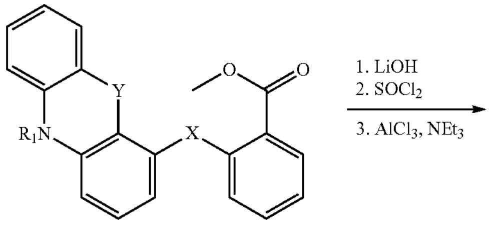

Intermediate A-2

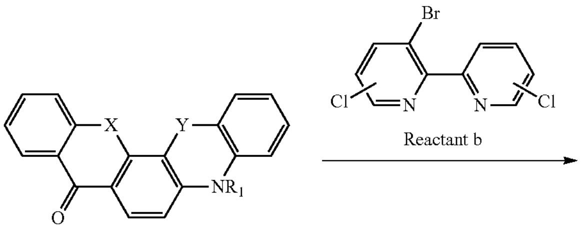

Intermediate A-3

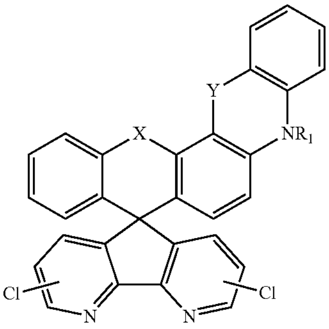

Intermediate A

1) Synthesis of the intermediate A-2: 10 mmol intermediate A-1, 12 mmol reactant a, 10 mmol potassium carbonate and 160 mL of DMSO were added into a 250 mL three mouth flask, heated to 120° C., stirred to perform reaction for 10 hours, and cooled to room temperature. The resulting mixture was added to water of three times of volume, stirred to precipitate solid and filtered. The filter cake was washed with water to neutral, completely dissolved by adding dichloromethane, washed with water to neutral, dried with anhydrous $Na_2SO_4$, concentrated, and passed through a silica gel column, to obtain the intermediate A-2 with a yield of 86%.

2) Synthesis of the intermediate A-3: 20 mmol intermediate A-2, 140 mL tetrahydrofuran (THF), and 35 mL water were added into a 250 mL three-necked flask. Then the resulting mixture was added with 0.1 mol potassium hydroxide, stirred at room temperature to perform reaction for 8 hours. After the raw materials were completely reacted, the resulting mixture was added with hydrochloric acid to adjust the pH to acidity, allowed standing for layering. The organic phase was separated and washed with water to neutral. The aqueous phase was extracted with dichloromethane. The organic phase was combined, dried and the solvent was evaporated to dryness. The resulting solid was added to 100 ml dichlorosulfoxide to perform reaction under reflux for 3 hours. The solvent was evaporated, and the resulting mixture was added to 140 mL tetrahydrofuran, filled with nitrogen, and added with 0.12 mol $AlCl_3$, 0.1 mol potassium carbonate, and 0.06 mol triethylamine, heated to 80° C., stirred to perform reaction for 8 hours, poured into ice water, and allowed standing for layering. The organic phase was washed with water to neutral. The aqueous phase was extracted with dichloromethane. The organic phase was combined, dried with anhydrous $Na_2SO_4$, and then passed through a column, to obtain the intermediate A-3 with a yield of 58%.

3) Synthesis of the intermediate A: A 250 mL three-necked flask was filled with nitrogen, added with 0.07 mol Mg, a grain of iodine and a small amount of THE, and dropped with a small amount of THE solution of reactant b. After the reaction was initiated, 120 mL THE solution containing 0.05 mol reactant b was slowly dropped to the flask. The reaction was performed under reflux. When the Mg chips were completely consumed, the resulting mixture was cooled, added with 0.03 mol intermediate A-3, cooled to room temperature after the reaction was performed under reflux for 8 hours, and added with 2N hydrochloric acid solution to quench the reaction, and distilled under a reduced pressure to remove the solvent. The resulting solid was added with 120 mL acetic acid, heated to perform reaction under reflux for 2 hours, cooled to room temperature, added to water of the same volume to precipitate solid, and filtered. The filter cake was washed with water to neutral, dried, dissolved in 120 mL THF solution, slowly added with methanol of the same volume, and stirred to precipitate the intermediate A with a yield of 70%.

Preparation of the Intermediate B

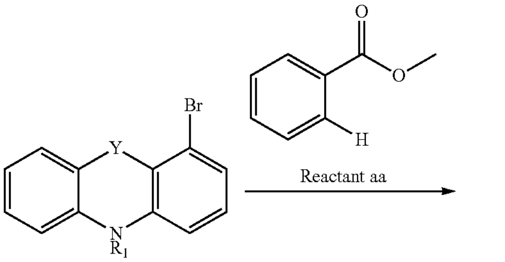

Intermediate B-1

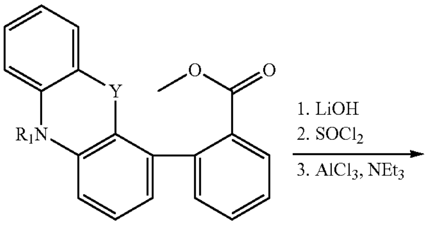

Intermediate B-2

-continued

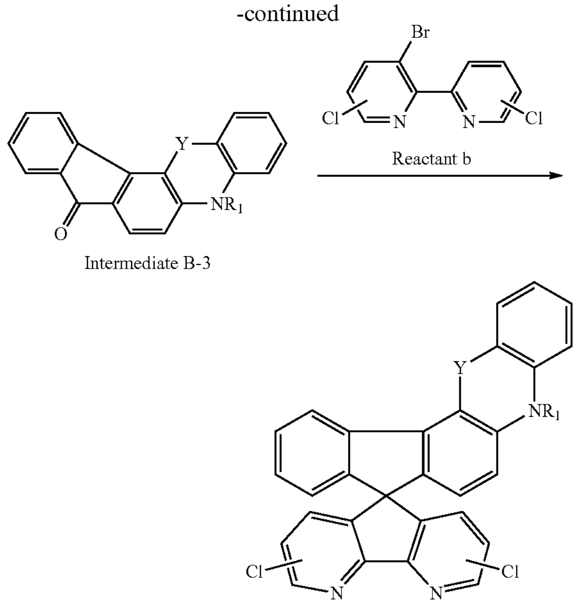

Intermediate B-3

Intermediate B

The synthesis of the intermediate B was similar to that of the intermediate A, except that the reactant a in step 1) was replaced by equimolar reactant aa.

Example 1

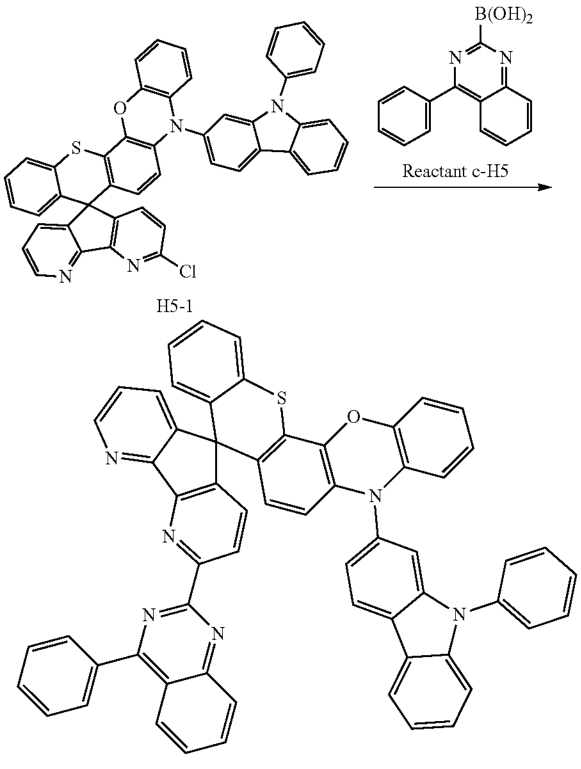

H5-1

H5

In a 250 mL round bottom flask, 10 mmol reactant H5-1, 12 mmol reactant c-H5 and 80 mmol $Na_2CO_3$ were added to a solvent of toluene/EtOH (anhydrous ethanol)/$H_2O$ (75/25/50, mL) to form a mixed solution. Then the mixed solution was added with 0.48 mmol catalyst $Pd(PPh_3)_4$ and reflux reaction was performed under a nitrogen atmosphere for 20 hours to obtain an intermediate. The intermediate was cooled to room temperature, added to water, filtered with a diatomite pad, extracted with dichloromethane, washed with water, dried with anhydrous $MgSO_4$, filtered, and evaporated. The crude product was purified with silica gel column chromatography to obtain the product $H_5$.

MALDI-TOF: m/z: calculated value: $C_{61}H_{36}N_6OS$: 900.27, measured value: 900.45

Results of elemental analysis of the compound: calculated value: $C_{61}H_{36}N_6OS$ (%): C, 81.31; H, 4.03; N, 9.33; O, 1.78; and S, 3.56; measured value: C, 81.29; H, 4.04; N, 9.34; O, 1.78; and S, 3.55.

Example 2

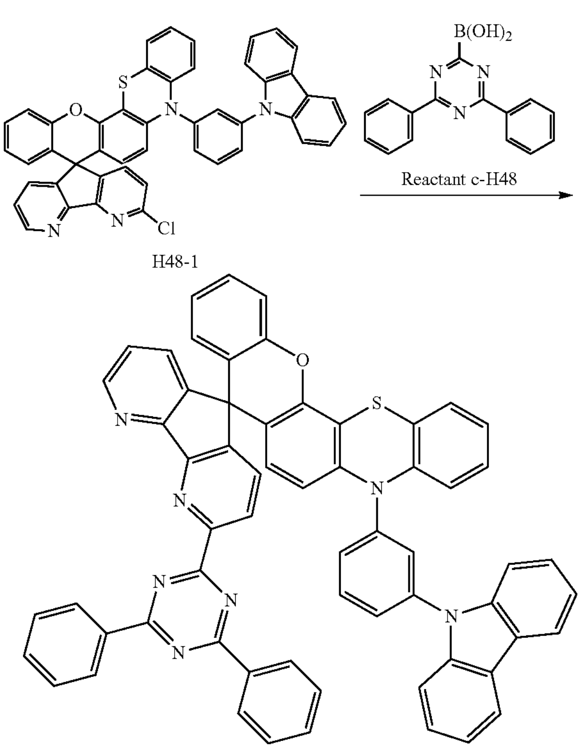

H48-1

H48

In a 250 mL round bottom flask, 10 mmol reactant $H_{48}$-1, 12 mmol reactant c-H48 and 80 mmol $Na_2CO_3$ were added to a solvent of toluene/EtOH (anhydrous ethanol)/$H_2O$ (75/25/50, mL) to form a mixed solution. Then the mixed solution was added with 0.48 mmol catalyst $Pd(PPh_3)_4$ and reflux reaction was performed under a nitrogen atmosphere for 20 hours to obtain an intermediate. The intermediate was cooled to room temperature, added to water, filtered with a diatomite pad, extracted with dichloromethane, washed with water, dried with anhydrous $MgSO_4$, filtered, and evaporated. The crude product was purified with silica gel column chromatography to obtain the product $H_{48}$.

MALDI-TOF: m/z: calculated value: $C_{62}H_{37}N_7OS$: 927.28, measured value: 927.45

Results of elemental analysis of the compound: calculated value: $C_{62}H_{37}N_7OS$ (%): C, 80.24; H, 4.02; N, 10.56; O, 1.72; and S, 3.46; measured value: C, 80.25; H, 4.01; N, 10.57; O, 1.72; and S, 3.45.

Example 3

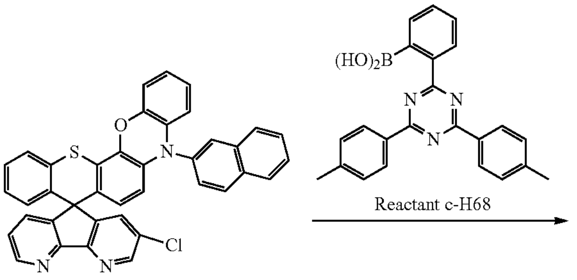

H68-1

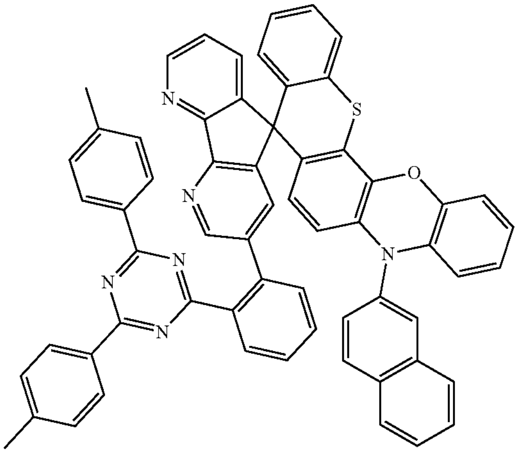

H68

In a 250 mL round bottom flask, 10 mmol reactant $H_{68}$-1, 12 mmol reactant c-H68 and 80 mmol $Na_2CO_3$ were added to a solvent of toluene/EtOH (anhydrous ethanol)/$H_2O$ (75/25/50, mL) to form a mixed solution. Then the mixed solution was added with 0.48 mmol catalyst $Pd(PPh_3)_4$ and reflux reaction was performed under a nitrogen atmosphere for 20 hours to obtain an intermediate. The intermediate was cooled to room temperature, added to water, filtered with a diatomite pad, extracted with dichloromethane, washed with water, dried with anhydrous $MgSO_4$, filtered, and evaporated. The crude product was purified with silica gel column chromatography to obtain the product $H_{68}$.

MALDI-TOF: m/z: calculated value: $C_{62}H_{40}N_6OS$: 916.30, measured value: 916.42

Results of elemental analysis of the compound: calculated value: $C_{62}H_{40}N_6OS$ (%): C, 81.20; H, 4.40; N, 9.16; O, 1.74; S, and 3.50; measured value: C, 81.22; H, 4.39; N, 9.15; O, 1.74; and S, 3.51.

Example 4

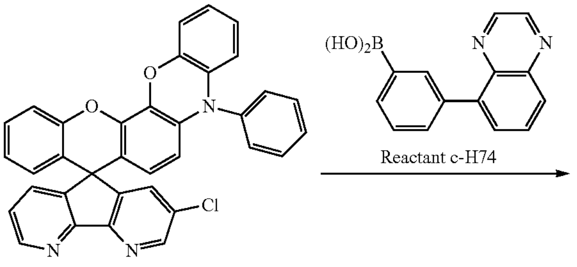

H74-1

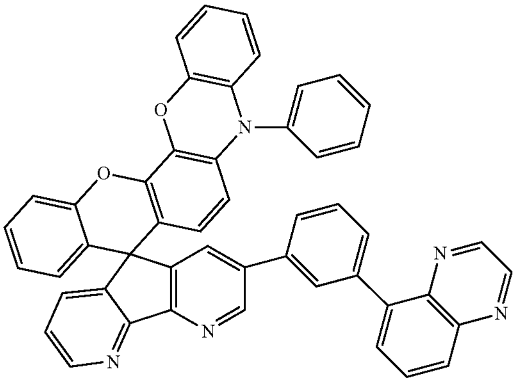

H74

The synthesis of compound H74 was similar to that of compound H5, except that the reactants c-H5 and $H_5$-1 were respectively replaced by equimolar reactants c-H74 and H74-1.

MALDI-TOF: m/z: calculated value: $C_{49}H_{29}N_5O_2$: 719.23, measured value: 719.38

Results of elemental analysis of the compound: calculated value: $C_{49}H_{29}N_5O_2$ (%): C, 81.76; H, 4.06; N, 9.73; and O, 4.45; measured value: C, 81.74; H, 4.07; N, 9.74; and O, 4.44.

Example 5

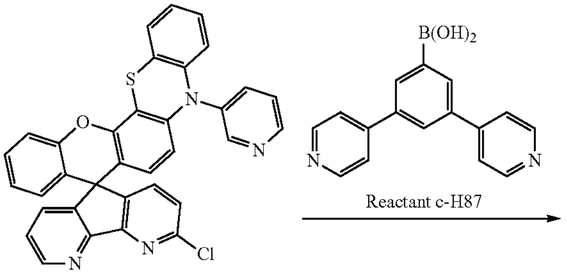

H87-1

-continued
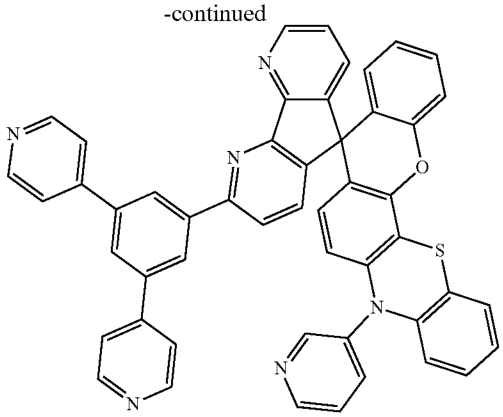
H87
The synthesis of compound H87 was similar to that of compound H5, except that the reactants c-H5 and $H_5$-1 were respectively replaced by equimolar reactants c-H87 and $H_{87}$-1.
MALDI-TOF: m/z: calculated value: $C_{50}H_{30}N_6OS$: 762.22, measured value: 762.43
Results of elemental analysis of the compound: calculated value: $C_{50}H_{30}N_6OS$ (%): C, 78.72; H, 3.96; N, 11.02; O, 2.10; and S, 4.20; measured value: C, 78.74; H, 3.95; N, 11.03; O, 2.10; and S, 4.19.
Example 6
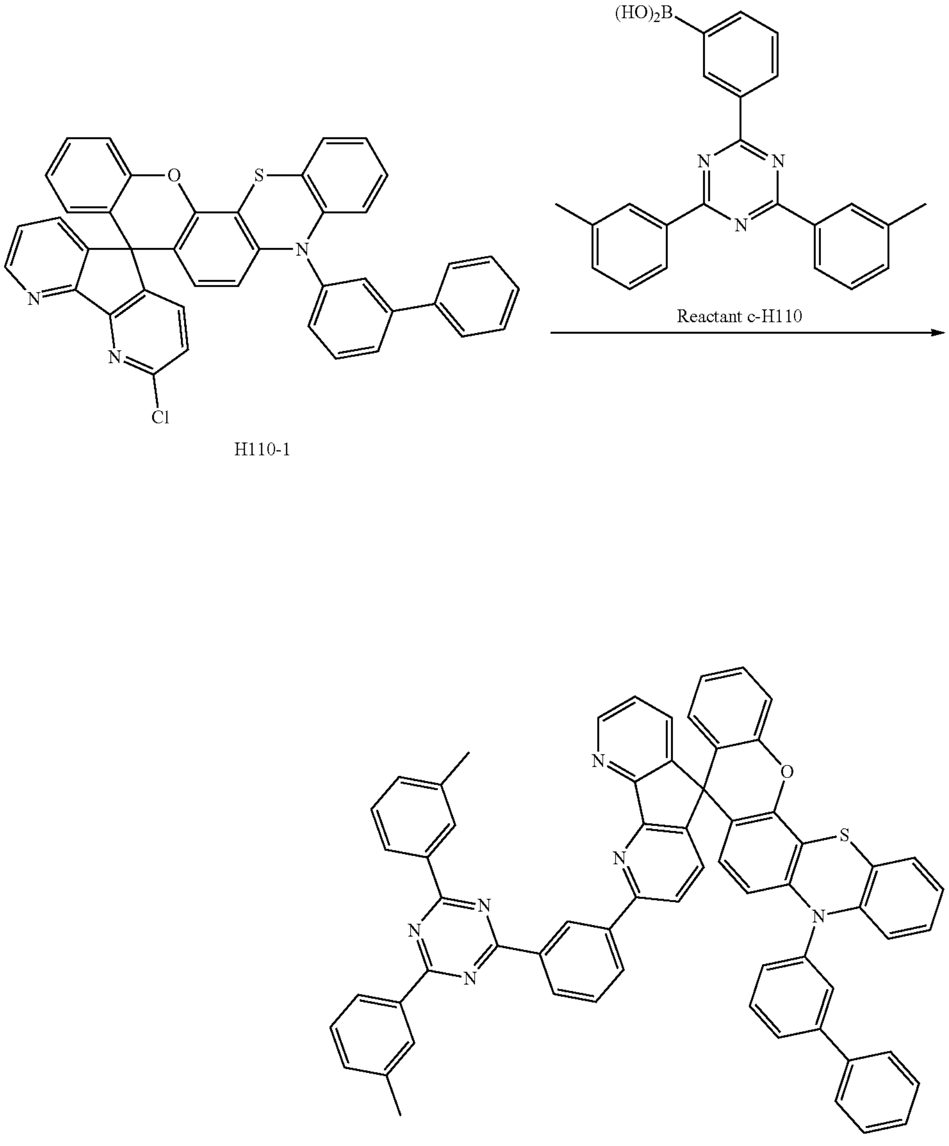
H110-1
H110

The synthesis of compound H110 was similar to that of compound H5, except that the reactants c-H5 and $H_5$-1 were respectively replaced by equimolar reactants c-H110 and $H_{110}$-1.

MALDI-TOF: m/z: calculated value: $C_{64}H_{42}N_6OS$: 942.31, measured value: 942.54

Results of elemental analysis of the compound: calculated value: $C_{64}H_{42}N_6OS$ (%): C, 81.50; H, 4.49; N, 8.91; O, 1.70; and S, 3.40; measured value: C, 81.51; H, 4.48; N, 8.92; 0, 1.70; and S, 3.39.

Example 7

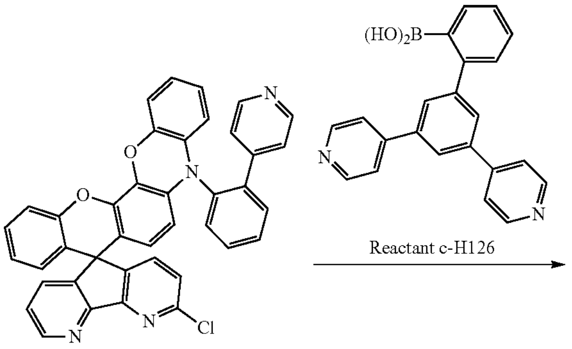

H126-1

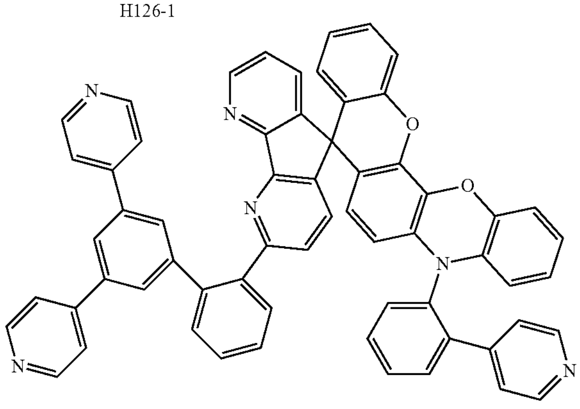

H126

The synthesis of compound H126 was similar to that of compound H5, except that the reactants c-H5 and $H_5$-1 were respectively replaced by equimolar reactants c-H126 and H126-1.

MALDI-TOF: m/z: calculated value: $C_{62}H_{38}N_6O_2$: 898.31, measured value: 898.45

Results of elemental analysis of the compound: calculated value: $C_{62}H_{38}N_6O_2$ (%): C, 82.83; H, 4.26; N, 9.35; and O, 3.56; measured value: C, 82.81; H, 4.27; N, 9.36; and O, 3.55.

Example 8

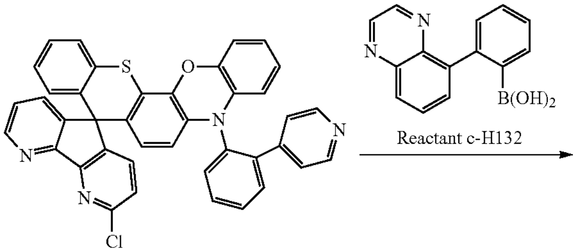

H132-1

-continued

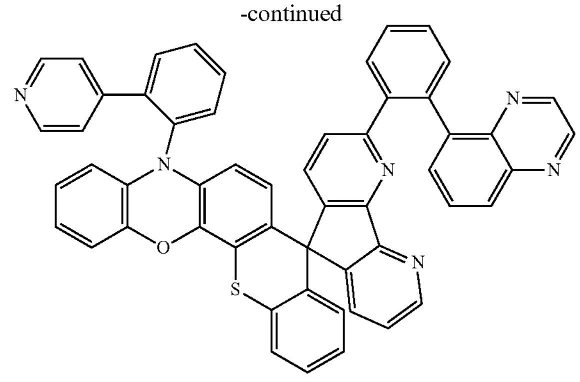

H132

The synthesis of compound H132 was similar to that of compound H5, except that the reactants c-H5 and $H_5$-1 were respectively replaced by equimolar reactants c-H132 and H132-1.

MALDI-TOF: m/z: calculated value: $C_{54}H_{32}N_6OS$: 812.24, measured value: 812.42

Results of elemental analysis of the compound: calculated value: $C_{54}H_{32}N_6OS$ (%): C, 79.78; H, 3.97; N, 10.34; O, 1.97; and S, 3.94; measured value: C, 79.76; H, 3.98; N, 10.35; 0, 1.97; and S, 3.93.

Example 9

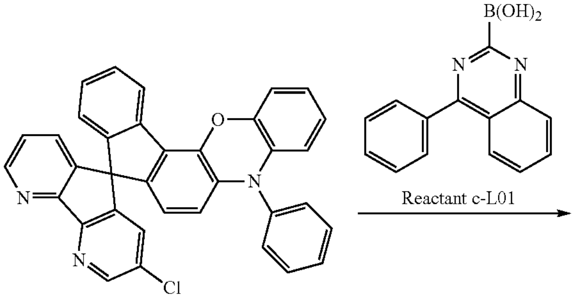

L01-1

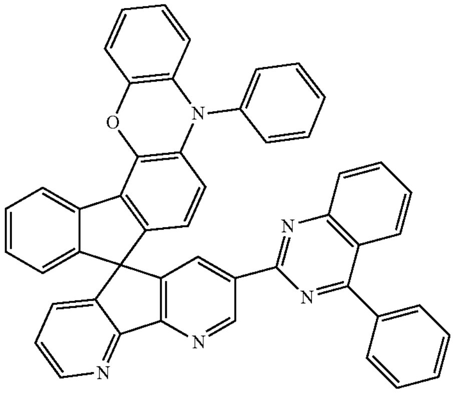

L01

The synthesis of compound L01 was similar to that of compound H5, except that the reactants c-H5 and $H_5$-1 were respectively replaced by equimolar reactants c-L01 and L01-1.

MALDI-TOF: m/z: calculated value: $C_{49}H_{29}N_5O$: 703.24, measured value: 703.29

Results of elemental analysis of the compound: calculated value: $C_{49}H_{29}N_5O$ (%): C, 83.62; H, 4.15; N, 9.95; and O, 2.27; measured value: C, 83.64; H, 4.14; N, 9.96; and O, 2.26.

Example 10

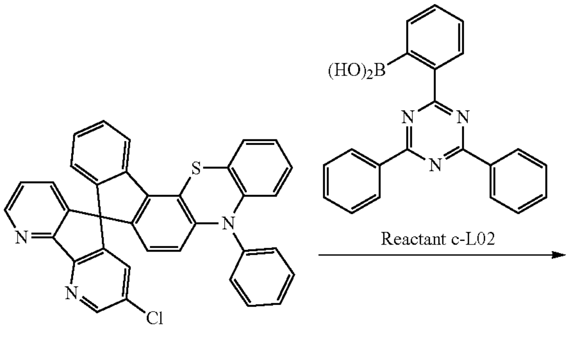

L02-1

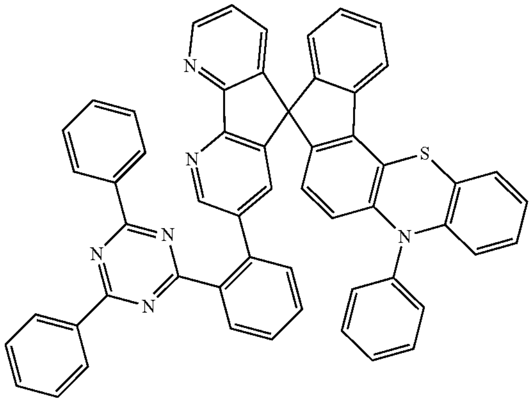

L02

The synthesis of compound L02 was similar to that of compound H5, except that the reactants c-H5 and $H_5$-1 were respectively replaced by equimolar reactants c-L02 and L02-1.

MALDI-TOF: m/z: calculated value: $C_{56}H_{34}N_6S$: 822.26, measured value: 822.32 Results of elemental analysis of the compound: calculated value: $C_{56}H_{34}N_6S$ (%): C, 81.73; H, 4.16; N, 10.21; and S, 3.90; measured value: C, 81.71; H, 4.17; N, 10.21; and S, 3.91.

Example 11

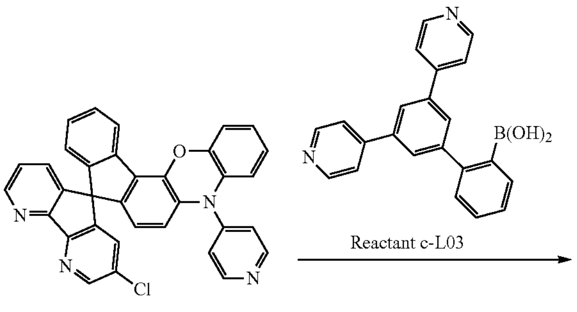

L03-1

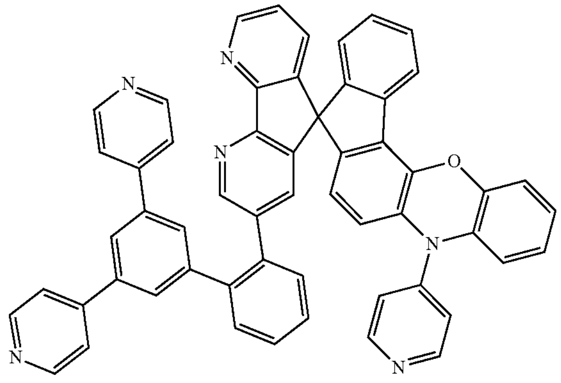

L03

The synthesis of compound L03 was similar to that of compound H5, except that the reactants c-H5 and $H_5$-1 were respectively replaced by equimolar reactants c-L03 and L03-1.

MALDI-TOF: m/z: calculated value: $C_{56}H_{34}N_6O$: 806.28, measured value: 806.36

Results of elemental analysis of the compound: calculated value: $C_{56}H_{34}N_6O$ (%): C, 83.36; H, 4.25; N, 10.42; and O, 1.98; measured value: C, 83.34; H, 4.26; N, 10.41; and O, 1.99.

Example 12

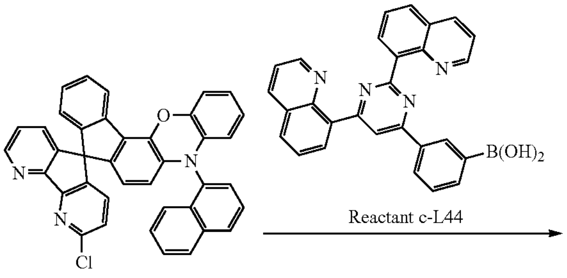

L44-1

-continued

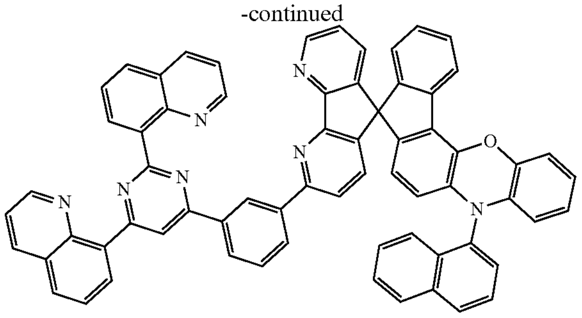

L44

The synthesis of compound L44 was similar to that of compound H5, except that the reactants c-H5 and $H_5$-1 were respectively replaced by equimolar reactants c-L44 and L44-1.

MALDI-TOF: m/z: calculated value: $C_{67}H_{39}N_7O$: 957.32, measured value: 957.40 Results of elemental analysis of the compound: calculated value: $C_{67}H_{39}N_7O$ (%): C, 83.99; H, 4.10; N, 10.23; and O, 1.67; measured value: C, 83.98; H, 4.11; N, 10.22; and O, 1.68.

Example 13

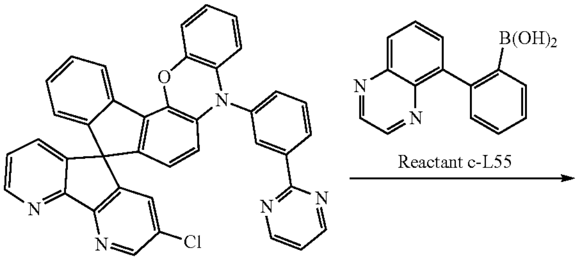

L55-1

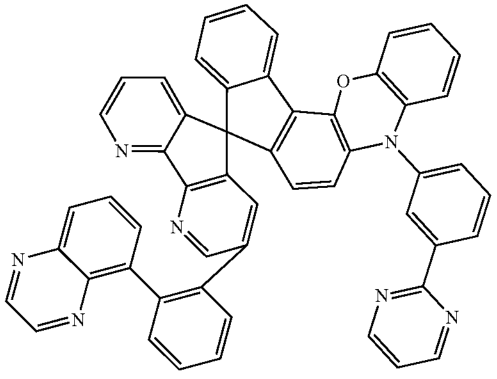

L55

The synthesis of compound L55 was similar to that of compound H5, except that the reactants c-H5 and $H_5$-1 were respectively replaced by equimolar reactants c-L55 and L55-1.

MALDI-TOF: m/z: calculated value: $C_{53}H_{31}N_7O$: 781.26, measured value: 781.35

Results of elemental analysis of the compound: calculated value: $C_{53}H_{31}N_7O$ (%): C, 81.42; H, 4.10; N, 12.54; and O, 2.05; measured value: C, 81.41; H, 4.01; N, 12.54; and O, 2.04.

Example 14

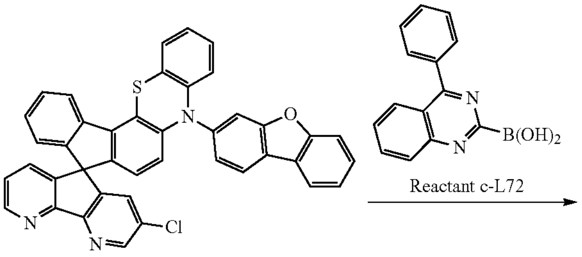

L72-1

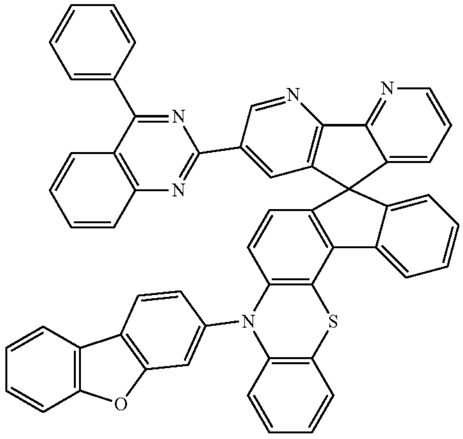

L72

The synthesis of compound L72 was similar to that of compound H5, except that the reactants c-H5 and $H_5$-1 were respectively replaced by equimolar reactants c-L72 and L72-1.

MALDI-TOF: m/z: calculated value: $C_{55}H_{31}N_5OS$: 809.22, measured value: 809.41

Results of elemental analysis of the compound: calculated value: $C_{55}H_{31}N_5OS$ (%): C, 81.56; H, 3.86; N, 8.65; O, 1.98; and S, 3.96; measured value: C, 81.55; H, 3.87; N, 8.64; O, 1.98; and S, 3.96.

Device Example 1

An organic light-emitting device is provided according to this example. The device has a structure of:

ITO (10 nm)/HAT-CN (10 nm)/NPB (40 nm)/TAPC (10 nm)/compound H5: $Ir(MDQ)_2(acac)$ (20 nm)/TPBi (30 nm)/LiF (2 nm)/Al (100 nm).

In the above structure of the device, ITO serves as an anode material. HAT-CN serves as a hole injection layer material, NPB and TAPC respectively serve as a first hole transport layer material and a second hole transport layer material, the light-emitting layer is obtained by doping a guest material ($Ir(MDQ)_2(acac)$) into a host material (compound H5) in a certain proportion, TPBi serves as an electron transport layer material, LiF serves as an electron injection layer material, and Al serves as a cathode material.

The organic light-emitting device was prepared by performing the following steps.

1) A glass substrate 1 was cut to a size of 50 mm×50 mm×0.7 mm, ultrasonically cleaned in acetone, isopropanol and deionized water for 30 minutes, and then cleaned in UV ozone for 30 minutes, and glass substrate with an indium tin oxide (ITO) anode 2 of a thickness of 10 nm obtained by magnetron sputtering was installed on a vacuum deposition apparatus;

2) The hole injection layer material HAT-CN was deposited on the ITO anode layer 2 by vacuum evaporation deposition to form a hole injection layer 3 with a thickness of 10 nm;

3) The hole transport layer material NPB was deposited on the hole injection layer 3 by vacuum evaporation deposition to form a first hole transport layer 4 with a thickness of 40 nm;

4) The hole transport layer material TAPC was deposited on the first hole transport layer 4 by vacuum evaporation deposition to form a second hole transport layer 5 with a thickness of 10 nm;

5) A light-emitting layer 6 with a thickness of 20 nm was deposited on the second hole transport layer 5 by vacuum evaporation deposition, and compound H5 according to the present disclosure served as the host material, and $Ir(MDQ)_2(acac)$ served as the doping material (guest material), and a doping ratio was 3% (mass ratio);

6) The electron transport layer material TPBi was deposited on the light-emitting layer 6 by vacuum evaporation deposition to form an electron transport layer 7 with a thickness of 30 nm;

7) The electron injection layer material LiF was deposited on the electron transport layer 7 by vacuum evaporation deposition to form an electron injection layer 8 with a thickness of 2 nm; and 8) An aluminum (Al) electrode was deposited on the electron transport layer 8 to form a cathode 9 with a thickness of 100 nm.

The structures of the compounds used in the preparation of the OLED device are as follows:

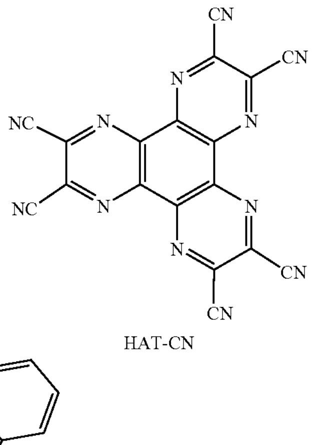

HAT-CN

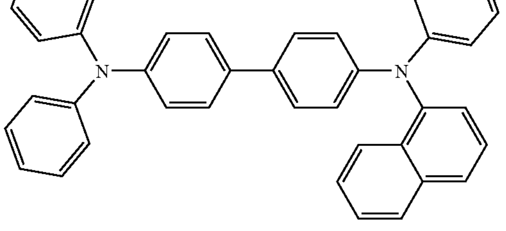

NPB

-continued

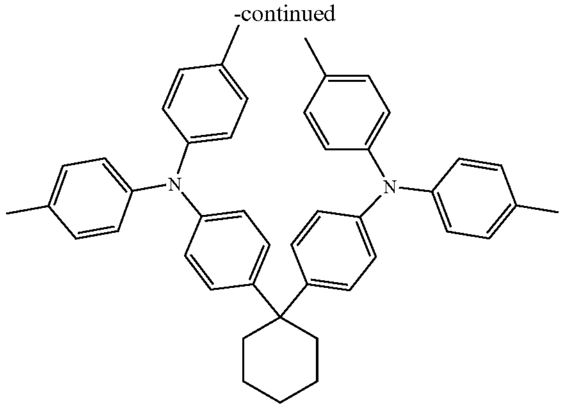

TAPC

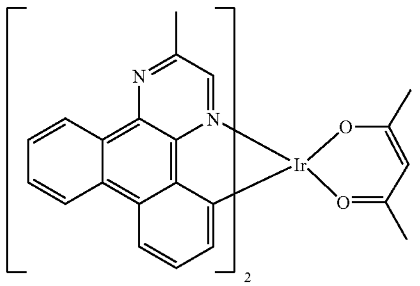

$Ir(MDQ)_2acac$

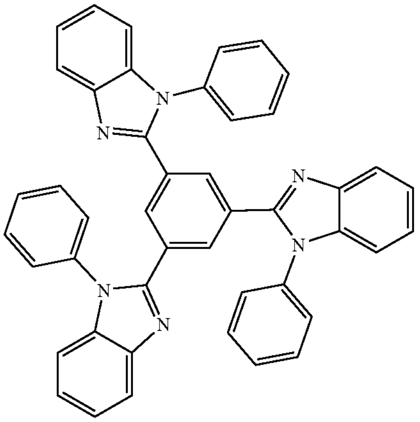

TPBI

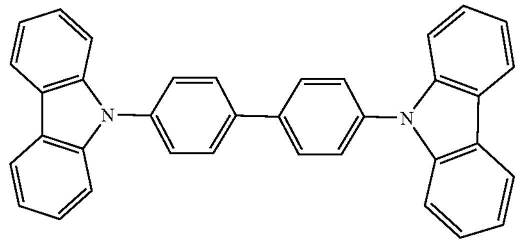

CBP

Device Examples 2 to 14

The organic compound H5 in step (5) of the device Example 1 was replaced with the same amount of compound H48, H68, H74, H87, H110, H126, H132, L01, L02, L03, L44, L55 or L72, and other preparation steps were the same as those of Device Example 1.

Device Reference Example

This example differed from Device Example 1 in that the host material in step (4) was replaced with the same amount of reference compound CBP, and other raw materials and preparation steps were the same as those of Device Example 1.

Evaluation of Performance of the OLED Device:

Currents of the OLED device under different voltages were tested by a Keithley 2365A digital nanovoltmeter, and the currents were divided by a light-emitting area to obtain current densities of the OLED device under different voltages. Brightness and radiant energy flux densities of the OLED device under different voltages were measured by a Konicaminolta CS-2000 spectroradiometer. According to the current densities and brightness of the OLED device under different voltages, a lighting voltage and a current efficiency (CE, Cd/A) under the same current density (10 $mA/cm^2$) were obtained. VON represents the lighting voltage under brightness of $1Cd/m^2$. A service life LT95 (under a test condition of 50 $mA/cm^2$) was obtained by measuring the time that brightness of the OLED device reached 95% of the initial brightness. Taking the test data of lighting voltage Von, the current efficiency CE and the service life LT95 in the device reference Example (REF) as 100%, each of the Von, the CE and the LT95 in each of the device Examples 1 to 14 is a ratio of test data thereof to the test data of Device Reference Example, that is, a relative value compared with the value in the Device Reference Example. Specific data are as shown in Table 1.

TABLE 1

Test results of performance of the OLED device

| OLED device | Material of the light-emitting layer | $V_{on}/V_{REF}$ | $CE/CE_{REF}$ | $LT95/LT95_{REF}$ |
|---|---|---|---|---|
| Device Example 1 | H5 | 96.5% | 106.2% | 105.3% |
| Device Example 2 | H48 | 95.5% | 110.1% | 106.6% |
| Device Example 3 | H68 | 95.7% | 109.2% | 107.4% |
| Device Example 4 | H74 | 96.1% | 107.4% | 106.8% |
| Device Example 5 | H87 | 95.1% | 108.8% | 105.4% |
| Device Example 6 | H110 | 95.4% | 110.6% | 108.2% |
| Device Example 7 | H126 | 95.8% | 109.9% | 108.4% |
| Device Example 8 | H132 | 96.6% | 107.1% | 103.8% |
| Device Example 9 | L01 | 95.9% | 107.8% | 105.0% |
| Device Example 10 | L02 | 95.5% | 110.1% | 106.5% |
| Device Example 11 | L03 | 95.9% | 108.2% | 107.1% |
| Device Example 12 | L44 | 97.1% | 107.5% | 104.8% |
| Device Example 13 | L55 | 96.9% | 108.2% | 104.0% |
| Device Example 14 | L72 | 95.6% | 107.2% | 106.3% |
| Device Reference Example(REF) | CBP | 100% | 100% | 100% |

As can be seen from Table 1, compared with the organic light-emitting device prepared based on the conventional host material CBP, the organic light-emitting device prepared based on the host material according to the present disclosure shows excellent properties in terms of driving voltage, light-emitting efficiency and service life and particularly shows good performance in efficiency. In addition, the host material according to the present disclosure has TADF feature, which is mainly due to the special fused ring and spiro skeleton of the material according to the present disclosure, and overlap of a HOMO energy level and a LUMO energy level of a molecule is small. The spiro structure further enables the compound to obtain a high thermal stability and glass transition temperature Tg. In addition, the compound containing a spiro structure further has appropriate spatial distortion, which reduces a molecular force and intermolecular stacking, and reducing concentration quenching. The compound has a bipolar feature of transporting hole and an electron at the same time, and the compound is conducive to a charge transfer balance in the light-emitting layer, and broadening an exciton recombination region and improving the efficiency of the device.

The invention claimed is:

1. A nitrogen-containing spiral organic compound having a structure shown in Formula I or Formula II:

Formula I

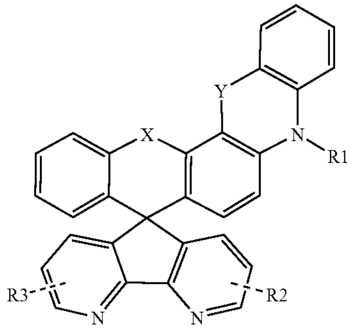

Formula II

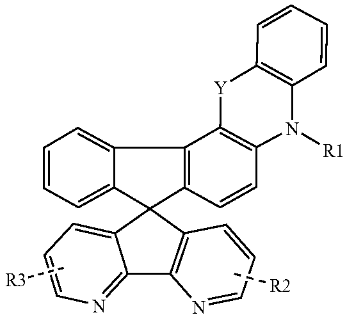

wherein:

X and Y are independently selected from O and S;

$R_1$ is selected from substituted or unsubstituted aryl and heteroaryl; and $R_2$ and $R_3$ are independently selected from H, and substituted or unsubstituted aryl or heteroaryl, and $R_2$ and $R_3$ are not both H.

2. The nitrogen-containing spiral organic compound according to claim 1, wherein the substituent of the substituted aryl or heteroaryl is one or more selected from halogen, cyano, $C_1$-$C_6$ alkyl, $C_1$-$C_6$ alkoxyl, and substituted or unsubstituted aryl, heteroaryl and arylamino.

3. The nitrogen-containing spiral organic compound according to claim 2, wherein the substituent of the substituted aryl or heteroaryl is one or more selected from F, Cl, Br, cyano, methyl, ethyl, n-propyl, isopropyl, n-butyl, isobutyl, t-butyl, methoxy, ethoxy, n-propoxy, and substituted or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl and quinazolinyl.

4. The nitrogen-containing spiral organic compound according to claim 3, wherein the substituent of the substituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl and quinazolinyl is one or more selected from phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl, or quinazolinyl.

5. The nitrogen-containing spiral organic compound according to claim 1, wherein R1 is selected from substituted or unsubstituted monocyclic aryl, monocyclic heteroaryl, fused ring aryl, and fused ring heteroaryl, or is a group formed by connecting any one or more of substituted or unsubstituted monocyclic aryl, monocyclic heteroaryl, fused ring aryl and fused ring heteroaryl through a single bond or an N atom.

6. The nitrogen-containing spiral organic compound according to claim 5, wherein the monocyclic aryl is phenyl;

the monocyclic heteroaryl is selected from pyridyl, pyrazinyl, pyrimidinyl, pyridazinyl, 1,2,3-triazine, 1,3,5-triazide, and 1,3,4-triazide;

the fused ring aryl is selected from naphthyl, anthracenyl, phenanthrenyl, pyrenyl and fluorenyl; and the fused ring heteroaryl is selected from carbazolyl, dibenzofuranyl, dibenzothiophenyl, quinolinyl, isoquinolinyl, quinoxalinyl and quinazolinyl.

7. The nitrogen-containing spiral organic compound according to claim 5, wherein the one or more means one, two, three, or four.

8. The nitrogen-containing spiral organic compound according to claim 1, wherein R1 is selected from a first substituent-containing or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, quinolinyl, isoquinolinyl, quinoxalinyl and quinazolinyl;

the first substituent is one or more selected from F, Cl, Br, cyano, methyl, ethyl, n-propyl, isopropyl, n-butyl, isobutyl, t-butyl, methoxy, ethoxy, n-propoxy, and a second substituent-containing or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl and quinazolinyl; and the second substituent is one or more selected from phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl and quinazolinyl.

9. The nitrogen-containing spiral organic compound according to claim 1, wherein R1 is selected from any one of the following structures:

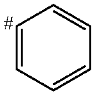
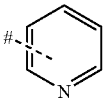
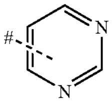
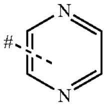

-continued

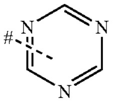
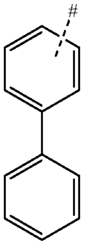
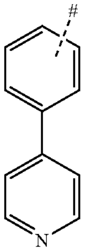
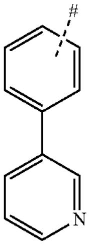
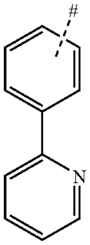
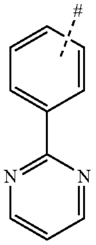
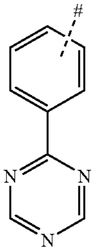
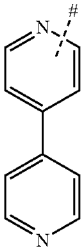
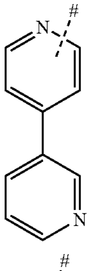
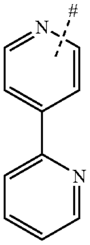
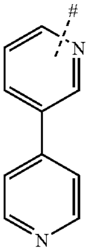
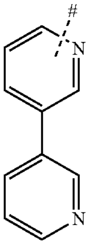
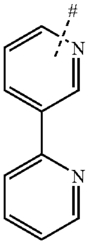
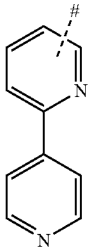
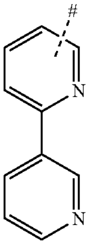
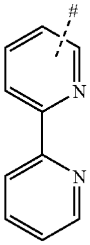
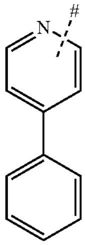
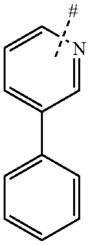
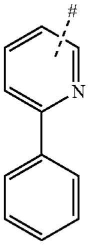
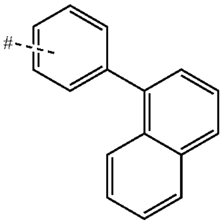
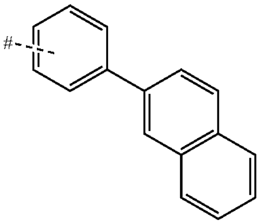
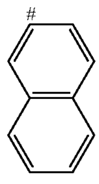
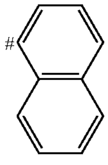
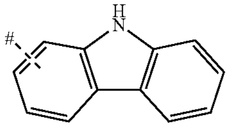
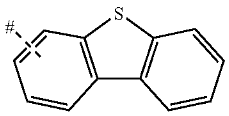
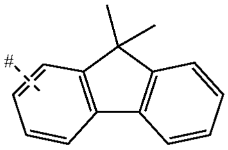
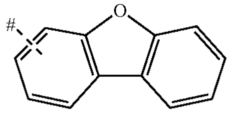

-continued

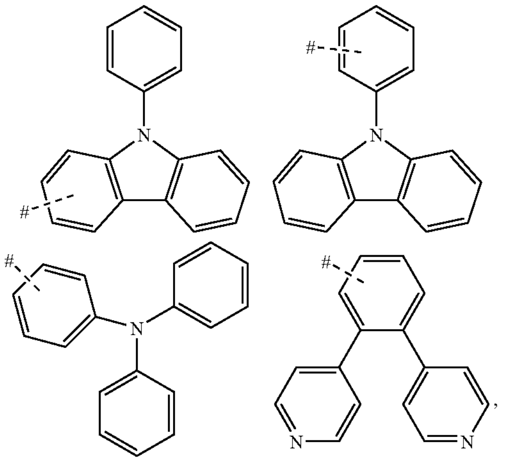

wherein #represents a connection position.

10. The nitrogen-containing spiral organic compound according to claim 1, wherein R2 and R3 are independently selected from H, substituted or unsubstituted monocyclic aryl, monocyclic heteroaryl, fused ring aryl, and fused ring heteroaryl, or are groups formed by connecting any one or more of substituted or unsubstituted monocyclic aryl, monocyclic heteroaryl, fused ring aryl and fused ring heteroaryl through a single bond or an N atom, and R2 and R3 are not both H.

11. The nitrogen-containing spiral organic compound according to claim 10, wherein the monocyclic aryl is phenyl;

the monocyclic heteroaryl is selected from pyridyl, pyrazinyl, pyrimidinyl, pyridazinyl, 1,2,3-triazine, 1,3,5-triazide, and 1,3,4-triazide;

the fused ring aryl is selected from naphthyl, anthracenyl, phenanthrenyl, pyrenyl and fluorenyl; and the fused ring heteroaryl is selected from carbazolyl, dibenzofuranyl, dibenzothiophenyl, quinolinyl, isoquinolinyl, quinoxalinyl and quinazolinyl.

12. The nitrogen-containing spiral organic compound according to claim 10, wherein the one or more means one, two, one or three, or one or four.

13. The nitrogen-containing spiral organic compound according to claim 1, wherein R2 and R3 are independently selected from H, a first substituent-containing or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, quinolinyl, isoquinolinyl, quinoxalinyl and quinazolinyl;

the first substituent is one or more selected from F, Cl, Br, cyano, methyl, ethyl, n-propyl, isopropyl, n-butyl, isobutyl, t-butyl, methoxy, ethoxy, n-propoxy, and a second substituent-containing or unsubstituted phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl and quinazolinyl;

the second substituent is one or more selected from halogen, cyano, $C_1$-$C_6$ alkyl, $C_1$-$C_6$ alkoxyl, phenyl, naphthyl, pyridyl, pyrazinyl, pyrimidinyl, pyridazinyl, 1,2,3-triazinyl, 1,3,5-triazinyl, 1,3,4-triazinyl, carbazolyl, fluorenyl, dibenzofuranyl, dibenzothiophenyl, phenylamino, N,N-diphenylamino, quinolinyl, isoquinolinyl, quinoxalinyl and quinazolinyl; and $R_2$ and $R_3$ are not both H.

14. The nitrogen-containing spiral organic compound according to claim 1, wherein any one or both of R2 and R3 are selected from any one of the following structures:

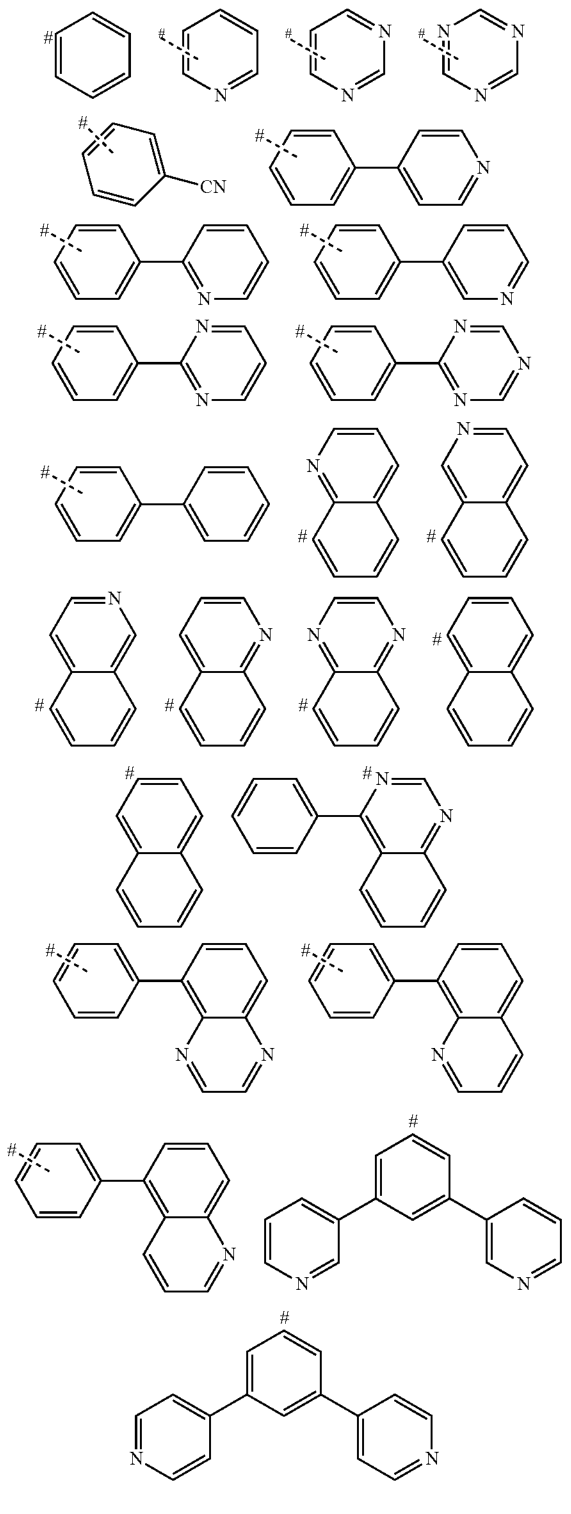

-continued
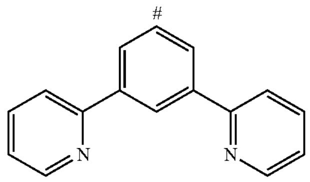
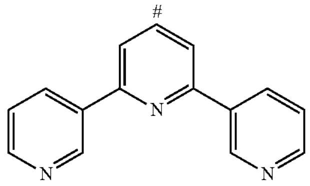
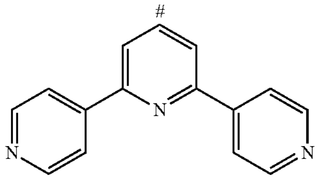
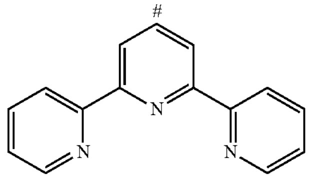
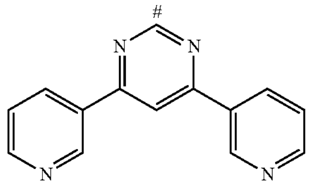
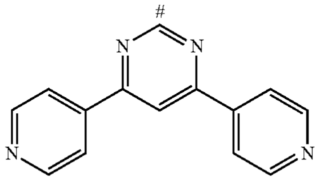
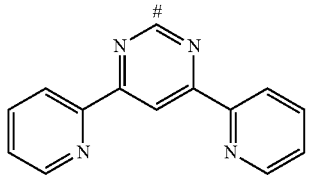
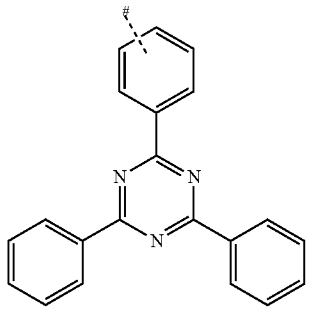
-continued
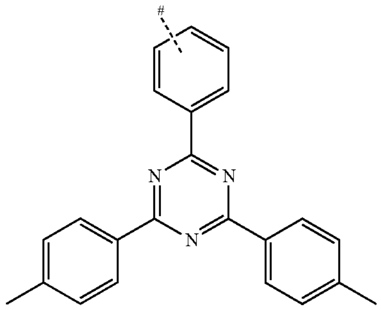
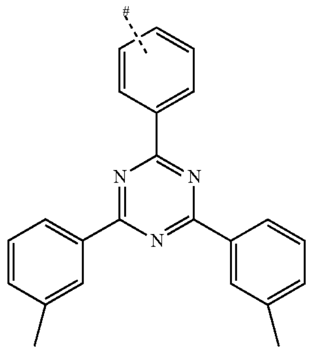
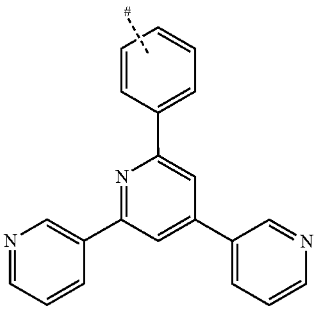
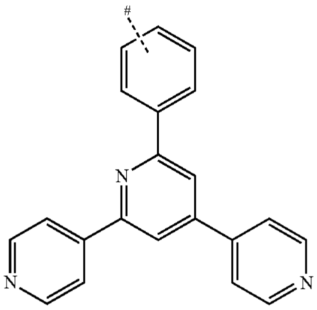
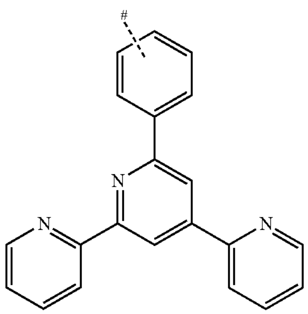

-continued
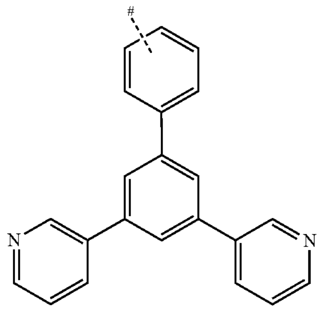
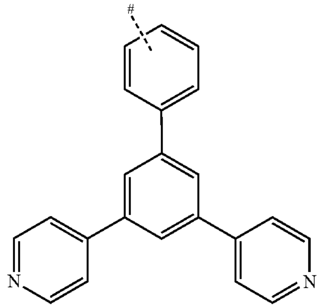
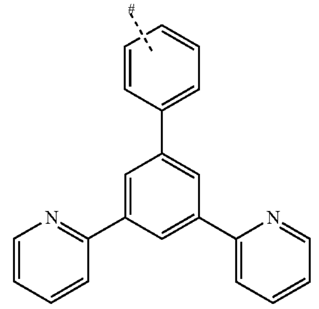
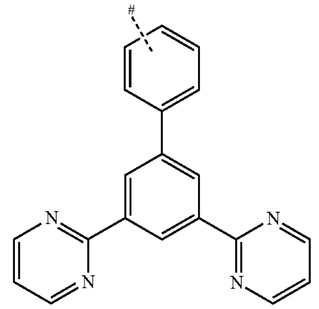
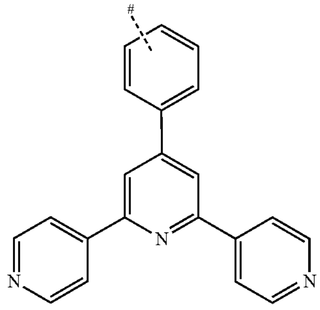
-continued
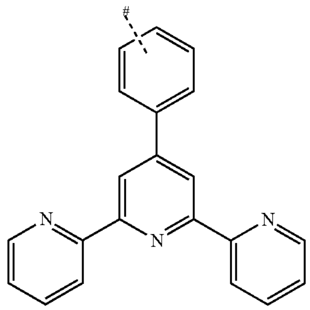
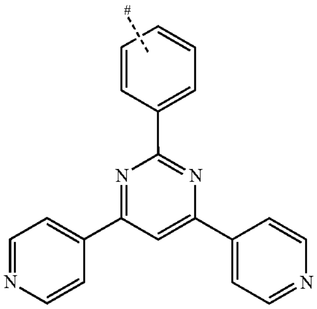
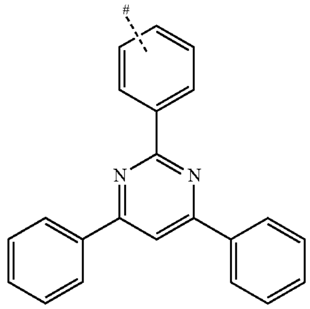
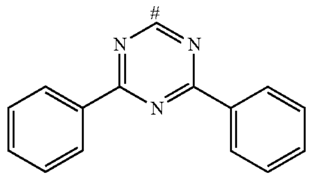
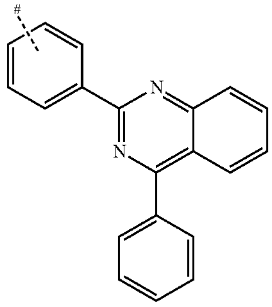

-continued
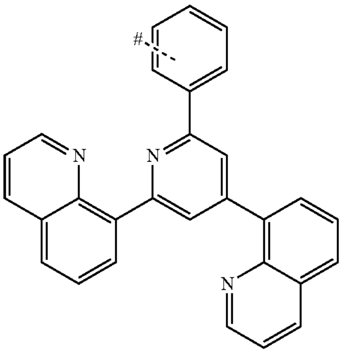
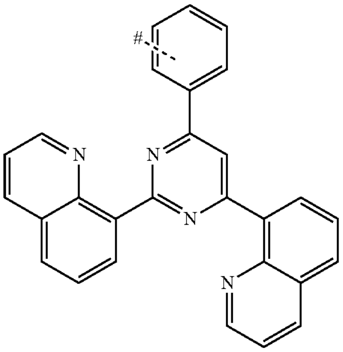
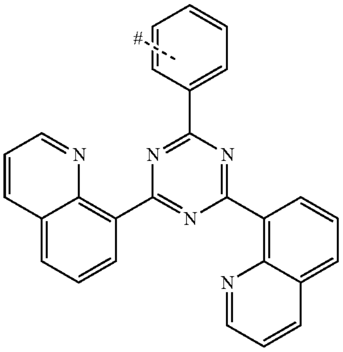
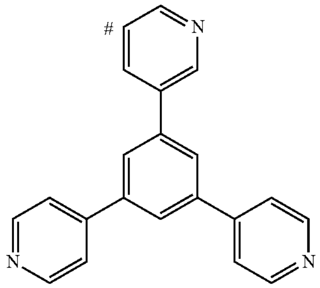
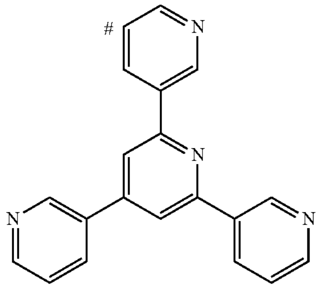
-continued
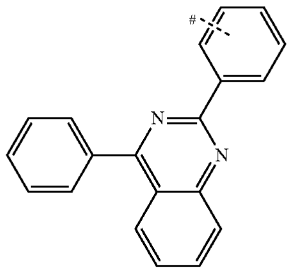
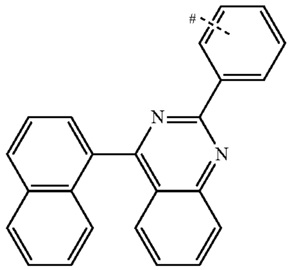
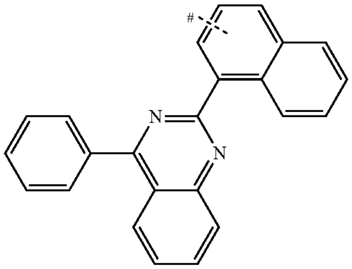
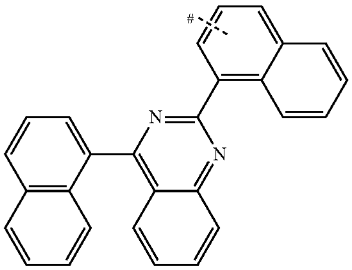
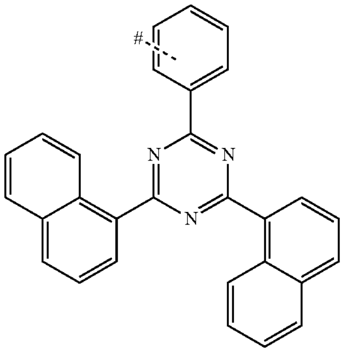
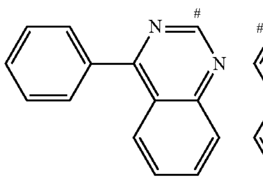
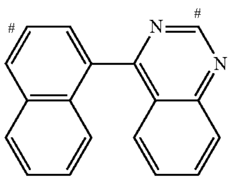

-continued
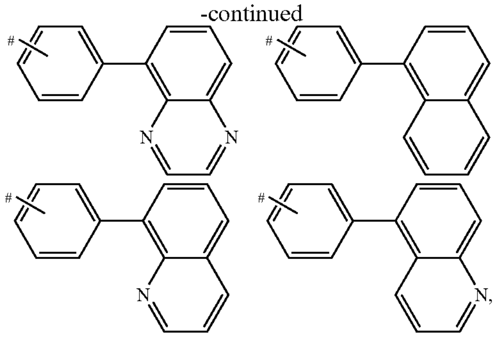
wherein #represents a connection position.
15. The nitrogen-containing spiral organic compound according to claim 1, wherein R3 is H.
16. The nitrogen-containing spiral organic compound according to claim 1, which has any one of the following structures:
H1
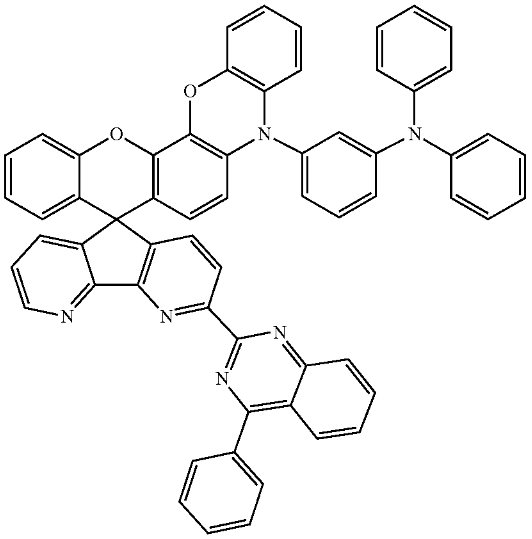
H2
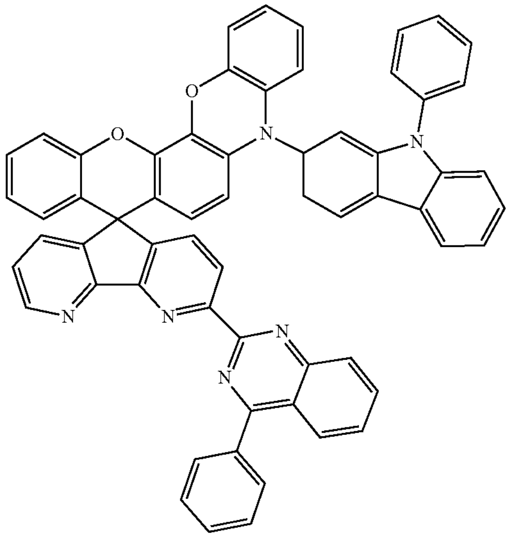
-continued
H3
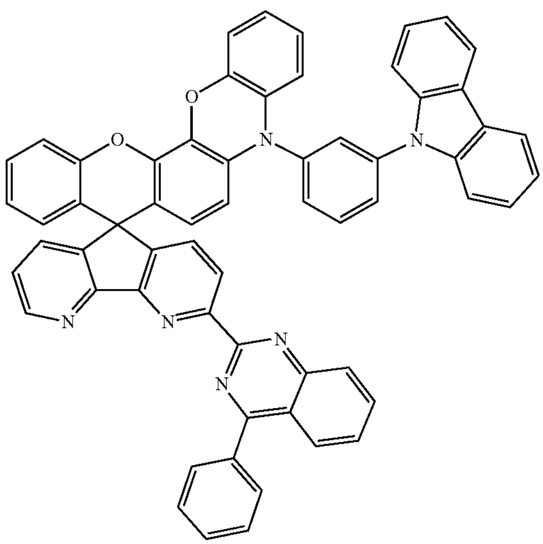
H4
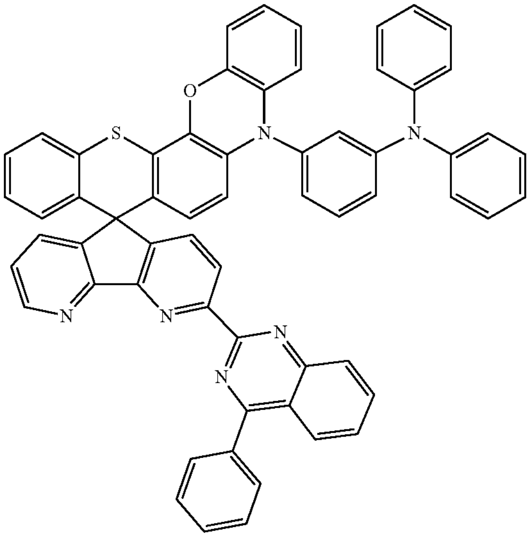
H5
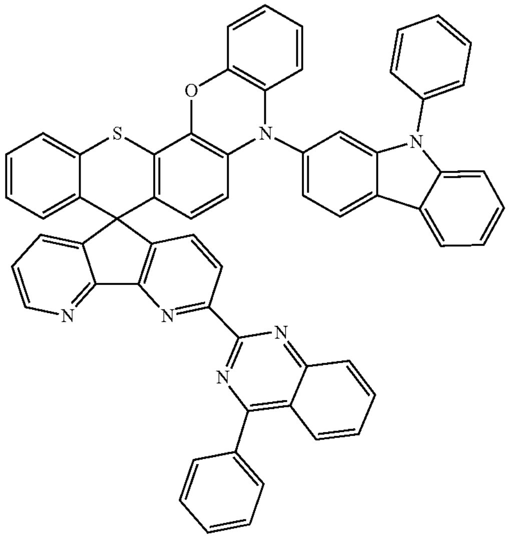

-continued
H6
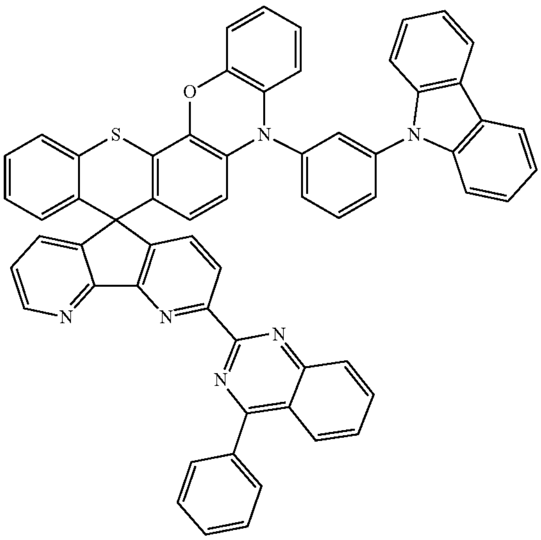
H7
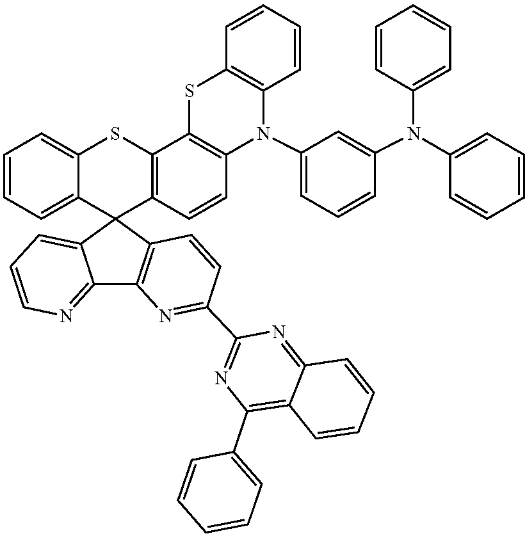
H8
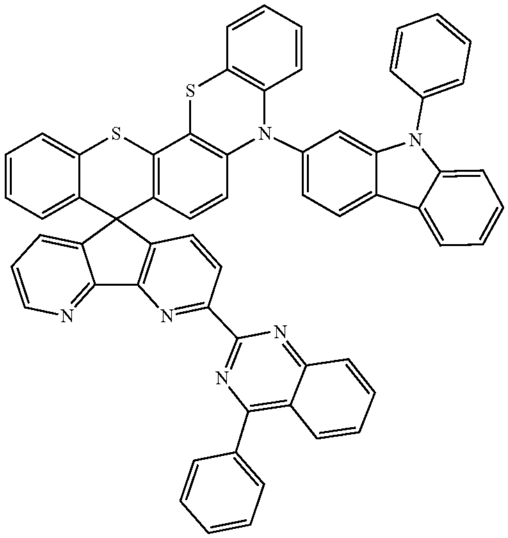
-continued
H9
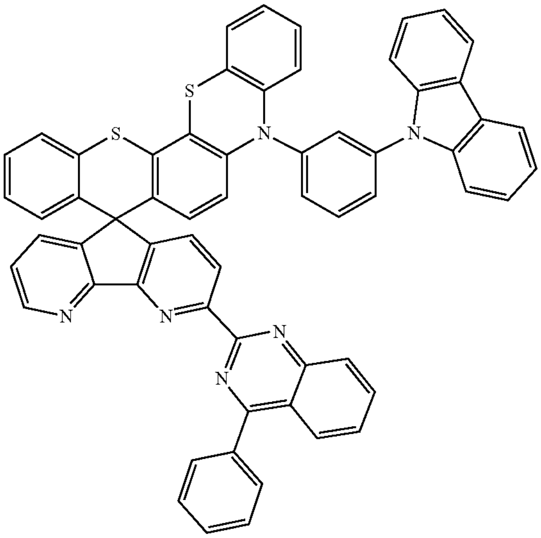
H10
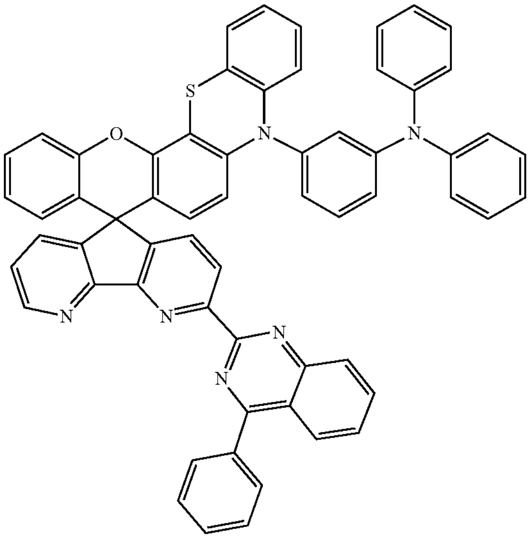
H11
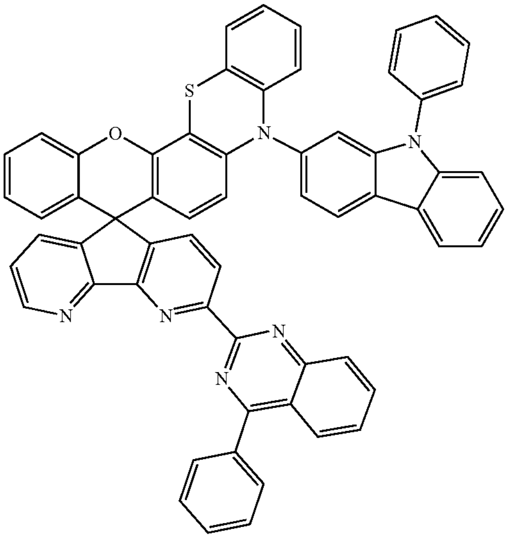

H12
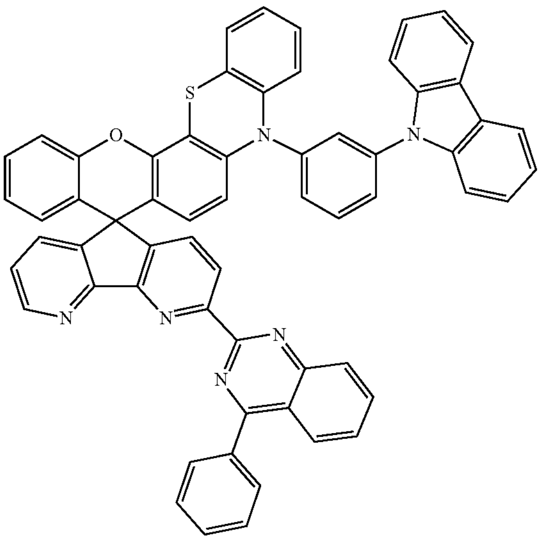
H13
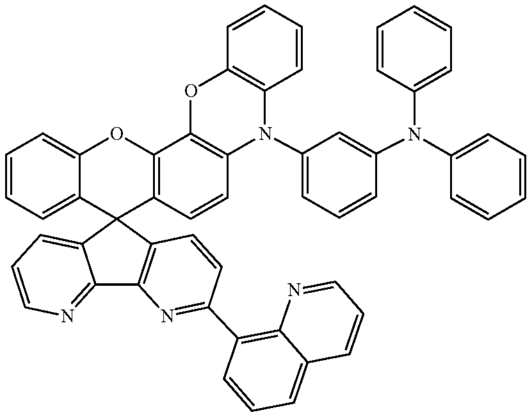
H14
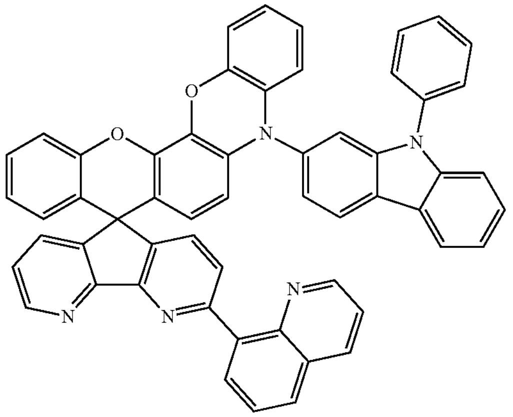
H15
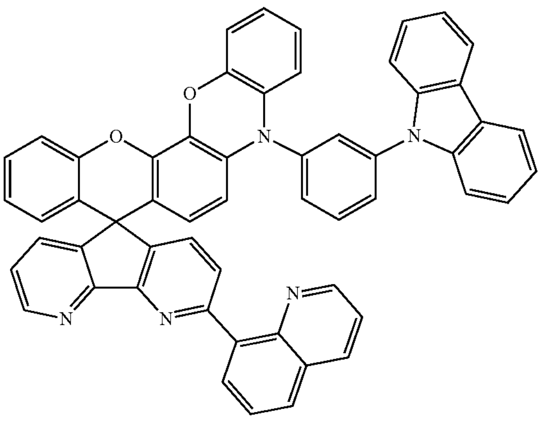
H16
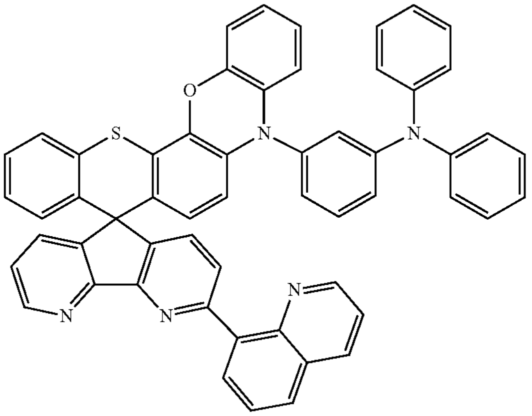
H17
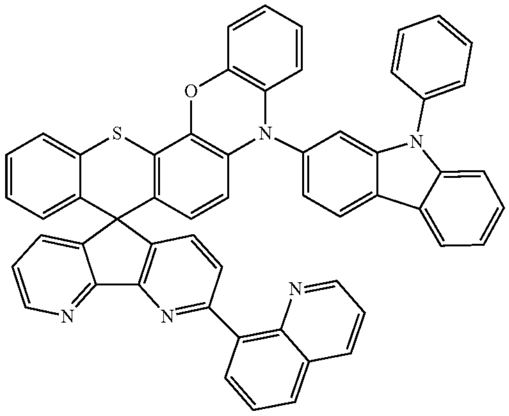

-continued
H18
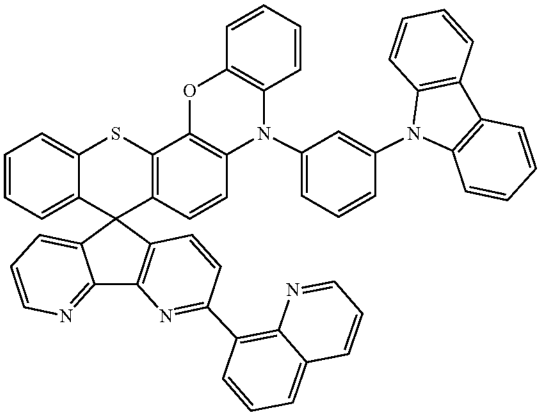
H19
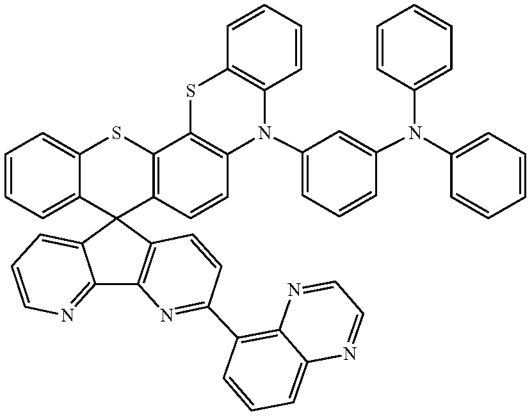
H20
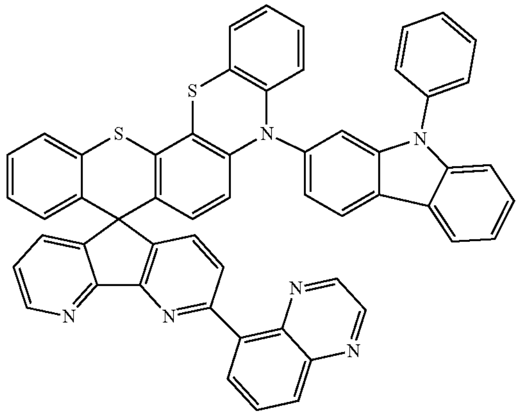
-continued
H21
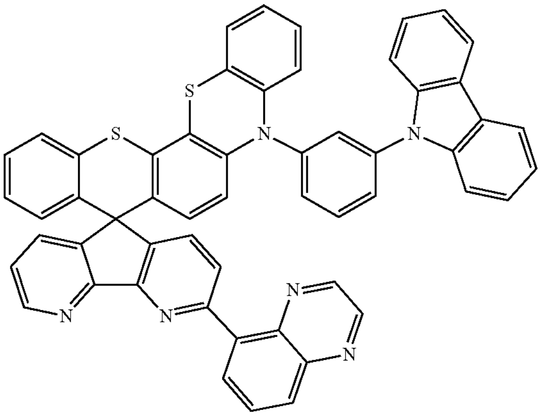
H22
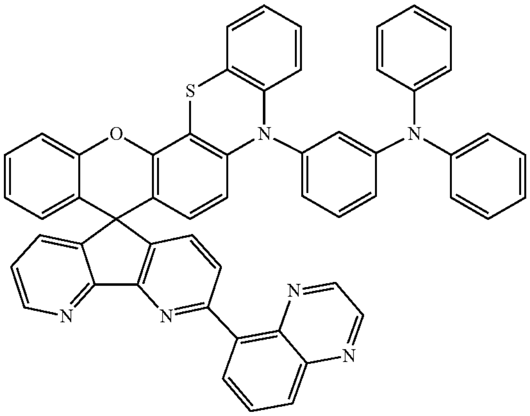
H23
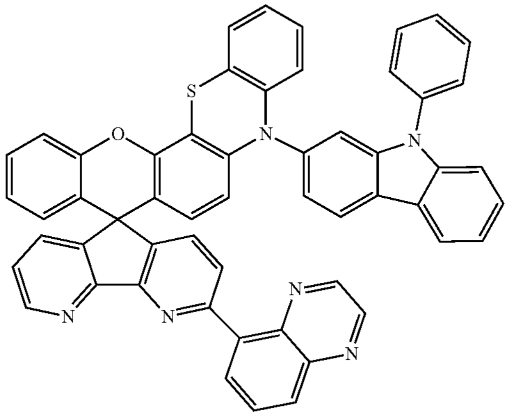

-continued
H24
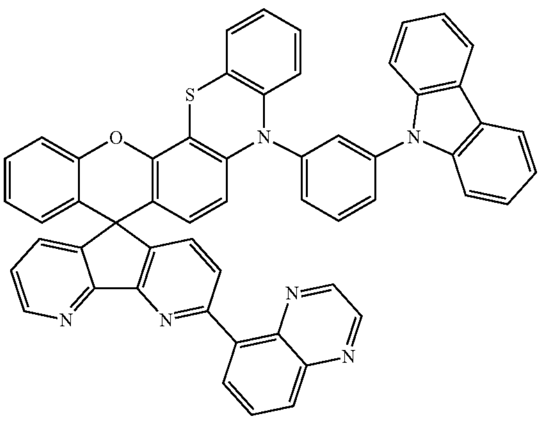
H25
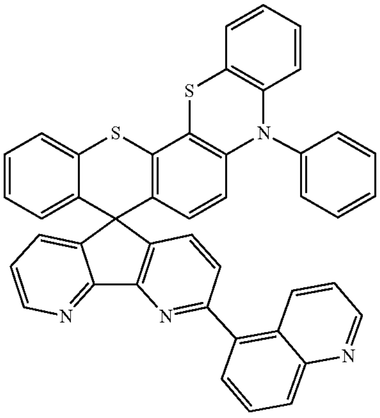
H26
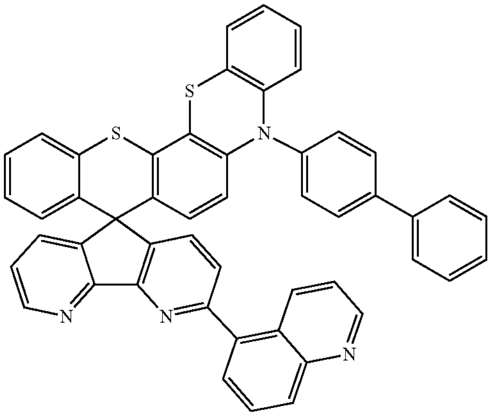
-continued
H27
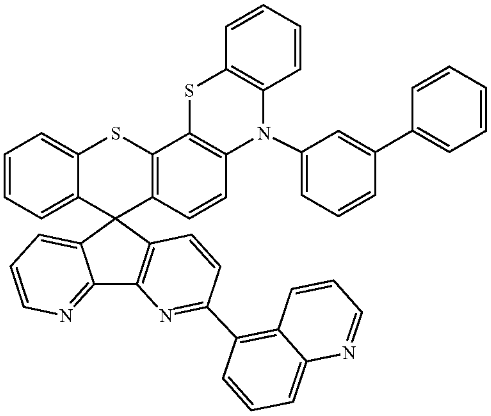
H28
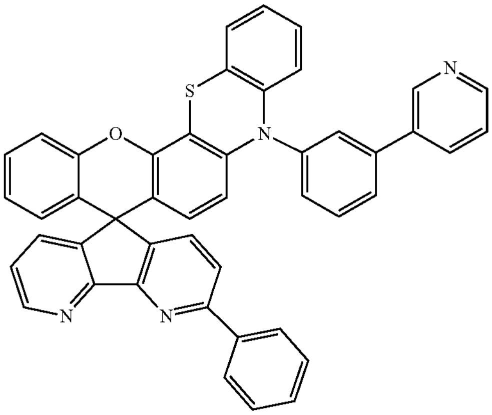
H29
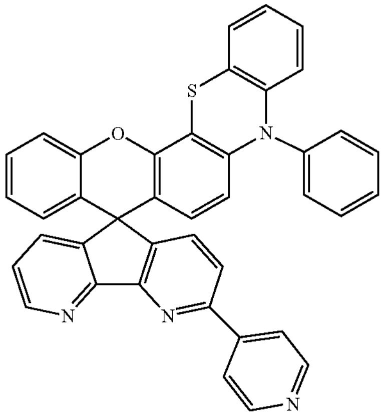

-continued
H30
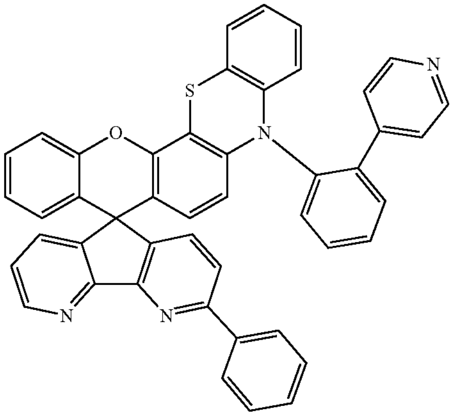
H31
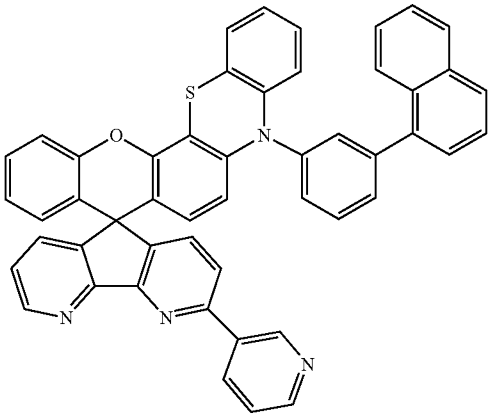
H32
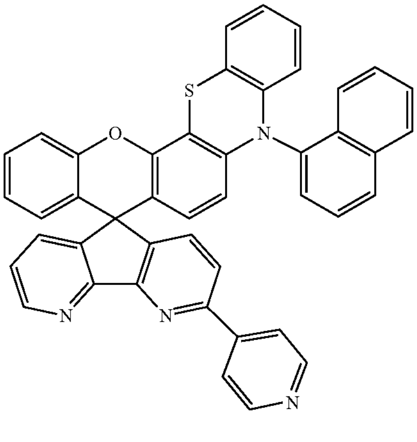
-continued
H33
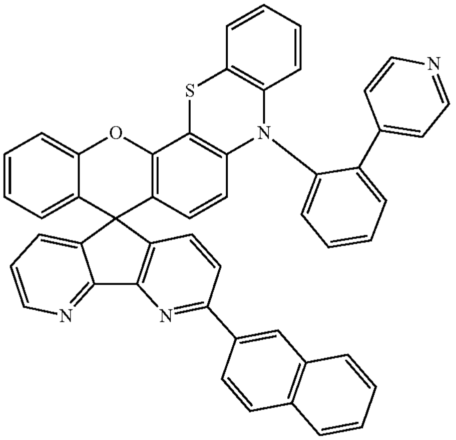
H34
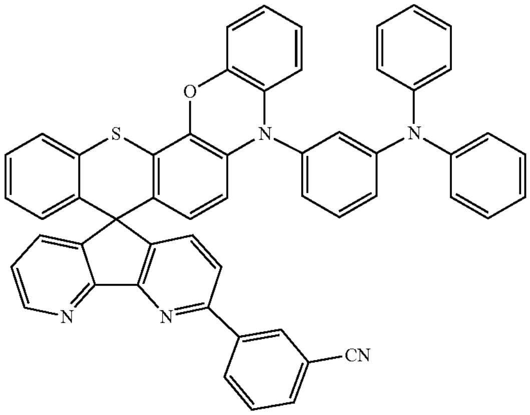
H35
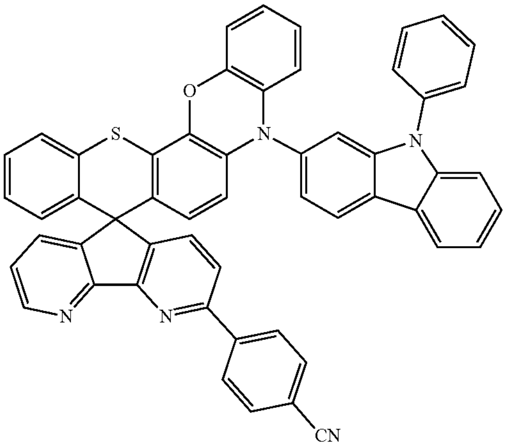

-continued
H36
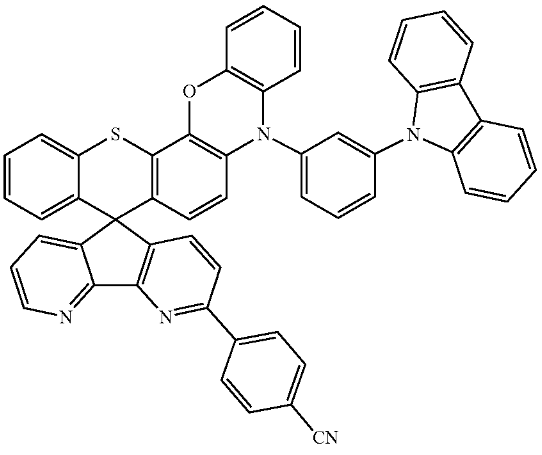
H37
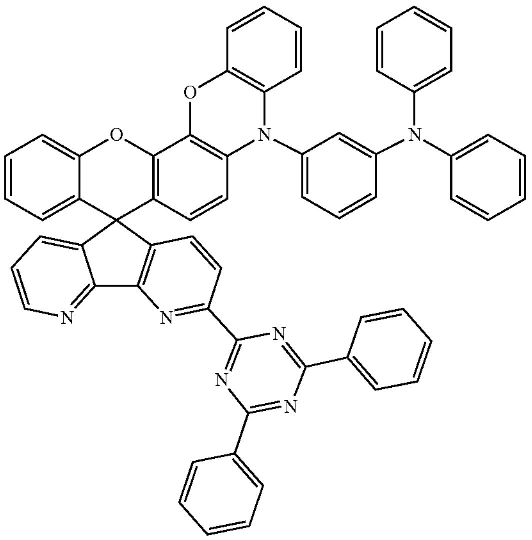
H38
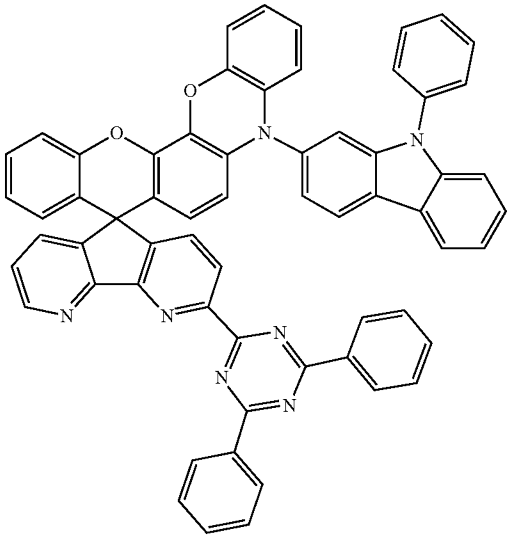
-continued
H39
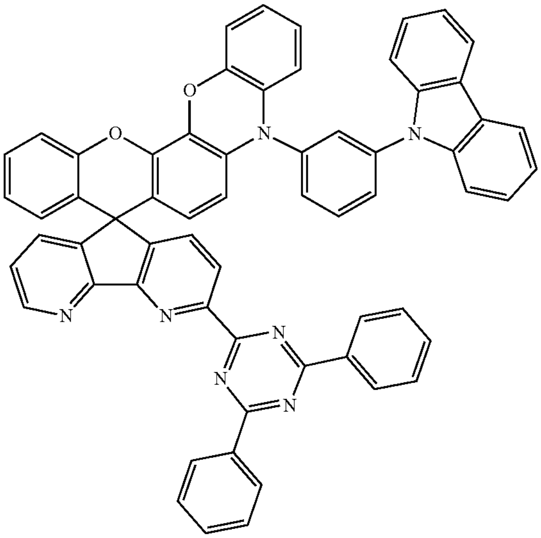
H40
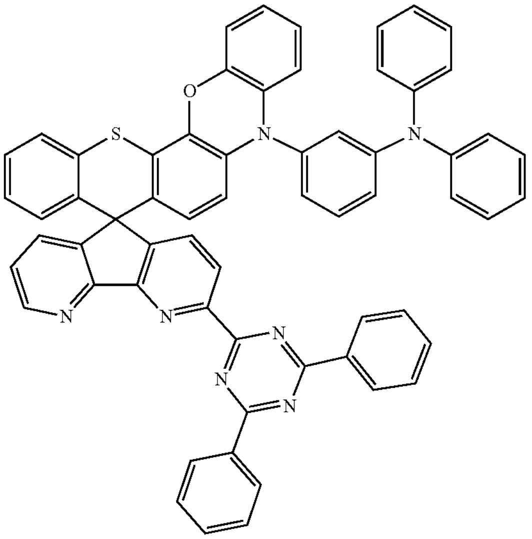
H41
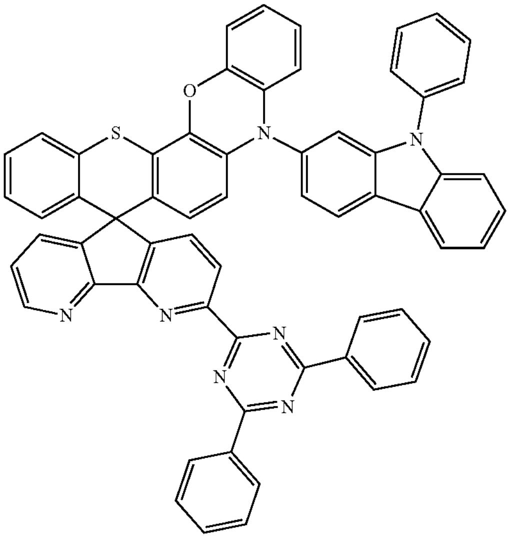

-continued
H42
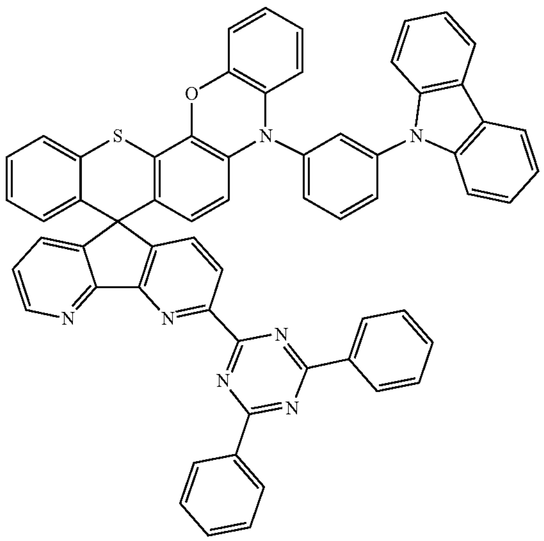
H43
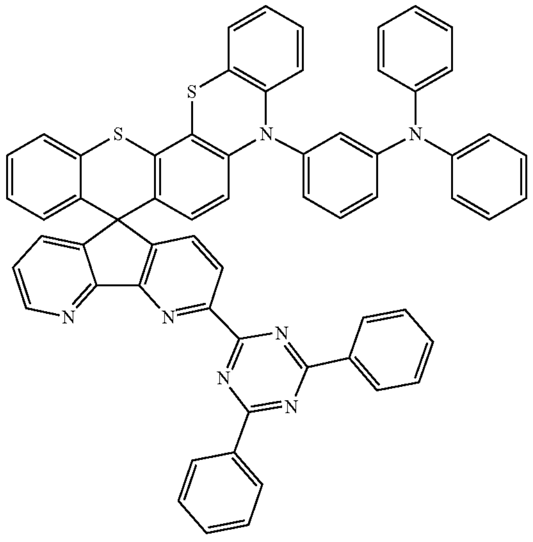
-continued
H44
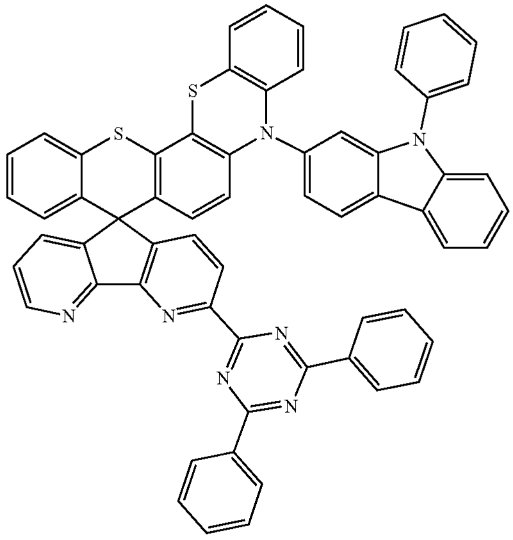
H45
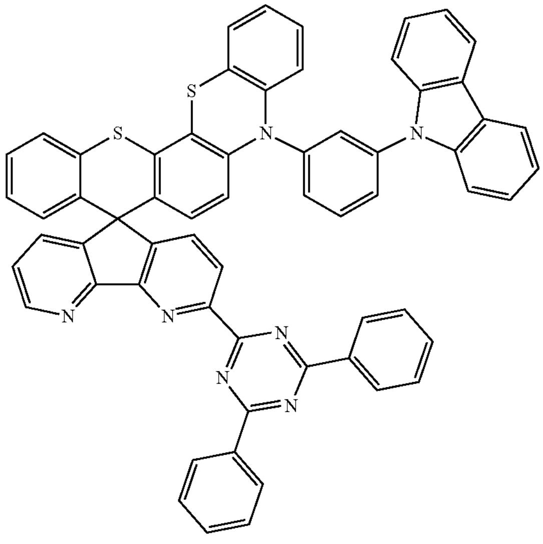

-continued
H46
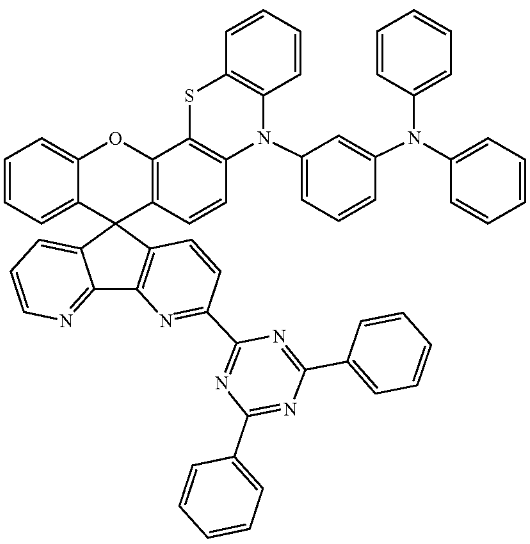
H47
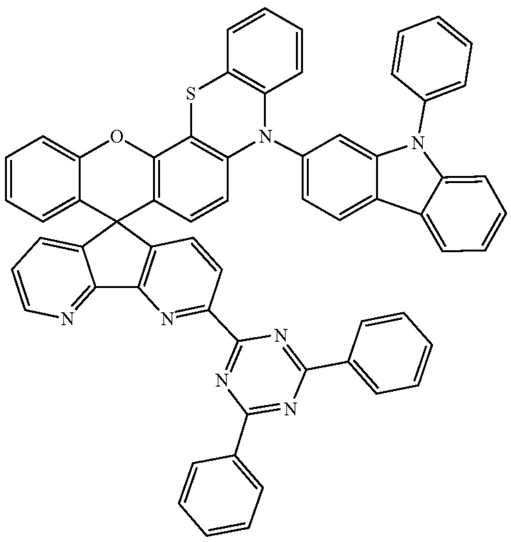
H48
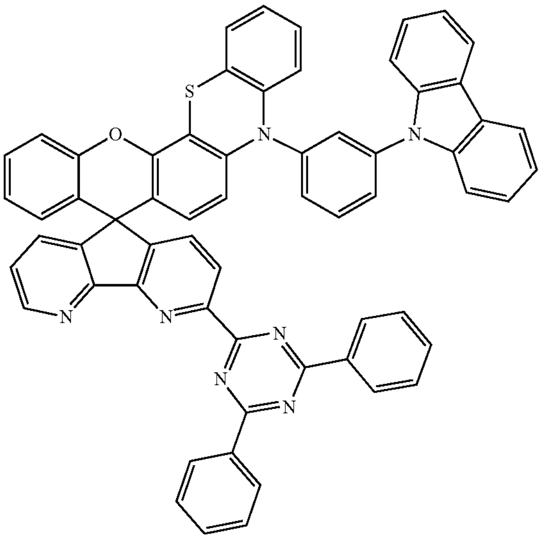
-continued
H49
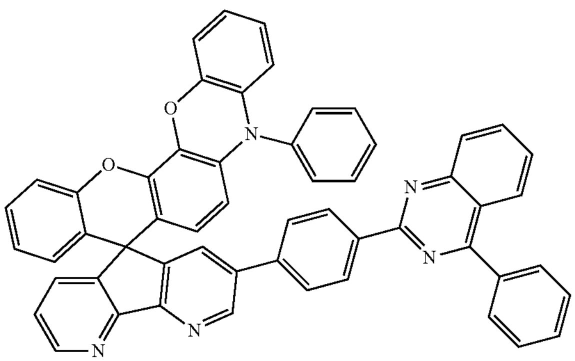
H50
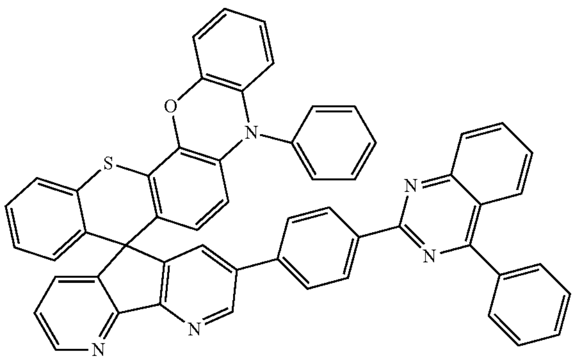
H51
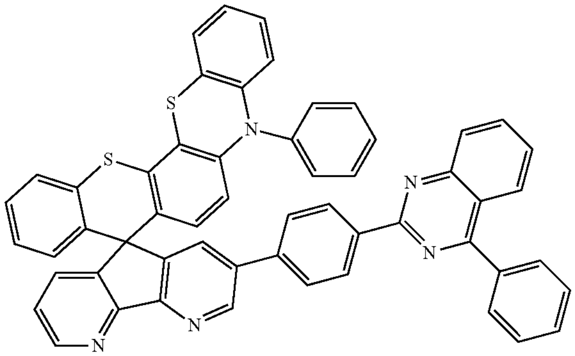
H52
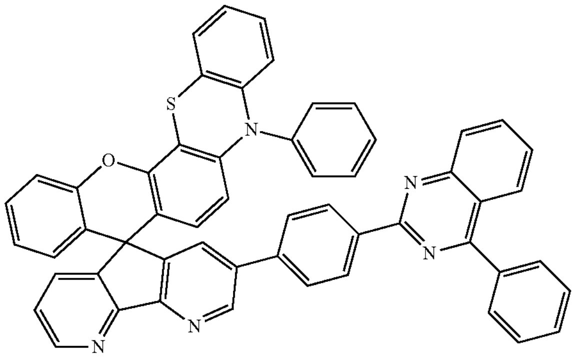

-continued
H53
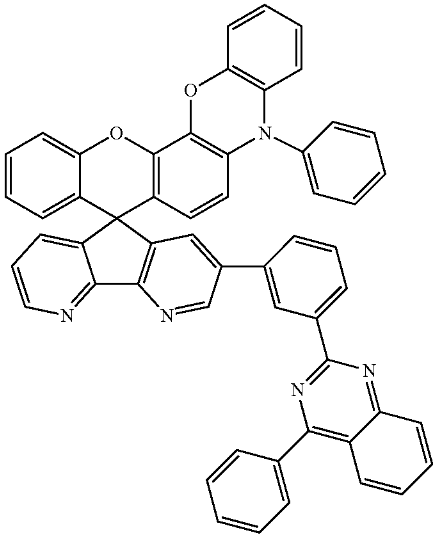
H54
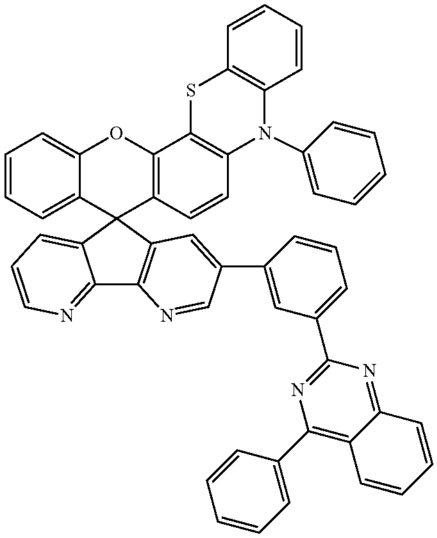
H55
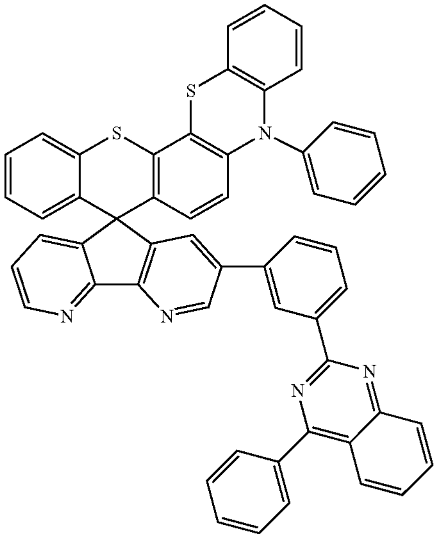
-continued
H56
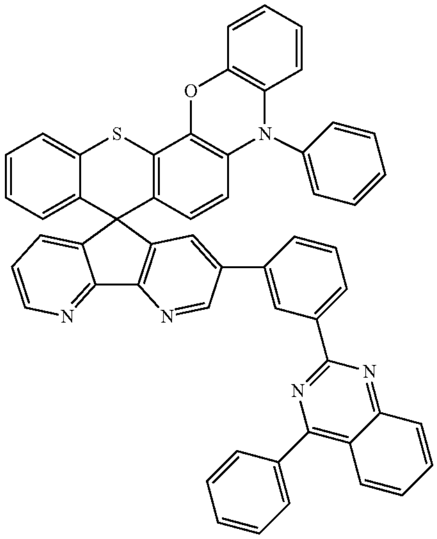
H57
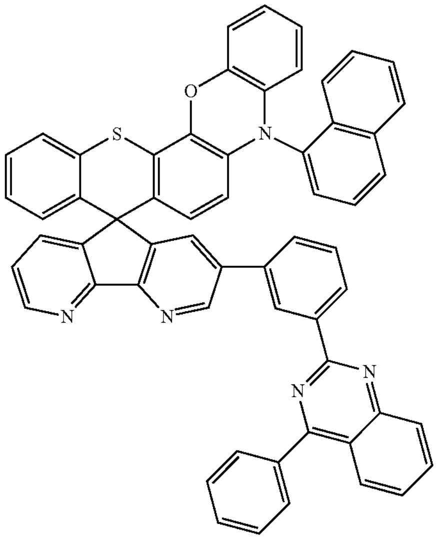
H58
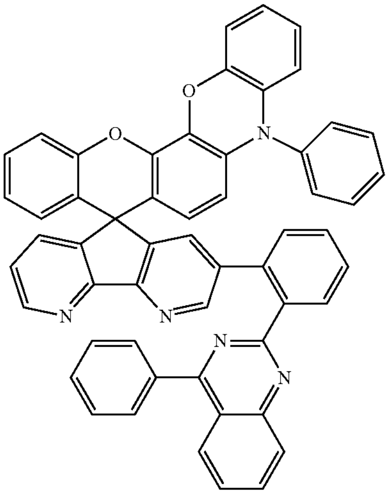

H59
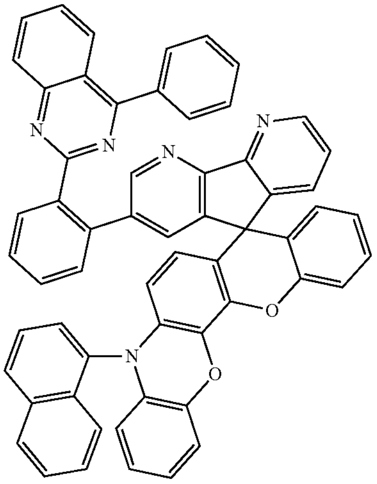
H60
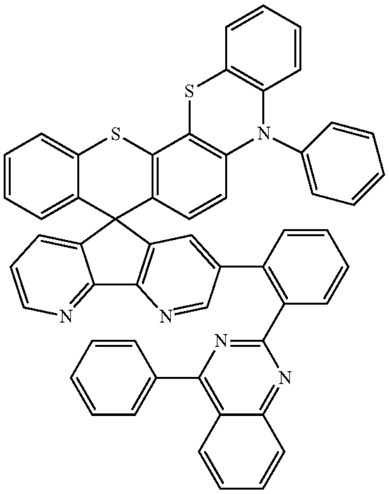
H61
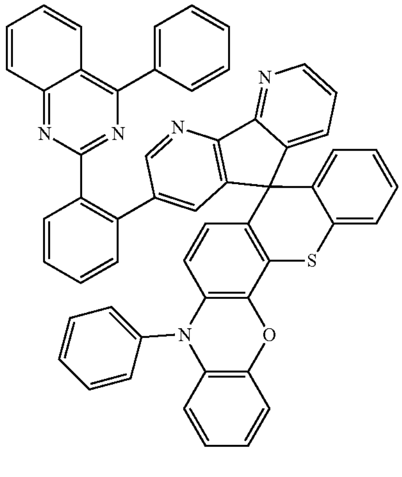
H62
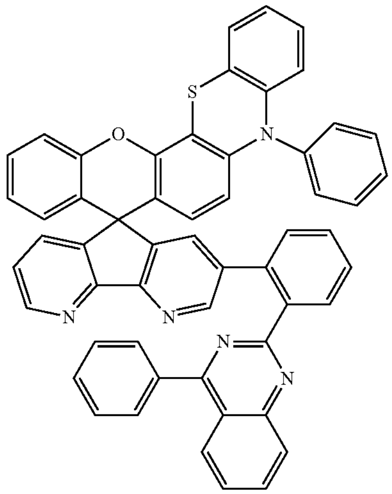
H63
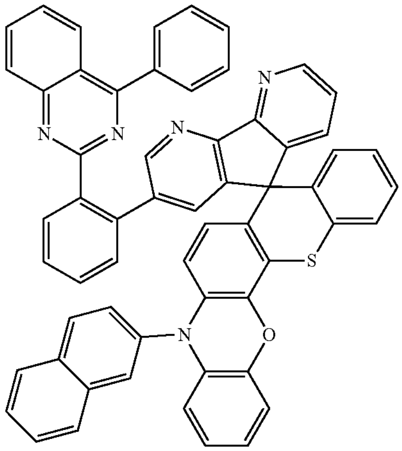
H64
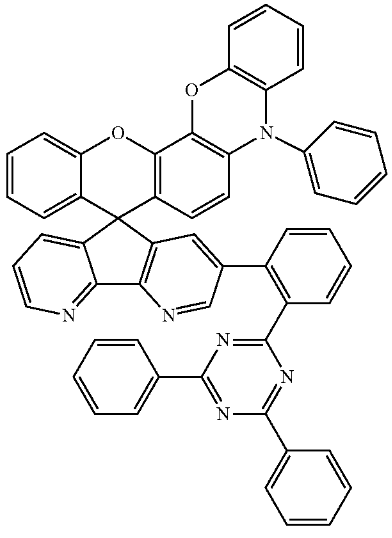

-continued
H65
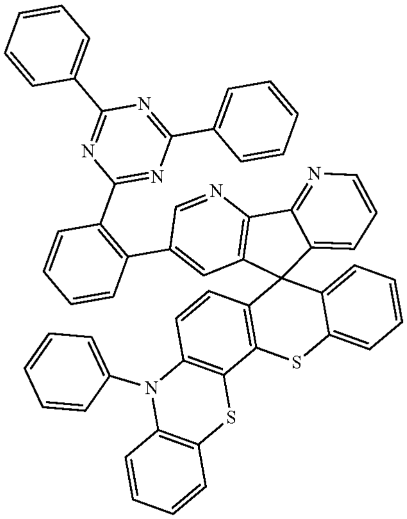
H66
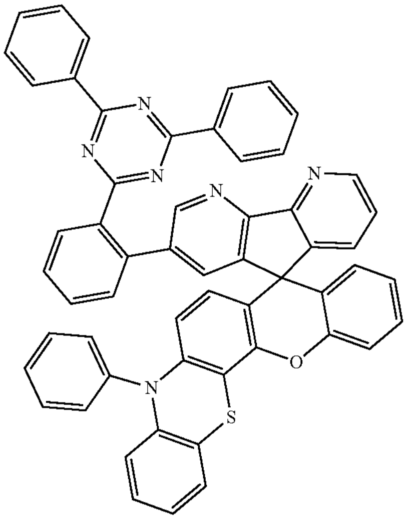
H67
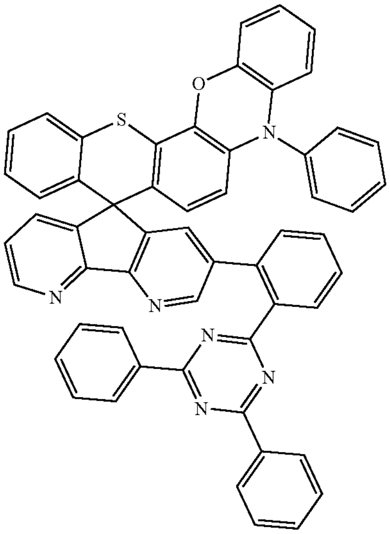
-continued
H68
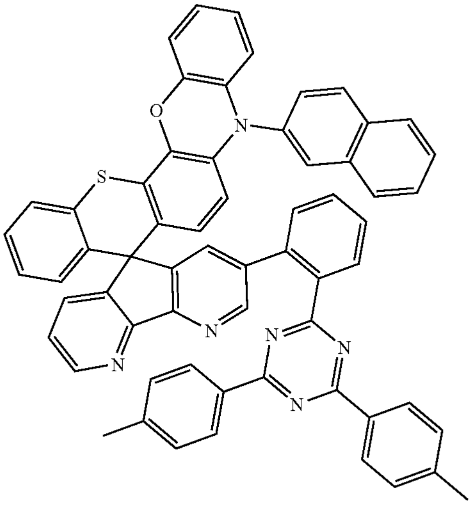
H69
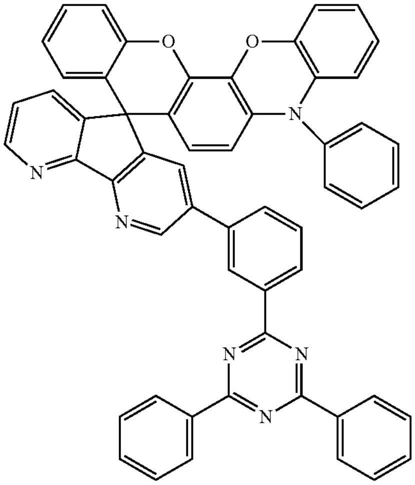
H70
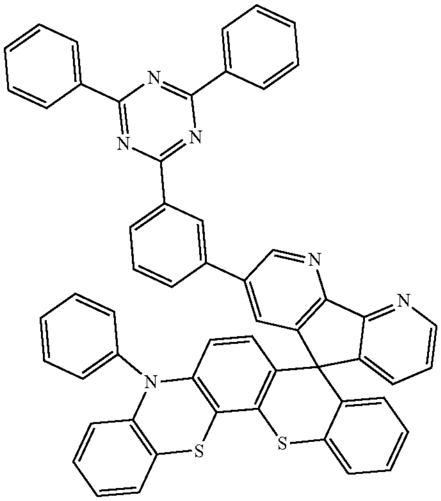

-continued
H71
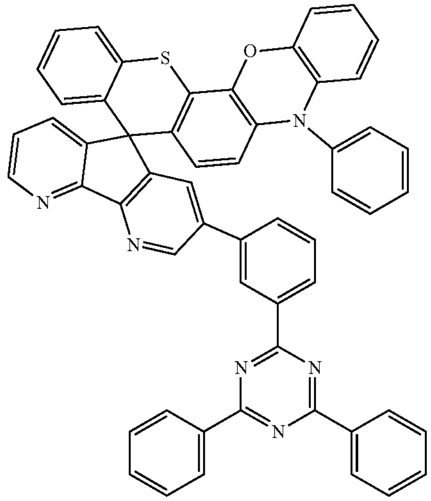
H72
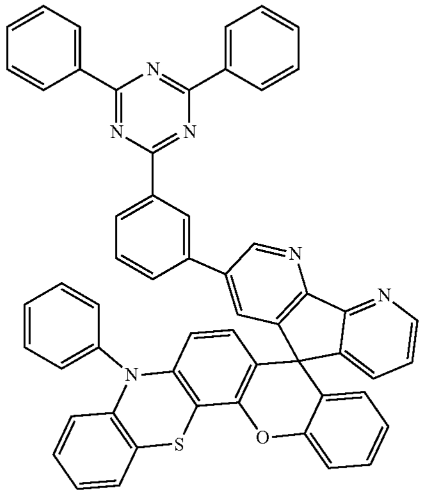
H73
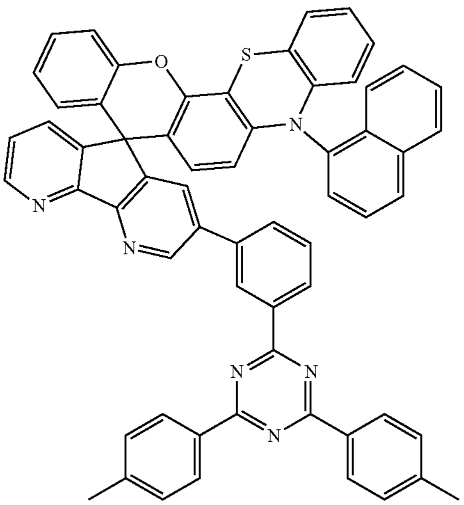
-continued
H74
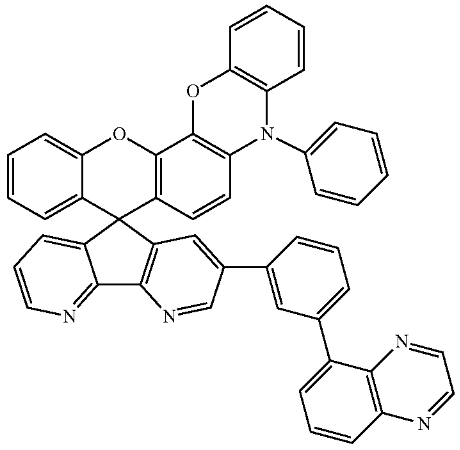
H75
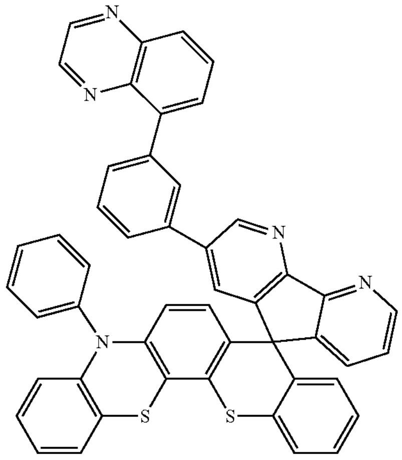
H76
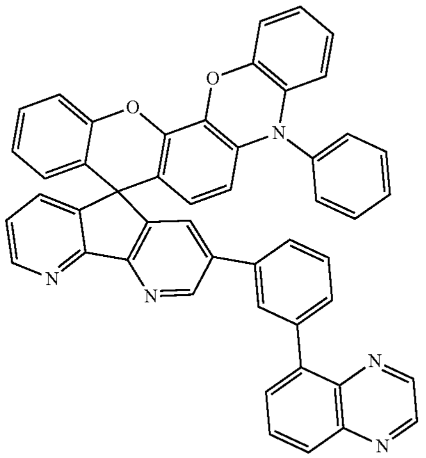

-continued
H77
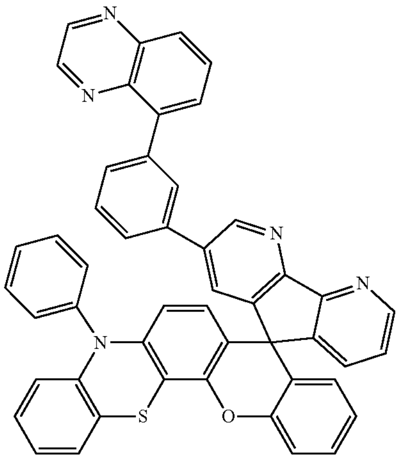
H78
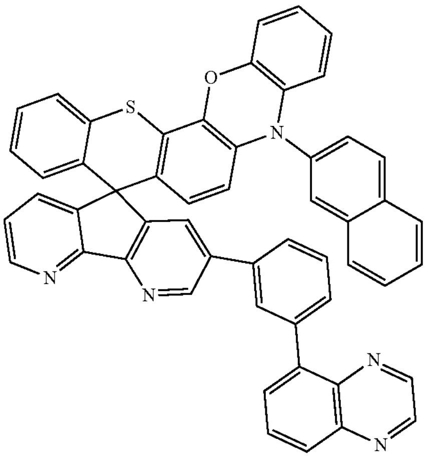
H79
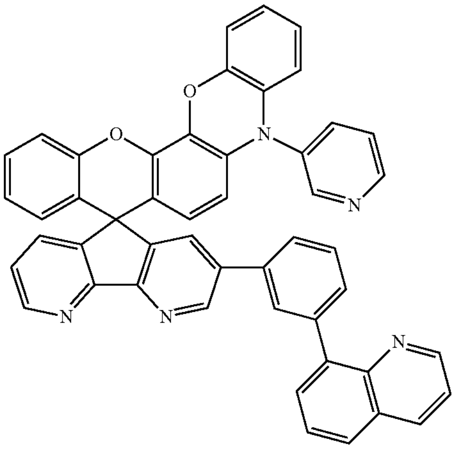
-continued
H80
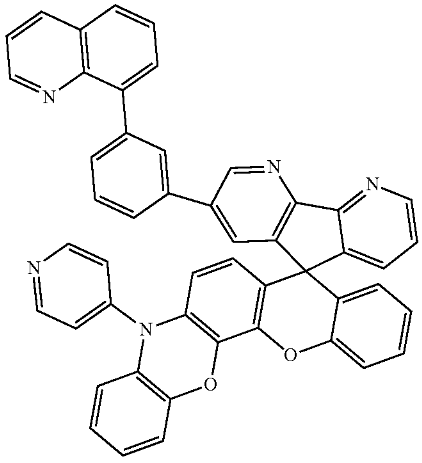
H81
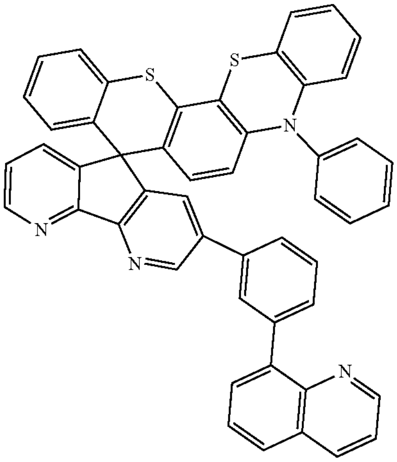
H82
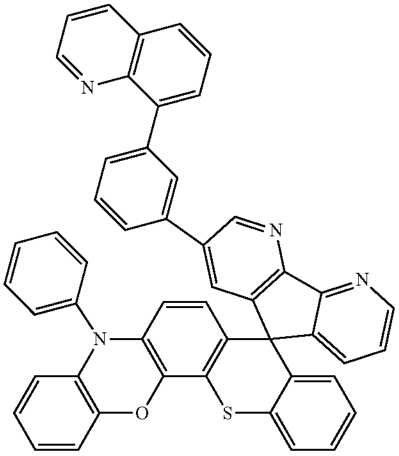

-continued
H83
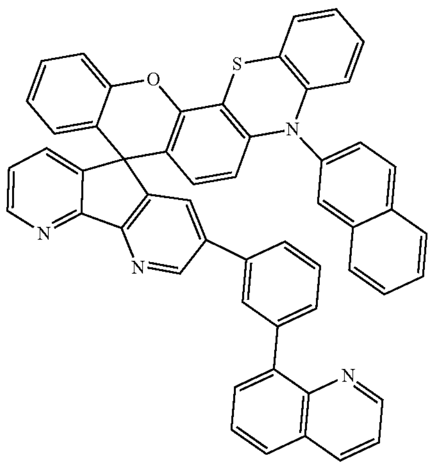
H84
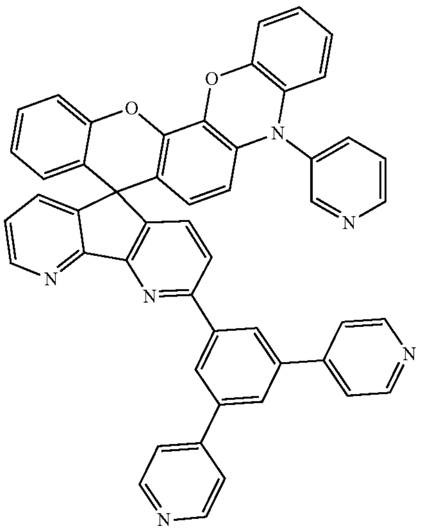
H85
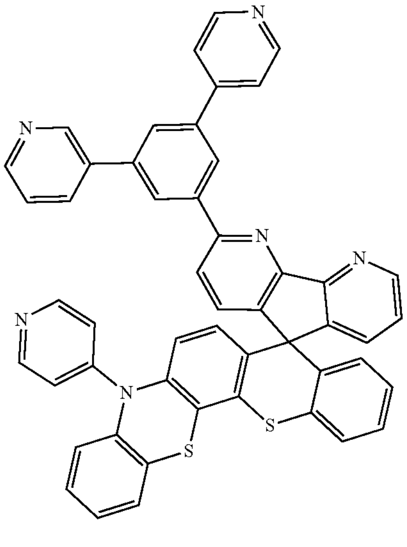
-continued
H86
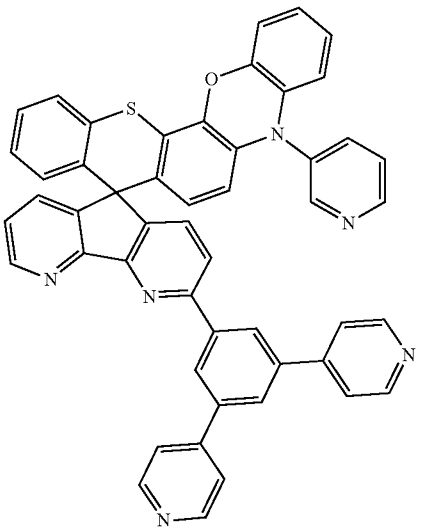
H87
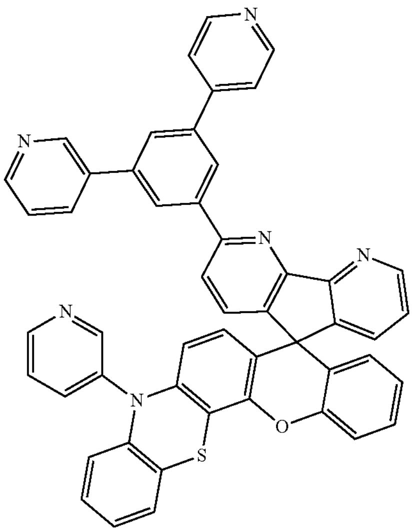
H88
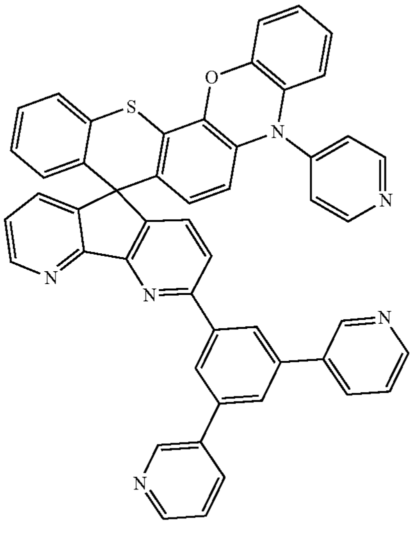

-continued
H89
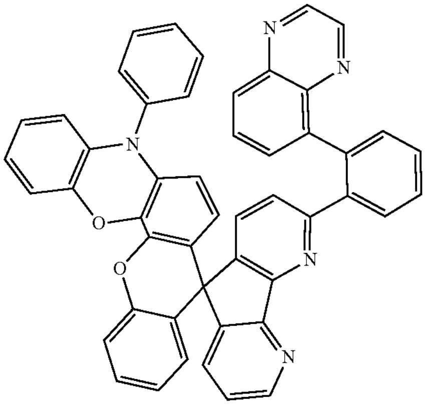
H90
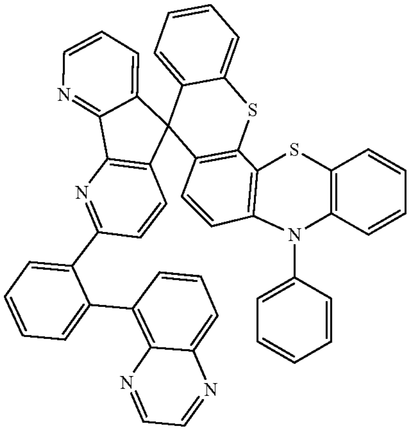
H91
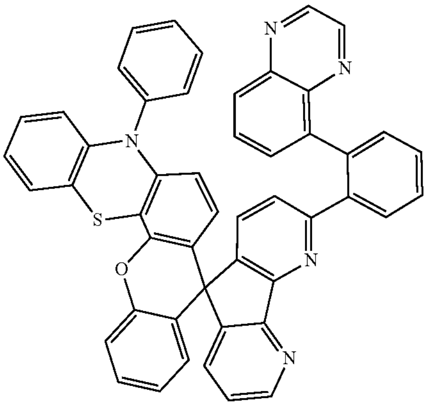
-continued
H92
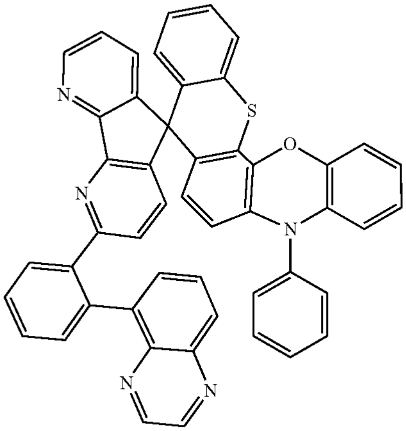
H93
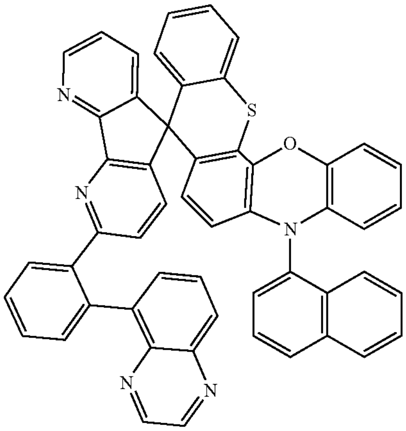
H94
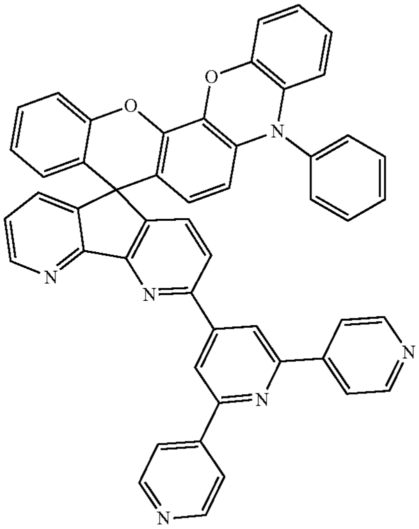

-continued
H95
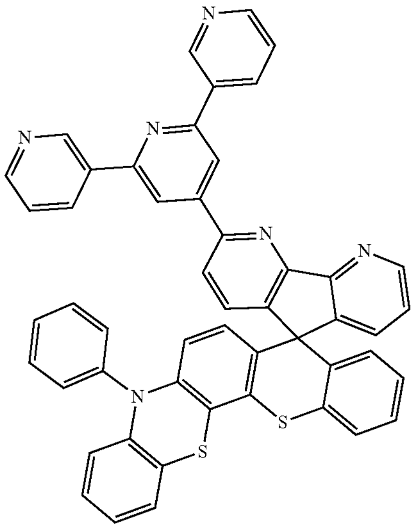
H96
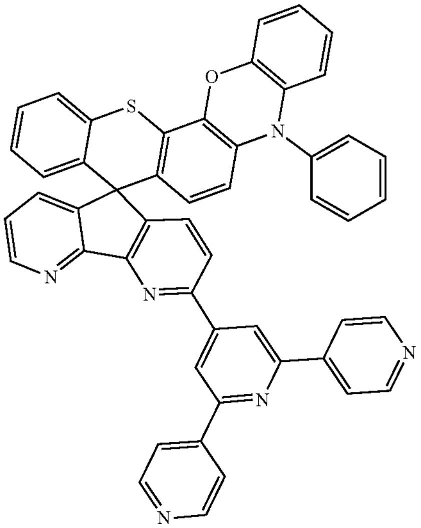
H97
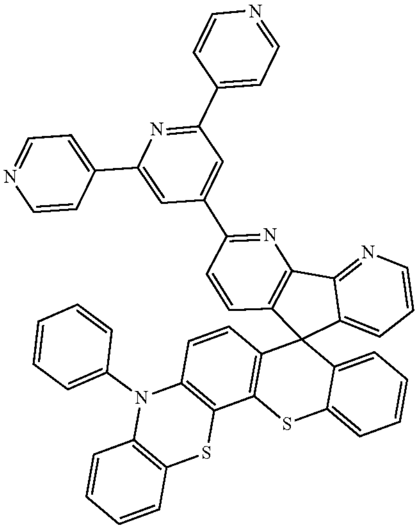
-continued
H98
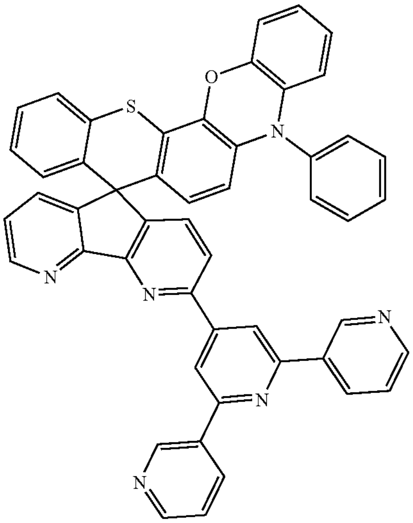
H99
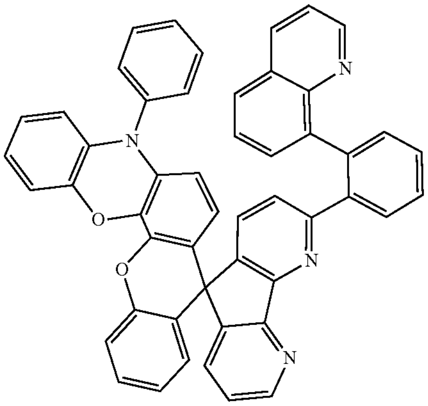
H100
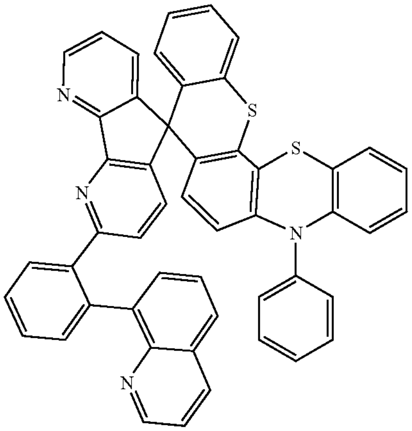

-continued
H101
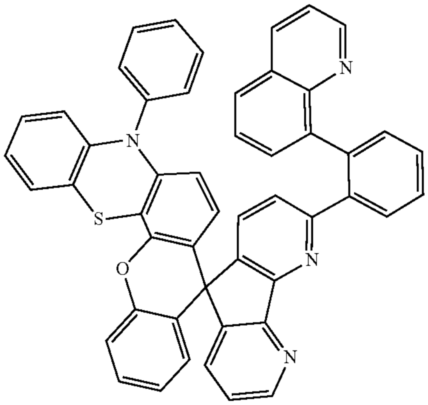
H102
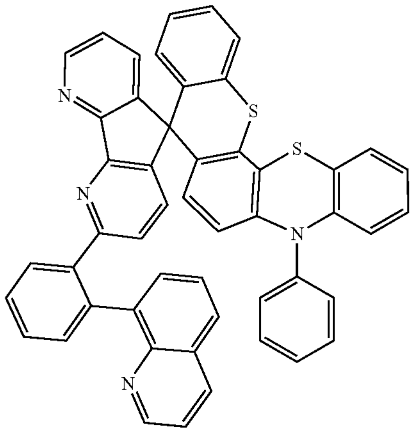
H103
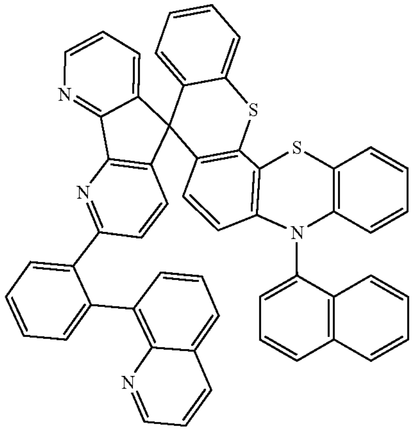
H104
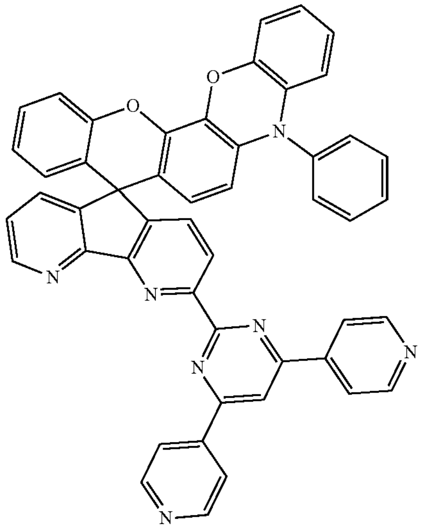
H105
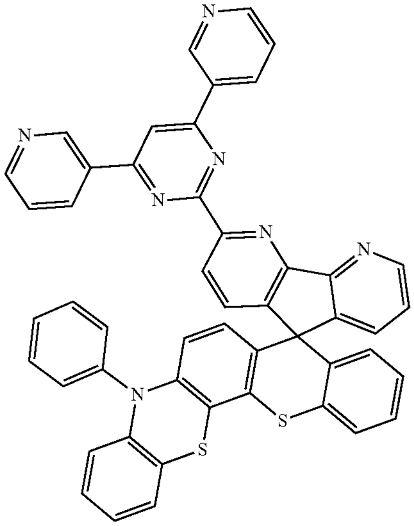
H106
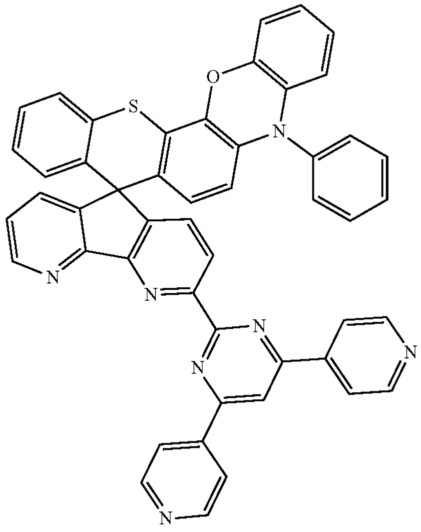

-continued
H107
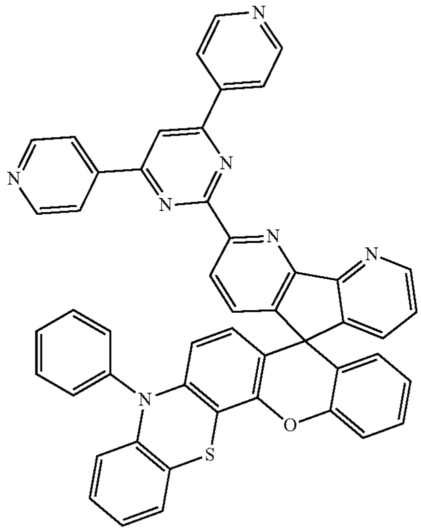
H108
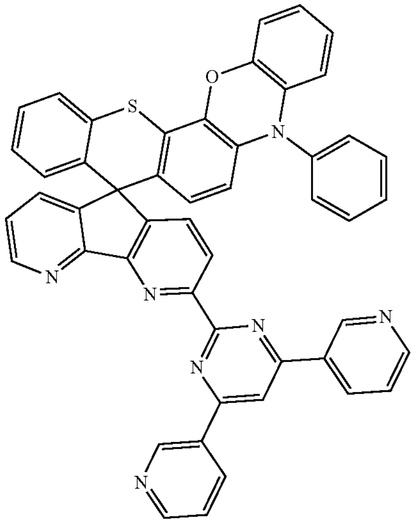
H108
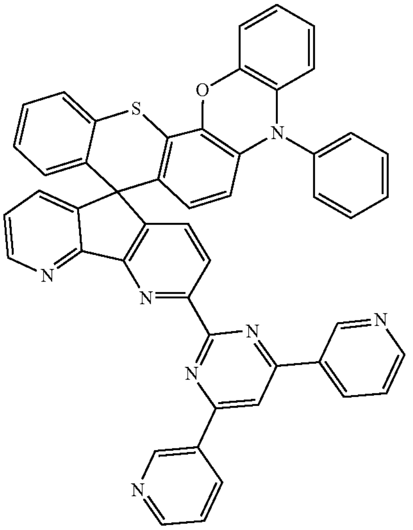
-continued
H109
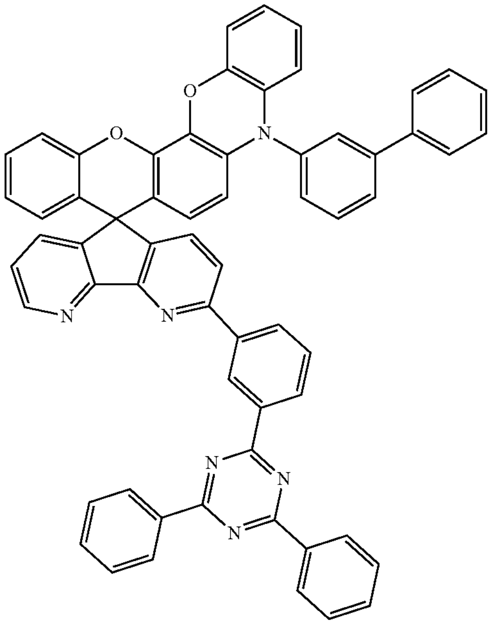
H110
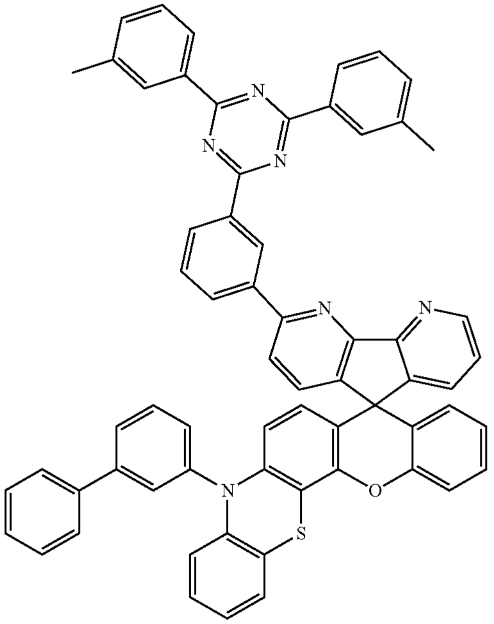

-continued
H111
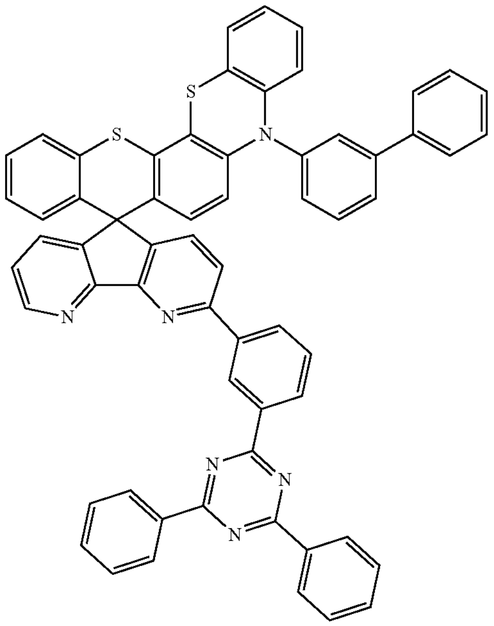
H112
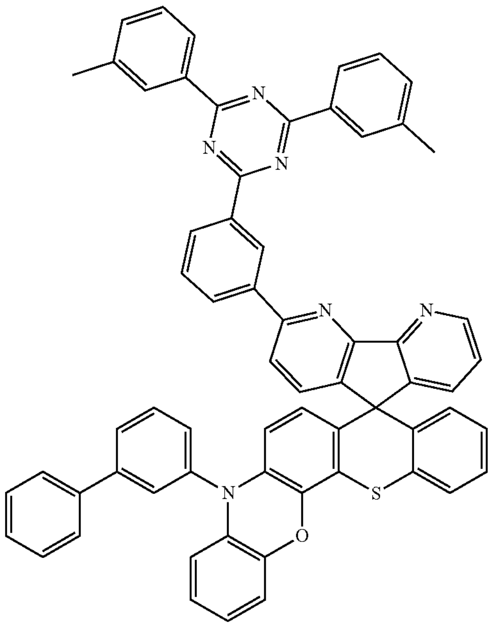
-continued
H113
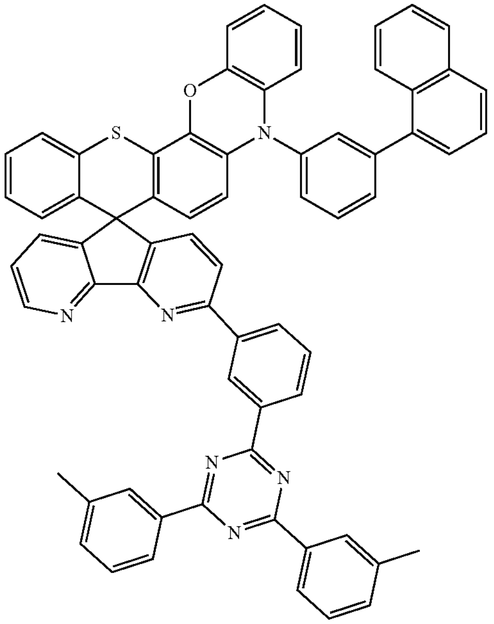
H114
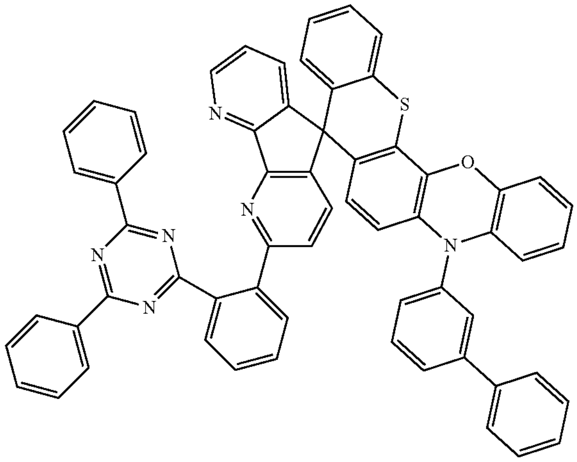
H115
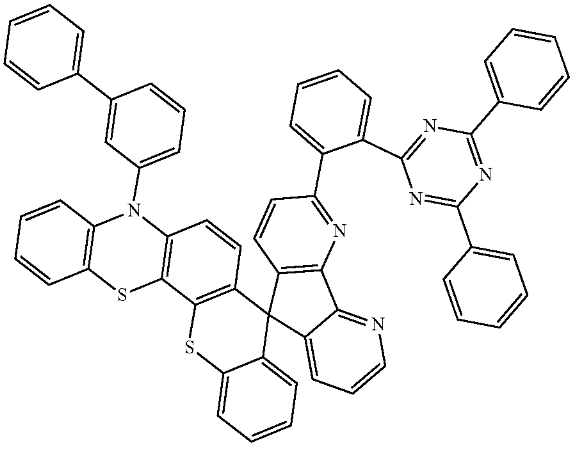

-continued
H116
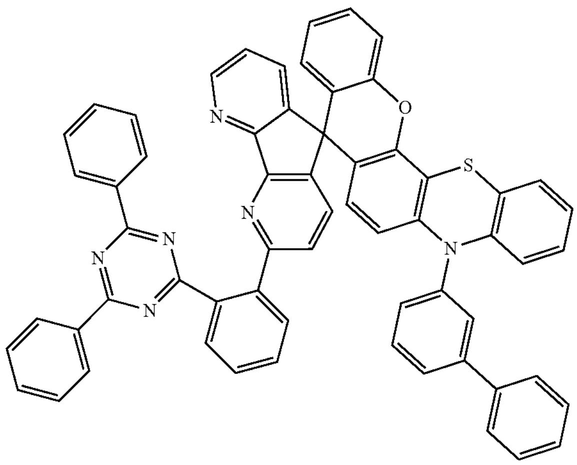
H117
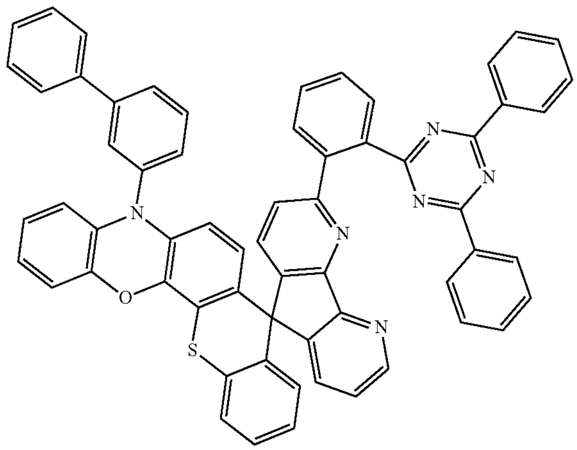
H118
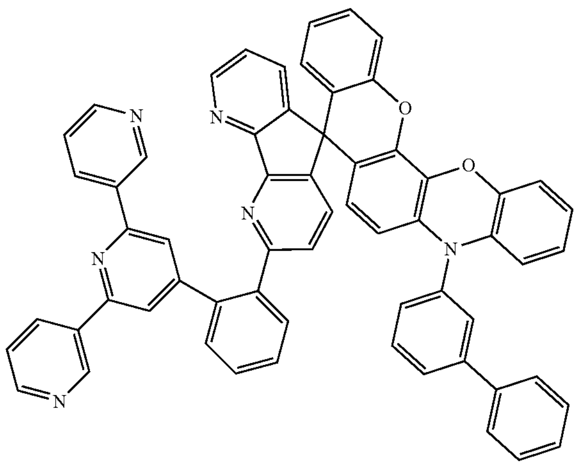
-continued
H119
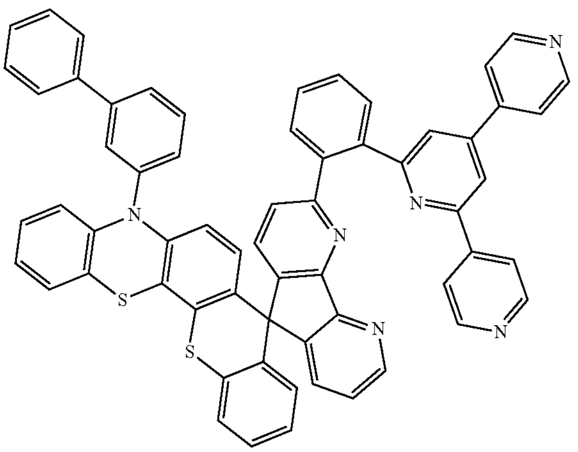
H120
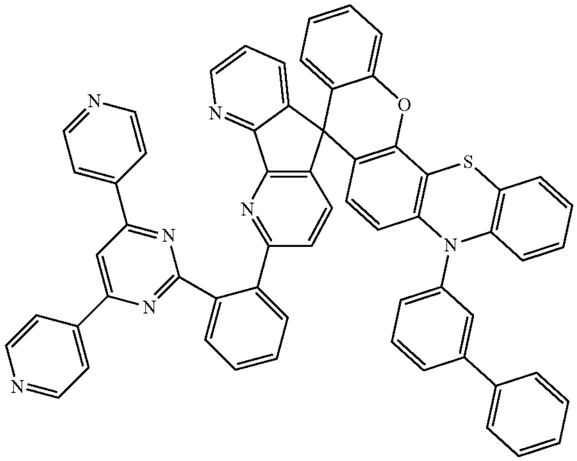
H121
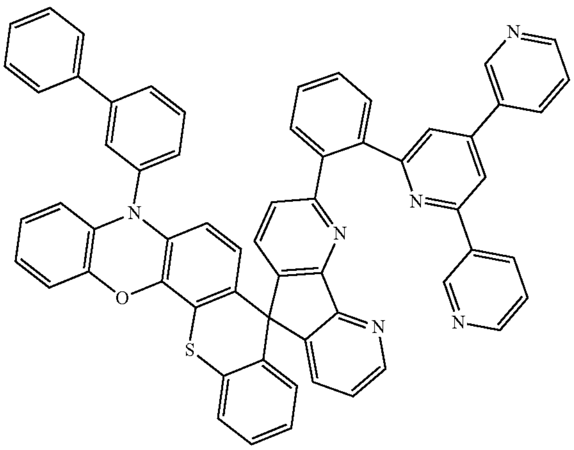

-continued
H122
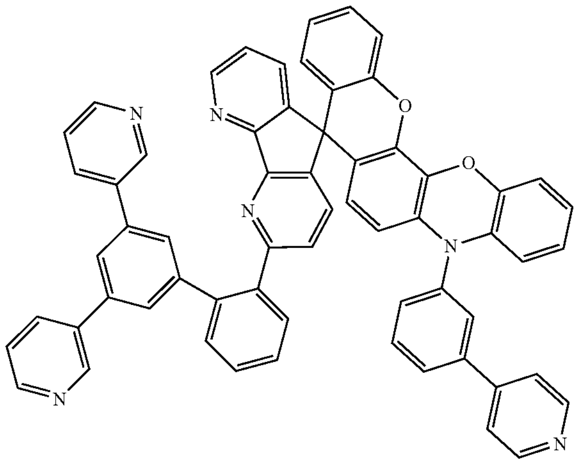
H123
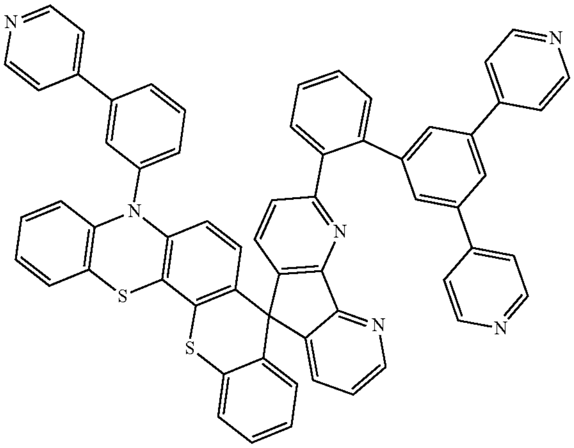
H124
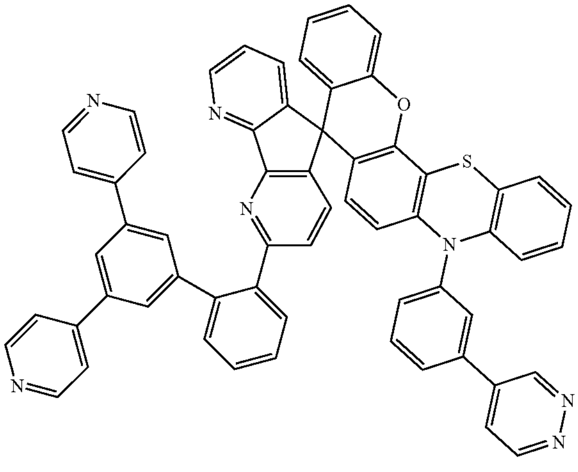
-continued
H125
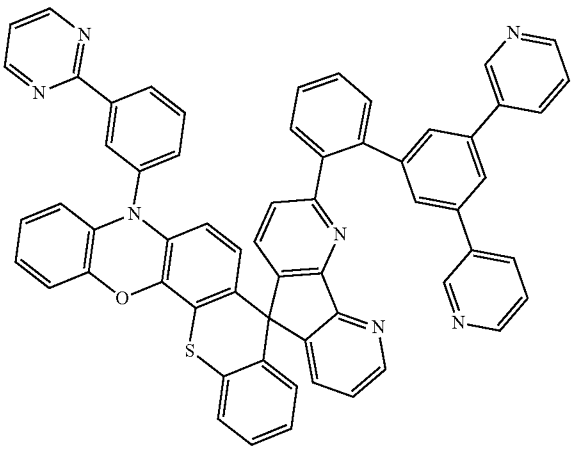
H126
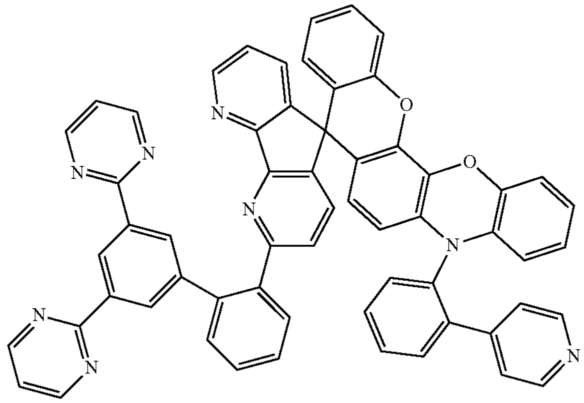
H127
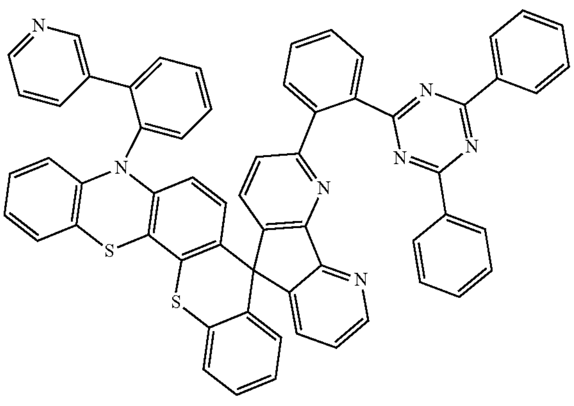

-continued
H128
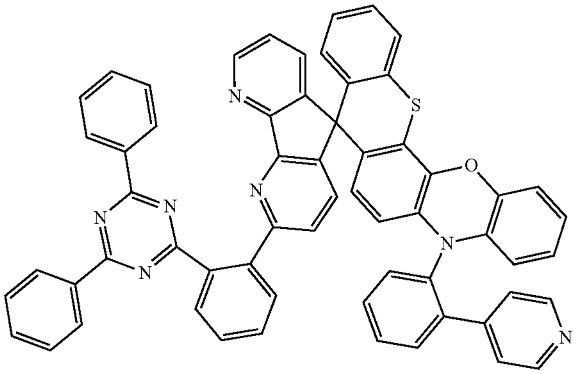
H129
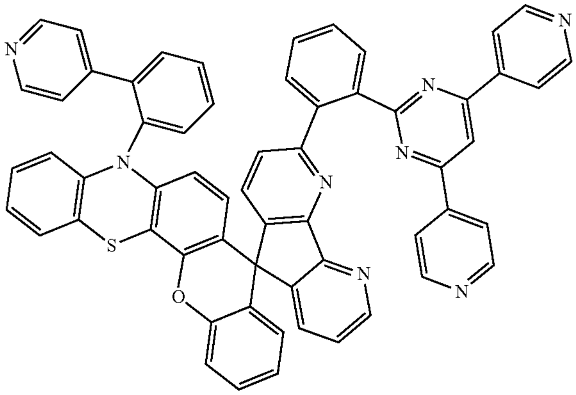
H130
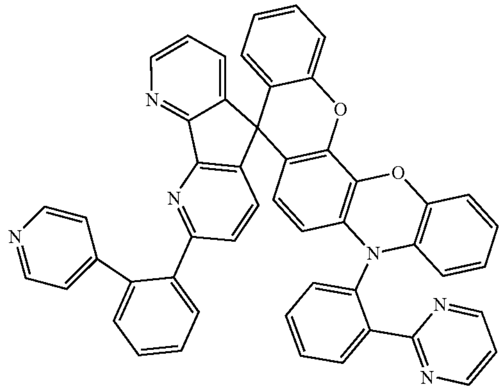
H131
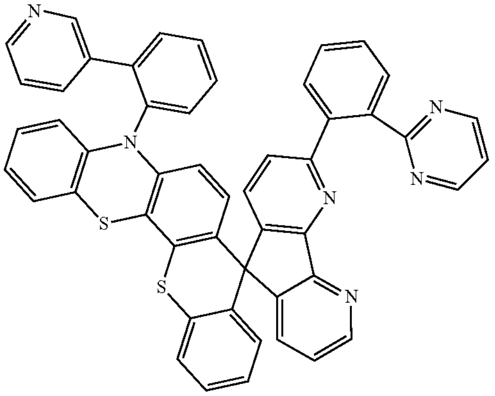
-continued
H132
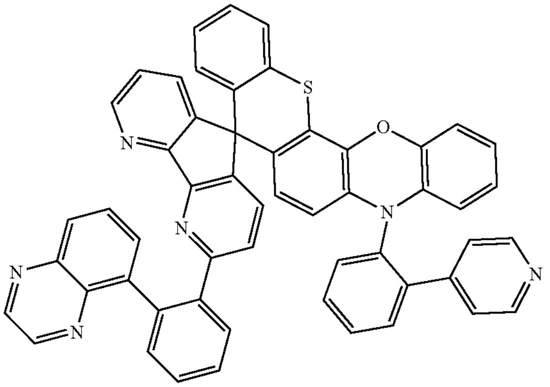
H133
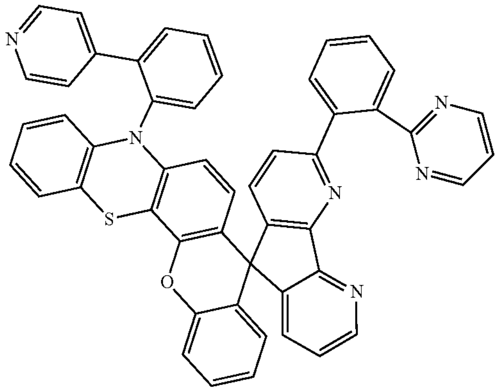
H134
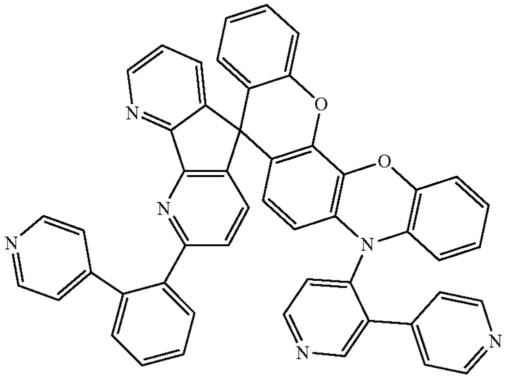

-continued
H135
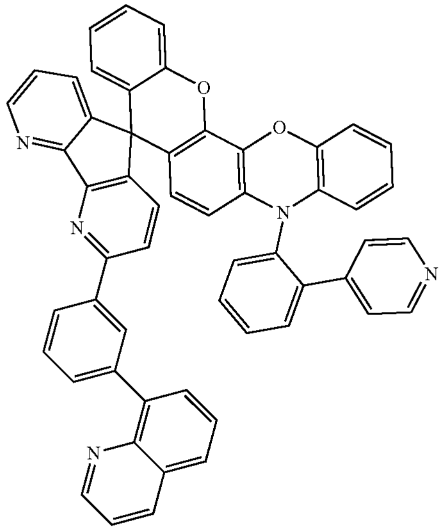
H136
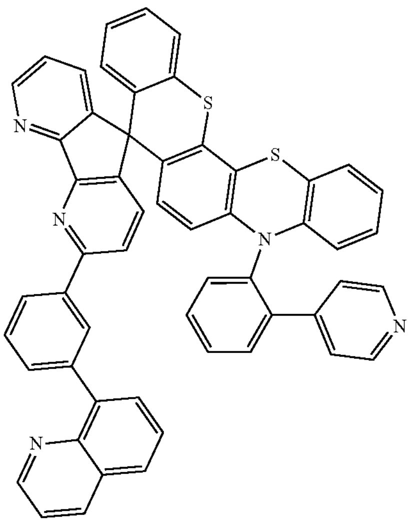
H137
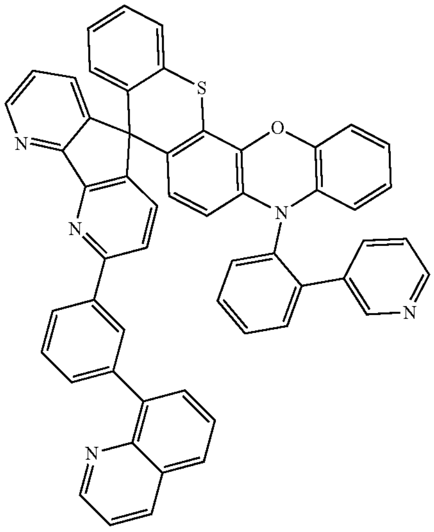
-continued
H138
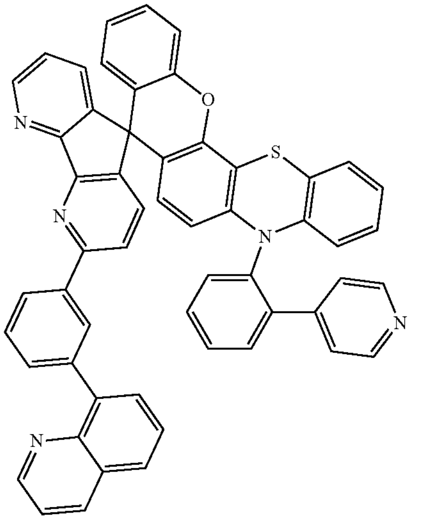
H139
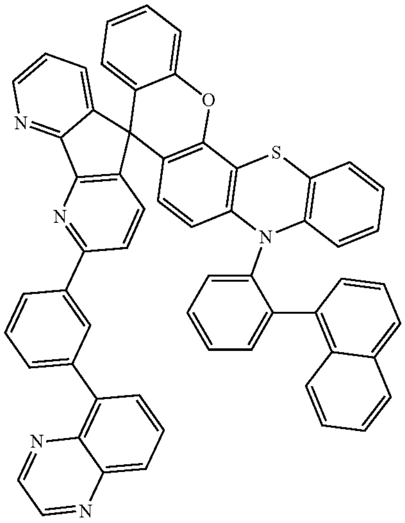
H140
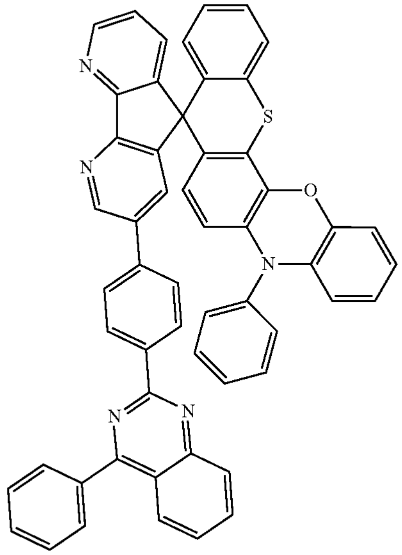

-continued
H141
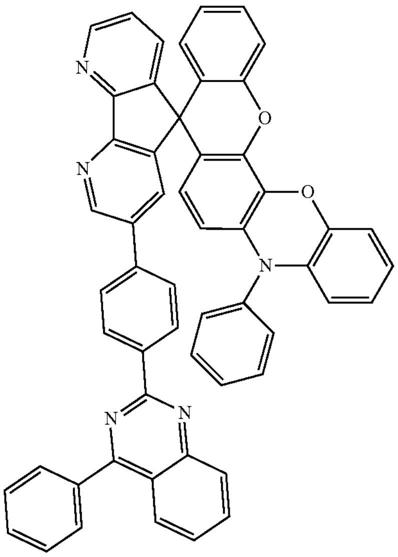
H142
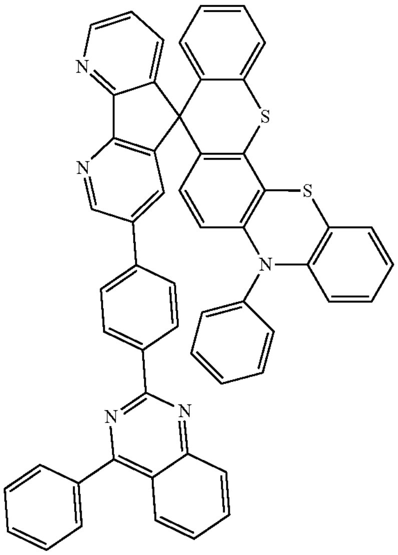
H143
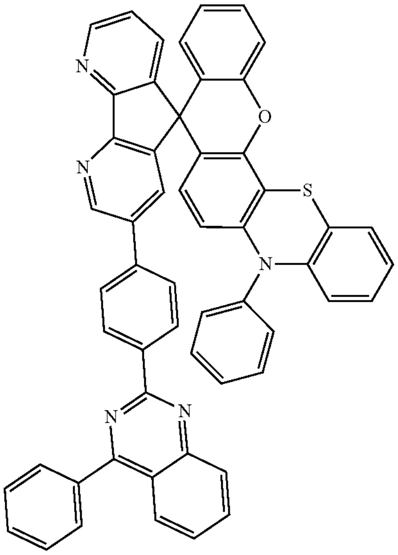
-continued
H144
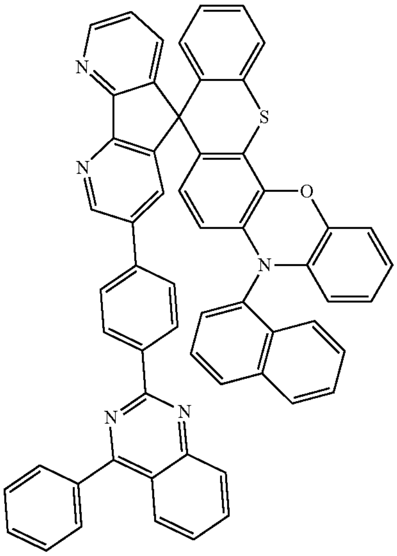
H145
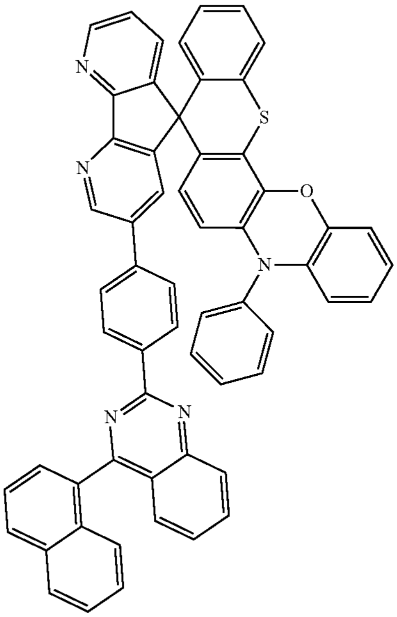
H146
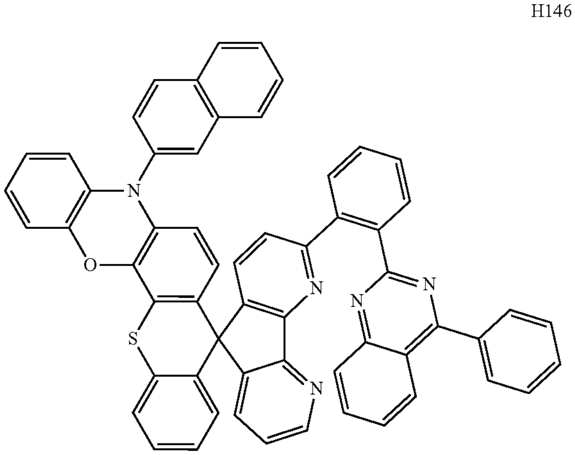

-continued
H147
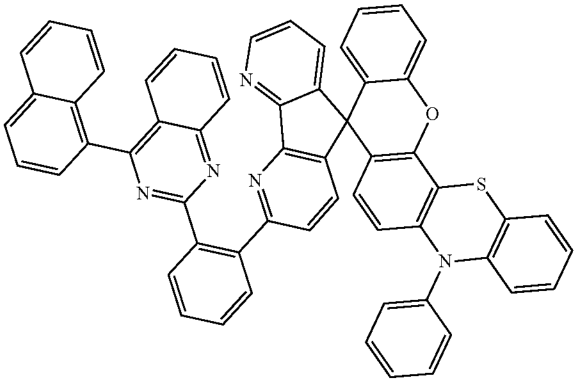
H148
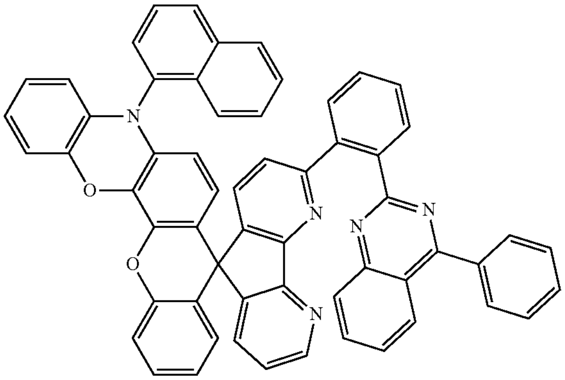
H149
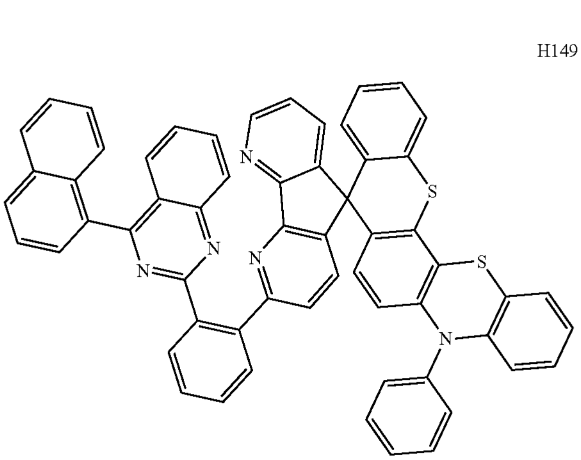
-continued
H150
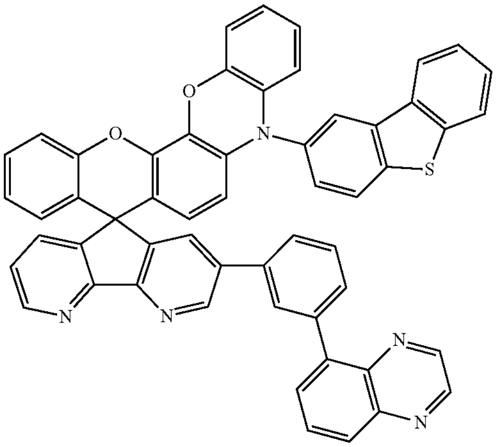
H151
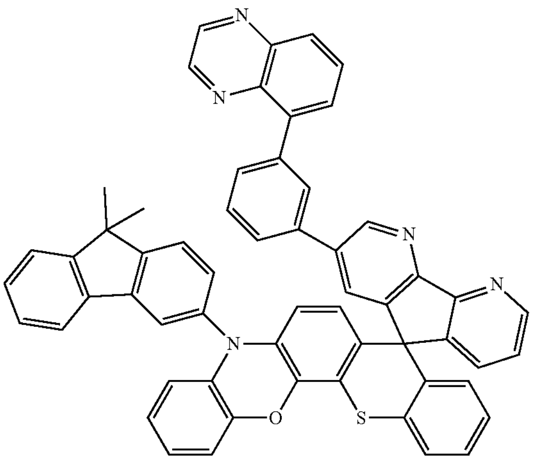
H152
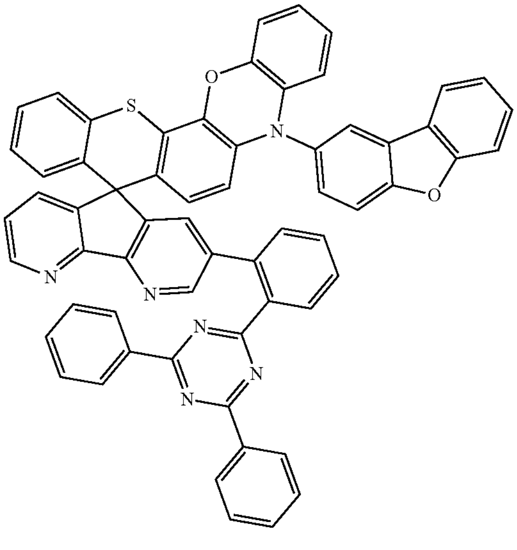

-continued
H153
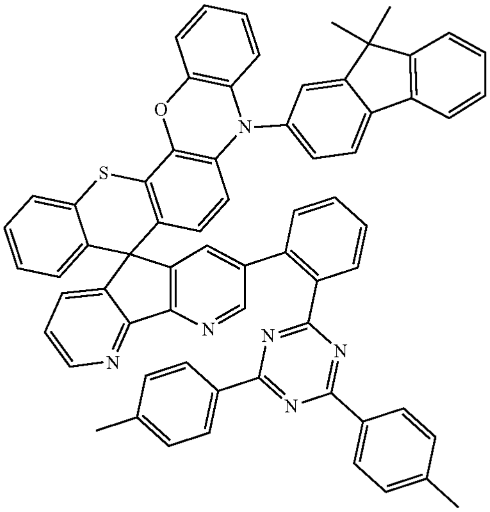
H154
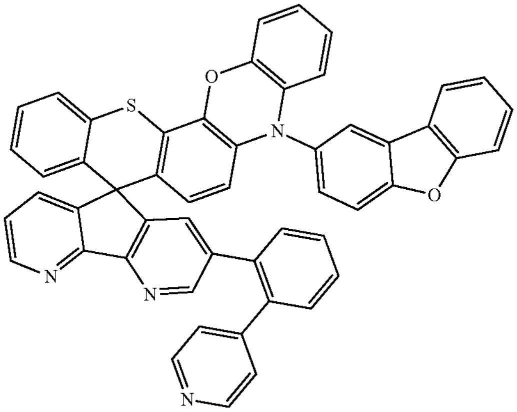
H155
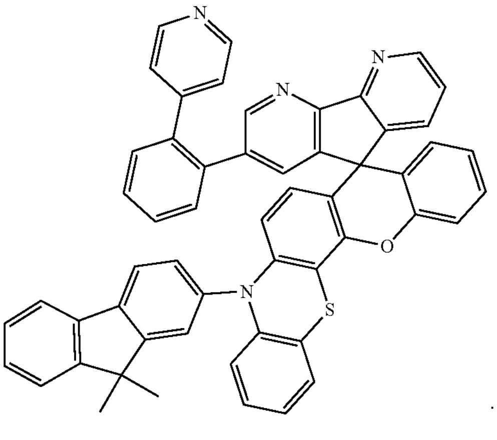
.
17. The nitrogen-containing spiral organic compound according to claim 1, which has any one of the following structures:
L01
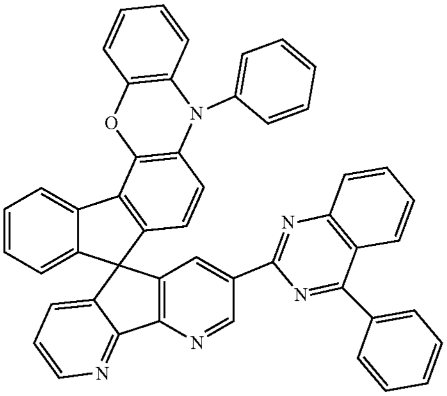
L02
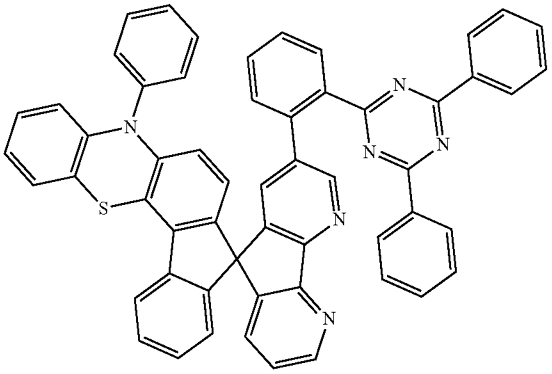
L03
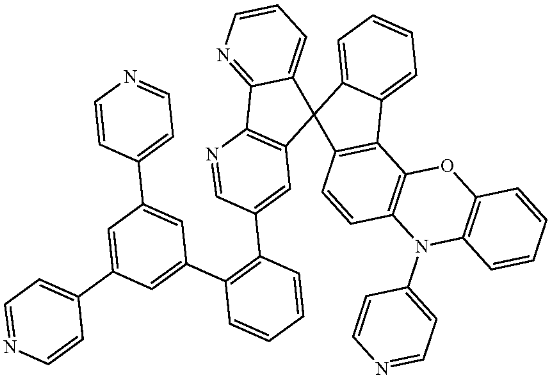
L04
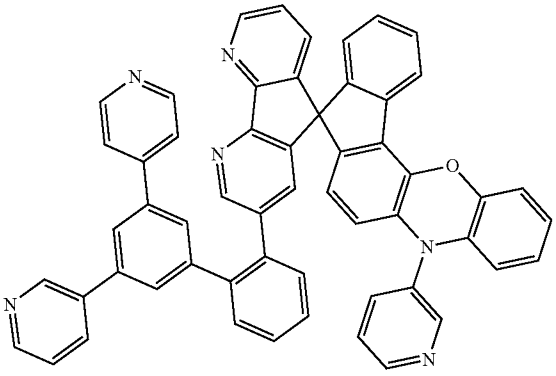

-continued
L05
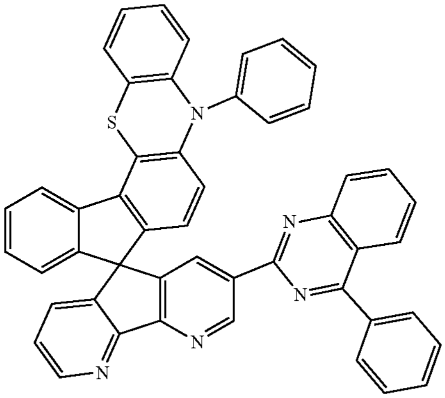
L06
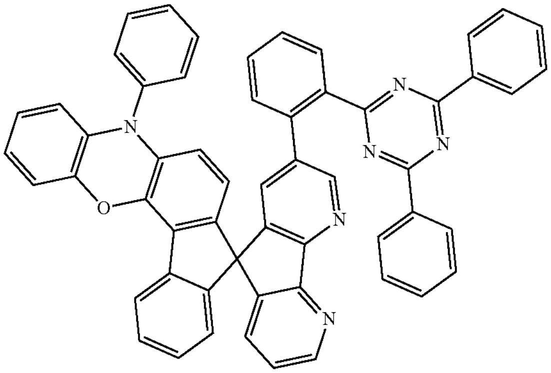
L07
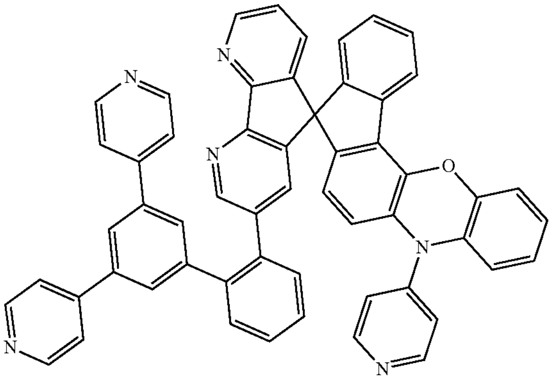
L08
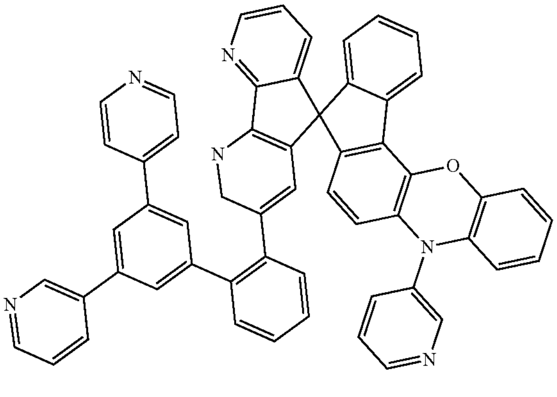
-continued
L09
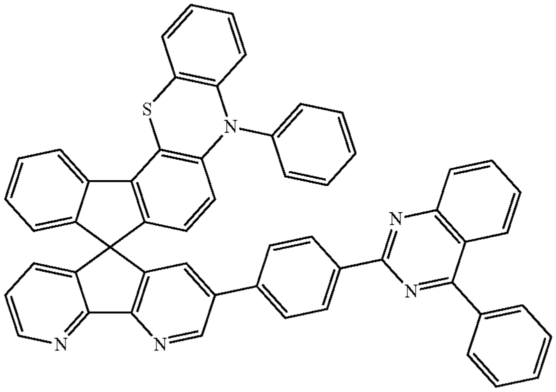
L10
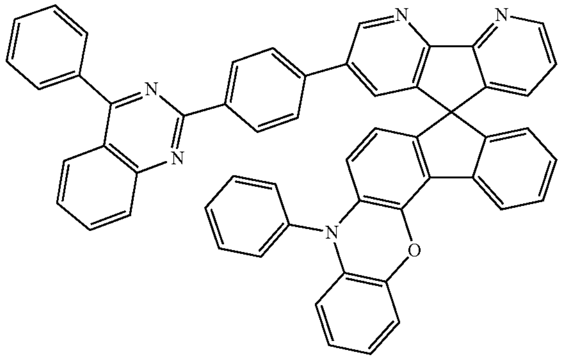
L11
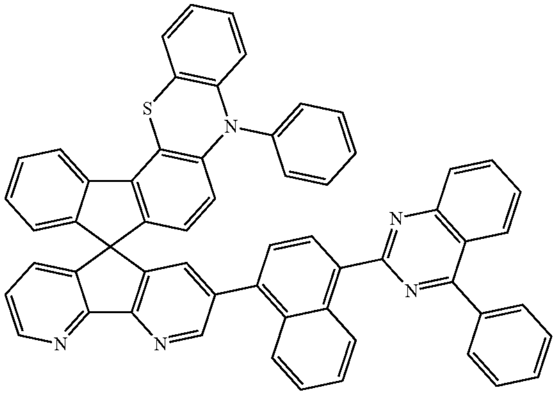
L12
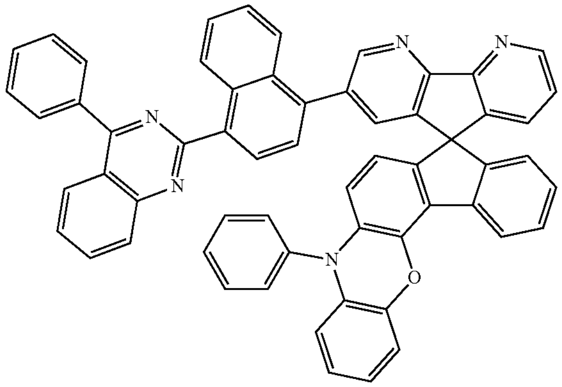

-continued
L13
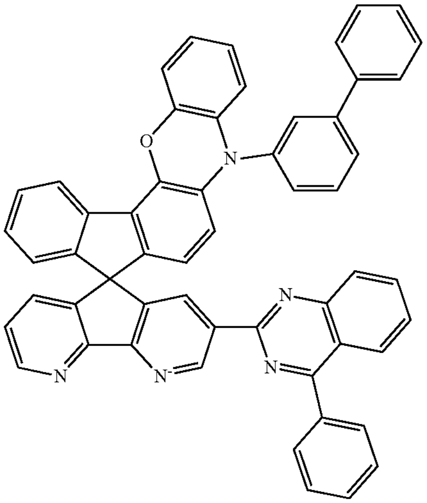
L14
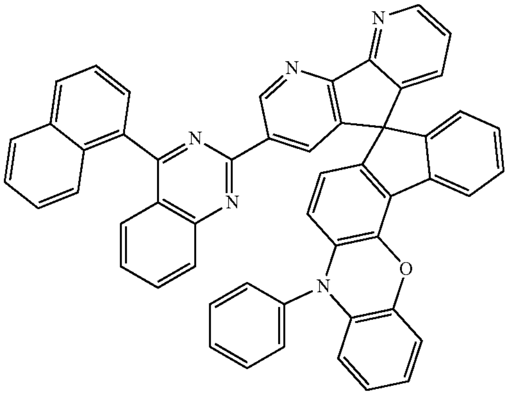
L15
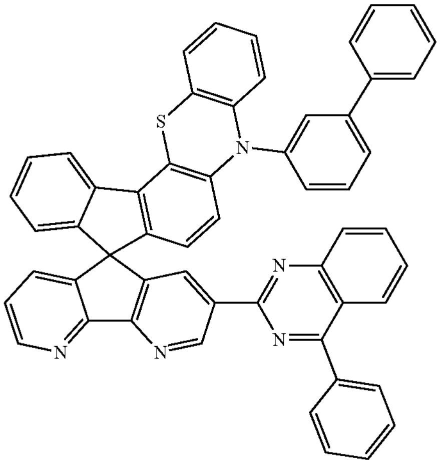
-continued
L16
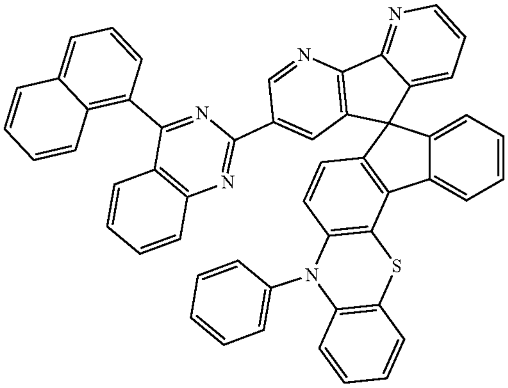
L17
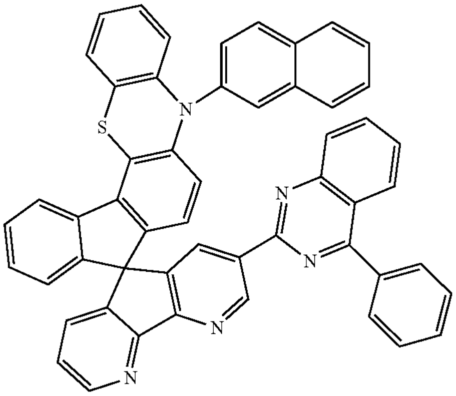
L18
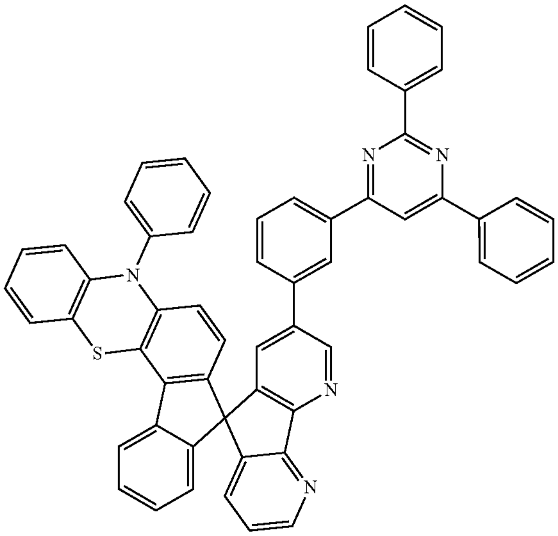

-continued
L19
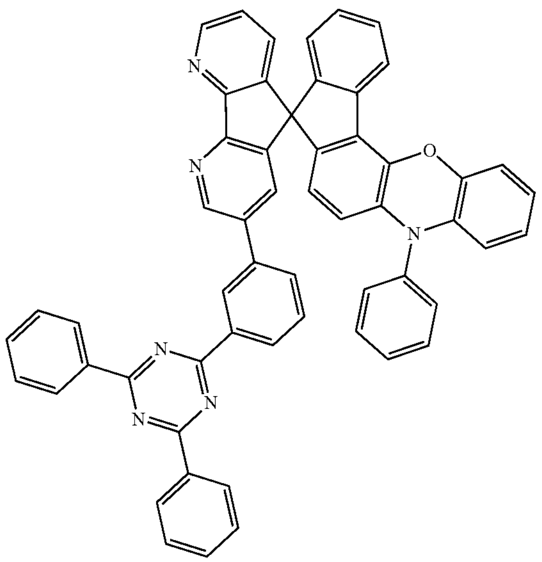
L20
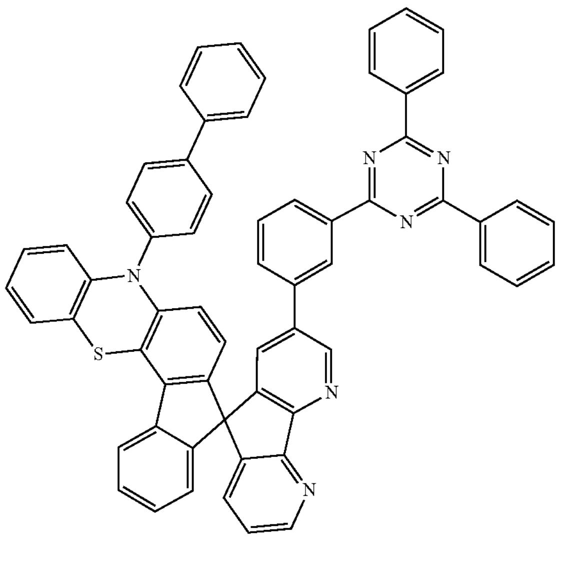
-continued
L21
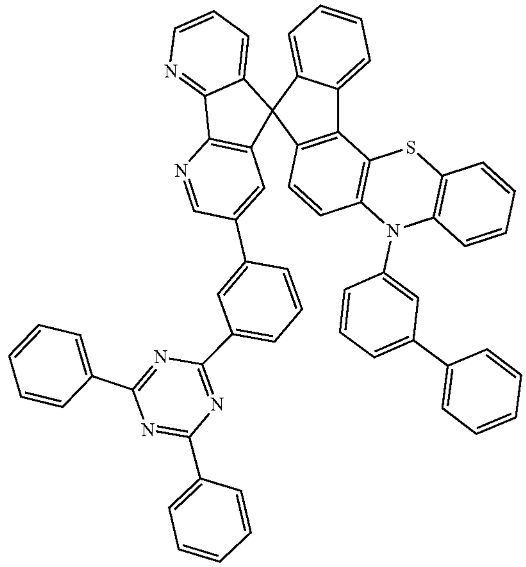
L22
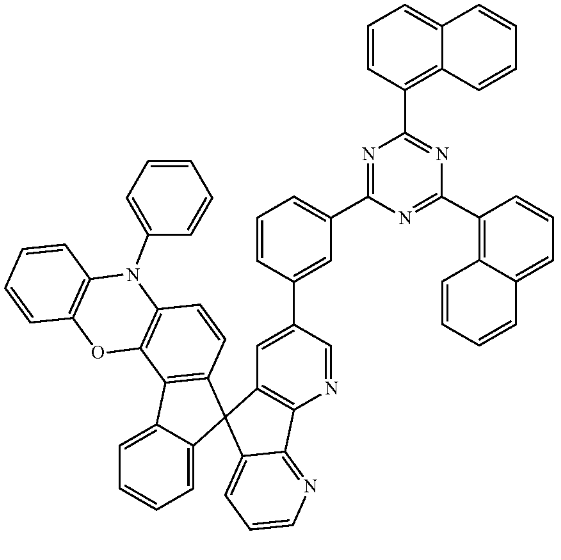

-continued
L23
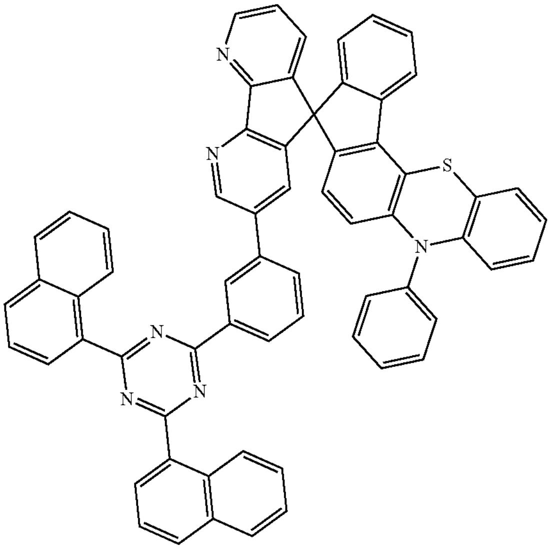
-continued
L25
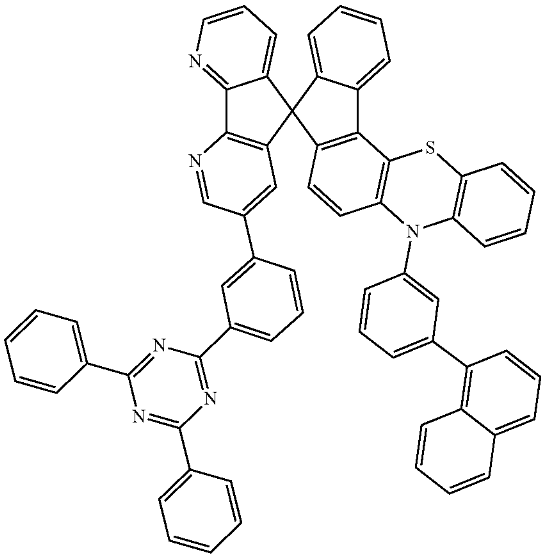
L24
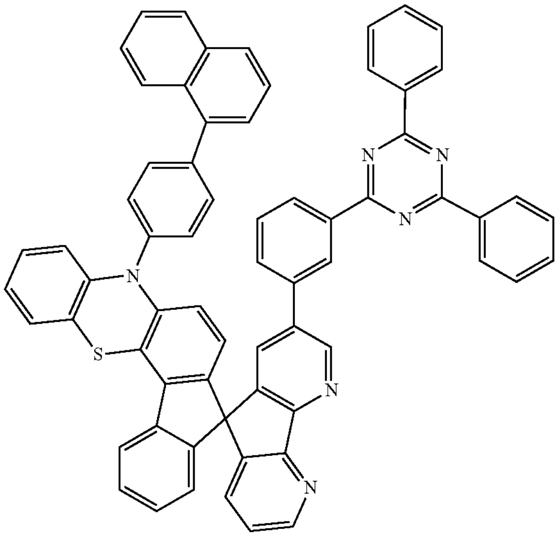
L26
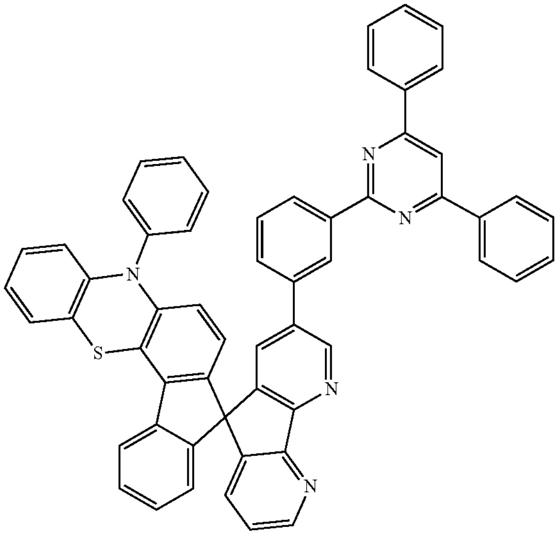

L27
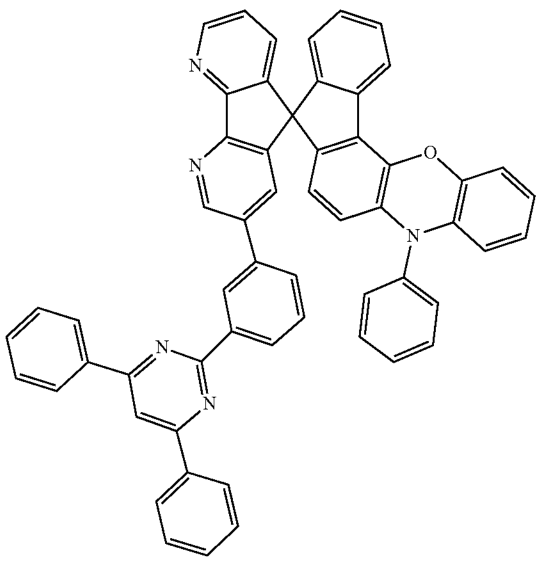
L28
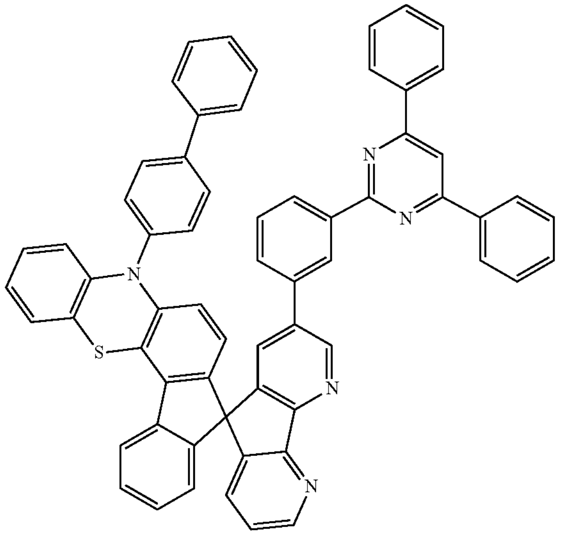
L29
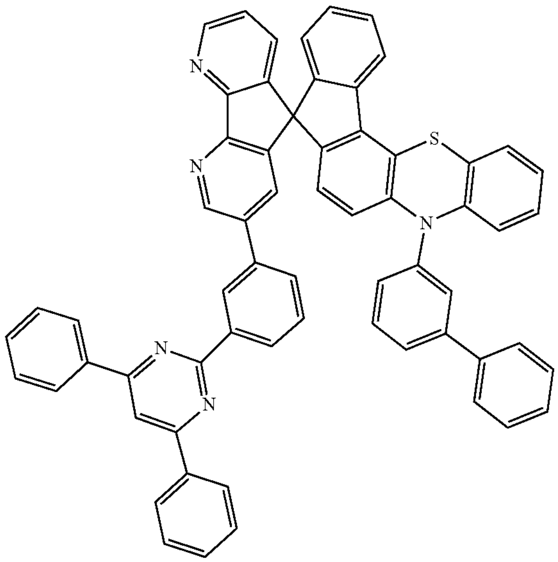
L30
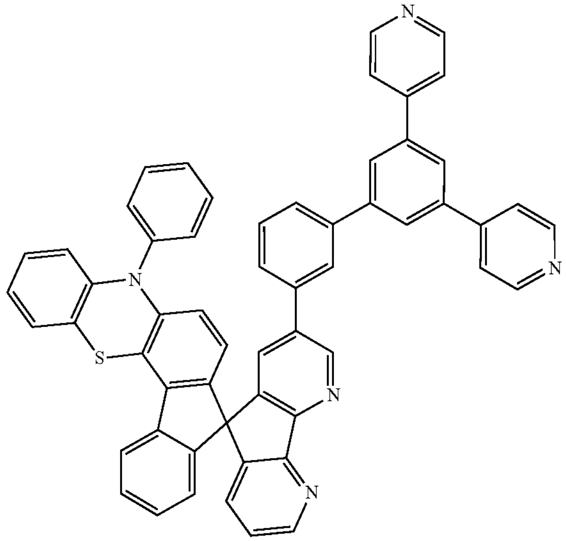

-continued
L31
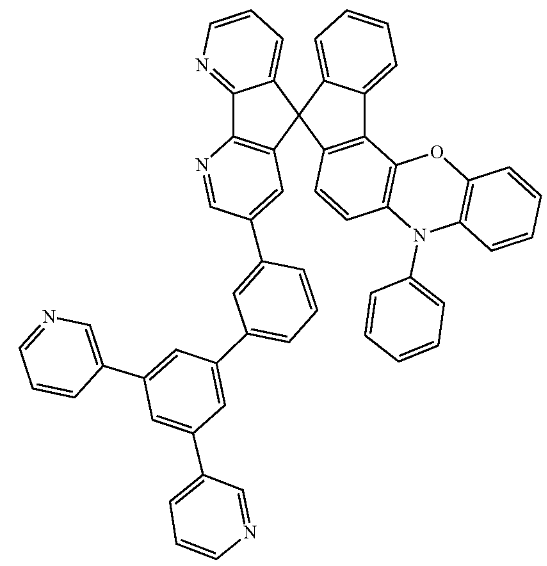
L33
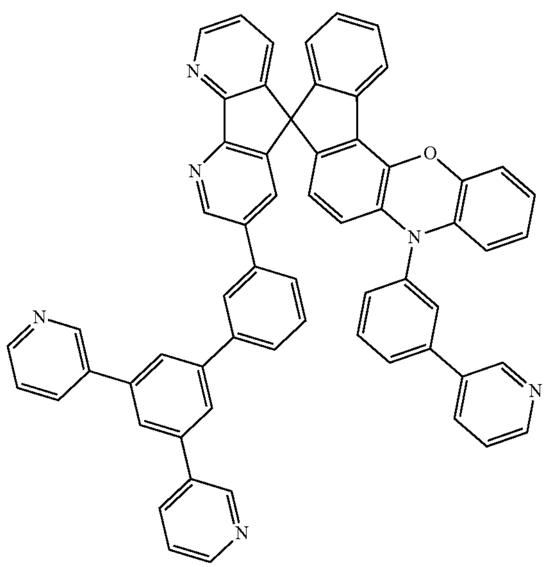
L32
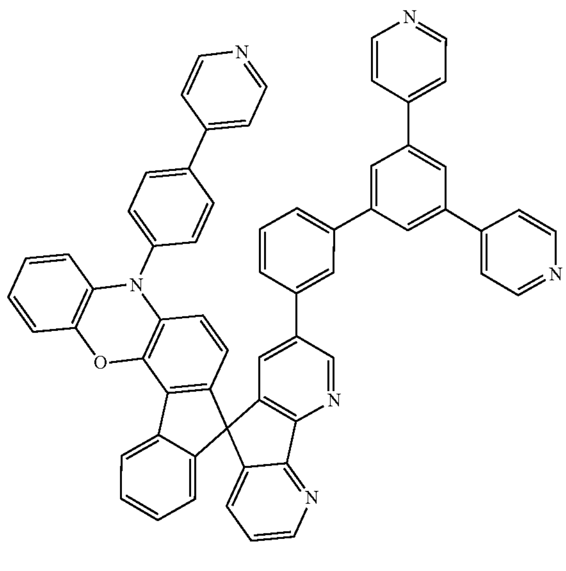
L34
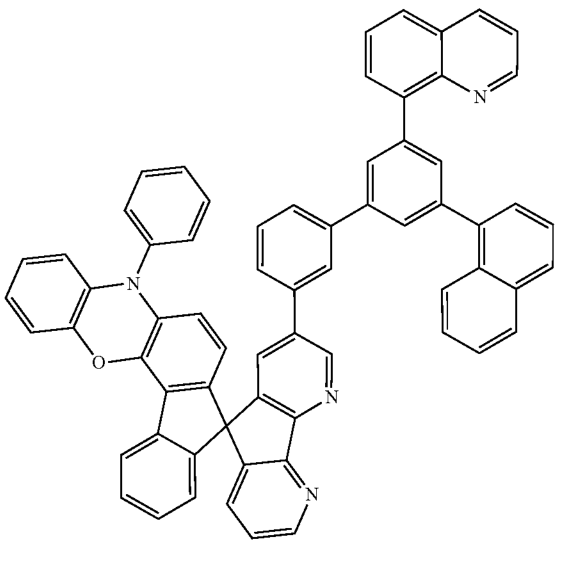

-continued
L35
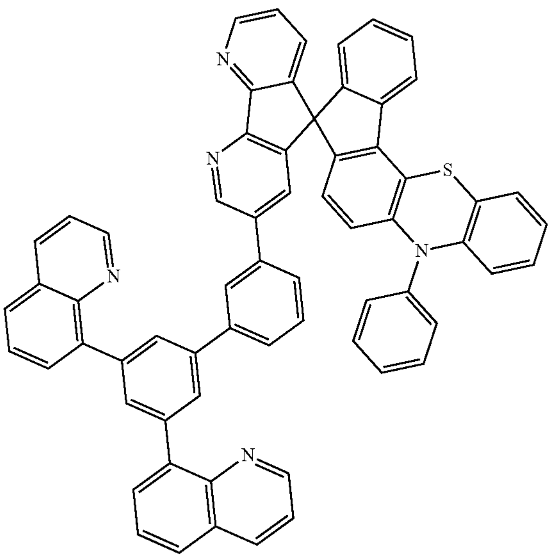
L36
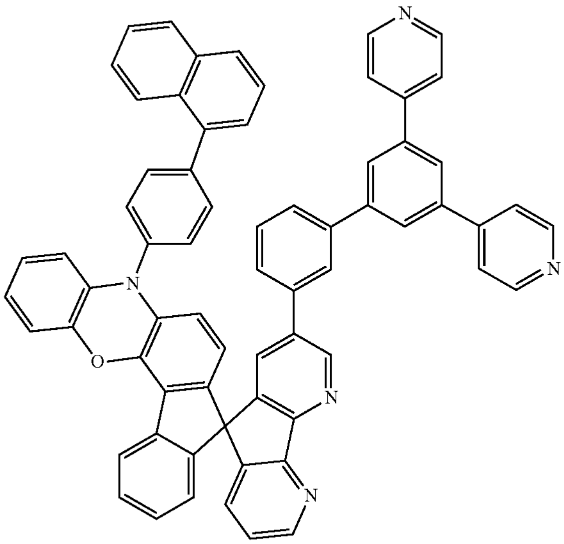
-continued
L37
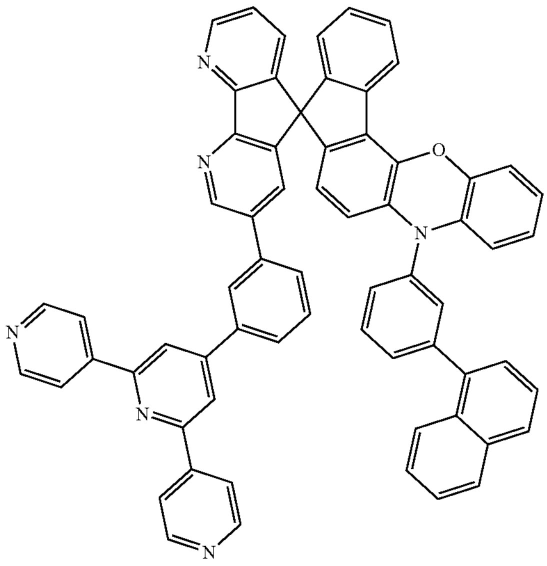
L38
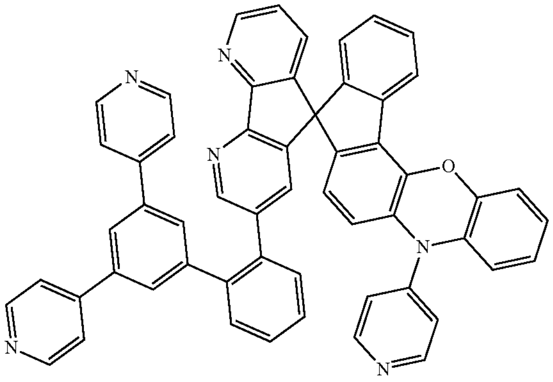
L39
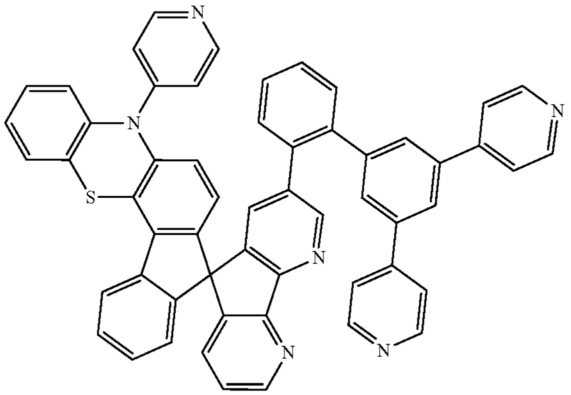

-continued
L40
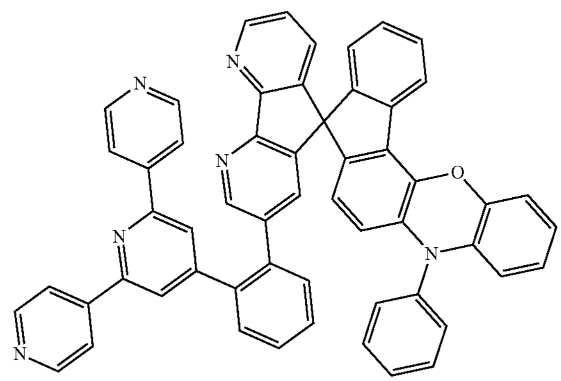
L41
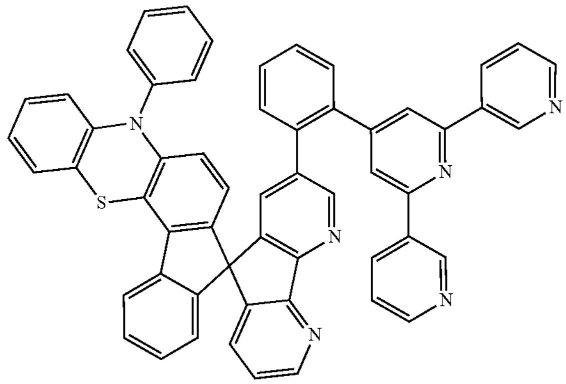
L42
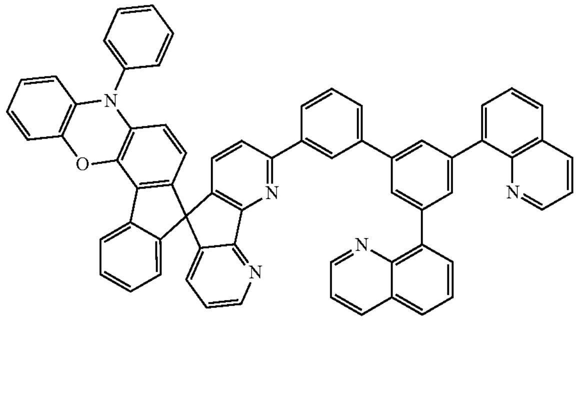
L43
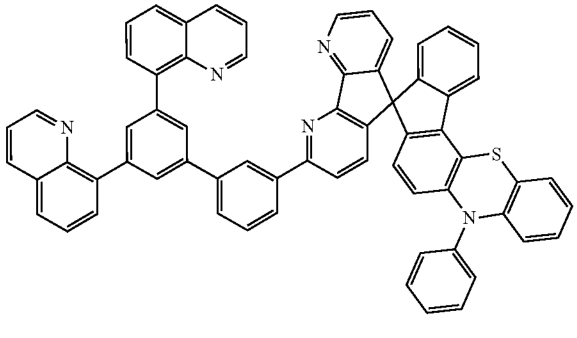
-continued
L44
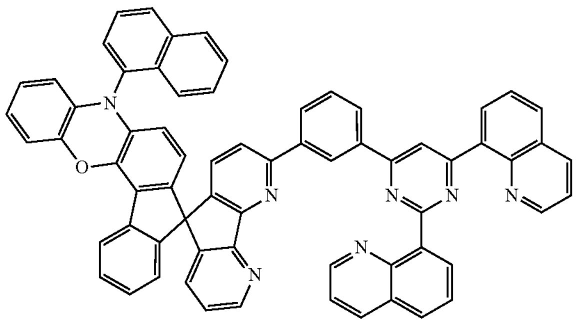
L45
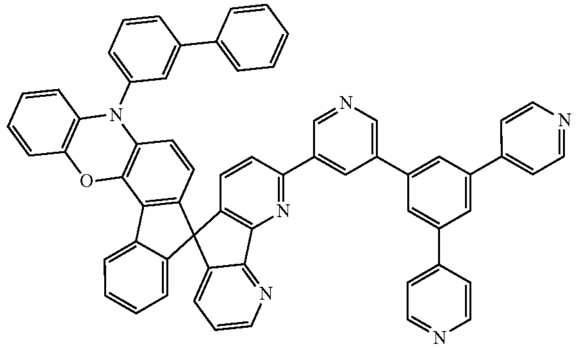
L46
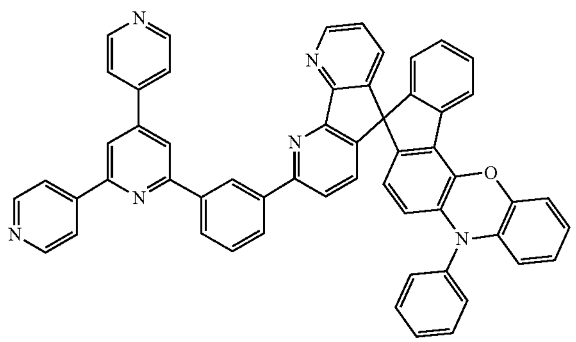
L47
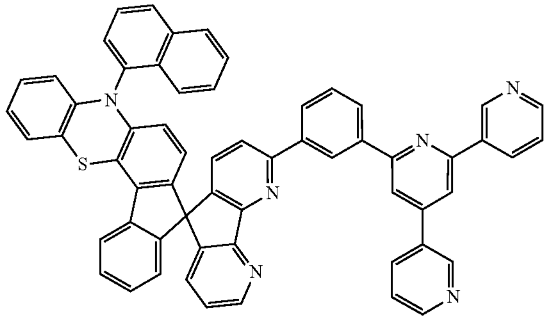

-continued
L48
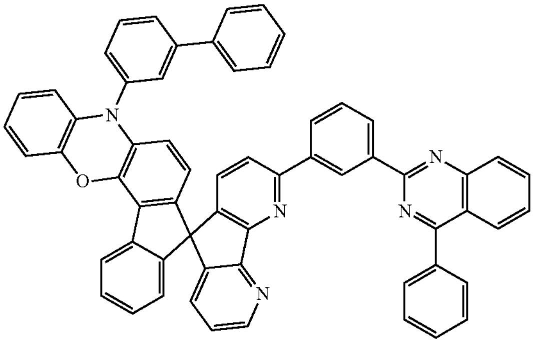
L49
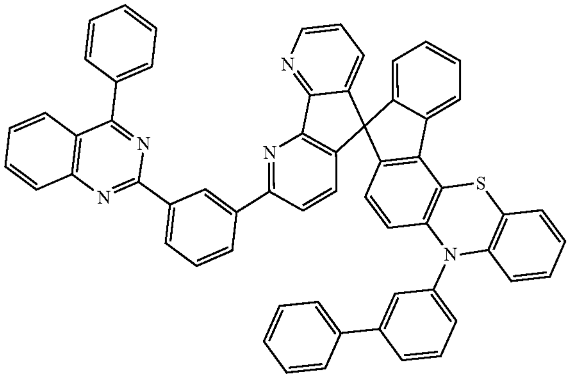
L50
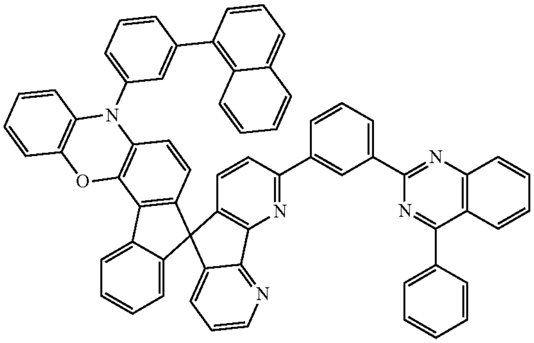
L51
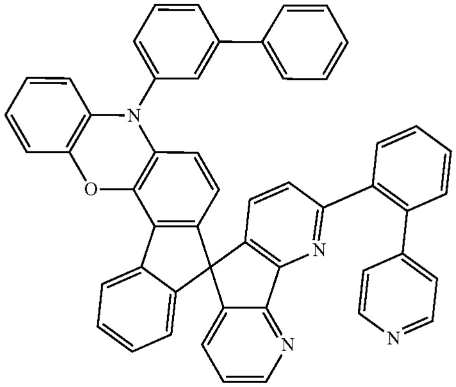
-continued
L52
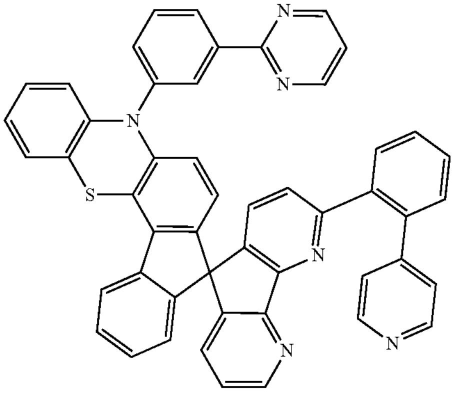
L53
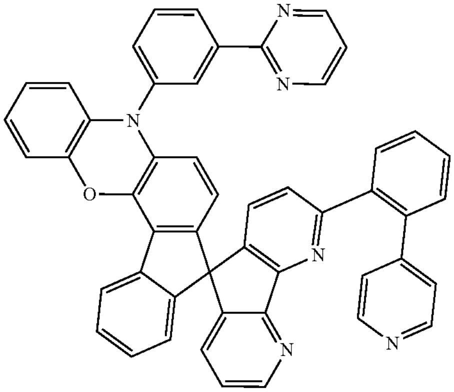
L54
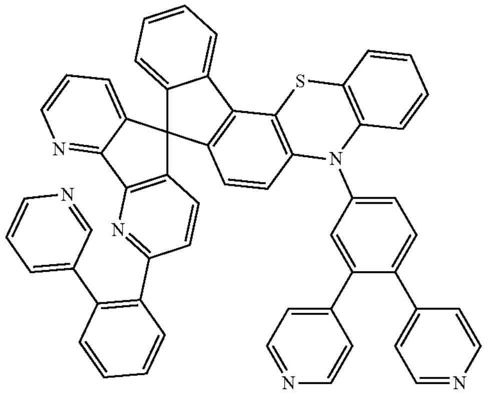
L55
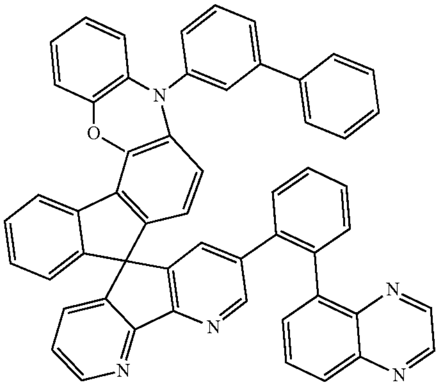

-continued
L56
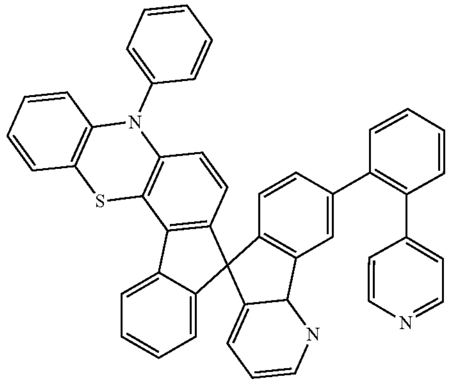
L57
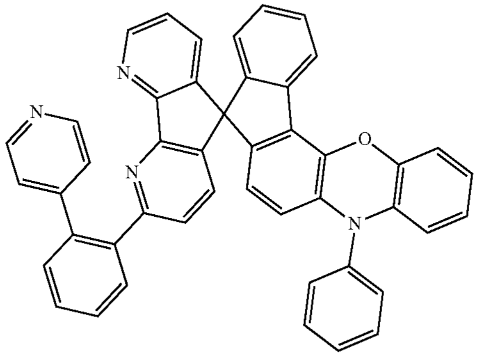
L58
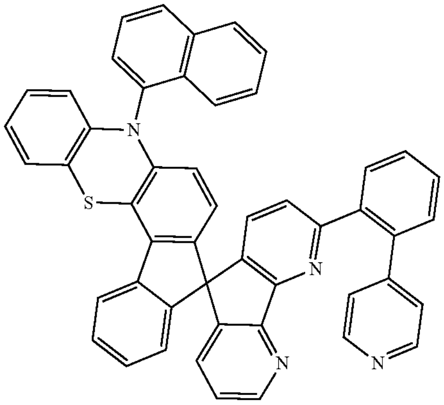
L59
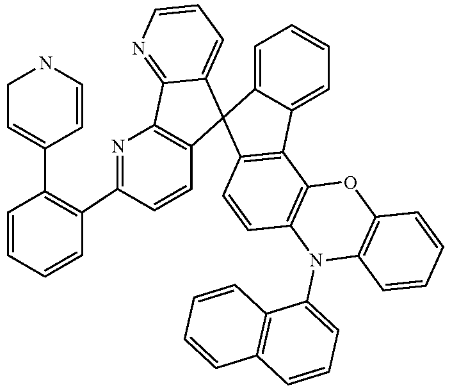
-continued
L60
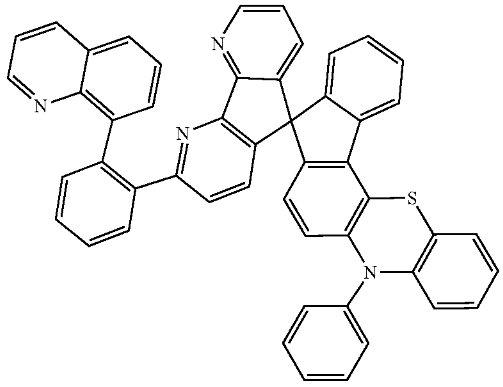
L61
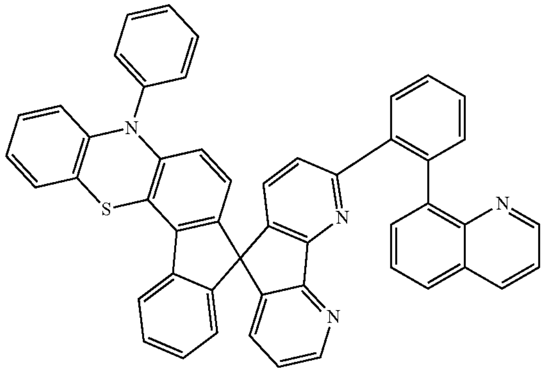
L62
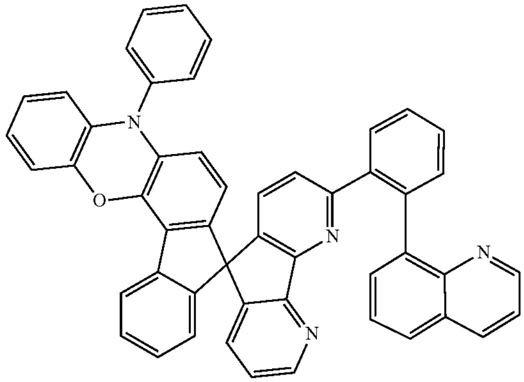
L63
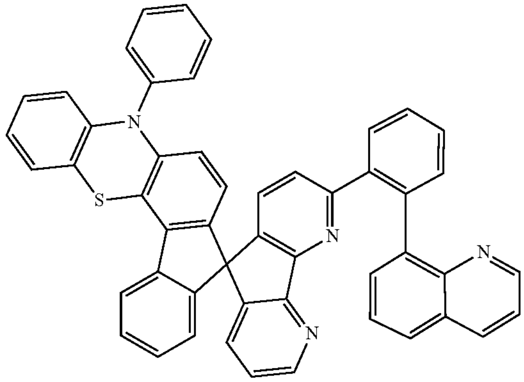

L64
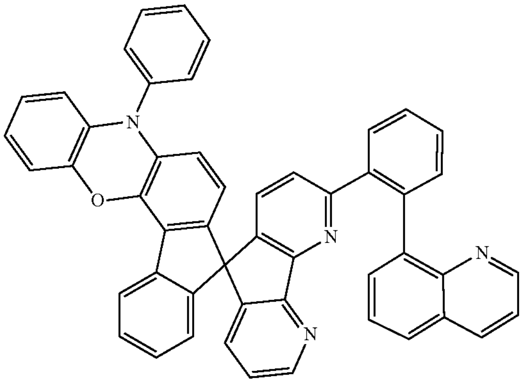
L65
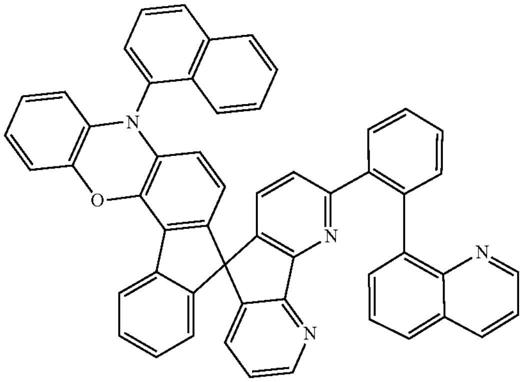
L66
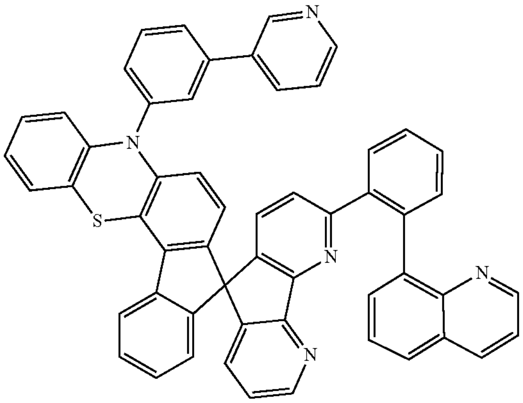
L67
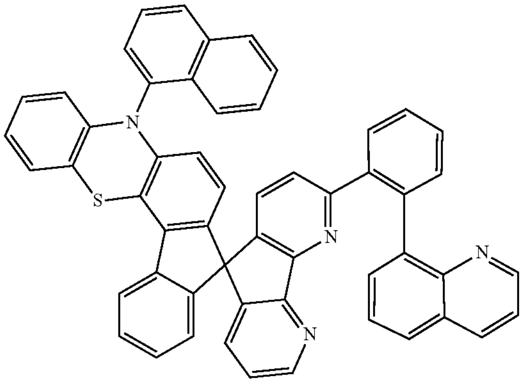
L68
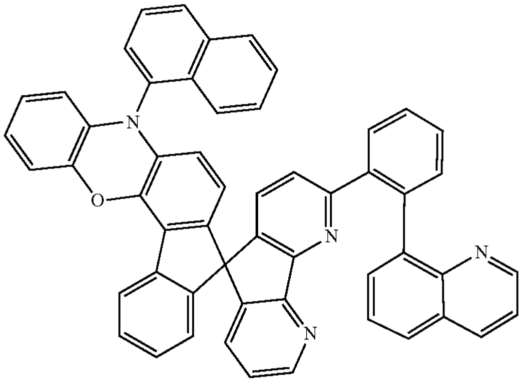
L69
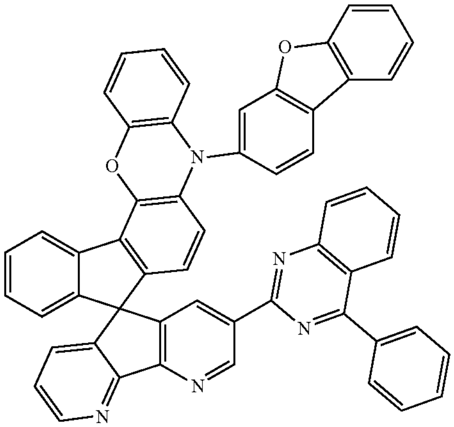
L70
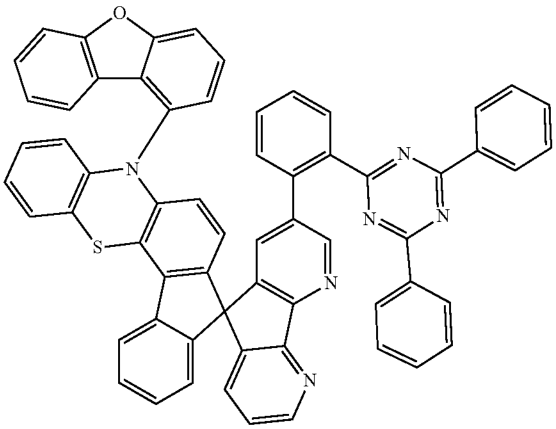

-continued

L71

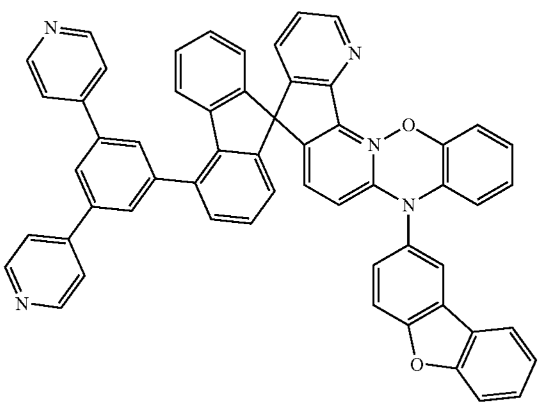

L72

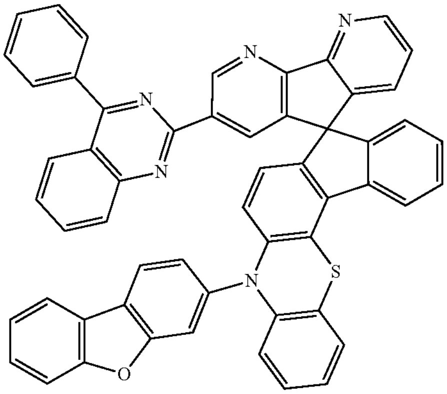

L73

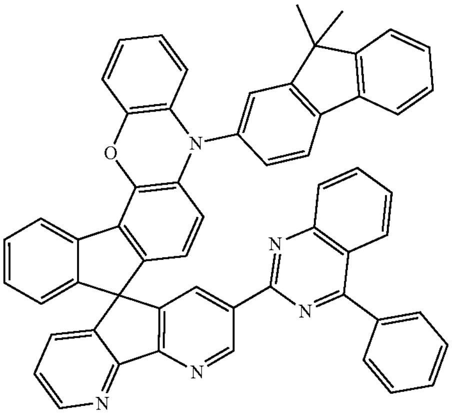

-continued

L74

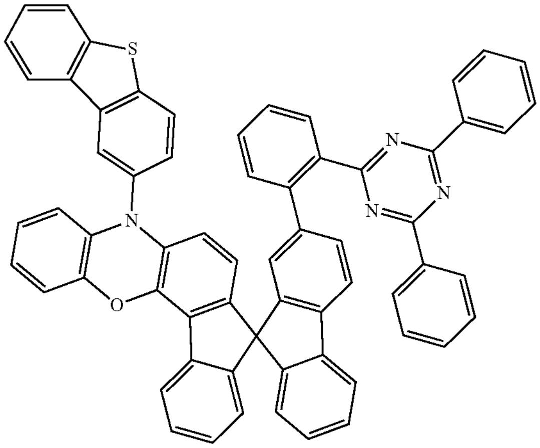

L75

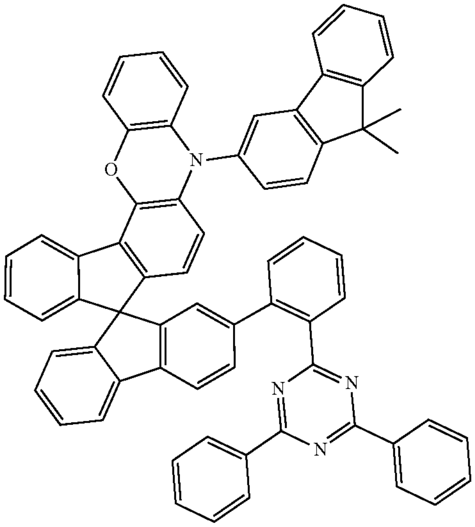

L76

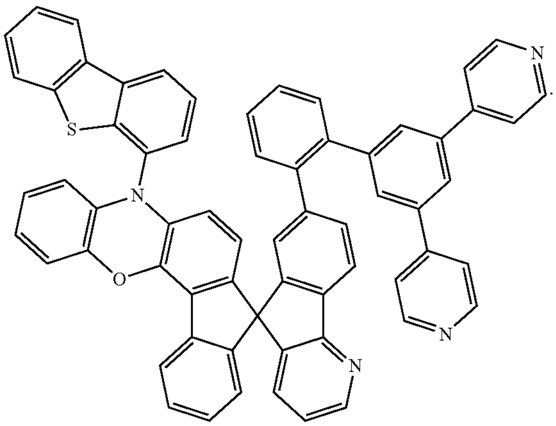

18. An organic light-emitting device, comprising an anode, a cathode and an organic thin film layer between the anode and the cathode, wherein the organic thin film layer comprises a light-emitting layer, and the light-emitting layer comprises at least one of the nitrogen-containing spiral organic compound according to claim 1.

19. The organic light-emitting device according to claim 18, wherein the organic thin film layer comprises a phosphorescent light-emitting layer, and the phosphorescent light-emitting layer comprises at least one of the nitrogen-containing spiral organic compound according to claim 1.

20. A display panel, comprising the organic light-emitting device according to claim 18.

* * * * *